US012780916B2

(12) United States Patent
Yao et al.

(10) Patent No.: US 12,780,916 B2
(45) Date of Patent: Nov. 3, 2026

(54) BINDING AGENTS TARGETING TUMORS AND/OR IMMUNE CELLS

(71) Applicant: KisoJi Biotechnology Inc., Montréal (CA)

(72) Inventors: Shugang Yao, Montréal (CA); Richard Wargachuk, Montréal (CA); Wenyang Hou, Montréal (CA); Luis Da Cruz, Montréal (CA); David S. Young, Montréal (CA)

(73) Assignee: KisoJi Biotechnology Inc., Montréal (CA)

( * ) Notice: Subject to any disclaimer, the term of this patent is extended or adjusted under 35 U.S.C. 154(b) by 398 days.

(21) Appl. No.: 18/283,579

(22) PCT Filed: Mar. 25, 2022

(86) PCT No.: PCT/CA2022/050442

§ 371 (c)(1),
(2) Date: Sep. 22, 2023

(87) PCT Pub. No.: WO2022/204793

PCT Pub. Date: Oct. 6, 2022

(65) Prior Publication Data

US 2024/0166739 A1 May 23, 2024

Related U.S. Application Data

(60) Provisional application No. 63/301,305, filed on Jan. 20, 2022, provisional application No. 63/249,784, filed on Sep. 29, 2021, provisional application No. 63/168,606, filed on Mar. 31, 2021.

(51) Int. Cl.
*C07K 16/28* (2006.01)
*A61P 35/02* (2006.01)
*A61K 39/00* (2006.01)

(52) U.S. Cl.
CPC .......... *C07K 16/2803* (2013.01); *A61P 35/02* (2018.01); *C07K 16/2809* (2013.01); *C07K 16/2818* (2013.01); *A61K 2039/505* (2013.01); *C07K 2317/24* (2013.01); *C07K 2317/31* (2013.01); *C07K 2317/524* (2013.01); *C07K 2317/526* (2013.01); *C07K 2317/53* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 2014/0348839 A1 | 11/2014 | Chowdhury et al. |
| 2017/0198051 A1 | 7/2017 | Eckelman et al. |
| 2018/0222966 A1 | 8/2018 | Verhessen et al. |
| 2019/0345235 A1 | 11/2019 | Hollands et al. |
| 2020/0030356 A1 | 1/2020 | Jandaghi et al. |

FOREIGN PATENT DOCUMENTS

| | | | |
|---|---|---|---|
| EP | 3998287 A1 | 5/2022 |
| WO | 2007035092 A2 | 3/2007 |
| WO | 2011051327 A2 | 5/2011 |
| WO | 2013/012733 A1 | 1/2013 |
| WO | 2016124768 A1 | 8/2016 |
| WO | 2016192613 A1 | 12/2016 |
| WO | 2019179434 A1 | 9/2019 |
| WO | 2021004480 A1 | 1/2021 |
| WO | 2021/119832 A1 | 6/2021 |
| WO | 2022204793 A1 | 10/2022 |

OTHER PUBLICATIONS

Muyldermans et al (ARB:82:775-797, 2013).*
Bonuccelli et al (Parkinsonism and Related Disorders, 15S:s44-s53, 2009).*
"International Search Report and Written Opinion" for International Application No. PCTCA2022050442 dated Jul. 8, 2022 (19 pages).
Angal, et al., "A Single Amino Acid Substitution Abolishes the Heterogeneity of Chimeric Mouse/Human (IgG4) Antibody", Molecular Immunology, vol. 30, No. 1, Sep. 8, 1992 (pp. 105-108).
Arai, et al., "Design of the Linkers which Effectively Separate Domains of a Bifunctional Fusion Protein", Protein Engineering, Design and Selection, vol. 14, No. 8, 2001, pp. 529-532, DOI: 10.1093/protein/14.8.529, (4 pages).
Chen, et al., "Fusion Protein Linkers: Property, Design and Functionality", Advanced Drug Delivery Reviews, vol. 65, No. 10, 2013, DOI: 10.1016/j.addr.2012.09.039 (pp. 1357-1369).
Conrath ELS, et al., "Camel Single-domain Antibodies as Modular Building Units in Bispecific and Bivalent Antibody Constructs", The Journal of Biological Chemistry, vol. 276, No. 10, 2001 (pp. 7346-7350).
Coppieters, et al., "Formatted Anti-Tumor Necrosis Factor a VHH Proteins Derived from Camelids Show Superior Potency and Targeting to Inflamed Joints in a Murine Model of Collagen-Induced Arthritis", Arthritis & Rheumatism, vol. 54, DOI 10.1002/art.21827, No. 6, Jun. 2006 (pp. 1856-1866).
De Vlieger, et al., "Single-Domain Antibodies and Their Formatting to Combat Viral Infections", Antibodies, vol. 8, No. 1, 2019, DOI: 10.3390/antib8010001, (22 pages).
Detalle et al., "Generation and Characterization of ALX-0171, a Potent Novel Therapeutic Nanobody for the Treatment of Respiratory Syncytial Virus Infection", Antimicrobial Agents and Chemotherapy, vol. 60, No. 1, Jan. 2016, DOI: 10.1128/AAC.01802-15, (8 pages).

(Continued)

*Primary Examiner* — Brad Duffy
(74) *Attorney, Agent, or Firm* — Proskauer Rose LLP

(57) ABSTRACT

The present disclosure generally relates to binding agents that are capable of targeting tumor cells and/or immune cells. The binding agents of the present disclosure comprise one or more antigen binding domains of heavy chain antibodies (HcAb) which are capable of binding to DR2, to PD-1 and/or to CD47. The binding agents of the present disclosure may be in the form of monomers or multimers and may be monospecific or multispecific.

32 Claims, 34 Drawing Sheets

Specification includes a Sequence Listing.

(56) References Cited

OTHER PUBLICATIONS

Duggan, "Caplacizumab: First Global Approval", Adisinsight Report Drug (2018) 78:1639-1642; http//doi.org.10.1007/s40265-0989-0, Oct. 8, 2018 (pp. 1639-1642).
Fleischmann, et al., "A Novel Individualized Treatment Approach in Open-Label Extension Study of Ozoralizumab (ATN-103) in Subjects with Rheumatoid Arthritis on a Background of Methotrexate", 2012 ACR/ARHP Annual Meeting, Abstract No. 1311, (4 pages).
Fridy, et al., "A Robust Pipeline for Rapid Production of Versatile Nanobody Repertoires", Nature Methods, vol. 11, No. 12, Dec. 2014, DOI: 10.1038/nmeth.3170, Author Manuscript (pp. 1253-1260).
Godar, et al., "Therapeutic Bispecific Antibody Formats: A Patent Applications Review (1994-2017) ", Expert Opinion on Therapeutic Patents, vol. 28, No. 3, 2018, DOI: 10.1080/13543776.2018.1428307 (pp. 251-276).
Ha, et al., "Immunoglobulin Fc Heterodimer Platform Technology: From Design to Applications in Therapeutic Antibodies and Proteins", Frontiers in Immunology, vol. 7, Article No. 394, Oct. 6, 2016, DOI: 10.3389/fimmu.2016.00394 (16 pages).
Hamers-Casterman, et al., "Naturally occurring antibodies devoid of light chains", Nature, vol. 363, Jun. 3, 1993, DOI: 10.1038/363446a0 (pp. 446-448).
Hmila, et al., "VHH, Bivalent Domains and Chimeric Heavy Chain-only Antibodies with High Neutralizing Efficacy for Scorpion Toxin Aahi", Molecular Immunology, vol. 45, No. 14, 2008, DOI: 10.1016/j.molimm.2008.04.011 (pp. 3847-3856).
Hultberg, et al., "Llama-Derived Single Domain Antibodies to Build Multivalent, Superpotent and Broadened Neutralizing Anti-Viral Molecules", PLoS One, vol. 6, No. 4, Apr. 2011, e17665, DOI: 10.1371/journal.pone.0017665 (12 pages).
Jähnichen, et al., "CXCR4 nanobodies (VHH-based single variable domains) potently inhibit chemotaxis and HIV-1 replication and mobilize stem cells", Proceedings of the National Academy of Science, vol. 107, No. 47, Nov. 23, 2010 (pp. 20565-20570).
Khan, et al., "Prominence of Dopamine D2 Short Isoform in Dopaminergic Pathways", Proc. Natl. Acad. Sci. USA, vol. 95, Jun. 1998 (pp. 7731-7736).
Kovalenko, et al., "Atypical Antigen Recognition Mode of a Shark Immunoglobulin New Antigen Receptor (IgNAR) Variable Domain Characterized by Humanization and Structural Analysis", Journal of Biological Chemistry, vol. 288, No. 24, Jun. 14, 2013, DOI: 10.1074/jbc.M112.435289 (pp. 17408-17419).
Laursen, et al., "Universal Protection Against Influenza Infection by a Multidomain Antibody to Influenza Hemagglutinin", Science, vol. 362, No. 6414, Nov. 2, 2018: 598-602, DOI: 10.1126/science.aaq0620, Author Manuscript (pp. 598-602).
Muyldermans, et al., "Distinct antibody species: structural differences creating therapeutic opportunities", Current Opinion in Immunology, vol. 40, Jun. 2016, DOI: 10.1016/j.coi.2016.02.003, (pp. 7-13).
Muyldermans, et al., "Sequence and Structure of VH Domain from Naturally Occurring Camel Heavy Chain Immunoglobulins Lacking Light Chains", Protein Engineering, vol. 7, No. 9, 1994 (pp. 1129-1135).
Saunders, "Conceptual Approaches to Modulating Antibody Effector Functions and Circulation Half-Life", Frontiers in Immunology, vol. 10, Article No. 1296, Jun. 7, 2019, DOI: 10.3389/fimmu.2019.01296, (20 pages).
Schoen, et al., "Anti-RANKL nanobody ALX-0141 shows sustained biomarker inhibition in a Phase I study in healthy postmenopausal Women", Bone Abstracts, 1, pp. 135, 2013, DOI: 10.1530/boneabs.1.PP135 (1 page).
Simmons, et al., "Dimerisation Strategies for Shark IgNAR Single Domain Antibody Fragments", Journal of Immunological Methods 315, Aug. 28, 2006, (pp. 171-184).
Svecova, et al., "A Randomized, Double-blind, Placebo-controlled Phase 1 Study of Multiple Ascending Doses of Subcutaneous M1095, an Anti-interleukin 17A/F Nanobody, in Moderate-to-severe Psoriasis", Journal of the American Academy of Dermatology, vol. 81, No. Jul. 1, 2019, DOI: 10.1016/j.jaad.2019.03.056, (pp. 196-203).
Tatusova, et al., "Blast 2 Sequences, a new tool for comparing protein and nucleotide sequences", FEMS Microbiology Letters, vol. 174, No. 2, Mar. 18, 1999, DOI: 10.1111/j.1574-6968.1999.tb13575.x (pp. 247-250).
Van Roy, et al., "The preclinical pharmacology of the high affinity anti-IL-6R Nanobody® ALX-0061 supports its clinical development in rheumatoid arthritis", Arthritis Research & Therapy, vol. 17, Article No. 135, 2015, DOI: 10.1186/s13075-015-0651-0, (16 pages).
Vincke, et al., "General Strategy to Humanize a Camelid Single-domain Antibody and Identification of a Universal Humanized Nanobody Scaffold", Journal of Biological Chemistry, vol. 284, No. 5, Jan. 30, 2009, DOI: 10.1074/jbc.M806889200, (pp. 3273-3284).
Vu, et al., "Comparison of Llama Vh Sequences from Conventional and Heavy Chain Antibodies", Molecular Immunology, vol. 34, No. 16-17, Dec. 4, 1997 (pp. 1121-1131).
Wang, et al., "Design and Characterization of Mouse Igg1 and Igg2a Bispecific Antibodies for use in Syngeneic Models", mAbs, vol. 12, No. 1, 2019, e1685350 (12 pages).
Wei, et al., "Structural Basis of a Novel Heterodimeric Fc for Bispecific Antibody Production", Oncotarget, vol. 8, No. 31, 2017, DOI: 10.18632/oncotarget.17558, (pp. 51037-51049).
Anoynmous, "Anti-Dopamine D2 Receptor Antibody / AB1158—Millipore", XP003031281; http://www.millipore.com/catalogue.item/ab1558 (2012) (3 pages).
Simmons et al., "Dimerisation Strategies for Shark IgNAR Single Domain Antibody Fragments", Journal of Immunological Methods 315, Aug. 28, 2006, (pp. 171-184) (14 pages).
Svecova et al., "A Randomized, Double-blind, Placebo-controlled Phase 1 Study of Multiple Ascending Doses of Subcutaneous M1095, an Anti-interleukin 17A/F Nanobody, in Moderate-to-severe Psoriasis", Journal of the American Academy of Dermatology, vol. 81, No. 1, Jul. 2019, DOI: 10.1016/j.jaad.2019.03.056, (pp. 196-203) (8 pages).
Tatusova et al., "Blast 2 Sequences, a new tool for comparing protein and nucleotide sequences", FEMS Microbiology Letters, vol. 174, No. 2, Mar. 18, 1999, DOI: 10.1111/j.1574-6968.1999.tb13575.x (pp. 247-250) (4 pages).
Vincke et al., "General Strategy to Humanize a Camelid Single-domain Antibody and Identification of a Universal Humanized Nanobody Scaffold", Journal of Biological Chemistry, vol. 284, No. 5, Jan. 30, 2009, DOI: 10.1074/jbc.M806889200, (pp. 3273-3284) (12 pages).
Vu et al., "Comparison of Llama Vh Sequences from Conventional and Heavy Chain Antibodies", Molecular Immunology, vol. 34, No. 16-17, Dec. 4, 1997 (pp. 1121-1131) (11 pages).
Wei et al., "Structural Basis of a Novel Heterodimeric Fc for Bispecific Antibody Production", Oncotarget, vol. 8, No. 31, 2017, DOI: 10.18632/oncotarget.17558, (pp. 51037-51049) (13 pages).
Weissenrieder, Jillian S. et al., "Cancer and the Dopamine D2 Receptor: A Pharmacological Perspective", J Pharmacol Exp Ther 370:111-126, Jul. 2019; https://doi.org.10.1124/jpet.119.256818 (16 pages).
Yao Shugang et al., "Abstract P200: Pre-clinical development of a dopamine receptor 2, PD-1 and CD47 trispecific antibody for treatment of small cell lung cancer", Mol Cancer Ther (2021) 20 (12_Supplement): P200; https://doi.org/10.1158/1535-7163.TARG-21-P200 (4 pages).
International Search Report for International Application No. PCT/CA2023/051305 dated Jan. 6, 2024 (6 pages).
Kaur, et al., "A Function-blocking CD47 Antibody Suppresses Stem Cell and EGF Signaling in Triple-Negative Breast Cancer", Oncotarget, vol. 7, No. 9, Jan. 31, 2016, DOI: 10.18632/oncotarget.7100, pp. 10133-10152 (20 pages).
Schimid, et al., "Pembrolizumab for Early Triple-Negative Breast Cancer", New England Journal of Medicine, vol. 382, No. 9, Feb. 27, 2020, DOI: 10.1056/NEJMoa1910549, pp. 810-821 (12 pages).

* cited by examiner

Figure 2

| Name | KC018 | | Dopamine | | KC011 | | KC012 | | KC013 | | KC014 | |
|---|---|---|---|---|---|---|---|---|---|---|---|---|
| Biosensor | $EC_{50}$ (pM) | | $EC_{50}$ (pM) | | $EC_{50}$ (pM) | | $EC_{50}$ (pM) | | $EC_{50}$ (pM) | | $EC_{50}$ (pM) | |
| Gαz | -- | -- | 9.18 | 9.13 | -- | 7.04 | -- | 7.00 | 6.57 | 6.04 | 7.19 | 6.91 |
| Gαs | -- | -- | -- | -- | -- | -- | -- | -- | -- | -- | -- | -- |
| Gαq | -- | -- | -- | -- | -- | -- | -- | -- | -- | -- | -- | -- |
| Gα15/16 | -- | -- | -- | -- | -- | -- | -- | -- | -- | -- | -- | -- |
| Gαi2 | -- | -- | 8.25 | 8.21 | -- | -- | NS | NS | -- | -- | -- | -- |
| GαoA | -- | -- | 8.98 | 8.64 | -- | -- | -- | -- | -- | -- | -- | -- |
| Gα13 | -- | -- | -- | -- | -- | -- | -- | -- | -- | -- | -- | -- |
| Barr2 | -- | -- | 7.45 | 7.84 | -- | -- | -- | -- | -- | -- | -- | -- |

*NS: non-saturated curve*

*--: No detection*

LOG2 transformation of transcript reads (all FDR<0.05, 825 genes), with Complete linkage clustering, Pearson distance measurement

** t=3h are used for all subsequent analyses

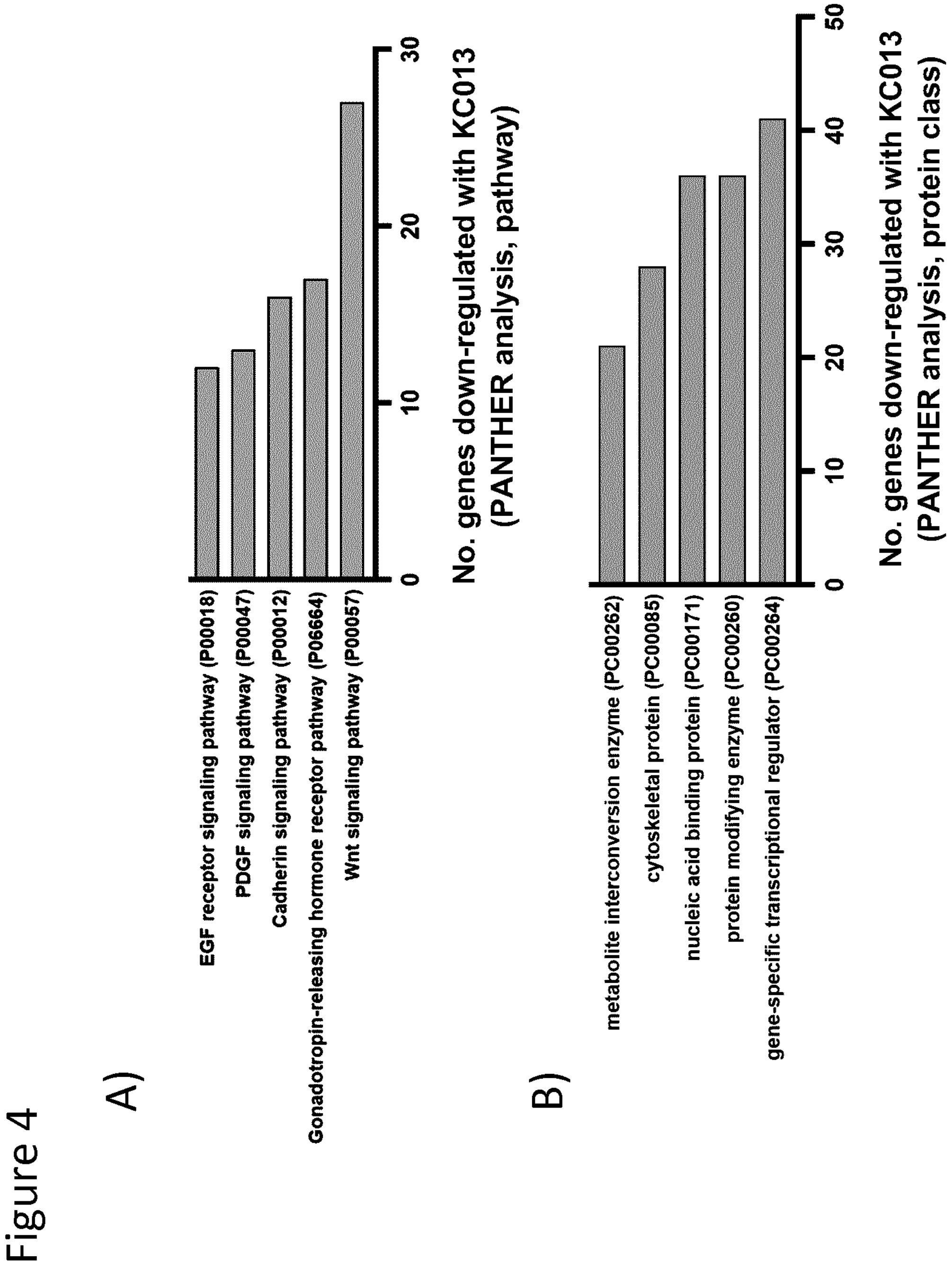
Figure 4
A)
EGF receptor signaling pathway (P00018)
PDGF signaling pathway (P00047)
Cadherin signaling pathway (P00012)
Gonadotropin-releasing hormone receptor pathway (P06664)
Wnt signaling pathway (P00057)
0
10
20
30
No. genes down-regulated with KC013
(PANTHER analysis, pathway)
B)
metabolite interconversion enzyme (PC00262)
cytoskeletal protein (PC00085)
nucleic acid binding protein (PC00171)
protein modifying enzyme (PC00260)
gene-specific transcriptional regulator (PC00264)
0
10
20
30
40
50
No. genes down-regulated with KC013
(PANTHER analysis, protein class)

Figure 6
A)
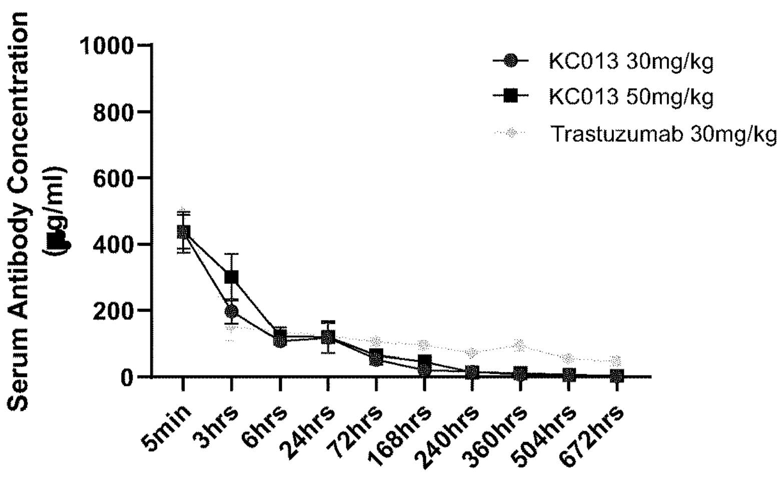
| Molecule | Cmax* (mg/mL) | T1/2* (hour) |
|---|---|---|
| KC013 | 436 | 214 |
| Trastuzumab | 496 | 441 |
*From 30mg/kg single dose
B)
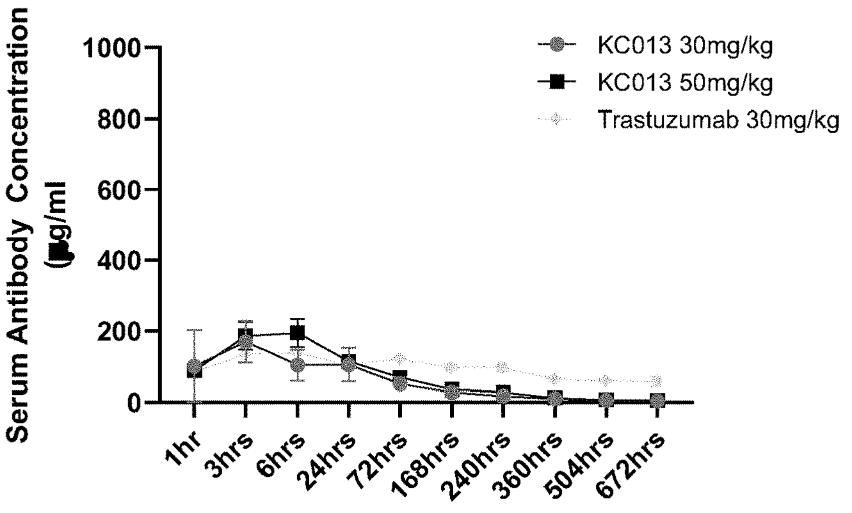
| Molecule | Cmax* (mg/mL) | T1/2* (hour) |
|---|---|---|
| KC013 | 170 | 159 |
| Trastuzumab | 139 | 528 |

Figure 8

| | | TGI (%) | | | | |
|---|---|---|---|---|---|---|
| | sdAb ID | NCI-H69 | NCI-H510A | NCI-H727 (1M) | NCI-H727 (6M) | PANC1 (5M) |
| DR2 | KC013 | **46** | **77** | **54** | **49** | -29 |
| | KC014 | **57** | **67** | 26 | 12 | 9 |
| | KC011 | **53** | **76** | 31 | -2 | 11 |
| | KC012 | **43** | **61** | **43** | 35 | **55** |

A)

B)

C)

D)

E)

Figure 15
A)
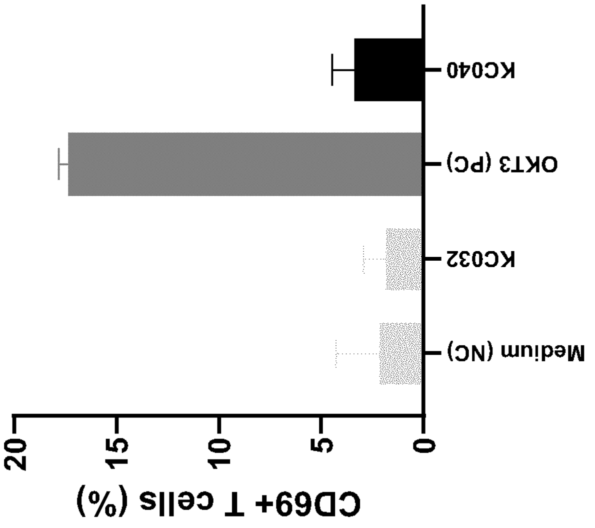
B)
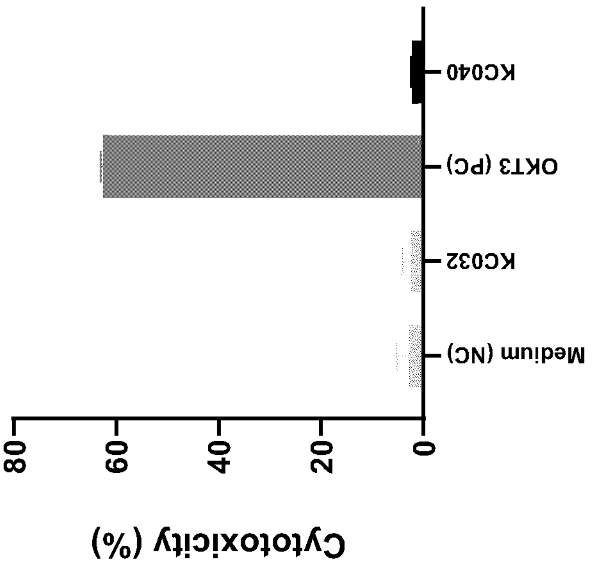

A)

B)

| Protein ID | Anti-D2 Module | TGI (%) | P value (TT) |
|---|---|---|---|
| KC020 | KC001 | 74.02 | 0.001 |
| KC024 | KC007 | 63.02 | 0.001 |
| KC022 | KC005 | 59.78 | 0.002 |
| KC025 | KC003 | 52.05 | 0.008 |
| KC023 | KC006 | 47.17 | 0.016 |
| KC026 | KC004 | 46.07 | 0.016 |

A)

B)

| Tumor | Model | TGI |
|---|---|---|
| NCI-H69 | PBMC pre-engrafted | 53.11% |
| NCI-H82 | Co-engraftment | 74.2% |
| SCLC-21H | PBMC pre-engrafted | 55.64% |
| RKO | PBMC pre-engrafted | 49.32% |

C)

C)

BINDING AGENTS TARGETING TUMORS AND/OR IMMUNE CELLS

CROSS-REFERENCE TO RELATED APPLICATIONS

This application is a 35 U.S.C. § 371 National Stage Application of International Application No. PCT/CA2022/050442, filed on Mar. 25, 2022, which claims priority to U.S. Provisional Patent Application Nos. 63/168,606, filed Mar. 31, 2021, 63/249,784, filed Sep. 29, 2021, 63/301,305, filed Jan. 20, 2022, all of which are incorporated by reference herein in their entireties for all purposes.

INCORPORATION BY REFERENCE OF SEQUENCE LISTING

The instant application contains a Sequence Listing which has been submitted electronically in TXT format and is hereby incorporated by reference in its entirety. Said TXT copy, created on Apr. 28, 2022, is named 17500-005-PCT-_SL.txt and is 251 kilobytes in size.

TECHNICAL FIELD

The present disclosure generally relates to binding agents that are capable of targeting tumor cells and/or immune cells. The binding agents of the present disclosure comprise one or more antigen binding domains of VHH antibodies which are capable of binding to DR2, to PD-1 and/or to CD47. The binding agents of the present disclosure may be in the form of monomers or multimers and may be monospecific or multispecific.

BACKGROUND

Camelids and cartilaginous fishes naturally produce antibodies composed of functional homodimeric heavy chain only antibodies (HCAbs) (Hamers-Casterman et al., 1993; Muyldermans and Smider, 2016). The heavy chains of HCAbs lack the first constant domain (CH1) and differs from classical antibodies by only a few amino acids substitutions normally involved in light chain pairing (Muyldermans et al., 1994; Vu et al., 1997). These substitutions (Val37Phe/Tyr, Gly44Glu, Leu45Arg, and Trp47Gly) are present in framework region 2 (FR2). The antigen-binding fragment of HCAbs is referred to as, VHH or Nanobody®. VHHs have a molecular weight of around 15 kDa which makes them amenable to applications that require enhanced tissue penetration or rapid clearance, such as radioisotope-based imaging. However, for therapeutic applications, the VHH half-life usually needs to be increased so as to minimize renal clearance and optimize therapeutic efficacy (De Vlieger et al., Antibodies 8(1), 1-22, 2019). Although methods to increase VHH half-life such as PEGylation, N-glycosylation, HSA or other carrier protein fusions have been exploited, such construct can introduce immunogenicity or have limited success.

VHHs have been exploited as building blocks to make bispecific and multispecific antibodies. In some studies, bivalent constructs have been shown to be have increased avidity or affinity compared to the monovalent form (Conrath et al., 2001; Coppieters et al., 2006; Hmila et al., 2008; Simmons et al., 2006 and Hultberg et al., 2011, Jähnichen et al. (2010), Fridy et al., 2014).

A number of VHH-based therapeutics are currently in late investigational stage or have been approved by FDA. These include the bivalent monospecific antibody Caplacizumab against antigen vWF approved for Thrombotic thrombocytopenic purpura (Duggan, 2018). A Trivalent nanobody complex, ALX-0171 against RSV is at late-stage development for Respiratory syncytial virus infection (Detallea et al., 2015). ALX-0061 is a monovalent against antigen IL-6R but attached with HSA nanobody to extend half-life and is at clinical development stage for RA and SLE indications (Van Roy et al., 2015). The investigational drug ALX-0761 contains three nanobodies against antigens IL-17A, IL-17F and HAS and is being developed for Psoriasis (Svecova et., 2019). Anti-RANKL, ALX-0141 is a bivalent for antigen RANKL and attached to HSA to extend half-life (Schoen et al., 2013). Ozoralizumab is bivalent nanobody against antigen TNFα and attached to HSA to extend half-life (Fleischmann et al., 2012).

The Applicant has developed novel binding agents that targets tumors cells and/or immune cells that contains one or more antigen binding domains.

SUMMARY

The present disclosure generally relates to binding agents that are capable, amongst other things, of targeting tumor cells and/or immune cells.

In some embodiments, the binding agents of the present disclosure are capable of binding to DR2, to PD-1 and/or to CD47. In other embodiments of the present disclosure, the binding agents may bind to cells expressing DR2, to cells expressing PD-1 and/or to cells expressing CD47.

In some embodiments, the cells expressing DR2 comprise tumor cells.

In some embodiments, the cells expressing PD-1 comprises immune cells.

In some embodiments, the cells expressing CD47 comprises immune cells or tumor cells.

Accordingly, in some embodiments, the binding agent may comprise an antigen binding domain capable of binding to DR2 or to cells expressing DR2, an antigen binding domain capable of binding to PD-1 or to cells expressing PD-1 and/or an antigen binding domain capable of binding to CD47 or to cells expressing CD47. In accordance with the present disclosure, the binding agent may also comprise additional antigen binding domains.

In some embodiments, the antigen binding domain capable of binding to DR2 or to cells expressing DR2 is an antigen binding domain 1 (ABD1) as described herein. In some embodiments, the antigen binding domain capable of binding to DR2 or to cells expressing DR2 is not limited to antigen binding domain 1 (ABD1).

Accordingly, in some embodiments, the binding agent may comprise at least one antigen binding domain 1 (ABD1).

In some embodiment, the binding agent may comprise at least one antigen binding domain 1 (ABD1) and at least one other antigen binding domain.

In some instances, the binding agent may comprise at least one antigen binding domain 1 (ABD1) and may also bind to immune cells. Accordingly, in some embodiments, the binding agent comprises comprise at least one antigen binding domain 1 (ABD1) and at least one antigen binding domain that binds to immune cells.

In some embodiments, the antigen binding domain capable of binding to PD-1 or to cells expressing PD-1 is an antigen binding domain 2 (ABD2) as described herein. In some embodiments, the antigen binding domain capable of binding to PD-1 or to cells expressing PD-1 is not limited to antigen binding domain 2 (ABD2).

Accordingly, in some embodiments, the binding agent may comprise at least one antigen binding domain 2 (ABD2).

In some embodiment, the binding agent may comprise at least one antigen binding domain 2 (ABD2) and at least one other antigen binding domain.

In some instances, the binding agent may comprise at least one antigen binding domain 2 (ABD2) and may also bind to tumor cells. Accordingly, in some embodiments, the binding agent comprises at least one antigen binding domain 2 (ABD2) and at least one antigen binding domain that binds tumor cells.

In some embodiments, the antigen binding domain capable of binding to CD47 or to cells expressing CD47 is an antigen binding domain 3 (ABD3) as described herein. In some embodiments, the antigen binding domain capable of binding to CD47 or to cells expressing CD47 is not limited to ABD3.

Accordingly, in some embodiments, the binding agent may comprise at least one antigen binding domain 3 (ABD3).

In some embodiment, the binding agent may comprise at least one antigen binding domain 3 (ABD3) and at least one other antigen binding domain.

In some instances, the binding agent may comprise at least one antigen binding domain 3 (ABD3) and may also bind to tumor cells. Accordingly, in some embodiments, the binding agent comprises at least one antigen binding domain 3 (ABD3) and at least one antigen binding domain that binds to tumor cells In other instances, the binding agent may comprise at least one antigen binding domain 3 (ABD3) and may also bind to immune cells. In some embodiments, the binding agent comprises at least one antigen binding domain 3 (ABD3) and at least one antigen binding domain that binds to immune cells.

In some instances, the binding agent is capable of binding to DR2 and to PD-1. Accordingly, in some embodiments, the binding agent comprises at least one antigen binding domain that binds to DR2 and at least one antigen binding domain that binds to PD-1.

In some instances, the binding agent is capable of binding to DR2 and to CD47. Accordingly, in some embodiments, the binding agent comprises at least one antigen binding domain that binds to DR2 and at least one antigen binding domain that binds to CD47.

In some instances, the binding agent is capable of binding to DR2, PD-1 and to CD47. Accordingly, in some embodiments, the binding agent comprises at least one antigen binding domain that binds to DR2, at least one antigen binding domain that binds to PD-1 and at least one antigen binding domain that binds to CD47.

In some instances, the binding agent is capable of binding to PD-1 and to CD47. Accordingly, in some embodiments, the binding agent comprises at least one antigen binding domain that binds to PD-1 and at least one antigen binding domain that binds to CD47.

In some instances, the binding agent is capable of binding to PD-1, to CD47 and to tumor cells. Accordingly, in some embodiments, the binding agent comprises at least one antigen binding domain that binds to PD-1, at least one antigen binding domain that binds to CD47 and at least one antigen binding domain that binds to tumor cells.

In some instances, the binding agent is capable of binding to PD-1 and to tumor cells. Accordingly, in some embodiments, the binding agent comprises at least one antigen binding domain that binds to PD-1 and at least one antigen binding domain that binds to tumor cells.

In some instances, the binding agent is capable of binding to CD47 and to tumor cells. Accordingly, in some embodiments, the binding agent comprises at least one antigen binding domain that binds to CD47 and at least one antigen binding domain that binds to tumor cells.

In some instances, the binding agent is capable of binding to CD47 and to immune cells. Accordingly, in some embodiments, the binding agent comprises at least one antigen binding domain that binds to CD47 and at least one antigen binding domain that binds to immune cells.

In some embodiments, the binding agent comprises one or more antigen binding domains, wherein at least one of the antigen binding domains is an antigen binding domain 1 (ABD1).

In some embodiments, the binding agent comprises one or more antigen binding domains, wherein at least one of the antigen binding domains is an antigen binding domain 2 (ABD2).

In some embodiments, the binding agent comprises one or more antigen binding domains, wherein at least one of the antigen binding domains is an antigen binding domain 3 (ABD3).

In some embodiments, the binding agent comprises one or more antigen binding domains, wherein at least one of the antigen binding domains is selected from:

an antigen binding domain 1 (ABD1), an antigen binding domain 2 (ABD2) or, an antigen binding domain 3 (ABD3).

In some embodiments, the binding agent may comprise an antigen binding domain that targets epitopes other than those covered by ABD1, ABD2 and ABD3. The binding agent may thus comprise an antigen binding domain that has the same or different specificity as that of ABD1, ABD2 and/or ABD3.

In some embodiments, the binding agent may comprise more than one antigen binding domains.

For example, in some embodiments, the binding agent may comprise comprises two antigen binding domains or more, three antigen binding domains or more, four antigen binding domains or more, five antigen binding domains or more, six antigen binding domains or more, seven antigen binding domains or more, eight antigen binding domains or more, nine antigen binding domains or more, ten antigen binding domains or more.

In some embodiments, the binding agent may comprise between one and twelve antigen binding domains.

In some embodiments, the binding agents of the present disclosure may be monospecific.

In some embodiments, the binding agents of the present disclosure may be multispecific.

In some embodiments, the binding agents of the present disclosure may be monovalent.

In some embodiments, the binding agents of the present disclosure may be multivalent.

In some embodiments, the binding agents of the present disclosure may be in the form of a monomer.

In some embodiments, the binding agents of the present disclosure may be in the form of a dimer or higher order form such as trimer, four-mer, five-mer and the like (e.g., multimer).

In some instances, the antigen binding domain of the binding agent originates from a heavy chain antibody. In some instances, the heavy chain antibodies may be obtained by immunization of camelids or transgenic animals.

In some embodiments, the binding agent comprises at least one antigen binding domain that binds to DR2 and that comprises complementarity determining regions set forth herein.

In some embodiments, the binding agent comprises at least one antigen binding domain that binds to PD-1 and that comprises complementarity determining regions set forth herein.

In some embodiments, the binding agent comprises at least one antigen binding domain that binds to CD47 and that comprises complementarity determining regions set forth herein.

In some embodiments, the antigen binding domains are on one or more polypeptide chains.

In some embodiments, the antigen binding domains antigen are on same polypeptide chain.

In some embodiments, the binding agent comprises a single polypeptide chain.

In some embodiments, the binding agent comprises two polypeptide chains. Accordingly, the binding agent may be in the form of a dimer.

In some embodiments, the binding agent comprises more than two polypeptide chains, such as three polypeptide chains or more, four polypeptide chains or more, five polypeptide chains or more, six polypeptide chains or more, seven polypeptide chains or more, eight polypeptide chains or more, nine polypeptide chains or more, ten polypeptide chains or more. Accordingly, the binding agent may be in the form of a multimer. For example, a binding agent that comprises three polypeptide chains is referred herein as a trimer, a binding agent that comprises four polypeptide chains is referred herein as a four-mer, and the like.

In some embodiments, the binding agent comprises at least two polypeptide chains that are capable of assembling to form a dimer and wherein each polypeptide chain comprises one or more antigen binding domains.

In some embodiments, the two polypeptide chains are capable of assembling to form a dimer and each polypeptide chain comprises different antigen binding domains.

In some embodiments, the two polypeptide chains are capable of assembling to form a dimer and each polypeptide chain comprises the same antigen binding domains.

In some embodiments, each polypeptide chain comprises identical antigen binding domain 1 (ABD1).

In some embodiments, each polypeptide chain comprises identical antigen binding domain 2 (ABD2).

In some embodiments, each polypeptide chain comprises identical antigen binding domain 3 (ABD3).

In some exemplary embodiments, the binding agent comprises at least two polypeptide chains that assemble to form a dimer and each polypeptide chain comprises identical antigen binding domain 1 (ABD1) and identical antigen binding domain 2 (ABD2).

In other exemplary embodiments, the binding agent comprises at least two polypeptide chains that assemble to form a dimer and each polypeptide chain comprises identical antigen binding domain 1 (ABD1) and identical antigen binding domain 3 (ABD3).

In further exemplary embodiments, the binding agent comprises at least two polypeptide chains that assemble to form a dimer and each polypeptide chain comprises identical antigen binding domain 2 (ABD2) and identical antigen binding domain 3 (ABD3).

In yet further exemplary embodiments, the binding agent comprises at least two polypeptide chains that assemble to form a dimer and each polypeptide chain comprises identical antigen binding domain 1 (ABD1), identical antigen binding domain 2 (ABD2) and identical antigen binding domain 2 (ABD3).

In some instances, the antigen binding domain 1 (ABD1), antigen binding domain 2 (ABD2) and antigen binding domain 2 (ABD3) may occupy the same position on each of the two polypeptide chains.

In some instances, the antigen binding domain 1 (ABD1), antigen binding domain 2 (ABD2) and antigen binding domain 2 (ABD3) may occupy different positions on each of the two polypeptide chains.

In some embodiments, each polypeptide chains of the binding agent are the same.

In some embodiments, each polypeptide chains of the binding agent are different.

In some embodiments, the two polypeptide chains are capable of assembling to form a homodimer.

In some embodiments, the two polypeptide chains are capable of assembling to form a heterodimer.

In some embodiments, antigen binding domains are separated by an amino acid sequence.

In some embodiments, the amino acid sequence is a linker.

Binding agents of the present disclosure encompass for example the antigen binding domains disclosed herein, single polypeptide chain disclosed herein, dimers of the polypeptide chains disclosed herein or multimers of the polypeptide chains disclosed herein.

Accordingly, binding agents of the present disclosure may have a format of an antibody and antigen binding fragment thereof, an antibody-like molecule (Fc-, CH3-fusions and the like), a fusion with protein scaffolds, immune cell modulating agents and the like.

Advantageously, the binding agents of the present disclosure may have a format as disclosed in PCT/CA2020/051753 filed on Dec. 18, 2020 (the entire content of which is incorporated herein by reference) as formula Ia, formula Ib, formula Ic, formula II, formula III, formula IV, formula V, formula VI, formula VII or formula VIII and the like or formula I, formula II, formula III, formula IIIa and formula IIIb, formula IV, formula V, formula VI, formula VII or formula VIII disclosed herein.

In some embodiments, the binding agents are composed of polypeptide chains comprising one or more antigen binding domains and a dimerization domain allowing at least two polypeptide chains to form dimers.

In some embodiments, the binding agent of the present disclosure may comprise one or more polypeptide chains each independently comprising in a N- to C-terminal fashion an amino acid sequence of formula I:

$$X\text{-}[(Ab_a)\text{-}(L_b)]_m\text{-}(DD)\text{-}[(L_c)\text{-}(Ab_d)]_n\text{-}Y$$

Wherein m is 0, 1, 2 or an integer greater than 2;

Wherein n is 0, 1, 2 or an integer greater than 2;

Wherein m and n are not 0 simultaneously;

Wherein $Ab_a$, $Ab_d$, each represents an antigen binding domain wherein at least one of the antigen binding domains is an antigen binding domain 1 (ABD1), an antigen binding domain 2 (ABD2) or an antigen binding domain 3 (ABD3);

Wherein X or Y are independently present or absent and comprises an amino acid sequence;

Wherein $L_b$, $L_c$, each independently comprises one or more linkers; and

Wherein DD represents a dimerization domain.

In some embodiments the polypeptide chain comprises two antigen binding domains or more, three antigen binding domains or more, four antigen binding domains or more, five antigen binding domains or more, six antigen binding domains or more, etc.

In some embodiments the polypeptide chain comprises between one and twelve antigen binding domains.

In some embodiments, the binding agent comprises one polypeptide chain.

In some embodiments, the binding agent comprises two polypeptide chains, three polypeptide chains, four polypeptide chains, five polypeptide chains, six polypeptide chains, seven polypeptide chains, eight polypeptide chains, nine polypeptide chains, ten polypeptide chains or more than ten polypeptide chains.

In some embodiment, the polypeptide chains may be covalently linked.

In some embodiment, the polypeptide chains may be non-covalently linked.

In some embodiment, the polypeptide chains may be associated via electrostatic interaction(s).

In some embodiments where m is 2 or an integer greater than 2, the [$(Ab_a)$-$(L_b)$] units is the same or different.

In some embodiments where n is 2 or an integer greater than 2, the [$(L_c)$-$(Ab_d)$] units are the same or different.

In some embodiments, where m is 2 or an integer greater than 2, each $Ab_a$ is the same or different.

In some embodiments, where n is 2 or an integer greater than 2, each $Ab_d$ is the same or different.

In some embodiments, $Ab_a$ represents ABD1, ABD2 or ABD3.

In some embodiments, $Ab_d$ represents ABD1, ABD2 or ABD3.

In embodiments, the one or more polypeptide chain further comprises a hinge region of an antibody or antigen binding fragment thereof. For example, in some embodiments $L_b$ is a hinge region of an antibody or antigen binding fragment thereof.

In some embodiments, the hinge region is a natural hinge region from an IgG1, IgG2, IgG3 or IgG4.

In some embodiments, the hinge region is a mutated hinge region having at least 70% identity with a natural hinge region from an IgG1, IgG2, IgG3 or IgG4.

In some embodiments each of the one or more linkers independently has at least 5, 10, 15, 20, 25, 30, 35, 40, 45 or 50 amino acid residues in length.

In some embodiments, each of the one or more linkers is independently a flexible linker, a helical linker, or a rigid linker.

In some embodiments, the flexible linker is a GS linker. In some embodiments, the flexible linker comprises one or more units of GGGGS as described herein.

In some embodiments the rigid linker comprises multiple PA repeats as described herein.

In some embodiments, the helical linker comprises one or more units of EAAAK as described herein.

In some embodiments the binding agent comprises one or more polypeptide chains wherein at least one of the polypeptide chains comprises formula II: X-$(Ab_{a1})$-$(L_{b1})$-(DD)-$(L_{c1})$-$(Ab_{d1})$-Y (formula II).

In some embodiments the binding agent comprises one or more polypeptide chains wherein at least one of the polypeptide chains comprises formula III: X-$(Ab_{a1})$-$(L_{b1})$-(DD)-$(L_{c1})$-$(Ab_{d1})$-$(L_{c2})$-$(Ab_{d2})$-Y (formula III).

In some embodiments the binding agent comprises one or more polypeptide chains wherein at least one of the polypeptide chains comprises formula IV: X-$(Ab_{a1})$-$(L_{b2})$-$(Ab_{a2})$-$(L_{b1})$-(DD)-$(L_{c1})$-$(Ab_{d1})$-Y (formula IV).

In some embodiments the binding agent comprises one or more polypeptide chains wherein at least one of the polypeptide chains comprises formula V: X-$(Ab_{a1})$-$(L_{b2})$-$(Ab_{a2})$-$(L_{b1})$-(DD)-$(L_{c1})$-$(Ab_{d1})$-$(L_{c2})$-$(Ab_{d2})$-Y (formula V).

In some embodiments the binding agent comprises one or more polypeptide chains wherein at least one of the polypeptide chains comprises formula VI: X-$(Ab_{a1})$-$(L_{b2})$-$(Ab_{a2})$-$(L_{b1})$-(DD)-$(L_{c1})$-$(Ab_{d1})$-$(L_{c2})$-$(Ab_{d2})$-$(L_{c3})$-$(Ab_{d3})$-Y (formula VI).

In some embodiments the binding agent comprises one or more polypeptide chains wherein at least one of the polypeptide chains comprises formula VII: X-$(Ab_{a1})$-$(L_{b3})$-$(Ab_{a2})$-$(L_{b2})$-$(Ab_{a3})$-$(L_{b1})$-(DD)-$(L_{c1})$-$(Ab_{d1})$-$(L_{c2})$-$(Ab_{d2})$-Y (formula VII).

In some embodiments the binding agent comprises one or more polypeptide chains wherein at least one of the polypeptide chains comprises formula VIII: X-$(Ab_{a1})$-$(L_{b3})$-$(Ab_{a2})$-$(L_{b2})$-$(Ab_{a3})$-$(L_{b1})$-(DD)-$(L_{c1})$-$(Ab_{d1})$-$(L_{c2})$-$(Ab_{d2})$-$(L_{c3})$-$(Ab_{d3})$-Y (formula VIII).

In some embodiments $Ab_{a1}$, $Ab_{a2}$, $Ab_{a3}$, $Ab_{d1}$, $Ab_{d2}$, or $Ab_{d3}$, each independently comprises an antigen binding domain.

In some embodiments $Ab_{a1}$, $Ab_{a2}$, $Ab_{a3}$, Abdi, $Ab_{d2}$, or $Ab_{d3}$, each independently represents an antigen binding domain.

In some embodiments, at least one of $Ab_{a1}$, $Ab_{a2}$, $Ab_{a3}$, Abdi, $Ab_{d2}$, or $Ab_{d3}$ is an antigen binding domain 1 (ABD1), an antigen binding domain 2 (ABD2) or an antigen binding domain 3 (ABD3).

In some embodiments, at least one of $Ab_{a1}$, $Ab_{a2}$, $Ab_{a3}$, Abdi, $Ab_{d2}$, or $Ab_{d3}$ is not an antigen binding domain 1 (ABD1), an antigen binding domain 2 (ABD2) or an antigen binding domain 3 (ABD3).

In some embodiments $L_{b1}$ comprises a linker or linkers and/or a hinge region of an antibody or antigen binding fragment thereof. In some embodiments, the hinge region is a natural hinge region as disclosed herein. In other embodiments, the hinge region is a mutated hinge region as disclosed herein.

In some embodiments $L_{b2}$, $L_{b3}$ $L_{c1}$, $L_{c2}$, and $L_{c3}$ each independently comprise a linker or linkers as disclosed herein.

In some embodiments, the polypeptide chain comprises the antigen binding domain ABD1 as disclosed herein and an antigen binding domain that binds to an immune cell.

In some embodiments, the polypeptide chain comprises the antigen binding domain ABD2 as disclosed herein and an antigen binding domain that binds to a tumor cell.

In some embodiments, the polypeptide chain comprises the antigen binding domain ABD3 as disclosed herein and an antigen binding domain that binds to a tumor cell.

In some embodiments, the polypeptide chain comprises the antigen binding domain ABD3 as disclosed herein and an antigen binding domain that binds to immune cells.

In some embodiments, the polypeptide chain comprises at least one antigen binding domain selected from ABD1, ABD2 and ABD3 as disclosed herein.

In some embodiments, the polypeptide chain comprises at least two antigen binding domains selected from ABD1, ABD2 and ABD3 as disclosed herein.

In some embodiments, the polypeptide chain comprises at least three antigen binding domains selected from ABD1, ABD2 and ABD3 as disclosed herein.

In some embodiments, the dimerization domain comprises an immunoglobulin dimerization domain. Other dimerization domains known to a person skilled in the art are contemplated herein including leucine zippers, etc.

In some embodiments, the dimerization domain comprises an IgG, IgM, IgA, IgD or IgE dimerization domain (from human or animal IgGss, IgM, IgAs, IgDs or IgEs).

In some embodiments, the dimerization domain comprises a CH3 domain of an antibody.

The dimerization domain may also comprise a CH2 domain of an antibody.

In some exemplary embodiments, the dimerization domain comprises a natural CH3 domain.

In some exemplary embodiments, the dimerization domain comprises a mutated CH3 domain.

In some embodiments, the dimerization domain comprises a natural CH2 and a natural CH3 domain.

In some embodiments, the dimerization domain comprises a natural CH2 and a mutated CH3 domain.

In some embodiments, the dimerization domain comprises a mutated CH2 and a mutated CH3 domain.

In some embodiments, the dimerization domain comprises a mutated CH2 and a natural CH3 domain.

In some embodiments, the dimerization domain does not comprise a CH1 domain.

In some embodiments, the dimerization domain does not comprise a CH4 domain.

In some embodiments, the dimerization domain comprises a Fc region of an antibody or a portion thereof.

In some embodiments, the polypeptide chain comprises at least two or at least three antigen binding domains and a dimerization domain that allow assembly of two polypeptide chains to form a multivalent and/or multispecific binding agent.

In embodiments, the antigen binding domain comprises or consist of an antigen binding domain of a single domain antibody (sdAb).

In embodiments, the antigen binding domain comprises a heavy chain variable region (VH or VHH).

In some embodiment the VHH is derived from humans, from a mouse, from a rat etc.

In some embodiment, the VHH is from a transgenic mouse or rat capable of expressing camelized mouse or rats VHHs, VHHs from other species (e.g., humans etc.) or camelized VHHs from other species (e.g., camelized human VHH etc.).

In some embodiments, the binding agent does not comprise a light chain variable region (VL or VLL).

In embodiments, the binding agent comprises a light chain variable region (VL or VLL).

In embodiments, the antigen binding domain is a single chain variable fragment (ScFv).

In embodiments, the antigen binding domain is from a $V_{NAR}$ fragment.

In other embodiments, the antigen binding domains of the polypeptide chain comprises a combination of any antigen binding domain of single domain antibodies (sdAbs), heavy chain variable regions (VHs or VHHs), light chain variable regions (VLs or VLLs), single chain variable fragments (ScFvs) and/or VNAR fragments.

In some embodiments, the sdAb or VHH is from a Camelidae antibody.

In embodiments, the Camelidae antibody is from a dromedary, a camel, a llama, an alpaca etc.

In other embodiments, the sdAb or VHH is from a cartilaginous fish antibody.

In embodiments, the cartilaginous fish antibody is a shark antibody.

In some embodiments, each antigen binding domain specifically binds to a different epitope.

In other embodiments, each antigen binding domain specifically binds to a different antigen.

In yet other embodiments, each antigen binding domain specifically binds to a different protein.

In some embodiments, the binding agent comprises a polypeptide chain comprising at least one antigen binding domain that binds to a protein expressed by a tumor. In other embodiments, the binding agent comprises a polypeptide chain comprising at least one antigen binding domain that binds to a protein expressed by a tumor and that modulates its activity.

In some embodiments, the binding agent comprises a polypeptide chain comprising at least one antigen binding domain that binds to an immune checkpoint protein. In other embodiments, the binding agent comprises a polypeptide chain comprising at least one antigen binding domain that binds to an immune checkpoint protein and that modulates its activity.

In some embodiments, the binding agent comprises a polypeptide chain comprising at least one antigen binding domain that binds to an immune cell protein. In other embodiments, the binding agent comprises a polypeptide chain comprising at least one antigen binding domain that binds to an immune cell protein and that modulates its activity. Yet in other embodiments, the binding agent comprises a polypeptide chain comprising at least one antigen binding domain that binds to or engages and recruits or redirects immune cells.

In some embodiments, the binding agent comprises a polypeptide chain comprising at least one antigen binding domain that binds to peripheral blood mononuclear cells (PBMCs). In other embodiments, the binding agent comprises a polypeptide chain comprising at least one antigen binding domain that binds to PBMCs and that modulates its activity. Yet in other embodiments, the binding agent comprises a polypeptide chain comprising at least one antigen binding domain that binds to PBMCs and that recruits or redirects PBMCs.

In some embodiments, the binding agent comprises a polypeptide chain comprising at least one antigen binding domain that binds to a T cell protein. In other embodiments, the binding agent may bind to a T cell protein and may modulate its activity. Yet in other embodiments, the binding agent may bind to a T cell protein and may recruit or redirect T cells. In some embodiments the binding agent may bind to activated T cells and/or may modulate the activity of activated T cells.

In some embodiments, the binding agent comprises a polypeptide chain comprising at least one antigen binding domain that binds to a protein expressed by a tumor and at least one antigen binding domain that binds to and recruits or redirects an immune cell.

In some embodiments, the binding agent comprises a polypeptide chain comprising at least one antigen binding domain that binds to a protein expressed by a tumor, at least one antigen binding domain that binds to an immune check point protein and at least one antigen binding domain that binds to and recruits or redirects an immune cell.

In some embodiments, the binding agent comprises a polypeptide chain comprising at least one antigen binding domain that modulates immune checkpoint inhibitors.

In some embodiments, the binding agent comprises a polypeptide chain comprising at least one antigen binding domain that binds to a tumor antigen, at least one antigen binding domain that binds to an immune check point protein and at least one antigen binding domain that binds to a T cell.

In some embodiments, the binding agent comprises a polypeptide chain comprising at least one antigen binding domain that binds to a tumor antigen, at least one antigen binding domain that binds to an immune check point protein and at least one antigen binding domain that binds to CD47.

In some embodiments, the binding agent comprises a polypeptide chain comprising at least one antigen binding domain that modulates CD47 function.

In some embodiments, the binding agent comprises a polypeptide chain comprising at least one antigen binding domain that binds CD47 and enhances macrophage function by blocking SIRPα/CD47 interaction.

In some embodiments, the binding agent comprises a polypeptide chain comprising an antigen binding domain that specifically binds to a receptor.

In some embodiments, the binding agent comprises a polypeptide chain comprising an antigen binding domain that specifically binds to a tumor antigen and an antigen binding domain that specifically binds to an immunomodulator.

In some embodiments the antigen binding domain that specifically binds to a tumor antigen is N-terminal to the dimerization domain and the antigen binding domain that specifically binds to an immunomodulator is C-terminal to the dimerization domain.

In some embodiments, the immunomodulator is an immune checkpoint protein, a cytokine, a chemokine or an immune receptor or coreceptor.

It is to be understood herein, that a given antigen binding domain may bind to an epitope that exists in different proteins. As such, in some embodiments, the antigen binding domain, or the binding agent comprising same, may bind to more than one protein. In some embodiments, the antigen binding domain, or the binding agent, may have affinity for more than one protein.

In some embodiments, the binding agent comprises at least two polypeptide chains which are capable of forming dimers.

In some embodiments, the two polypeptide chains are the same.

In some embodiments, the two polypeptide chains are different.

In some embodiments, the polypeptide chains are the same, and the binding agent is a homodimer.

In some embodiments, the polypeptide chains are different, and the binding agent is a heterodimer.

In some embodiments, the binding agent is multispecific.

In some embodiments, the binding agent is bispecific, trispecific or tetra specific.

In some embodiments, the binding agent comprises one or more polypeptide chains that are multispecific.

In some embodiments, the binding agent comprises one or more polypeptide chains that are bispecific, trispecific or tetra specific.

In some embodiments, the one or more polypeptide chains have the same valency and specificity.

In some embodiments, the one or more polypeptide chains have different valency and specificity.

In some embodiments, the one or more polypeptide chains each is an antibody heavy chain.

The binding agent of any of the preceding claims, wherein the binding agent is an antibody or an antigen binding fragment thereof.

In some embodiments, the binding agent is a bispecific antibody.

In some embodiments, the bispecific antibody further comprises a first antibody light chain and a second antibody light.

In some embodiments, one or more of the antigen binding domains is humanized.

In some embodiments, one or more of the antigen binding domains is partially humanized.

In some embodiments, the antigen binding domains comprise one or more human frameworks.

In some embodiments, X or Y are independently selected from a linker, a cytokine, a chemokine, a tag, a masking domain, a phage coat protein (pIII, pVI, pV, pVII or pIX), an antigen binding domain or combination thereof.

In some embodiments, the polypeptide chain is conjugated to a therapeutic moiety.

In some embodiments, the polypeptide chain is conjugated to a detectable moiety.

In some embodiments, the polypeptide chain is conjugated to a protein allowing an extended half-life.

In some embodiments, the polypeptide chain is attached to nanoparticles.

Other aspects and embodiments of the present disclosure relate to a composition comprising at least one of the binding agents disclosed herein.

In some embodiments, the composition comprises monomers, dimers and mixture thereof.

In some embodiments, greater than 70%, 75%, 80%, 85%, 90%, 95%, 96%, 97%, 98%, or 99% of the first and second polypeptide chains exist as dimers in the composition.

In some embodiments, greater than 70%, 75%, 80%, 85%, 90%, 95%, 96%, 97%, 98%, or 99% of the first and second polypeptide chains exist as homodimers in the composition.

In some embodiments, greater than 70%, 75%, 80%, 85%, 90%, 95%, 96%, 97%, 98%, or 99% of the first and second polypeptide chains exist as heterodimers in the composition.

Other aspects and embodiments of the present disclosure relate to a pharmaceutical composition comprising a binding agent disclosed herein and a pharmaceutically acceptable carrier.

Yet other aspects and embodiments of the present disclosure relate to a nucleic acid or set of nucleic acids encoding the polypeptide chains and/or the binding agent disclosed herein.

The nucleic acid may be in the form of DNA segments as disclosed herein.

Additional aspects and embodiments of the present disclosure relate to a vector comprising a nucleic disclosed herein or a set of vectors each comprising a nucleic acid disclosed herein Further aspects and embodiments of the present disclosure relate to a cell expressing the polypeptide chains or binding agents disclosed herein.

Additional aspects and embodiments of the present disclosure relate to a cell comprising the nucleic acid or the vector disclosed herein.

Further aspects and embodiments of the present disclosure relate to a kit comprising the binding agent disclosed herein.

Yet further aspects and embodiments of the present disclosure relate to a kit comprising the nucleic acid disclosed herein.

Yet further aspects and embodiments of the present disclosure relate to a kit comprising the vector disclosed herein.

Yet further aspects and embodiments of the present disclosure relate to a kit comprising the cells disclosed herein.

In an additional aspect and embodiments, the present disclosure relates to a method of treating a disorder or disease comprising administering the binding agent disclosed herein.

In further aspects and embodiments, the present disclosure relates to a method of treating a disorder or disease comprising administering the composition disclosed herein.

In further aspects and embodiments, the present disclosure relates to a method of treating a disorder or disease comprising administering the pharmaceutical composition disclosed herein.

In some embodiments, the disorder or disease is cancer.

In some embodiments, the disorder or disease is a solid tumor.

In some embodiments, the disorder or disease is advanced metastatic solid cancer.

In some embodiments, the disorder or disease is hematogenous cancer.

In some embodiments, the disorder or disease is lung cancer.

In some embodiments, the lung cancer is metastatic.

In some embodiments, the disorder of disease is small cell lung cancer.

In some embodiments, the disorder of disease is non small cell lung cancer.

In some embodiments, the disorder or disease is myeloma.

In some embodiments, the disorder or disease is prostate cancer.

In some embodiments, the disorder or disease is breast cancer.

In some embodiments, the disorder or disease is rectal cancer.

In some embodiments, the disorder or disease is pancreatic cancer.

In some embodiments, the disorder or disease is glioblastoma.

In some embodiments, the disorder or disease is an infection.

In some embodiments, the disorder or disease is immune dysregulation.

In other aspects and embodiments, the present disclosure relates to a method of making the binding agent disclosed herein, the method comprising transforming cells with one or more vectors comprising the nucleic acid disclosed herein.

In some embodiments, the method may further comprise isolating and/or purifying the binding agent from impurities.

In other embodiments, the method may further comprise isolating and/or purifying heterodimers from monomers and/or homodimers.

In other embodiments, the method may further comprise isolating and/or purifying homodimers from monomers and/or heterodimers.

In some embodiments, the method further comprises conjugating the binding agent with a therapeutic moiety, detectable moiety, or a protein allowing an extended half-life or to nanoparticles.

Further scope, applicability and advantages of the present disclosure will become apparent from the non-restrictive detailed description given hereinafter. It should be understood, however, that this detailed description, while indicating exemplary embodiments of the disclosure, is given by way of example only, with reference to the accompanying drawings.

BRIEF DESCRIPTION OF THE DRAWINGS

FIG. 2: Table listing the EC50 of D2-specific binding agents (VHH-hinge-CH2-CH3) in the GPCR BRET assays transfected with various G protein sensors. Dopamine was used as a positive control to show the GPCR response with G proteins including Gαz, Gαi2, GαoA, and Barr2. Negative control is 4HEM-specific binding agent (VHH-hinge-CH2-CH3) comprising the antigen binding domain set forth in SEQ ID NO:114 (KC018).

FIG. 4: graph representing the downregulated signaling pathways and protein classes from the PANTHER analysis of the RNAseq result of FIG. 3.

FIGS. 6A-6B: graph representing the pharmacokinetics of binding agent comprising D2-specific antigen binding domain (VHH-hinge-CH2-CH3) (KC013; SEQ ID NO:73) and Trastuzumab in SCID mice with single-dose injection (FIG. 6A: IV injection) (FIG. 6B: IP injection).

FIG. 8: table listing the percentage of tumor growth inhibition in various tumor prevention SCLC tumor models in SCID mice upon treatment with D2-specific binding agents (VHH-hinge-CH2-CH3) that comprises the amino acid sequence set forth in SEQ ID NO:71 (KC011), SEQ ID NO:72 (KC012), SEQ ID NO:73 (KC013), or SEQ ID NO:74 (KC014).

FIGS. 15A-15B: graph representing the T cell activation (FIG. 15A) and T cell-dependent cytotoxicity (FIG. 15B) at the E to T ratio of 5:1 induced by binding agent comprising anti-D2-, and anti-CD47 antigen binding domains on human T cells (KC040: SEQ ID NO:84). Controls include, medium only (negative control), binding agent comprising anti-HEWL antigen binding domains and the same anti-D2 antigen binding domain (negative control KC032; SEQ ID NO:90) and OKT3 (positive control).

DETAILED DESCRIPTION

Definitions

Figure 1:
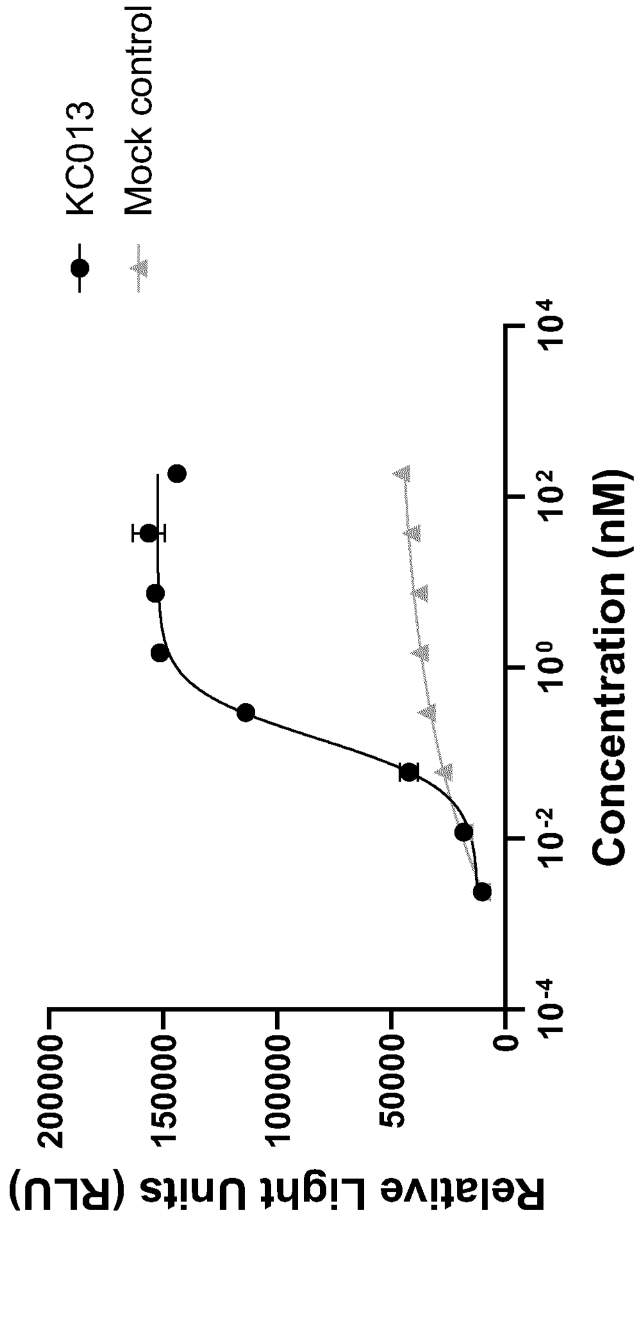
FIG. 1: graph representing the binding curve of D2-specific binding agent (VHH-hinge-CH2-CH3) on D2 proteoliposomes. Mock proteoliposomes were included as negative control.

Unless indicated otherwise, the amino acid numbering indicated for the dimerization domain are in accordance with the EU numbering system.

The use of the terms "a" and "an" and "the" and similar referents in the context of describing embodiments (especially in the context of the claims) are to be construed to cover both the singular and the plural, unless otherwise indicated herein or clearly contradicted by context.

Unless specifically stated or obvious from context, as used herein the term "or" is understood to be inclusive and covers both "or" and "and".

The term "and/or" where used herein is to be taken as specific disclosure of each of the specified features or components with or without the other.

The terms "comprising", "having", "including", and "containing" are to be construed as open-ended terms (i.e., meaning "including, but not limited to") unless otherwise noted. The term "consisting of" is to be construed as close-ended.

The term "treatment" for purposes of this disclosure refers to both therapeutic treatment and prophylactic or tumor prevention measures. Those in need of treatment include those already with the disorder as well as those prone to have the disorder or those in whom the disorder is to be prevented.

The term "about" or "approximately" with respect to a given value means that variation in the value is contemplated. In some embodiments, the term "about" or "approximately" shall generally mean a range within +/−10 percent, within +/−5 percent, within +/−4 percent, within +/−3 percent, within +/−2 percent or within +/−1 percent of a given value or range.

The term "functionally active" with reference to an antigen binding domain means that the antigen binding domain is capable of binding to its target and optionally that the antigen binding domain possesses one or more biological activities.

As used herein the term "flexible linker" refers to peptide comprising at least a portion composed of flexible amino acid residues that allow adjacent modules to move relative to one another.

As used herein the term "rigid linker" refers to peptide comprising at least a portion composed of amino acids that exhibit a rigid structure and that keeps a distance between two modules.

As used herein the term "helical linker" means a linker that is composed of amino acid residues that adopt a α-helical conformation.

As used herein the term "cleavable linker" refers to peptides that comprise an enzymatic cleavage site that is sensitive to proteases selected from ADAMS, ADAMTS, aspartate proteases, caspases, cysteine cathepsins, cysteine proteinases, metalloproteinases, serine proteases, coagulation factor proteases, Type II Transmembrane Serine Proteases (TTSPs) and combination thereof.

As used herein the term "monospecific" with respect to polypeptide chains or binding agents refers to polypeptide chains or binding agents that bind to a single antigen or epitope. A monospecific polypeptide chains or binding agents may thus have one antigen binding domain or more than one binding domains (which are the same or different) having the same specificity towards a given antigen or epitope.

As used herein the term "multispecific" with respect to polypeptide chains or binding agents refers to polypeptide chains or binding agents that bind to more than one antigen or epitope.

The term "multispecific" encompasses "bispecific", "trispecific", "tetraspecific", "pentaspecific", "hexaspecific" and the like.

As used herein in the context of binding agents the term "bispecific" designates a binding agent that binds to two different antigens or proteins or to two epitopes of the same antigen or protein.

As used herein, the expression "at least two polypeptide chains" and the like such as in the expression "binding agent comprises at least two polypeptide chains" and the like refers to a number of polypeptide chain species and not to an absolute numerical value.

It is to be understood herein, that expressions referring to ranges of values in the format such as "from A to B", include each individual value and any sub-range comprised and including such ranges. For example, the expression "from 1 to 10" includes sub-ranges such as and without limitations, "from 2 to 10", "from 2 to 9", "from 3 to 6", "from 5 to 7" and any individual values comprised between and including 1 and 10, i.e., 1, 2, 3, 4, 5, 6, 7, 8, 9 or 10.

It is to be understood herein that the term "at least" with respect to a given value intends to include the value and superior values. For example, the term "at least 80%"

include "at least 81%", "at least 82%", "at least 83%", "at least 84%", "at least 85%", "at least 86%", "at least 87%", "at least 88%", "at least 89%", "at least 90%", "at least 91%", "at least 92%", "at least 93%", "at least 94%", "at least 95%", "at least 96%", "at least 97%", "at least 98%", "at least 99%", "at least 99.1%", "at least 99.2%", at least 99.3%" at least 99.4%" at least 99.5%" at least 99.6%", at least 99.7%", at least 99.8%", at least 99.9%", and 100%.

Antigen Binding Domains (Abs)

As disclosed herein, the binding agent may comprise one or more antigen binding domains.

The antigen binding domains of the present disclosure may be selected for their ability to bind specific targets. The antigen binding domains may also be selected for their in vivo and/or in vitro functional properties or biological effects including, for example, their ability to modulate cellular processes such as gene expression, signal transduction, cell growth, cell viability and the like.

For example, the binding agents of the present disclosure comprise one or more antigen binding domains each independently comprising one or more complementarity determining region(s) (CDRs) of an antibody.

The specificity of the binding agents of the present disclosure may thus be conferred by their antigen binding domains.

The binding agent of the present disclosure may comprise an antigen binding domain capable of binding to DR2 or to cells expressing DR2, an antigen binding domain capable of binding to PD-1 or to cells expressing PD-1 and/or an antigen binding domain capable of binding to CD47 or to cells expressing CD47.

In some embodiments, the antigen binding domain is an antigen binding domain capable of binding to DR2 or to cells expressing DR2 and includes for example, antigen binding domain 1 (ABD1).

In some embodiments, the antigen binding domain is an antigen binding domain capable of binding to PD-1 or to cells expressing PD-1 and includes for example, antigen binding domain 2 (ABD2).

In some embodiments, the antigen binding domain is an antigen binding domain capable of binding to CD47 or to cells expressing CD47 and includes for example, antigen binding domain 3 (ABD3).

In some embodiments, the antigen binding domain targets the same epitope or antigen as ABD1, ABD2 and/or ABD3. In some embodiments, the antigen binding domain competes with ABD1, ABD2 and/or ABD3 for binding to their respective epitope or antigen.

In some embodiments, the antigen binding domain binds to at least one antigen that is not selected amongst DR2, PD-1 or CD47.

In some embodiments, the binding agent may comprise more than one antigen binding domains.

For example, in some embodiments, the binding agent may comprise comprises two antigen binding domains or more.

In some embodiments, the binding agent may comprise three antigen binding domains or more.

In some embodiments, the binding agent may comprise four antigen binding domains or more.

In some embodiments, the binding agent may comprise five antigen binding domains or more.

In some embodiments, the binding agent may comprise six antigen binding domains or more.

In some embodiments, the binding agent may comprise between one and twelve antigen binding domains, such as between one and two, between one and three, between one and four, between one and five, between one and six, between one and seven, between one and eight, between one and nine, between one and ten, between one and eleven, between one and twelve, between two and three, between two and four, between two and five, between two and six, between two and seven, between two and eight, between two and nine, between two and ten, between two and eleven, between two and twelve, between three and four, between three and five, between three and six, between three and seven, between three and eight, between three and nine, between three and ten, between three and eleven, between three and twelve, between four and five, between four and six, between four and seven, between four and eight, between four and nine, between four and ten, between four and eleven, between four and twelve, between five and six, between five and seven, between five and eight, between five and nine, between five and ten, between five and eleven, between five and twelve, between six and seven, between six and eight, between six and nine, between six and ten, between six and eleven, between six and twelve, between seven and eight, between seven and nine, between seven and ten, between seven and eleven, between seven and twelve, between eight and nine, between eight and ten, between eight and eleven, between eight and twelve, between nine and ten, between nine and eleven, between nine and twelve, between ten and eleven, between ten and twelve, or between eleven and twelve.

In some embodiments, the binding agents of the present disclosure may comprise one or more antigen binding domains and at least one of the antigen binding domains is capable of binding to tumor cells.

In some embodiments, the binding agents of the present disclosure may comprise one or more antigen binding domains and at least one of the antigen binding domains is capable of binding to an immunomodulator. In some embodiments, at least one of the antigen binding domains is capable of binding to an immune checkpoint protein. In some embodiments, the immune checkpoint protein is PD-1.

In some embodiments, the binding agents of the present disclosure may comprise one or more antigen binding domains and at least one of the antigen binding domains is capable of binding to immune cells. In some embodiments, at least one of the antigen binding domains is capable of binding to a protein expressed at the surface of immune cells (e.g., T cells, NK-cells, monocytes, macrophages etc.).

In some embodiments, the binding agents of the present disclosure may be multivalent and may comprise at least one antigen binding domain that binds tumor cells and at least one antigen binding domain that binds immune cells.

In some embodiments, the protein expressed at the surface of immune cells is selected from CD47 or CD3.

In some embodiments, the protein expressed at the surface of immune cells is CD47.

In some embodiments, the protein expressed at the surface of immune cells is CD3.

The antigen binding domains may be derived from a natural antibody (of human or animal origin) or from a synthetic antibody.

In some embodiments, antigen binding domains of a natural antibody are engineered so as to form a single chain.

In some embodiments, antigen binding domains may be obtained from IgGs such as IgG1, IgG2, IgG3 or IgG4. In particular embodiments, antigen binding domains are derived from a human IgG heavy chain.

In some embodiments, the antigen binding domains may be obtained from heavy chain only antibodies (HCAbs).

Exemplary embodiments of antigen binding domains include for example and without limitation a single domain antibody (sdAb), a heavy chain variable region (VH or VHH), a light chain variable region (VL or VLL), a single chain variable fragment (scFv), a $V_{NAR}$ fragment, and combinations thereof.

In some embodiments the antigen binding domain of the binding agents disclosed herein is a VHH.

In some embodiments the antigen binding domain of the binding agents disclosed herein is a VHH that comprises the complementarity determining regions of the VHH disclosed herein.

In some embodiments the complementarity determining regions (CDRs) of the VHH disclosed herein correspond to Kabat CDRs.

In some embodiments the complementarity determining regions (CDRs) of the VHH disclosed herein correspond to IMGT CDRs.

In a particular embodiment, the binding agents of the present disclosure may comprise an antigen binding domain VHH derived from humans or a mouse or rat or from a transgenic mouse or rat wherein a mouse or rat VHH has been camelized, a human VHH, a human VHH which has been camelized, of an IgG1, IgG2a, IgG2b, IgG2c or IgG3 or combination thereof. The antibodies may be obtained by immunizing a mouse or a rat or a transgenic mouse or rat which is lacking a functional CH1 domain in any of its heavy chains, IgG1, IgG2a, IgG2b, IgG2c or IgG3 or combination thereof, or a combination of the VHH described above, with an antigen of interest.

In a particular embodiment, the polypeptide chains of the present disclosure may comprise an antigen binding domain of a camelid antibody such as VHH of an IgG2 or IgG3. The camelid antibodies may be obtained by immunizing a dromedary, a camel, a llama or an alpaca with an antigen of interest.

In some embodiments, the camelid antibodies may originate from the so-called old-world camelids such as *Camelus bactrianus, Camelus dromaderus* or from new-world camelids such as *Lama pacos, Lama glama* and *Lama vicugna.*

In another particular embodiment, the polypeptide chains of the present disclosure may comprise an antigen binding domain of a cartilaginous fish such as a $V_{NAR}$ fragment of IgNAR. The $V_{NAR}$ fragment may originate from shark antibodies.

If desired, the antigen binding domain of a non-human antibody may be humanized. For example, the framework region of non-human VH, VHH or HCAbs may be modified so as to render them more human-like. Humanization of camelid antibodies is discussed for example in Vincke C. et al. (J. Biol Chem. 2009, 284(5):3273-3284), the entire content of which is incorporated herein by reference. Humanized camelid antibodies may be obtained, for example, by CDR grating onto a universal humanized nanobody scaffold (e.g., h-NbBcII$10_{FGLA}$ disclosed in Vincke C. et al.). $V_{NAR}$ antibodies can be humanized by converting non-CDR residues to those of human germline Vκ1 sequence DPK9 as discussed in Kovalenko O V et al. (J Biol Chem. 2013, 288:17408-17419) the entire content of which is incorporated herein by reference. The polypeptide chains of the present disclosure therefore encompass humanized antigen binding domains.

In yet another particular embodiment, the antigen binding domain may comprise a human VH (modified or not). Human VH may be obtained for example, from synthetic human VH libraries. Modified human VH include those in which some amino acid residues have been modified to render them more camel-like (i.e., by camelization).

A person skilled in the art will understand that the antigen binding domains may be incorporated into an antibody, antigen binding fragment or an antibody-like molecule including without limitations, single domain antibodies (sdAb), VHH, conventional antibodies or antigen binding fragments thereof, bispecific antibodies, single chain Fv-CH3 (scFv-CH3) fusion, tandem-scFv-CH3 (TaFv-CH3) fusion, diabody-CH3 (db-CH3) fusion, tandem db-CH3 (TaDb-CH3) fusion, single chain db-CH3 fusion (scDb-CH3), Fab-CH3 fusion, single chain Fab-CH3 fusion, Fab-scFv-CH3 fusion, dual affinity retargeting (DART)-CH3 fusion, Fab-DART-CH3 fusion, single chain Fv-Fc (scFv-Fc) fusion, tandem-scFv-Fc (TaFv-Fc) fusion, diabody-Fc (db-Fc) fusion, tandem db-Fc (TaDb-Fc) fusion, single chain db-Fc fusion (scDb-Fc), Fab-Fc fusion, single chain Fab-Fc fusion, Fab-scFv-Fc fusion, dual affinity retargeting (DART)-Fc fusion, Fab-DART-Fc fusion etc. These antibody formats may have natural CH3, mutated CH3 domains, natural CH2-CH3 domains or mutated CH2-CH3 domains disclosed herein.

Exemplary Embodiments of ABD1

Antigen binding domain 1 (ABD1) may be selected, for example, from antigen binding domains that bind DR2, some non-limiting exemplary embodiments of which is provided herein.

In some exemplary embodiments, the binding agent of the present disclosure may comprise one or more antigen binding domains, wherein at least one of the antigen binding domains is an antigen binding domain 1 (ABD1) and comprises a heavy chain complementarity determining region 1 (CRDH1) having the amino acid sequence set forth in SEQ ID NO:1, a heavy chain complementarity determining region 2 (CDRH2) having the amino acid sequence set forth in SEQ ID NO:2 and a heavy chain complementarity determining region 3 (CDRH3) having the amino acid sequence set forth in SEQ ID NO:3.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:4, a CDRH2 having the amino acid sequence set forth in SEQ ID NO:5 and a CDRH3 having the amino acid sequence set forth in SEQ ID NO:6.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:8, a CDRH2 having the amino acid sequence set forth in SEQ ID NO:9 and a CDRH3 having the amino acid sequence set forth in SEQ ID NO:10.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:11, a CDRH2 having the amino acid sequence set forth in SEQ ID NO:12 and a CDRH3 having the amino acid sequence set forth in SEQ ID NO:13.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:15, a CDRH2 having the amino acid sequence set forth in SEQ ID NO:16 and a CDRH3 having the amino acid sequence set forth in SEQ ID NO:17.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:18, a CDRH2 having the amino acid sequence set forth in SEQ ID NO:19 and a CDRH3 having the amino acid sequence set forth in SEQ ID NO:20.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:22, a CDRH2 having the amino acid sequence set forth in SEQ ID NO:23 and a CDRH3 having the amino acid sequence set forth in SEQ ID NO:24.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:25, a CDRH2 having the amino acid sequence set forth in SEQ ID NO:26 and a CDRH3 having the amino acid sequence set forth in SEQ ID NO:27.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:29, a CDRH2 having the amino acid sequence set forth in SEQ ID NO:30 and a CDRH3 having the amino acid sequence set forth in SEQ ID NO:31.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:32, a CDRH2 having the amino acid sequence set forth in SEQ ID NO:33 and a CDRH3 having the amino acid sequence set forth in SEQ ID NO:34.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:36, a CDRH2 having the amino acid sequence set forth in SEQ ID NO:37 and a CDRH3 having the amino acid sequence set forth in SEQ ID NO:38.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:39, a CDRH2 having the amino acid sequence set forth in SEQ ID NO:40 and a CDRH3 having the amino acid sequence set forth in SEQ ID NO:41.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:43, a CDRH2 having the amino acid sequence set forth in SEQ ID NO:44 and a CDRH3 having the amino acid sequence set forth in SEQ ID NO:45.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:46, a CDRH2 having the amino acid sequence set forth in SEQ ID NO:47 and a CDRH3 having the amino acid sequence set forth in SEQ ID NO:48.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:50, a CDRH2 having the amino acid sequence set forth in SEQ ID NO:51 and a CDRH3 having the amino acid sequence set forth in SEQ ID NO:52.

In some exemplary embodiments, the binding agent of the present disclosure may comprise one or more antigen binding domains, wherein at least one of the antigen binding domains is an antigen binding domain 1 (ABD1) and comprises a CRDH1 having the amino acid sequence set forth in SEQ ID NO:53, a CDRH2 having the amino acid sequence set forth in SEQ ID NO:54 and a CDRH3 having the amino acid sequence set forth in SEQ ID NO:55.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:7.

In some embodiments, the amino acid variation may be located in one or more framework regions of SEQ ID NO:7.

In some embodiment, the heavy chain comprises an amino acid sequence at least 75%, 80% 85%, 90%, 95% identical to the amino acid sequence set forth in SEQ ID NO:7 and CDRs identical to the Kabat CDRs of SEQ ID NO:7.

In some embodiment, the heavy chain comprises an amino acid sequence at least 75%, 80% 85%, 90%, 95% identical to the amino acid sequence set forth in SEQ ID NO:7 and CDRs identical to the IMGT CDRs of SEQ ID NO:7.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:7.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:14.

In some embodiments, the amino acid variation may be located in one or more framework regions of SEQ ID NO:14.

In some embodiment, the heavy chain comprises an amino acid sequence at least 75%, 80% 85%, 90%, 95% identical to the amino acid sequence set forth in SEQ ID NO:14 and CDRs identical to the Kabat CDRs of SEQ ID NO:14.

In some embodiment, the heavy chain comprises an amino acid sequence at least 75%, 80% 85%, 90%, 95% identical to the amino acid sequence set forth in SEQ ID NO:14 and CDRs identical to the IMGT CDRs of SEQ ID NO:14.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:14.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:21.

In some embodiments, the amino acid variation may be located in one or more framework regions of SEQ ID NO:21.

In some embodiment, the heavy chain comprises an amino acid sequence at least 75%, 80% 85%, 90%, 95% identical to the amino acid sequence set forth in SEQ ID NO:21 and CDRs identical to the Kabat CDRs of SEQ ID NO:21.

In some embodiment, the heavy chain comprises an amino acid sequence at least 75%, 80% 85%, 90%, 95% identical to the amino acid sequence set forth in SEQ ID NO:21 and CDRs identical to the IMGT CDRs of SEQ ID NO:21.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:21.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:28.

In some embodiments, the amino acid variation may be located in one or more framework regions of SEQ ID NO:28.

In some embodiment, the heavy chain comprises an amino acid sequence at least 75%, 80% 85%, 90%, 95% identical to the amino acid sequence set forth in SEQ ID NO:28 and CDRs identical to the Kabat CDRs of SEQ ID NO:28.

In some embodiment, the heavy chain comprises an amino acid sequence at least 75%, 80% 85%, 90%, 95% identical to the amino acid sequence set forth in SEQ ID NO:28 and CDRs identical to the IMGT CDRs of SEQ ID NO:28.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:28.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:35.

In some embodiments, the amino acid variation may be located in one or more framework regions of SEQ ID NO:35.

In some embodiment, the heavy chain comprises an amino acid sequence at least 75%, 80% 85%, 90%, 95% identical to the amino acid sequence set forth in SEQ ID NO:35 and CDRs identical to the Kabat CDRs of SEQ ID NO:35.

In some embodiment, the heavy chain comprises an amino acid sequence at least 75%, 80% 85%, 90%, 95% identical to the amino acid sequence set forth in SEQ ID NO:35 and CDRs identical to the IMGT CDRs of SEQ ID NO:35.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:35.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:42.

In some embodiments, the amino acid variation may be located in one or more framework regions of SEQ ID NO:42.

In some embodiment, the heavy chain comprises an amino acid sequence at least 75%, 80% 85%, 90%, 95% identical to the amino acid sequence set forth in SEQ ID NO:42 and CDRs identical to the Kabat CDRs of SEQ ID NO:42.

In some embodiment, the heavy chain comprises an amino acid sequence at least 75%, 80% 85%, 90%, 95% identical to the amino acid sequence set forth in SEQ ID NO:42 and CDRs identical to the IMGT CDRs of SEQ ID NO:42.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:42.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:49.

In some embodiments, the amino acid variation may be located in one or more framework regions of SEQ ID NO:49.

In some embodiment, the heavy chain comprises an amino acid sequence at least 75%, 80% 85%, 90%, 95% identical to the amino acid sequence set forth in SEQ ID NO:49 and CDRs identical to the Kabat CDRs of SEQ ID NO:49.

In some embodiment, the heavy chain comprises an amino acid sequence at least 75%, 80% 85%, 90%, 95% identical to the amino acid sequence set forth in SEQ ID NO:49 and CDRs identical to the IMGT CDRs of SEQ ID NO:49.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:49.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence at least 75%, 80% 85%, 90%, 95% identical to the amino acid sequence set forth in SEQ ID NO:56.

In some embodiments, the amino acid variation may be located in one or more framework regions of SEQ ID NO:56.

In some embodiment, the heavy chain comprises an amino acid sequence at least 75%, 80% 85%, 90%, 95% identical to the amino acid sequence set forth in SEQ ID NO:56 and CDRs identical to the Kabat CDRs of SEQ ID NO:56.

In some embodiment, the heavy chain comprises an amino acid sequence at least 75%, 80% 85%, 90%, 95% identical to the amino acid sequence set forth in SEQ ID NO:56 and CDRs identical to the IMGT CDRs of SEQ ID NO:56.

In some exemplary embodiments, the binding agent of the present disclosure may comprise one or more antigen binding domains, wherein at least one of the antigen binding domains is an antigen binding domain 1 (ABD1) and comprises a heavy chain having an amino acid sequence as set forth in SEQ ID NO:56.

Exemplary Embodiments of ABD2

Antigen binding domain 2 (ABD2) may be selected, for example, from antigen binding domains that bind PD-1, some non-limiting exemplary embodiments of which is provided herein.

In some exemplary embodiments, the binding agent of the present disclosure may comprise one or more antigen binding domains, wherein at least one of the antigen binding domains is an antigen binding domain 2 (ABD2) and comprises a heavy chain complementarity determining region 1 (CRDH1) having the amino acid sequence set forth in SEQ ID NO:57, a heavy chain complementarity determining region 2 (CDRH2) having the amino acid sequence set forth in SEQ ID NO:58 and a heavy chain complementarity determining region 3 (CDRH3) having the amino acid sequence set forth in SEQ ID NO:59.

In some exemplary embodiments, the binding agent of the present disclosure may comprise one or more antigen binding domains, wherein at least one of the antigen binding domains is an antigen binding domain 2 (ABD2) and comprises a CRDH1 having the amino acid sequence set forth in SEQ ID NO:60, a CDRH2 having the amino acid sequence set forth in SEQ ID NO:61 and a CDRH3 having the amino acid sequence set forth in SEQ ID NO:62.

In some exemplary embodiments, the binding agent of the present disclosure may comprise one or more antigen binding domains, wherein at least one of the antigen binding domains is an antigen binding domain 2 (ABD2) and comprises a heavy chain having an amino acid sequence at least 75%, 80% 85%, 90%, 95% identical to the amino acid sequence set forth in SEQ ID NO:63.

In some embodiments, the amino acid variation may be located in one or more framework regions of SEQ ID NO:63.

In some embodiment, the heavy chain comprises an amino acid sequence at least 75%, 80% 85%, 90%, 95% identical to the amino acid sequence set forth in SEQ ID NO:63 and CDRs identical to the Kabat CDRs of SEQ ID NO:63.

In some embodiment, the heavy chain comprises an amino acid sequence at least 75%, 80% 85%, 90%, 95% identical to the amino acid sequence set forth in SEQ ID NO:63 and CDRs identical to the IMGT CDRs of SEQ ID NO:63.

In some exemplary embodiments, the binding agent of the present disclosure may comprise one or more antigen binding domains, wherein at least one of the antigen binding domains is an antigen binding domain 2 (ABD2) and comprises a heavy chain having an amino acid sequence as set forth in SEQ ID NO:63.

Exemplary Embodiments of ABD3

Antigen binding domain 3 (ABD3) may be selected, for example, from antigen binding domains that bind CD47, some non-limiting exemplary embodiments of which is provided herein.

In some exemplary embodiments, the binding agent of the present disclosure may comprise one or more antigen binding domains, wherein at least one of the antigen binding domains is an antigen binding domain 3 (ABD3) and comprises a heavy chain complementarity determining region 1 (CRDH1) having the amino acid sequence set forth in SEQ ID NO:64, a heavy chain complementarity determining region 2 (CDRH2) having the amino acid sequence set forth in SEQ ID NO:65 and a heavy chain complementarity determining region 3 (CDRH3) having the amino acid sequence set forth in SEQ ID NO:66.

In some exemplary embodiments, the binding agent of the present disclosure may comprise one or more antigen binding domains, wherein at least one of the antigen binding domains is an antigen binding domain 3 (ABD3) and comprises a CRDH1 having the amino acid sequence set forth in SEQ ID NO:67, a CDRH2 having the amino acid sequence set forth in SEQ ID NO:68 and a CDRH3 having the amino acid sequence set forth in SEQ ID NO:69.

In some exemplary embodiments, the binding agent of the present disclosure may comprise one or more antigen binding domains, wherein at least one of the antigen binding domains is an antigen binding domain 3 (ABD3) and comprises a heavy chain having an amino acid sequence at least 75%, 80% 85%, 90%, 95% identical to the amino acid sequence set forth in SEQ ID NO:70.

In some embodiments, the amino acid variation may be located in one or more framework regions of SEQ ID NO:70.

In some embodiment, the heavy chain comprises an amino acid sequence at least 75%, 80% 85%, 90%, 95% identical to the amino acid sequence set forth in SEQ ID NO:70 and CDRs identical to the Kabat CDRs of SEQ ID NO:70.

In some embodiment, the heavy chain comprises an amino acid sequence at least 75%, 80% 85%, 90%, 95% identical to the amino acid sequence set forth in SEQ ID NO:70 and CDRs identical to the IMGT CDRs of SEQ ID NO:70.

In some exemplary embodiments, the binding agent of the present disclosure may comprise one or more antigen binding domains, wherein at least one of the antigen binding domains is an antigen binding domain 3 (ABD3) and comprises a heavy chain having an amino acid sequence as set forth in SEQ ID NO:70.

Exemplary Embodiments of Other Antigen Binding Domains

In some embodiments, the binding agent comprises one or more antigen binding domains, wherein at least one of the antigen binding domains is an antigen binding domain 1 (ABD1), an antigen binding domain 2 (ABD2) or an antigen binding domain 3 (ABD3) and wherein at least one antigen binding domains binds to a different antigen.

In some embodiments, the binding agents may thus comprise an antigen binding domain that binds to CD3. Such antigen binding domains include those known to a person skilled in the art. An exemplary embodiment of an antigen binding domain that binds to CD3 is provided in SEQ ID NO:115.

Accordingly, in some embodiments, the binding agents may comprise an antigen binding domain that binds to DR2, PD-1 and/or CD3. In other embodiments, the binding agents may comprise an antigen binding domain that binds to DR2 and/or CD3. In yet other embodiments, the binding agents may comprise an antigen binding domain that binds to PD-1 and/or CD3.

In some embodiments, the binding agent comprises one or more antigen binding domains, wherein at least one of the antigen binding domains is an antigen binding domain 1 (ABD1), an antigen binding domain 2 (ABD2) or an antigen binding domain 3 (ABD3) and wherein at least one of the antigen binding domains is selected, for example and without limitations, from antigen binding domains that specifically bind to CD3, CD36, DRD1, DRD2, DRD3, DRD4, DRD5, PD-L1, TROP2, CD147, MCT1, IL1RAP, AMIGO2, PTK7, MCT2, MCT4, NHE1, H+/K+-ATPase, LAP, HLA-I A2, CD73, CD98, CEACAM5/6, ICAM-1, MCSP, fibronectin, Beta 1 Integrin, Tetraspanin 8, CD164, CD59, CD63, CD44, CD166, cWF, TNF, IL-17A, IL17-F, IL-6R, BCMA, TNF, RANKL, ADAMTS5, VEGF, Ang2, $CX_3CR1$, CXCR4, TfR1 (CD71), CXCR2, CD3, PD1, PDL-1, CTLA-4, CD8, LAG-3, OX40, CD27, CD122/IL2RB, TLR8/CD288, TIM-3, ICOS/CD278, NKG2A, A2AR, B7-H3, B7-H4, GITR/TNFRSF18, 4-IBB/CD137, KIR2DL1, KIR3DL2, SIRPα, CD47, VISTA, CD40, CD112, CD96, TOGOT, BTLA, TIGIT, CD4, VEGFR2, CD19, IGFR1, EpCAM, EGFR, DLL3, CGRP, CD79b, CD28, CCR5, ErbB3, ErbB2, TGFβ1, TGFβ2, TGFβ3, TGFβR1, TGFβR2, IDO1, IDO2, TLR-4, TLR-7, TLR-8, TLR-9, NOX2, or SIGLEC-7.

Polypeptide Chain(s)

The binding agents of the present disclosures comprise one or more polypeptide chains.

Segments of DNA encoding desired polypeptide chain sequences may be synthesized in vitro. The different DNA modules are assembled into a single piece in an organized and directional manner which is then cloned into an expression vector. The resulting polypeptide chains are therefore composed of different modules forming a single chain.

The polypeptide chains of the present disclosure include, for example and without limitation, antigen binding domains, linkers and a dimerization domain that promote assembly of at least two polypeptide chains.

In some embodiments, the polypeptide chain of the present disclosure may be monospecific.

In some embodiments, the polypeptide chain of the present disclosure may be multispecific.

In some embodiments, the polypeptide chain of the present disclosure may be monovalent.

In some embodiments, the polypeptide chain of the present disclosure may be multivalent.

In some instances, the polypeptide chain does not comprise a dimerization domain.

In some instances, the polypeptide chain comprises a dimerization domain.

In some aspects of the disclosure, the polypeptide chains may be monospecific.

An exemplary embodiment of a monospecific polypeptide chain includes a polypeptide chain that comprise one antigen binding domain. Another exemplary embodiment of a monospecific polypeptide chain includes a polypeptide chain that comprise more than one antigen binding domains, but the antigen binding domains have identical CDRs and framework regions. Yet another exemplary embodiment of a monospecific polypeptide chain includes a polypeptide chain that comprise more than one antigen binding domains, but the antigen binding domains have identical CDRs and different framework regions. A further exemplary embodiment of a monospecific polypeptide chain includes a polypeptide chain that comprise antigen binding domains that differ in the amino acid sequence of one or more of their CDRs (e.g., conservative substitution in one or more CDRs) without affecting their ability to bind to the same antigen or epitope.

In some aspects of the disclosure, the polypeptide chains may be multispecific. The polypeptide chains may encompass for example, bispecific polypeptide chains, trispecific polypeptide chains, tetraspecific polypeptide chains, pentaspecific polypeptide chains, hexaspecific polypeptide chains, biparatopic polypeptide chains, multiparatopic polypeptide chains and the like.

In an exemplary configuration, one or more antigen binding domains may be located at the N-terminus, at the C-terminus or on each side of the dimerization domain.

In another exemplary configuration, the polypeptide chains may comprise at least one antigen binding domain at the N-terminus of the dimerization domain and at least one antigen binding domain at the C-terminus of the dimerization domain.

In a further exemplary configuration, the polypeptide chains may comprise one antigen binding domain at the N-terminus of the dimerization domain and at least two antigen binding domains at the C-terminus of the dimerization domain.

In yet a further exemplary configuration, the polypeptide chains may comprise two antigen binding domains at the N-terminus of the dimerization domain and two antigen binding domains at the C-terminus of the dimerization domain.

The polypeptide chains may comprise in a N- to C-terminal fashion an amino acid sequence of formula I:

$$X\text{-}[(Ab_a)\text{-}(L_b)]_m\text{-}(DD)\text{-}[(L_c)\text{-}(Ab_d)]_n\text{-}Y$$

Wherein m is 0, 1, 2 or an integer greater than 2;

Wherein n is 0, 1, 2 or an integer greater than 2;

Wherein m and n are not 0 simultaneously;

Wherein $Ab_a$, $Ab_d$, each represents an antigen binding domain wherein at least one of the antigen binding domains is an antigen binding domain 1 (ABD1), an antigen binding domain 2 (ABD2) or an antigen binding domain 3 (ABD3);

Wherein X or Y are independently present or absent and comprises an amino acid sequence;

Wherein $L_b$, $L_c$, each independently comprises one or more linkers; and

Wherein DD represents a dimerization domain.

In some embodiments $L_b$ may be absent.

In some embodiments $L_c$ may be absent.

In some embodiments both $L_b$ and $L_c$ may be absent.

In some embodiments the polypeptide chain comprises more than one antigen binding domains.

In some embodiments where m is 2 or an integer greater than 2, the $[(Ab_a)-(L_b)]$ units is the same.

In other embodiments where m is 2 or an integer greater than 2, the $[(Ab_a)-(L_b)]$ units of the polypeptide chain or binding agent is different.

In other embodiments where m is an integer greater than 2, the $[(Ab_a)-(L_b)]$ units of the polypeptide chain or binding agent may comprise the same and different units.

In some embodiments where n is 2 or an integer greater than 2, the $[(L_c)-(Ab_d)]$ units are the same.

In other embodiments where n is 2 or an integer greater than 2, the $[(L_c)-(Ab_d)]$ units are different.

In other embodiments where n is 2 or an integer greater than 2, the $[(L_c)-(Ab_d)]$ units comprise the same and different units.

In some embodiments, where m is 2 or an integer greater than 2, each $Ab_a$ is the same or different.

In some embodiments, where n is 2 or an integer greater than 2, each $Ab_d$ is the same or different.

In some embodiments, $Ab_a$ represents ABD1.

In some embodiments, $Ab_d$ represents ABD2.

In some embodiments, $Ab_d$ represents ABD3.

In some embodiments, m is 1 and $Ab_a$ represents ABD1.

In some embodiments, n is 2 and one of $Ab_d$ represents ABD2.

In some embodiments, n is 2 and one of $Ab_d$ represents ABD3.

In some embodiments, n is 2 and one of $Ab_d$ represents ABD2 and the other $Ab_d$ represents ABD3.

In some embodiments, m is 2, 3, 4, 5 or an integer greater than 5.

In some embodiments m is 2.

In other embodiments m is 3.

In yet other embodiments m is 4.

In further embodiments m is 5 In other embodiments m is an integer greater than 5.

In some embodiments, n is 2, 3, 4, 5 or an integer greater than 5.

In some embodiments n is 2.

In other embodiments n is 3.

In additional embodiments n is 4.

In further embodiments n is 5.

In other embodiments n is an integer greater than 5.

In embodiments, the one or more polypeptide chain further comprises a hinge region of an antibody or antigen binding fragment thereof.

In some embodiments, the hinge region is at the N-terminus of the dimerization domain.

In some embodiments $L_b$ is a hinge region of an antibody or antigen binding fragment thereof.

In some embodiments, the hinge region is a natural human IgG1 hinge region. In other embodiments the hinge region is a mutated human IgG1 hinge region.

In other embodiments, the hinge region is a natural human IgG2 hinge region. In other embodiments, the hinge region is a mutated human IgG2 hinge region.

In other embodiments, the hinge region is a natural human IgG3 hinge region. In other embodiments, the hinge region is a mutated human IgG3 hinge region.

In yet other embodiments, the hinge region is a natural human IgG4 hinge region. In other embodiments, the hinge region is a mutated human IgG4 hinge region.

In some embodiments each of the one or more linkers independently has at least 5, 10, 15, 20, 25, 30, 35, 40, 45 or 50 amino acid residues in length.

In some embodiments, each of the one or more linkers is independently a flexible linker, a helical linker, or a rigid linker.

In some embodiments, the linker $L_c$ is a rigid linker.

In some embodiments, $L_c$ comprises a non-cleavable linker. In other embodiments, $L_c$ consists of a non-cleavable linker.

In some embodiments the one or more linkers comprise a flexible linker.

In some embodiments the one or more linkers comprise a rigid linker.

In some embodiments, the flexible linker is a GS linker.

In some embodiments, the flexible linker comprises one or more units of GGGGS.

In some embodiments, the flexible linker comprises at least 2, 3, 4, 5, or more units of GGGGS.

In some embodiments the rigid linker comprises multiple PA repeats.

In some embodiments, the rigid linker is selected from PAPAPKA (SEQ ID NO:105); APAPAPAPAPKA (SEQ ID NO:106); APAPAPAPAPAPAPAPAPAPKA (SEQ ID NO:107); or combinations thereof.

In some embodiments, the helical linker comprises one or more units of EAAAK.

In some embodiments, the helical linker is selected from AEAAAKEAAAKA (SEQ ID NO:109); AEAAAKEAAAKEAAAKA (SEQ ID NO:110); AEAAAKEAAAKEAAAKEAAAKEAAAKA (SEQ ID NO:111); or combinations thereof.

In some embodiments, the dimerization domain comprises an amino acid sequence at least 80%, 85%, 90%, 95%, 96%, 97%, 98%, or 99% identical to SEQ ID NO:116.

In some embodiments the dimerization domain further comprises an amino acid sequence at least 80%, 85%, 90%, 95%, 96%, 97%, 98%, or 99% identical to SEQ ID NO:117.

In other exemplary embodiments, the polypeptide chain comprises formula II:

$$X-(Ab_{a1})-(L_{b1})-(DD)-(L_{c1})-(Ab_{d1})-Y \quad \text{(formula II).}$$

In yet other exemplary embodiments, the polypeptide chain comprises formula III:

$$X-(Ab_{a1})-(L_{b1})-(DD)-(L_{c1})-(Ab_{d1})-(L_{c2})-(Ab_{d2})-Y \quad \text{(formula III).}$$

In further exemplary embodiments, the polypeptide chain comprises formula IV:

$$X-(Ab_{a1})-(L_{b2})-(Ab_{a2})-(L_{b1})-(DD)-(L_{c1})-(Ab_{d1})-Y \quad \text{(formula IV).}$$

In additional exemplary embodiments the polypeptide chain comprises formula V:

$$X-(Ab_{a1})-(L_{b2})-(Ab_{a2})-(L_{b1})-(DD)-(L_{c1})-(Ab_{d1})-(L_{c2})-(Ab_{d2})-Y \quad \text{(formula V).}$$

In further exemplary embodiments, the polypeptide chain comprises formula VI:

$$X-(Ab_{a1})-(L_{b2})-(Ab_{a2})-(L_{b1})-(DD)-(L_{c1})-(Ab_{d1})-(L_{c2})-(Ab_{d2})-(L_{c3})-(Ab_{d3})-Y \quad \text{(formula VI)}.$$

In yet further exemplary embodiments, the polypeptide chain comprises formula VII:

$$X-(Ab_{a1})-(L_{b3})-(Ab_{a2})-(L_{b2})-(Ab_{a3})-(L_{b1})-(DD)-(L_{c1})-(Ab_{d1})-(L_{c2})-(Ab_{d2})-Y \quad \text{(formula VII)}.$$

In other exemplary embodiments, the polypeptide chain comprises formula VIII:

$$X-(Ab_{a1})-(L_{b3})-(Ab_{a2})-(L_{b2})-(Ab_{a3})-(L_{b1})-(DD)-(L_{c1})-(Ab_{d1})-(L_{c2})-(Ab_{d2})-(L_{c3})-(Ab_{d3})-Y \quad \text{(formula VIII)}.$$

In some embodiments $Ab_{a1}$, $Ab_{a2}$, $Ab_{a3}$, $Ab_{d1}$, $Ab_{d2}$, $Ab_{d3}$, each independently comprises an antigen binding domain.

In some embodiments $Ab_{a1}$, $Ab_{a2}$, $Ab_{a3}$, $Ab_{d1}$, $Ab_{d2}$, $Ab_{d3}$, each independently represents an antigen binding domain.

In some embodiments, at least one of the antigen binding domains is an antigen binding domain 1 (ABD1), an antigen binding domain 2 (ABD2) or an antigen binding domain 3 (ABD3) In some embodiments $L_{b1}$ comprises a linker or linkers and/or a hinge region of an antibody or antigen binding fragment thereof. In some embodiments, $L_{b1}$ is $L_b$.

In some embodiments $L_{b2}$, $L_{b3}$ $L_{c1}$, $L_{c2}$, and $L_{c3}$ each independently comprise a linker or linkers.

In some embodiments one or more of $L_{b1}$, $L_{b2}$ and/or $L_{b3}$ may be absent.

In some embodiments $L_{b2}$ and/or $L_{b3}$ may be absent.

In some embodiments, one or more of $L_{c1}$, $L_{c2}$, and/or $L_{c3}$ may be absent.

In some embodiments $L_{c2}$ and/or $L_{c3}$ may be absent.

In some embodiments, $L_{c1}$ is a rigid linker.

In some embodiments, $L_{c2}$ is a rigid linker.

In some embodiments, $L_{c3}$ is a rigid linker.

In some embodiments, $L_{c1}$, and $L_{c2}$ are rigid linkers.

In some embodiments, $L_{c1}$, $L_{c2}$ and $L_{c3}$ are rigid linkers.

In some embodiments $L_{c1}$, $L_{c2}$ and/or $L_{c3}$ may be absent.

In some embodiments $L_{c2}$, and/or $L_{c3}$ may be absent.

In some embodiments $L_{c1}$, and/or $L_{c3}$ may be absent.

In some embodiments $L_{c2}$ and/or $L_{c3}$ may be absent.

In some embodiments, $L_{c1}$, $L_{c2}$, and $L_{c3}$ may be absent.

The polypeptide chains of the present disclosure comprise antigen binding domains that are functionally active either as a single chain or when part of the binding agent disclosed herein.

For example, the antigen binding domain of the polypeptide chains may bind to its target and may biologically active.

In some embodiments, the biological activity of an antigen binding domain includes, for example and without limitation, blocking binding of a target to its natural receptor or ligand. Alternatively, the biological activity of an antigen binding domain includes its ability to sequester a target. Moreover, the biological activity of an antigen binding domain includes its ability to induce signalling.

A polypeptide chain that comprises more than one antigen binding domain is characterized as being multivalent.

The polypeptide chain of the present disclosure may comprise an additional amino acid sequence at its N- or C-terminus or at both ends (defined by X and Y respectively in the formulas disclosed herein).

In some embodiments, the amino acid sequence at the N-terminus (defined by X) may include a signal peptide, an exemplary embodiment of which is provided in SEQ ID NO:133.

In some embodiments, the amino acid sequence at the N-terminus (defined by X) or C-terminus (defined by Y) may independently include a linker, a cytokine, a chemokine, a tag (e.g., His tag (e.g. SEQ ID NO: 134), a masking domain, a phage coat protein, an antigen binding domain or combination thereof.

An exemplary embodiment of a multispecific polypeptide chain include a polypeptide chain that comprises at least two antigen binding domains that differ in the amino acid sequence of one or more of their CDRs leading to different binding specificities.

A polypeptide chain may more particularly be characterized as being bispecific when it binds to two different epitopes or antigens. A polypeptide chain may be characterized as being trispecific when it binds to three different epitopes or antigens. A polypeptide chain may be characterized as being tetraspecific when it binds to four different epitopes or antigens. A polypeptide chain may be characterized as being pentaspecific when it binds to five different epitopes or antigens. A polypeptide chain may be characterized as being hexaspecific when it binds to six different epitopes or antigens.

A polypeptide chain comprising two antigen binding domains that bind to two non-overlapping epitopes on the same target is characterized as being biparatopic. A polypeptide chain comprising antigen binding domains that bind to three, four or more epitopes on the same target is characterized as being multiparatopic.

The antigen binding domains of a given polypeptide chain will be selected based on the intended use such as detection, diagnostic and/or therapeutic use. Each of the antigen binding domains of a particular polypeptide chain may be selected so as to generate an additive or synergic effect.

In some embodiments the antigen binding domain may be selected for its ability to specifically binds a protein involved in a disease or condition.

For example, polypeptide chains of the present disclosure may comprise at least one antigen binding domain that specifically binds to an antigen expressed by tumor cells or by the tumor cell environment (i.e., tumor-specific antigen binding domains).

In other aspects and embodiments of the disclosure the polypeptide chains may comprise at least one antigen binding domain that specifically binds to an immunomodulator.

For example, the polypeptide chain may comprise one or more antigen binding domains that bind an immune checkpoint protein, a cytokine, a chemokine or an immune receptor or coreceptor etc. (e.g., immune-specific antigen binding domains).

In some exemplary embodiment, the antigen binding domain may bind to dopamine receptor D2 (DR2).

In some exemplary embodiment, the antigen binding domain may bind to PD1.

In some exemplary embodiment, the antigen binding domain may bind to CD47.

In an exemplary embodiment, the polypeptide chain of the present disclosure may comprise at least one tumor-specific antigen binding domain and at least one immune-specific antigen binding domain.

In some embodiments, the tumor-specific antigen binding domain(s) may be located at the N-terminus of the dimerization domain.

In some embodiments, the tumor-specific antigen binding domain(s) may be located at the C-terminus of the dimerization domain.

In some embodiments, the tumor-specific antigen binding domains may be located at both the N- and C-terminus of the dimerization domain.

In some embodiments, the more immune-specific antigen binding domain(s) may be located at the N-terminus of the dimerization domain.

In some embodiments, the immune-specific antigen binding domain(s) may be located at the C-terminus of the dimerization domain.

In some embodiments, the immune-specific antigen binding domains may be located at both the N- and C-terminus of the dimerization domain.

In exemplary and non-limiting embodiments, the polypeptide chain or binding agent may comprise two immune-specific antigen binding domains at the C-terminus of the dimerization domain. In some embodiments, the immune-specific antigen binding domain that is immediately adjacent to the C-terminal part of the dimerization domain may be linked via a non-cleavable linker.

Dimerization Domain (DD)

In some embodiments, the polypeptide chains of the present disclosure comprise a dimerization domain. As such, two polypeptide chains may assemble to form a binding agent. Exemplary embodiments of binding agent include homodimers and heterodimers.

The dimerization domain may comprise, for example and without limitation, constant regions of an immunoglobulin, including for example a Fc, CH2 and/or CH3 domain of a heavy chain immunoglobulin.

In certain embodiments and aspects of the present disclosure the dimerization domain may have a sequence identical to that of a natural IgG1, IgG2, IgG3 or IgG4 constant region or with their corresponding CH2 and/or CH3 domains.

Particularly encompassed by the present disclosure dimerization domains having a sequence identical to that of a natural human antibody. Exemplary embodiments of dimerization domains include for example a CH2-CH3 domain of a natural human heavy chain.

Accordingly, in some embodiments, the dimerization domain comprises a natural constant region of an antibody, such as for example, a natural human IgG1 constant region, a natural human IgG2 constant region, a natural human IgG3 constant region or a natural human IgG4 constant region.

Accordingly, in some embodiments, the dimerization domain comprises a natural CH3 domain.

In exemplary embodiments, the dimerization domain comprises a natural human CH3 domain.

In some embodiments, the dimerization domain comprises a natural CH2 domain and a natural CH3 domain.

In some embodiments, the natural CH3 domain is a natural IgG1 CH3 domain. In some embodiments, the natural CH3 domain is a natural human IgG1 CH3 (e.g., SEQ ID NO:116).

In some embodiments, the natural CH3 domain is a natural IgG2 CH3 domain. In other embodiments, the natural CH3 domain is a natural human IgG2 CH3 domain.

In some embodiments, the natural CH3 domain is a natural IgG3 CH3 domain. In other embodiments, the natural CH3 domain is a natural human IgG3 CH3 domain.

In some embodiments, the natural CH3 domain is a natural IgG4 CH3 domain. In some embodiments, the natural CH3 domain is a natural human IgG4 CH3 domain.

When the two polypeptide chains of the binding agent are composed of the same amino acid sequence, the binding agent will form a homodimer. However, co-expression of polypeptide chains having a CH2-CH3 domain of a natural antibody, but different amino acid sequence may result in a mixture of homodimers and heterodimers. The different binding agents present in a mixture may be separated by methods known in the art and including for example, size-exclusion chromatography.

Exemplary heterodimers of the present disclosure therefore include those having a CH3 domain or a CH2-CH3 domain of a natural antibody and that are formed by two polypeptide chains having different sequences or configurations.

In some embodiments, the polypeptide chains may have a mutated dimerization domain that comprises, for example, from 1 to 30, from 1 to 20, from 1 to 15, from 1 to 10, from 1 to 9, from 1 to 8, from 1 to 7, from 1 to 6, from 1 to 5, from 1 to 4, from 1 to 3 amino acid substitutions in comparison with a natural or wild type sequence.

In exemplary embodiments, mutated dimerization domains may comprise 1, 2, 3, 4, 5, 6, 7, 8, 9 or 10 amino acid substitutions. Amino acid substitutions may be conservatives or non-conservatives as outlined in Table 2.

In exemplary embodiments, the polypeptide chains may have a mutated dimerization domain having a sequence which is from 80% to 99% identical with that of a natural IgG1, IgG2, IgG3 or IgG4 constant region or with a CH2 and/or CH3 domain. Polypeptide chains encompassed by the present disclosure include those comprising a mutated dimerization domain that is from 85% to 99% identical, from 90% to 99% identical, from 95% to 99% identical with that of a natural IgG1, IgG2, IgG3 or IgG4 constant region or with a CH2 and/or CH3 domain.

In some embodiments, the polypeptide chains of the present disclosure may comprise a mutated dimerization domain comprising amino acid substitutions that favorize heterodimer formation. Heterodimers of the present disclosure may therefore be formed by polypeptide chains comprising such mutations.

Accordingly, in some embodiments, the dimerization domain comprises a mutated constant region of an antibody, such as for example, a mutated human IgG1 constant region, a mutated human IgG2 constant region, a mutated human IgG3 constant region or a mutated human IgG4 constant region. A mutated constant region may have one or more amino acid substitutions, amino acid insertion or amino acid deletion in comparison with a natural constant region.

Accordingly, in some embodiments, the dimerization domain comprises a mutated CH3 domain. A mutated CH3 domain may have one or more amino acid substitutions, amino acid insertion or amino acid deletion in comparison with a natural CH3 domain.

In some embodiments, the dimerization domain comprises a natural CH2 and a mutated CH3 domain.

In some embodiments, the dimerization domain comprises a mutated CH2 and a mutated CH3 domain. A mutated CH2 domain may have one or more amino acid substitutions, amino acid insertion or amino acid deletion in comparison with a natural CH2 domain.

In some embodiments, the mutated CH3 domain is a mutated IgG1 CH3 domain. In other embodiments, the mutated CH3 domain is a mutated human IgG1 CH3 domain.

In some embodiments, the mutated CH3 domain is a mutated IgG2 CH3 domain. In other embodiments, the mutated CH3 domain is a mutated human IgG2 CH3 domain.

In some embodiments, the mutated CH3 domain is a mutated IgG3 CH3 domain. In other embodiments, the mutated CH3 domain is a mutated human IgG3 CH3 domain.

In some embodiments, the mutated CH3 domain is a mutated IgG4 CH3 domain. In other embodiments, the mutated CH3 domain is a mutated human IgG4 CH3 domain.

In some embodiments, the mutated CH2 domain is a mutated IgG1 CH2 domain. In other embodiments, the mutated CH2 domain is a mutated human IgG1 CH2 domain.

In some embodiments, the mutated CH2 domain is a mutated IgG2 CH2 domain. In other embodiments, the mutated CH2 domain is a mutated human IgG2 CH2 domain.

In some embodiments, the mutated CH2 domain is a mutated IgG3 CH2 domain. In other embodiments, the mutated CH2 domain is a mutated human IgG3 CH2 domain.

In some embodiments, the mutated CH2 domain is a mutated IgG4 CH2 domain. In other embodiments, the mutated CH2 domain is a mutated human IgG4 CH2 domain.

In some embodiments, the Fc region may be modified so as to prevent glycosylation, to extend its half-life, to modulate receptor binding or effector function. Exemplary mutations are discussed in Saunders K. O. (Front. Immunol. 10:1296, 2019 the entire content of which is incorporated herein by reference) and include for example mutation of asparagine 297 (e.g., N297).

In accordance with the present disclosure, the mutated CH3 domain comprises one or more mutations in comparison with a natural CH3 domain. Accordingly, in some embodiments, the dimerization domain comprises a mutated CH3 domain comprising one or more mutations in comparison with a natural CH3 domain.

For example, the mutated CH3 domain may comprise one or more mutations in comparison with a natural CH3 domain of a human IgG1. In another example, the mutated CH3 domain may comprise one or more mutations in comparison with a natural CH3 domain of a human IgG2. In yet another example, the mutated CH3 domain may comprise one or more mutations in comparison with a natural CH3 domain of a human IgG3. In a further example, the mutated CH3 domain may comprise one or more mutations in comparison with a natural CH3 domain of a human IgG4.

In some embodiments, the mutated CH3 domain may include amino acid substitutions at position 356, 357, 370, 399 and/or 439 (in accordance with EU numbering system).

In some embodiments, the dimerization domain comprises a mutated CH3 domain comprising one or more mutations at positions corresponding to D399, D/E356 and/or K370 (in accordance with EU numbering system) in comparison with a natural CH3 domain of a human IgG1 or IgG4.

In other embodiments, the dimerization domain comprises a mutated CH3 domain comprising one or more mutations at positions corresponding to D399, E357 and/or K439 in accordance with EU numbering (in accordance with EU numbering system) in comparison with a natural CH3 domain of a human IgG1 or IgG4.

In some embodiments, the mutated CH3 domain further comprises one or more mutations at positions corresponding to Y349, T350, L351, P352, S354, R/Q355, T394 and/or P395 in accordance with EU numbering (in accordance with EU numbering system) in comparison with a natural CH3 domain of a human IgG1 or IgG4.

In exemplary embodiments, one polypeptide chain of a given binding agent may include a mutated CH3 domain having, for example, amino acid substitutions at positions 357, 399 and 439, whereas the other polypeptide chain of the binding agent may include a mutated CH3 domain having, for example, amino acid substitutions at positions 356, 370 and 399 (in accordance with EU numbering system).

In exemplary embodiments, one polypeptide chain of a given binding agent may include a mutated CH3 domain having, for example, amino acid substitutions at positions 357, 399 and 439, whereas the other polypeptide chain of the binding agent may include a mutated CH3 domain having, for example, amino acid substitutions at positions 356, 370 and 399 (in accordance with EU numbering system). One or both polypeptide chains of a given binding agent may optionally further comprise mutations at positions selected from 349, 350, 351, 352, 354, 355, 394 and/or 395. One polypeptide chain of a given binding agent may thus comprise a first dimerization domain ($DD_1$) having the amino acid sequence disclosed herein and the other polypeptide chain of a given binding agent may thus comprise a second dimerization domain ($DD_2$) having the amino acid sequence disclosed herein.

In some embodiments, the amino acid at position 356 may be replaced by a neutral amino acid. In some embodiments, the amino acid at position 370 may be replaced by a positively charged amino acid. In some embodiments, the amino acid at position 399 may be replaced by a neutral amino acid. In some embodiments, the amino acid at position 357 may be replaced by a neutral amino acid. In some embodiments, the amino acid at position 439 may be replaced by a negatively charged amino acid.

For example, in order to favorize heterodimer formation, one of the polypeptide chain may be mutated by replacing a) the aspartic acid (D) or glutamic acid (E) at position 356 for a neutral amino acid, b) the lysine (K) at position 370 for a positively charged amino acid and c) the aspartic acid (D) at position 399 for a neutral amino acid while the other polypeptide chain may be mutated by replacing a) the glutamic acid (E) at position 357 for a neutral amino acid, b) the aspartic acid (D) at position 399 for a neutral amino acid and c) the lysine (K) at position 439 for a negatively charged amino acid.

An exemplary embodiment of the polypeptide chains of the present disclosure may comprise a dimerization domain comprising a mutated CH3 domain in which the aspartic acid (D) or glutamic acid (E) at position 356 may be changed for glutamine (Q), the lysine (K) at position 370 may be changed for glutamic acid (E) and the aspartic acid (D) at position 399 may be changed for asparagine (N).

Another exemplary embodiment of the polypeptide chains of the present disclosure may comprise a dimerization domain comprising a mutated CH3 domain in which the glutamic acid (E) at position 357 may be changed for glutamine (Q), the aspartic acid (D) at position 399 may be changed for asparagine (N) and the lysine (K) at position 439 may be changed for glutamic acid (E).

In some embodiments, the dimerization domain comprises a mutated CH3 domain in which the amino acid substitution (in comparison with natural CH3 domain) is selected from:

a. an amino acid substitution at position D399;
b. an amino acid substitution at position D/E356;
c. an amino acid substitution at position E357;
d. an amino acid substitution at position K370;

e. amino acid substitution at position K439;
f. an amino acid substitution at position Y349;
g. an amino acid substitution at position T350;
h. an amino acid substitution at position L351;
i. an amino acid substitution at position P352;
j. an amino acid substitution at position S354;
k. an amino acid substitution at position R355;
l. an amino acid substitution at position Q355;
m. an amino acid substitution at position T394;
n. an amino acid substitution at position P395;
o. an amino acid substitution at position Y349; and
p. any combination of two or more of a. to o. thereof.

In some embodiments, the mutated CH3 domain may comprise amino acid substitutions at positions D399, D/E356, K370 and Y349.

In some embodiments, the mutated CH3 domain may comprise amino acid substitutions at positions D399, D/E356, K370 and T350.

In some embodiments, the mutated CH3 domain may comprise amino acid substitutions at positions D399, D/E356, K370 and L351.

In some embodiments, the mutated CH3 domain may comprise amino acid substitutions at positions D399, D/E356, K370 and P352.

In some embodiments, the mutated CH3 domain may comprise amino acid substitutions at positions D399, D/E356, K370 and S354.

In some embodiments, the mutated CH3 domain may comprise amino acid substitutions at positions D399, D/E356, K370 and R355.

In some embodiments, the mutated CH3 domain may comprise amino acid substitutions at positions D399, D/E356, K370 and Q355.

In some embodiments, the mutated CH3 domain may comprise amino acid substitutions at positions D399, D/E356, K370 and T394.

In some embodiments, the mutated CH3 domain may comprise amino acid substitutions at positions D399, D/E356, K370, Y349 and S354.

In some embodiments, the mutated CH3 domain may comprise amino acid substitutions at positions D399, K439, E357 and Y349.

In some embodiments, the mutated CH3 domain comprises amino acid substitutions at positions D399, E357, K439 and T350.

In some embodiments, the mutated CH3 domain comprises amino acid substitutions at positions D399, E357, K439E and L351.

In some embodiments, the mutated CH3 domain may comprise amino acid substitutions at positions D399, K439, E357 and P352.

In some embodiments, the mutated CH3 domain may comprise amino acid substitutions at positions D399, K439, E357 and S354.

In some embodiments, the mutated CH3 domain may comprise amino acid substitutions at positions D399, K439, E357 and R355.

In some embodiments, the mutated CH3 domain may comprise mutations at positions D399, K439, E357 and Q355.

In some embodiments, the mutated CH3 domain may comprise amino acid substitutions at positions D399, K439, E357 and P395.

In some embodiments, the mutated CH3 domain comprises amino acid substitutions at positions D399, E357, K439, Y349 and S354.

It is to be understood that other amino acid substitution (at other positions or same position with other amino acid residues) in the natural CH3 domain or mutated CH3 domain may be carried out without affecting the ability of the polypeptide chain to form a dimer.

In some embodiments, the amino acid substitution at position Y349 is selected from Y349K, Y349D or Y349R. More particularly, in some embodiments, the amino acid substitution at position Y349 is Y349K. In other embodiments, the amino acid substitution at position Y349 is Y349D.

In some embodiments, the amino acid substitution at position S354 is selected from S354K, S354D, S354W or S354M. More particularly, in some embodiments, the amino acid substitution at position S354 is S354K. In other embodiments, the amino acid substitution at position S354 is S354D. In other embodiments, the amino acid substitution at position S354 is S354M.

In some embodiments, the amino acid substitution at position L351 is L351Y, L351W, L351H, L351R, L351D, L351A, L351T. More particularly, in some embodiments, the amino acid substitution at position L351 is L351Y. In other embodiments, the amino acid substitution at position L351 is L351W. In other embodiments, the amino acid substitution at position L351 is L351R.

In some embodiments, the amino acid substitution at position T350 is T350L, T350I or T350V. More particularly, in some embodiments, the amino acid substitution at position T350 is T350I. In other embodiments, the amino acid substitution at position T350 is T350V.

In some embodiments, the amino acid substitution at position P352 is P352Y, P352V, P352R, P352T, P352L, P352G, P352E, P352C, P352K or P352D. More particularly, in some embodiments, the amino acid substitution at position P352 is P352R. In other embodiments, the amino acid substitution at position P352 is P352E.

In some embodiments, the amino acid substitution at position T394 is T394N.

In some embodiments, the amino acid substitution at position P395 is P395I. In other embodiments, the amino acid substitution at position P395 is P395G. In other embodiments, the amino acid substitution at position P395 is P395E.

In some embodiments, the amino acid substitution at position R355 is R355K. In other embodiments, the amino acid substitution at position R355 is R355W.

In some embodiments, the amino acid substitution at position Q355 is Q355K. In other embodiments, the amino acid substitution at position Q355 is Q355W.

In some embodiment, the mutated CH3 domain comprises mutations D399N, D/E356Q and K370E in accordance with EU numbering.

In some embodiment, the mutated CH3 domain comprises mutations D399Q, D/E356Q and K370E in accordance with EU numbering.

In other embodiments, the mutated CH3 domain comprises mutations D399N, E357Q and K439E in accordance with EU numbering.

In some embodiments, the mutated CH3 domain may comprise mutations D399Q, D/E356Q, K370E, Y349K and S354K.

In some embodiments, the mutated CH3 domain may comprise mutations D399N, D/E356Q, K370E and L351W.

In some embodiments, the mutated CH3 domain may comprise mutations D399N, D/E356Q, K370E and S354M.

In some embodiments, the mutated CH3 domain may comprise mutations D399N, D/E356Q, K370E and T350I.

In some embodiments, the mutated CH3 domain may comprise mutations D399N, D/E356Q, K370E and T350V.

In some embodiments, the mutated CH3 domain may comprise mutations D399N, D/E356Q, K370E and P352R.

In some embodiments, the mutated CH3 domain may comprise mutations D399N, D/E356Q, K370E and P352E.

In some embodiments, the mutated CH3 domain may comprise mutations D399Q, D/E356Q and K370E.

In some embodiments, the mutated CH3 domain may comprise mutations D399N, D/E356Q, K370E and L351Y.

In some embodiments, the mutated CH3 domain may comprise mutations D399N, D/E356Q, K370E, and L351H.

In some embodiments, the mutated CH3 domain may comprise mutations D399N, D/E356Q, K370E, and R355K.

In some embodiments, the mutated CH3 domain may comprise mutations D399N, D/E356Q, K370E, and Q355K.

In some embodiments, the mutated CH3 domain may comprise mutations D399N, D/E356Q, K370E and S354K.

In some embodiments, the mutated CH3 domain may comprise mutations D399N, D/E356Q, K370E and T350L.

In some embodiments, the mutated CH3 domain may comprise mutations D399N, D/E356Q, K370E and T394N.

In some embodiments, the mutated CH3 domain may comprise mutations D399N, D/E356Q, K370E and P352Y.

In some embodiments, the mutated CH3 domain may comprise mutations D399N, D/E356Q, K370E and P352V.

In some embodiments, the mutated CH3 domain may comprise mutations D399N, D/E356Q, K370E and P352T.

In some embodiments, the mutated CH3 domain may comprise mutations D399N, D/E356Q, K370E and P352L.

In some embodiments, the mutated CH3 domain may comprise mutations D399N, D/E356Q, K370E and P352G.

In some embodiments, the mutated CH3 domain may comprise mutations D399N, D/E356Q, K370E and P352C.

In some embodiments, the mutated CH3 domain may comprise mutations D399N, D/E356Q, K370E and L351T.

In some embodiments, the mutated CH3 domain may comprise mutations D399N, D/E356Q, K370E and L351A.

In some embodiments, the mutated CH3 domain comprises mutations D399Q, E357Q, K439E, Y349D and S354D.

In some embodiments, the mutated CH3 domain comprises mutations D399N, E357Q, K439E and L351R.

In some embodiments, the mutated CH3 domain comprises mutations D399N, E357Q, K439E and L351Y.

In some embodiments, the mutated CH3 domain comprises mutations D399N, E357Q, K439E and T350I.

In some embodiments, the mutated CH3 domain may comprise mutations D399N, E357Q, K439E and T350V.

In some embodiments, the mutated CH3 domain may comprise mutations D399Q, K439E, E357Q.

In some embodiments, the mutated CH3 domain may comprise mutations D399N, K439E, E357Q, S354K.

In some embodiments, the mutated CH3 domain may comprise mutations D399N, K439E, E357Q, S354W.

In some embodiments, the mutated CH3 domain may comprise mutations D399N, K439E, E357Q, Y349R.

In some embodiments, the mutated CH3 domain may comprise mutations D399N, K439E, E357Q, T350L.

In some embodiments, the mutated CH3 domain may comprise mutations D399N, K439E, E357Q, R355W.

In some embodiments, the mutated CH3 domain may comprise mutations D399N, K439E, E357Q, Q355W.

In some embodiments, the mutated CH3 domain may comprise mutations D399N, K439E, E357Q, P395I.

In some embodiments, the mutated CH3 domain may comprise mutations D399N, K439E, E357Q, P395G.

In some embodiments, the mutated CH3 domain may comprise mutations D399N, K439E, E357Q, P395E.

In some embodiments, the mutated CH3 domain may comprise mutations D399N, K439E, E357Q, P352K.

In some embodiments, the mutated CH3 domain may comprise mutations D399N, K439E, E357Q, P352D.

In some embodiments, the mutated CH3 domain may comprise mutations D399N, K439E, E357Q, L351D.

In some embodiments, the binding agent comprises two polypeptide chains, wherein;

- one of the two polypeptide chains comprises a first dimerization domain ($DD_1$) comprising a mutated CH3 domain comprising one or more amino acid substitutions at positions corresponding to D399, D/E356 and/or K370 in accordance with EU numbering, and;
- the other of the two polypeptide chains comprises a second dimerization domain ($DD_2$) comprising a mutated CH3 domain comprising one or more amino acid substitutions at positions corresponding to D399, E357 and/or K439 in accordance with EU numbering.

In some embodiments, the first dimerization domain ($DD_1$) comprises a mutated CH3 domain comprising mutations D399N, D/E356Q and K370E in accordance with EU numbering, and wherein the second dimerization domain ($DD_2$) comprises a mutated CH3 domain comprising mutations D399N, E357Q and K439E in accordance with EU numbering.

In some embodiments, the first dimerization domain ($DD_1$) and/or second dimerization domain ($DD_2$) comprises a mutated CH3 domain further comprising amino acid substitutions at positions corresponding to Y349, T350, L351, P352 and/or S354 in accordance with EU numbering.

In some embodiments, the first dimerization domain ($DD_1$) comprises a mutated CH3 domain comprising mutations D399Q, D/E356Q, K370E, Y349K and S354K in accordance with EU numbering and wherein the second dimerization domain ($DD_2$) comprises a mutated CH3 domain comprising mutations D399Q, E357Q, K439E, Y349D and S354D in accordance with EU numbering.

In some embodiments, the first dimerization domain ($DD_1$) comprises a mutated CH3 domain comprising mutations D399N, D/E356Q, K370E and L351W in accordance with EU numbering and wherein the second dimerization domain ($DD_2$) comprises a mutated CH3 domain comprising mutations D399N, E357Q, K439E and L351R in accordance with EU numbering.

In some embodiments, the first dimerization domain ($DD_1$) comprises a mutated CH3 domain comprising mutations D399N, D/E356Q, K370E and S354M in accordance with EU numbering and wherein the second dimerization domain ($DD_2$) comprises a mutated CH3 domain comprising mutations D399N, E357Q, K439E and L351Y in accordance with EU numbering.

In some embodiments, the first dimerization domain ($DD_1$) comprises a mutated CH3 domain comprising mutations D399N, D/E356Q, K370E and T350I in accordance with EU numbering and wherein the second dimerization domain ($DD_2$) comprises a mutated CH3 domain comprising mutations D399N, E357Q, K439E and T350I in accordance with EU numbering.

In some embodiments, the first dimerization domain ($DD_1$) comprises a mutated CH3 domain comprising mutations D399N, D/E356Q, K370E and T350V in accordance with EU numbering and wherein the second dimerization domain ($DD_2$) comprises a mutated CH3 domain comprising mutations D399N, E357Q, K439E and T350V in accordance with EU numbering.

In some embodiments, the first dimerization domain ($DD_1$) comprises a mutated CH3 domain comprising mutations D399N, D/E356Q, K370E and P352R in accordance with EU numbering and wherein the second dimerization domain ($DD_2$) comprises a mutated CH3 domain comprising mutations D399N, E357Q, K439E and L351R in accordance with EU numbering.

In some embodiments, the first dimerization domain ($DD_1$) comprises a mutated CH3 domain comprising mutations D399N, D/E356Q, K370E and P352E in accordance with EU numbering and wherein the second dimerization domain ($DD_2$) comprises a mutated CH3 domain comprising mutations D399N, E357Q, K439E and L351R in accordance with EU numbering.

In accordance with the present disclosure, binding agents may be composed of two different polypeptide chains that associates to from a dimer, herein referred as a heterodimer.

Heterodimers can be made by co-expressing two different polypeptide chains (e.g., Chain A and Chain B).

In some embodiments, the polypeptide chain may comprise a dimerization domain comprising a wild type human CH2 and a mutated human CH3 that favorizes the formation of heterodimers. In some instances, the polypeptide chains have the possibility of forming a homodimer when expressed alone or to form a heterodimer (or mixture of homodimer and heterodimers) when expressed with a complementary chain.

Heterodimers were particularly made by transfection of a set of polypeptide chains comprising CH3 mutations (Chain A and Chain B exemplified Table 1).

TABLE 1

Exemplary embodiments of Chain A and Chain B (natural human IgG1 CH2 and mutated IgG1 CH3)

| CHAIN ID | CH3 MUTATIONS |
|---|---|
| Chain A | D399N, K370E, E356Q |
| Chain A | D399Q, K370E, E356Q |
| Chain A | D399Q, K370E, E356Q, Y349K, S354K |
| Chain A | D399N, K370E, E356Q, L351Y |
| Chain A | D399N, K370E, E356Q, L351H |
| Chain A | D399N, K370E, E356Q, S354M |
| Chain A | D399N, K370E, E356Q, R355K |
| Chain A | D399N, K370E, E356Q, S354K |
| Chain A | D399N, K370E, E356Q, T350I |
| Chain A | D399N, K370E, E356Q, T350L |
| Chain A | D399N, K370E, E356Q, T350V |
| Chain A | D399N, K370E, E356Q, T394N |
| Chain A | D399N, K370E, E356Q, T394N |
| Chain A | D399N, K370E, E356Q, T394N |
| Chain A | D399N, K370E, E356Q, P352Y |
| Chain A | D399N, K370E, E356Q, P352V |
| Chain A | D399N, K370E, E356Q, P352T |
| Chain A | D399N, K370E, E356Q, P352R |
| Chain A | D399N, K370E, E356Q, P352R |
| Chain A | D399N, K370E, E356Q, P352R |
| Chain A | D399N, K370E, E356Q, P352L |
| Chain A | D399N, K370E, E356Q, P352G |
| Chain A | D399N, K370E, E356Q, P352E |
| Chain A | D399N, K370E, E356Q, P352C |
| Chain A | D399N, K370E, E356Q, P352C |
| Chain A | D399N, K370E, E356Q, L351W |
| Chain A | D399N, K370E, E356Q, L351T |
| Chain A | D399N, K370E, E356Q, L351A |
| Chain A | D399N, K370E, E356Q, P352Y |
| Chain A | D399Q, K370E, E356Q, Y349K, S354K |
| Chain A | D399Q, K370E, E356Q, Y349K, S354K |
| Chain B | D399N, K439E, E357Q |
| Chain B | D399Q, K439E, E357Q |
| Chain B | D399Q, K439E, E357Q, Y349D, S354D |
| Chain B | D399N, K439E, E357Q, S354K |
| Chain B | D399N, K439E, E357Q, S354W |
| Chain B | D399N, K439E, E357Q, L351Y |
| Chain B | D399N, K439E, E357Q, Y349R |
| Chain B | D399N, K439E, E357Q, T350L |
| Chain B | D399N, K439E, E357Q, T350I |
| Chain B | D399N, K439E, E357Q, R355W |
| Chain B | D399N, K439E, E357Q, T350V |
| Chain B | D399N, K439E, E357Q, P395I |
| Chain B | D399N, K439E, E357Q, P395G |
| Chain B | D399N, K439E, E357Q, P395E |
| Chain B | D399N, K439E, E357Q, P352K |
| Chain B | D399N, K439E, E357Q, P352K |
| Chain B | D399N, K439E, E357Q, P352K |
| Chain B | D399N, K439E, E357Q, P352K |
| Chain B | D399N, K439E, E357Q, P352D |
| Chain B | D399N, K439E, E357Q, L351R |
| Chain B | D399N, K439E, E357Q, P352K |
| Chain B | D399N, K439E, E357Q, P352K |
| Chain B | D399N, K439E, E357Q, L351R |
| Chain B | D399N, K439E, E357Q, P352K |
| Chain B | D399N, K439E, E357Q, P352D |
| Chain B | D399N, K439E, E357Q, L351R |
| Chain B | D399N, K439E, E357Q, P352K |
| Chain B | D399N, K439E, E357Q, L351R |
| Chain B | D399N, K439E, E357Q |
| Chain B | D399N, K439E, E357Q |
| Chain B | D399N, K439E, E357Q, L351R |

Mutations may be introduced into CH3 domains of human IgGs. Numbering of amino acid residues in accordance with EU numbering Depending on the ratio of Chain A over Chain B, it is also possible to form homodimers upon co-expression of two such polypeptide chains.

Accordingly, in some circumstances, co-expression of a polypeptide Chain A with polypeptide Chain B may therefore result in heterodimers of Chain A and Chain B, homodimers of Chain A, homodimers of Chain B and mixture thereof. It is also possible that residual monomers of Chain A and/or Chain B exist. Since the monomers, heterodimers and homodimers each contain antigen binding domains, each component of the mixture may have some level of activity.

Therefore, monomers, heterodimers and homodimers that comprise the CH3 mutations disclosed herein as well as mixture of such monomers, heterodimers and/or homodimers are encompassed by the present disclosure.

In other embodiments, the polypeptide chains disclosed herein may comprise a mutated dimerization domain that comprises mutations known in the art to favorize heterodimer formation.

For example, polypeptides chains of the present disclosure may comprise the configuration set forth in formula I, formula II, formula III, formula IIIa and formula IIIb, formula IV, formula V, formula VI, formula VII or formula VIII disclosed herein and mutations known in the art to favorize heterodimer formation.

Exemplary embodiments of such mutations are disclosed for example in Ha, J-H et al. (Front Immunol, 2016; 7:394) or Godar M et al. (Expert Opinion on Therapeutic patents, 2018; 28(3):251-276), the entire content of which is incorporated by reference and includes for example Knobs-into-holes (first CH3 domain mutation T366Y and second CH3 domain mutation Y407T, first CH3 domain mutation T366W and second CH3 domain mutations T366S, L368A, Y407V, or first CH3 domain mutations S354C, T366W and second CH3 domain mutations Y349C, T366S, L368A, Y407V), DD/KK mutations (first CH3 domain mutations K409D, K392D, second CH3 domain mutations D399K, E356K), asymmetric re-engineering technology (first CH3 domain mutations E356K, E357K, D399K and second CH3 domain mutations K439E, K370E, K409D), BiMAb mutations (first CH3 domain mutations K249E, K288E, second CH3 domain mutations E236K, D278K), XmAb mutations (first CH3 domain mutations S364H, F405A, second CH3 domain mutations Y349T, T394F), DuoBody mutations (first CH3 domain mutation F405L, second CH3 domain mutation K409R), Azymetric mutations (first CH3 domain mutations T350V, L351Y, S400E, F405A, Y407V, second CH3 domain mutations T350V, T366L, N390R, K392M, T394W), Biclonics mutations (first CH3 domain mutation T366K (+L351K), second CH3 domain mutations L351D or E or D at Y349, L368 or Y349+R355), ZW1 mutations (first CH3 domain mutations T350V, L351Y, F405A, Y407V second CH3 domain mutations T350V, T366L, K392L, T394W), 7.8.60 mutations (first CH3 domain mutations K360D, D399M, Y407A, second CH3 domain mutations E345R, Q347R, T366V, K409V), EW-RVT mutations (first CH3 domain mutations K360E, K409W and second CH3 domain mutations Q347R, D399V, F405T), EW-RVTs-s mutations (first CH3 domain mutations K360E, K409W, Y349C and second CH3 domain mutations Q347R, D399V, F405T, S354C), SEED mutations (first CH3 domain mutations IgA-derived 45 residues on IgG1 CH3 and second CH3 domain mutations IgG1-derived 57 residues on IgA CH3), A107 mutations (first CH3 domain mutations K370E, K409W, second CH3 domain mutations E357N, D399V, F405T) etc.

Linkers (L)

The different modules of the polypeptide chains disclosed herein may be associated to each other via linkers.

In some embodiments, the linkers used to join one or more modules of the polypeptide chain are not cleavable linkers.

In an exemplary embodiment, the linker located immediately adjacent to the C-terminal end of the dimerization domain (Lc) does not comprise a cleavable linker.

In another exemplary embodiment, at least one of the linkers located between two antigen binding domains do not comprise a cleavable linker.

In other embodiments the linkers used to join one or more modules of the polypeptide chain may include non-cleavable linkers.

In an exemplary embodiment, the linker located immediately adjacent to the C-terminal end of the dimerization domain is a non-cleavable linker.

In another exemplary embodiment, at least one of the linkers located between two antigen binding domains is a non-cleavable linker.

In a further exemplary embodiment, the linker located immediately adjacent to the C-terminal end of the dimerization domain and the linker joining the first two antigen binding domains located at the C-terminal end of the dimerization domain are non-cleavable linkers.

In some embodiment, the linker immediately adjacent to the N-terminal end of the dimerization domain may preferably comprise hinge region of an antibody.

In some embodiments, the hinge region is natural hinge region.

In some embodiments, the natural hinge region is a natural IgG1 hinge region. In some embodiments, the natural hinge region is a natural human IgG1 hinge region.

In some embodiments, the natural hinge region is a natural IgG2 hinge region. In other embodiments, the natural hinge region is a natural human IgG2 hinge region.

In some embodiments, the natural hinge region is a natural IgG3 hinge region. In other embodiments, the natural hinge region is a natural human IgG3 hinge region.

In some embodiments, the natural hinge region is a natural IgG4 hinge region. In some embodiments, the natural hinge region is a natural human IgG4 hinge region.

In some embodiments, the hinge region is a mutated hinge region.

In some embodiments, the mutated hinge region is a mutated IgG1 hinge region. In some embodiments, the mutated hinge region is a mutated human IgG1 hinge region.

In some embodiments, the mutated hinge region is a mutated IgG2 hinge region. In other embodiments, the mutated hinge region is a mutated human IgG2 hinge region.

In some embodiments, the mutated hinge region is a mutated IgG3 hinge region. In other embodiments, the mutated hinge region is a mutated human IgG3 hinge region.

In some embodiments, the mutated hinge region is a mutated IgG4 hinge region. In some embodiments, the mutated hinge region is a mutated human IgG4 hinge region.

In some embodiments, all modules of the polypeptide chain are linked via non-cleavable linkers.

Exemplary embodiments of non-cleavable linkers include those that remains substantially intact during protein expression or during manufacturing process. As used herein "substantially intact" means that linker cleavage occurs in 20% or less, in 15% or less, in 10% or less, in 7.5% or less, in 5% or less, in 4% or less, in 3% or less, in 2% or less, in 1% or less of the total polypeptide content of a given solution or composition.

Other exemplary embodiments of non-cleavable linkers also include linkers that do not comprise a specific cleavage site for one or more proteases present in human or animal blood or serum.

Additional exemplary embodiments of non-cleavable linkers further include linkers that retain their integrity for at least one, two, three, four, five, six, twelve, twenty-four, forty-eight hours or more after administration upon administration of the binding agent in individuals.

In further exemplary embodiments, a linker comprises both non-cleavable linkers and cleavable linkers.

In some embodiments, a linker is not cleavable.

In some instance cleavable linkers may be used for in vivo release of drugs (e.g., cytostatic molecules, cytotoxic molecules, chemotherapeutics etc.) or labels attached to the polypeptide chain of the present disclosure.

Exemplary embodiments of cleavable linkers are provided for example in US2019/0010242 and include linkers that are sensitive to cleavage by a protease, usually an extracellular protease, such as a protease that is produced by a tumor or an activated immune effector cell and include those having a site for specific cleavage by proteases selected from ADAMS, ADAMTS, e.g. ADAMS; ADAMS; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; cysteine proteinases, e.g., Cruzipain; Legumain; Otubain-2; KLKs, e.g., KLK4, KLK5, KLK6, KLK7, KLK8, KLK10, KLK11, KLK13, or KLK14; metalloproteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof. In some embodiments the polypeptide chains of the present disclosure do not include such linkers at position corresponding to Lc.

Exemplary embodiments of linkers include flexible linkers, rigid linkers, helical linkers and combination thereof. Linkers are discussed for example, in Chen X et al. (Adv Drug Deliv Rev. 2013; 65(10):1357-1369) the entire content of which is incorporated herein by reference.

In some embodiments, a hinge region or a portion thereof may be used to link a module to the dimerization domain and is considered herein as a linker. The hinge region may be derived from a natural antibody (of human or animal origin) or from a synthetic antibody. Hinge regions may be obtained, for example, from IgGs such as IgG1, IgG2, IgG3 or IgG4. Exemplary embodiments of hinge regions are provided in SEQ ID NO:98, SEQ ID NO:121, SEQ ID NO:125 and SEQ ID NO:129.

In some instances, the hinge region may have one or more amino acid substitutions, amino acid insertion and/or amino acid deletions in comparison with a natural hinge region. Mutated hinge region includes, for example, a sequence that is from 80% to 99% identical with that of a natural IgG1, IgG2, IgG3 or IgG4 hinge region (mutated hinge region). An exemplary and non-limiting embodiment of a mutated hinge region includes a hinge region of an IgG4 in which S228 is replaced with P (EU numbering) (Angal, S. et al., Mol Immunol 30, 105-108, 1993). Other exemplary embodiments of mutated hinge are provided in SEQ ID NOs: 118-120, 122-124, 126-128 and 130-132.

Flexible linkers are usually composed of small polar amino acids such as threonine or serine and glycine. Exemplary and non-limiting embodiments of flexible linkers include GS linkers (glycine/serine repeats) such as for example, $(GGGS)_n(GGGGS)_m$, $(GS)_n$, $(G_4S)_n$, $(GGS)_n$, $(GGGS)_n$, $(GGGGS)_n$, $(GGSG)_n$, $(GGGSS)_n$ wherein n and m may be an integer such as 1, 2, 3, 4, 5, 6, 7, 8, 9, 10 or more, such as 15, 20 or 25.

Specific exemplary and non-limiting embodiments of flexible linkers include those comprising of consisting of the amino acid sequence set forth in SEQ ID NO:100, SEQ ID NO:101, SEQ ID NO:102, SEQ ID NO:103 or SEQ ID NO:104.

It is to be understood that SEQ ID NO:104 may be represented by formula $(GGGGS)_n$ wherein n is an integer selected from 1 to 10 or alternatively by formula $GGGGSX_1$ wherein $X_1$ is absent or, if present is from 1 to 9 repeats of amino acid residues 1 to 5 of SEQ ID NO:104.

Rigid linkers of the present disclosure are usually composed of proline-rich sequences $(XP)_n$, wherein X designate any amino acid, preferably Ala, Lys or Glu and n is an integer such as 1, 2, 3, 4, 5, 6, 7, 8, 9, 10 etc. (Chen X et al., 2013).

Specific exemplary and non-limiting embodiments of rigid linkers include those comprising of consisting of the amino acid sequence set forth in SEQ ID NO:105, SEQ ID NO:106, SEQ ID NO:107 or SEQ ID NO:108.

It is to be understood that SEQ ID NO:108 may be represented by formula $(X(PAPAP))_nKA$ wherein n is an integer selected from 1 to 10, wherein X is present or absent and, if present, is A or, alternatively, SEQ ID NO:108 may be represented by formula $(XPAPAP)X_2KA$ wherein X may be present or absent and, if present, is A; and wherein $X_2$ is absent or, if present, is from 1 to 9 repeats of amino acid residues 1 to 6 of SEQ ID NO:108.

Helical linkers may sometimes be characterized as rigid but are herein being separated into a distinct linker family. Exemplary embodiments of helical linkers are discussed in Chen X et al., 2013 and comprise, for example, repeats of alanine residues flanked by a positively charged- and a negatively charged amino acid residue.

Specific exemplary and non-limiting embodiments of helical linkers include those comprising of consisting of the amino acid sequence set forth in SEQ ID NO:109, SEQ ID NO:110, SEQ ID NO:111 and SEQ ID NO:112.

It is to be understood that SEQ ID NO: 112 may be represented by formula $X(EAAAK)_nX_2$ wherein n is an integer selected from 1 to 10, more preferably 2-5 wherein X and $X_2$ are independently present or absent and, if present, is preferably A. Alternatively, SEQ ID NO:112 may be represented by formula $X(EAAAK)X_3X_2$, wherein X and $X_2$ are independently present or absent and, if present, is preferably A; and $X_3$ is absent or, if present, is from 1 to 9 repeats of amino acid residues 2 to 6 of SEQ ID NO:112.

In an exemplary embodiment the linker immediately adjacent to the C-terminal end of the dimerization domain (identified as $L_{c1}$ in formulas II to VIII) may comprise either a flexible linker, a rigid linker or a helical linker. Linkers that may be particularly selected to occupy this position include for example and without limitations, a linker comprising or consisting of the amino acid sequence set forth in SEQ ID NO:100-109, SEQ ID NO:111 or in SEQ ID NO:112 wherein n is 1.

In an exemplary embodiment the linker joining the first two antigen binding domains located at the C-terminal end of the dimerization domain (identified as $L_{c2}$ in formulas II to VIII) may comprise either a flexible linker, a rigid linker or a helical linker. Linkers that may be particularly selected to occupy this position include for example and without limitations, a linker comprising or consisting of the amino acid sequence set forth in SEQ ID NO:100-110, or in SEQ ID NO:112 wherein n is 1.

The present disclosure also provides linkers having an addition of from 1 to 10 amino acids (and any range or value comprised within 1 and 10 such as for example, from 1 to 5) at one or both the N- or C-terminus of any of SEQ ID NOs: 100 to 112. These additional amino acid residues may each independently be selected from any amino acid residues. These additional amino acid residues preferably form a non-cleavable sequence.

The present disclosure also provides linkers having a deletion of from 1, 2, 3, 4 or 5 amino acids (and any value comprised within 1 and 5) at one or both the N- or C-terminus of any of SEQ ID NOs: 100 to 112.

Suitable linkers may comprise, for example, an amino acid sequence comprising from about 3 to about 50, from about 3 to about 40, from about 3 to about 30, from about 3 to about 25, from about 3 to about 20, from about 3 to about 15, from about 3 to about 10 amino acid residues.

In exemplary embodiments, the length of each linker may independently range from about 5 to about 50 amino acid residues, including for example, from about 5 to about 40 amino acid residues, from about 10 to about 40 amino acid residues, from about 20 to about 40 amino acid residues, from about 20 to about 35 amino acid residues, from about 25 to about 30 amino acid residues and any sub-range comprised and including such ranges.

In some embodiments linkers that comprise the amino acid sequence set forth in SEQ ID NO:104, SEQ ID NO:108 or SEQ ID NO:112 may have a "n" value preferably from 1 to 10, more preferably from 2-5 including 2, 3, 4 or 5.

Binding Agents

Binding agents of the present disclosure encompass for example the antigen binding domains disclosed herein.

Binding agents of the present disclosure encompass for example the polypeptide chains disclosed herein.

Binding agents of the present disclosure encompass for example dimers of polypeptide chains disclosed herein.

Binding agents of the present disclosure encompass for example multimers of polypeptide chains disclosed herein.

Binding agents of the present disclosure may have a format of an antibody and antigen binding fragment thereof, an antibody-like molecule (Fc-, CH3-fusions and the like), a fusion with protein scaffolds, immune cell modulating agents and the like.

In some embodiments, the binding agent comprises an antibody or an antigen binding fragment thereof.

In some embodiments, the binding agent comprises an antibody-like molecule.

In some embodiments, the binding agent may be fused with protein scaffold.

In some embodiments, the binding agent comprises an immune cell modulating agent.

Accordingly, in some embodiments, binding agents include antibodies and antigen-binding fragments thereof such as, for example and without limitations, single domain antibodies from camelids or sharks, human antibodies including IgGs (including human IgG1, human IgG2, human IgG3, human IgG4), human IgMs, human IgAs (including human IgA1 and human IgA2), human IgEs, human IgDs, animal antibodies including for example, IgGs (IgG1, IgG2a, IgG2b, IgG2c, IgG3, IgG4), IgMs, IgAs, IgEs and IgDs.

In other embodiments, binding agents include antigen-binding fragments such as, for example and without limitations, Fab, Fab', $F(ab')_2$, complementarity determining regions, variable regions including VHs, VHHs, VLs, and the like.

Binding agents also include immune cell modulating agents such as for example, dual-affinity retargeting molecules (DARTs), chimeric antigen receptors (CAR) constructs, bispecific T cell engagers construct (BiTEs), bispecific killer cell engagers (BiKEs), trispecific killer cell engagers (TriKEs) containing scFvs or VHHs.

Binding agents also encompass fusion with protein scaffolds, including ankyrin repeat proteins, Z-domain of *Staphylococcus* protein-A, Type-III fibronetin, knottin and the like.

Exemplary embodiments of binding agents include mono-specific-, bispecifics (symmetric or asymmetric) trispecific-, or multispecific antibodies as well as monovalent, bivalent, trivalent or multivalent antibodies, single chain FVs (scFVs) and derivatives such diabody, triabody, tetrabody, tandem di-scFvs, tandem tri-scFvs, scFV-Fc, minibody (scFV-CH3), tandem diabody, di-diabody, bibody and the like, VH or VHHs and derivatives such as, tandem bispecific or multi-specific VHH, bivalent VHH-Fc fusions, VHH-hinge-CH2-CH3 fusions, bivalent CH3 fusions, VHH pentabody, decabody and the like.

In some embodiments, the binding agents of the present disclosure may have a format as disclosed in PCT/CA2020/051753 filed on Dec. 18, 2020 as formula Ia, formula Ib, formula Ic, formula II, formula III, formula IV, formula V, formula VI, formula VII or formula VIII and the like or formula I, formula II, formula III, formula IIIa and formula IIIb, formula IV, formula V, formula VI, formula VII or formula VIII disclosed herein.

The binding agents of the present disclosure may be formed by the assembly of two polypeptide chains having the same configuration (with same or different amino acid sequence) or having different configurations where the same or different configurations include the configuration set forth in formula I, formula II, formula III, formula IIIa and formula IIIb, formula IV, formula V, formula VI, formula VII or formula VIII disclosed herein.

The binding agent of the present disclosure may comprise for example, one or more polypeptide chains independently comprising in a N- to C-terminal fashion an amino acid sequence of formula I:

$$X\text{-}[(Ab_a)\text{-}(L_b)]_m\text{-}(DD)\text{-}[(L_c)\text{-}(Ab_d)]_n\text{-}Y$$

Wherein m is 0, 1, 2 or an integer greater than 2;

Wherein n is 0, 1, 2 or an integer greater than 2;

Wherein m and n are not 0 simultaneously;

Wherein $Ab_a$, $Ab_d$, each represents an antigen binding domain wherein at least one of the antigen binding domains is an antigen binding domain 1 (ABD1), an antigen binding domain 2 (ABD2) or an antigen binding domain 3 (ABD3);

Wherein X or Y are independently present or absent and comprises an amino acid sequence;

Wherein $L_b$, $L_c$, each independently comprises one or more linkers; and

Wherein DD represents a dimerization domain.

In some embodiments $L_b$ may be absent. In some embodiments $L_{b2}$ and/or $L_{b3}$ may be absent.

In some embodiments $L_c$ may be absent. In some embodiments, $L_{c1}$, $L_{c2}$, and/or $L_{c3}$ may be absent.

In some embodiments both $L_b$ and $L_c$ may be absent.

In some embodiments the polypeptide chain comprises more than one antigen binding domains.

In some embodiments the polypeptide chain comprises two antigen binding domains or more.

In some embodiments the polypeptide chain comprises three antigen binding domains or more.

In some embodiments the polypeptide chain comprises four antigen binding domains or more.

In some embodiments the polypeptide chain comprises five antigen binding domains or more.

In some embodiments the polypeptide chain comprises six antigen binding domains or more.

In some embodiments the polypeptide chain comprises between one and twelve antigen binding domains.

In some embodiments, the binding agent may comprise between one and twelve antigen binding domains, such as between one and two, between one and three, between one and four, between one and five, between one and six, between one and seven, between one and eight, between one and nine, between one and ten, between one and eleven, between one and twelve, between two and three, between two and four, between two and five, between two and six, between two and seven, between two and eight, between two and nine, between two and ten, between two and eleven, between two and twelve, between three and four, between three and five, between three and six, between three and seven, between three and eight, between three and nine, between three and ten, between three and eleven, between three and twelve, between four and five, between four and six, between four and seven, between four and eight, between four and nine, between four and ten, between four and eleven, between four and twelve, between five and six, between five and seven, between five and eight, between five and nine, between five and ten, between five and eleven, between five and twelve, between six and seven, between six and eight, between six and nine, between six and ten, between six and eleven, between six and twelve, between seven and eight, between seven and nine, between seven and ten, between seven and eleven, between seven and twelve, between eight and nine, between eight and ten, between eight and eleven, between eight and twelve, between nine and ten, between nine and eleven, between nine and twelve, between ten and eleven, between ten and twelve, or between eleven and twelve.

In some embodiments, the binding agent comprises one polypeptide chain.

In some embodiments, the binding agent comprises two polypeptide chains.

In some embodiments, the binding agent comprises three polypeptide chains.

In some embodiments, the binding agent comprises four polypeptide chains.

In some embodiments, the binding agent comprises five polypeptide chains.

In some embodiments, the binding agent comprises six polypeptide chains.

In some embodiments, the binding agent comprises seven polypeptide chains.

In some embodiments, the binding agent comprises eight polypeptide chains.

In some embodiments, the binding agent comprises nine polypeptide chains.

In some embodiments, the binding agent comprises ten polypeptide chains.

In some embodiments, the binding agent comprises more than ten polypeptide chains.

In some embodiments the binding agent comprises at least one polypeptide chain having formula II: X-($Ab_{a1}$)-($L_{b1}$)-(DD)-($L_{c1}$)-($Ab_{d1}$)-Y (formula II).

In some embodiments the binding agent comprises at least one polypeptide chain having formula III: X-($Ab_{a1}$)-($L_{b1}$)-(DD)-($L_{c1}$)-($Ab_{d1}$)-($L_{c2}$)-($Ab_{d2}$)-Y (formula III).

In some embodiments the binding agent comprises at least one polypeptide chain having formula IV: X-($Ab_{a1}$)-($L_{b2}$)-($Ab_{a2}$)-($L_{b1}$)-(DD)-($L_{c1}$)-($Ab_{d1}$)-Y (formula IV).

In some embodiments the binding agent comprises at least one polypeptide chain having formula V: X-($Ab_{a1}$)-($L_{b2}$)-($Ab_{a2}$)-($L_{b1}$)-(DD)-($L_{c1}$)-($Ab_{d1}$)-($L_{c2}$)-($Ab_{d2}$)-Y (formula V).

In some embodiments the binding agent comprises at least one polypeptide chain having formula VI: X-($Ab_{a1}$)-($L_{b2}$)-($Ab_{a2}$)-($L_{b1}$)-(DD)-($L_{c1}$)-($Ab_{d1}$)-($L_{c2}$)-($Ab_{d2}$)-($L_{c3}$)-($Ab_{d3}$)-Y (formula VI).

In some embodiments the binding agent comprises at least one polypeptide chain having formula VII: X-($Ab_{a1}$)-($L_{b3}$)-($Ab_{a2}$)-($L_{b2}$)-($Ab_{a3}$)-($L_{b1}$)-(DD)-($L_{c1}$)-($Ab_{d1}$)-($L_{c2}$)-($Ab_{d2}$)-Y (formula VII).

In some embodiments the binding agent comprises at least one polypeptide chain having formula VIII: X-($Ab_{a1}$)-($L_{b3}$)-($Ab_{a2}$)-($L_{b2}$)-($Ab_{a3}$)-($L_{b1}$)-(DD)-($L_{c1}$)-($Ab_{d1}$)-($L_{c2}$)-($Ab_{d2}$)-($L_{c3}$)-($Ab_{d3}$)-Y (formula VIII).

In some embodiments, the binding agent comprises one or more polypeptide chains each independently comprising in a N- to C-terminal fashion an amino acid sequence of formula III X-($Ab_{a1}$)-($L_{b1}$)-(DD)-($L_{c1}$)-($Ab_{d1}$)-($L_{c2}$)-($Ab_{d2}$)-Y (formula III);

wherein one of $Ab_{a1}$, $Ab_{d1}$ or $Ab_{d2}$ represents the antigen binding domain 1 (ABD1). In some embodiments, the binding agent comprises one or more polypeptide chains each independently comprising in N- to C-terminal fashion an amino acid sequence of formula III X-($Ab_{a1}$)-($L_{b1}$)-(DD)-($L_{c1}$)-($Ab_{d1}$)-($L_{c2}$)-($Ab_{d2}$)-Y (formula III);

wherein one of $Ab_{a1}$, Abdi or $Ab_{d2}$ represents the antigen binding domain 2 (ABD2).

In some embodiments, the binding agent comprises one or more polypeptide chains each independently comprising in a N- to C-terminal fashion an amino acid sequence of formula III X-($Ab_{a1}$)-($L_{b1}$)-(DD)-($L_{c1}$)-($Ab_{d1}$)-($L_{c2}$)-($Ab_{d2}$)-Y (formula III);

wherein one of $Ab_{a1}$, Abdi or $Ab_{d2}$ represents the antigen binding domain 3 (ABD3).

In some embodiments, the binding agent comprises one or more polypeptide chains each independently comprising in a N- to C-terminal fashion an amino acid sequence of formula III X-($Ab_{a1}$)-($L_{b1}$)-(DD)-($L_{c1}$)-($Ab_{d1}$)-($L_{c2}$)-($Ab_{d2}$)-Y (formula III);

wherein one of $Ab_{a1}$, Abdi or $Ab_{d2}$ represents the antigen binding domain 1 (ABD1), one of $Ab_{a1}$, Abdi or $Ab_{d2}$ represents the antigen binding domain 2 (ABD2) and one of $Ab_{a1}$, Abdi or $Ab_{d2}$ represents the antigen binding domain 3 (ABD3).

In some embodiments, the binding agent comprises one or more polypeptide chains each independently comprising in a N- to C-terminal fashion an amino acid sequence of formula III X-($Ab_{a1}$)-($L_{b1}$)-(DD)-($L_{c1}$)-($Ab_{d1}$)-($L_{c2}$)-($Ab_{d2}$)-Y (formula III);

wherein $Ab_{a1}$ represents the antigen binding domain 1 (ABD1), Abdi represents the antigen binding domain 2 (ABD2) and $Ab_{d2}$ represents the antigen binding domain 3 (ABD3).

In some embodiments, the binding agent comprises one or more polypeptide chains each independently comprising in a N- to C-terminal fashion an amino acid sequence of formula III, wherein $Ab_{a1}$ is an antigen binding domain that binds to DR2, Abdi is an antigen binding domain that binds to PD-1 and $Ab_{d2}$ is an antigen binding domain that binds to CD47.

In some embodiments, the binding agent comprises one or more polypeptide chains each independently comprising in a N- to C-terminal fashion an amino acid sequence of formula III, wherein $Ab_{a1}$ is an antigen binding domain that binds to DR2, Abdi is an antigen binding domain that binds to CD47 and $Ab_{d2}$ is an antigen binding domain that binds to PD-1.

In some embodiments, the binding agent comprises one or more polypeptide chains each independently comprising in a N- to C-terminal fashion an amino acid sequence of formula IIIa:

X-(ABD1)-($L_{b1}$)-(DD)-($L_{c1}$)-(ABD2)-($L_{c2}$)-(ABD3)-Y (formula IIIa).

In some embodiments, the binding agent comprises one or more polypeptide chains each independently comprising in a N- to C-terminal fashion an amino acid sequence of formula IIIb:

X-(ABD1)-($L_{b1}$)-(DD)-($L_{c1}$)-(ABD3)-($L_{c2}$)-(ABD2)-Y (formula IIIb).

In some embodiments, the binding agent comprises two identical polypeptide chains.

In some embodiments, both polypeptide chains of the binding agent may have the configuration set forth in formula II (with same or different amino acid sequence).

In some embodiments, both polypeptide chains of the binding agent may have the configuration set forth in formula III (with same or different amino acid sequence).

In some embodiments, both polypeptide chains of the binding agent may have the configuration set forth in formula IIIa (with same or different amino acid sequence).

In some embodiments, both polypeptide chains of the binding agent may have the configuration set forth in formula IIIb (with same or different amino acid sequence).

In some embodiments, one polypeptide chain may have the configuration set forth in formula IIIa one polypeptide chain may have the configuration set forth in formula IIIb (with antigen binding domains having same or different amino acid sequence).

In some embodiments, one of the polypeptide chains may have the configuration set forth in formula II, while the other may have the configuration set forth in formula III.

In some embodiments, one of the polypeptide chains may have the configuration set forth in formula II, while the other has the configuration set forth in formula IV.

In some embodiments, one of the polypeptide chains may have the configuration set forth in formula III, while the other has the configuration set forth in formula IV.

In some embodiments, one of the polypeptide chains may have the configuration set forth in formula IV, while the other has the configuration set forth in formula IV.

In some embodiments, the binding agents of the present disclosure is monospecific or multispecific.

Monospecific binding agents encompass binding agents that are specific for a single epitope of a given antigen.

An exemplary embodiment of a monospecific binding agent includes a binding agent that comprise one antigen binding domain. Another exemplary embodiment of a monospecific binding agent includes a binding agent that comprise more than one antigen binding domains, but the antigen binding domains have identical CDRs and framework regions. Yet another exemplary embodiment of a binding agent chain includes a binding agent that comprise more than one antigen binding domains, but the antigen binding domains have identical CDRs and different framework regions. A further exemplary embodiment of a monospecific binding agent includes a binding agent that comprise antigen binding domains that differ in the amino acid sequence of one or more of their CDRs (e.g., conservative substitution in one or more CDRs) without affecting their ability to bind to the same antigen or epitope.

Multispecific binding agents encompass binding agents that are specific for more than one epitope (of the same antigen or different antigens) or to more than one antigen. For example, a multispecific polypeptide chain or binding agent may thus have more than one antigen binding domains, at least two of which bind to different antigens or epitopes.

The binding agents of the present disclosure may thus be bispecific, trispecific, tetraspecific, pentaspecific, hexaspecific etc. In some embodiments, each antigen binding domain may be specific for a given antigen. In some embodiments, two or more antigen binding domains of a given binding agent may be specific for the same or different antigens. In some embodiments, three or more antigen binding domains of a given binding agent may be specific for the same or different antigens. In some embodiments, four or more antigen binding domains of a given binding agent may be specific for the same or different antigens. In some embodiments, five or more antigen binding domains of a given binding agent may be specific for the same or different antigens. In some embodiments, six or more antigen binding domains of a given binding agent may be specific for the same or different antigens. The specificity may depend on the number of antigen binding domains present in a given binding agent.

Exemplary non-limiting embodiments of multispecific binding agent include those composed of multispecific polypeptide chains. Other exemplary non-limiting embodiments of multispecific binding agent include those having two antigen binding domains of different specificities. Yet other exemplary non-limiting embodiments of multispecific binding agent include those having more than two antigen binding domains that bind to two different antigens, proteins or to two different epitopes on the same antigens or proteins.

In some embodiments, the binding agents of the present disclosure is monovalent or multivalent.

Exemplary non-limiting embodiments of multivalent binding agents include binding agents composed of multivalent polypeptide chains. Other non-limiting exemplary embodiments of multivalent binding agent include binding agents composed of more than one monovalent polypeptide chain.

In accordance with the present disclosure, a bispecific binding agent may be bivalent or multivalent depending on the number of antigen binding domains that it contains. Exemplary non-limiting embodiments of bispecific binding agent include those comprising two identical bispecific polypeptide chains that form a dimer.

Exemplary Embodiments of Monospecific Binding Agents

As indicated herein the binding agent of the present disclosure may be monospecific.

Exemplary and non-limiting exemplary embodiments of monospecific binding agents include are provided herein.

For example, the binding agent may comprise only one antigen binding domain.

Alternatively, the binding agent may comprise more than one identical antigen binding domains.

Exemplary embodiments of monospecific binding agents include the antigen binding domains disclosed herein including ABD1, ABD2, ABD3 or heavy chains disclosed herein.

In exemplary embodiments, the monospecific binding agents may comprise the antigen binding domains disclosed herein and a dimerization domain.

Exemplary embodiments of dimerization domains are provided throughout the specification and include without limitation a CH3 domain (including natural CH3 domain and natural human CH3 domain, mutated CH3 domain) may also include a CH2 domain (natural CH2 domain or mutated CH2 domain).

In some embodiments the dimerization domain is a Fc region of an antibody or a portion thereof.

In some embodiments the dimerization domain may also comprise a hinge region of an antibody or a portion thereof.

In some embodiments the hinge region or portion thereof is a human hinge region or a portion thereof.

In some embodiments, the binding agent may comprise ABD1 and a dimerization domain.

In some embodiments, the binding agent may comprise ABD2 and a dimerization domain.

In some embodiments, the binding agent may comprise ABD3 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:7 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:14 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:21 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:28 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:35 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:42 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:49 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:56 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:63 and a dimerization domain.

In some exemplary embodiments, the binding agent of the present disclosure may comprise a heavy chain having an amino acid sequence at least 75%, 80% 85%, 90%, 95% identical to the amino acid sequence set forth in SEQ ID NO:70 and a dimerization domain.

In some exemplary embodiments, the binding agent of the present disclosure may comprise an amino acid sequence at least 75%, 80% 85%, 90%, 95% identical to the amino acid sequence set forth in SEQ ID NO:71.

In some exemplary embodiments, the binding agent of the present disclosure may comprise an amino acid sequence at least 75%, 80% 85%, 90%, 95% identical to the amino acid sequence set forth in SEQ ID NO:72.

In some exemplary embodiments, the binding agent of the present disclosure may comprise an amino acid sequence at least 75%, 80% 85%, 90%, 95% identical to the amino acid sequence set forth in SEQ ID NO:73.

In some exemplary embodiments, the binding agent of the present disclosure may comprise an amino acid sequence at least 75%, 80% 85%, 90%, 95% identical to the amino acid sequence set forth in SEQ ID NO:74.

In some exemplary embodiments, the binding agent of the present disclosure may comprise an amino acid sequence at least 75%, 80% 85%, 90%, 95% identical to the amino acid sequence set forth in SEQ ID NO:75.

Other exemplary embodiments of monospecific binding agents are provided herein.

Exemplary Embodiments of Multispecific Binding Agents

As indicated herein the binding agent of the present disclosure may be multispecific.

Exemplary and non-limiting exemplary embodiments of multispecific binding agents include are provided herein.

For example, in some embodiment, the binding agent may comprise more than one antigen binding domains, wherein at least one of the antigen binding domains is an antigen binding domain 1 (ABD1) as set forth herein and at least one of the antigen binding domains is an antigen binding domain that is capable of binding to an immune checkpoint protein.

In other embodiments, the binding agent may comprise more than one antigen binding domains, wherein at least one of the antigen binding domains is an antigen binding domain 1 (ABD1) as set forth herein, at least one of the antigen binding domains is an antigen binding domain that is capable of binding to an immune checkpoint protein and at least one of the antigen binding domains is an antigen binding domain that is capable of binding to a protein expressed at the surface of immune cells.

In yet other embodiments, the binding agent may comprise more than one antigen binding domains, wherein at least one of the antigen binding domains is an antigen binding domain 1 (ABD1) as set forth herein, at least one of the antigen binding domains is an antigen binding domain that is capable of binding to an immune checkpoint protein and at least one of the antigen binding domains is an antigen binding domain that is capable of binding to a protein expressed at the surface of tumors cells.

In some embodiments, the binding agent comprises at least one antigen binding domain 1 (ABD1) and at least one antigen binding domain 2 (ABD2).

In some embodiments, the binding agent comprises at least one antigen binding domain 1 (ABD1) and at least one antigen binding domain 3 (ABD3).

In some embodiments, the binding agent comprises at least one antigen binding domain 2 (ABD2) and at least one antigen binding domain 3 (ABD3).

In some embodiments, the binding agent comprises at least one antigen binding domain 1 (ABD1), at least one antigen binding domain 2 (ABD2) and at least one antigen binding domain 3 (ABD3).

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:7, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:14, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:21, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:28, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:35, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:42, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:49, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more antigen binding domains, wherein at least one of the antigen binding domains is an antigen binding domain 1 (ABD1) and comprises a heavy chain having an amino acid sequence as set forth in SEQ ID NO:56, at least one of the antigen binding domains is an antigen binding domain 2 (ABD2) and comprises a heavy chain having an amino acid sequence as set forth in SEQ ID NO:63 and at least one of the antigen binding domains is an antigen binding domain 3 (ABD3) and comprises a heavy chain having an amino acid sequence as set forth in SEQ ID NO:70.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:77. In some embodiments, the binding agent comprises one polypeptide chain that has the amino acid sequence set forth in SEQ ID NO:77. In other embodiments, the binding agent comprises two polypeptide chains, having an amino acid sequence at least 75%, 80% 85%, 90%, 95%, 99% or 100% identical to the amino acid sequence set forth in SEQ ID NO:77. In yet other embodiments, the binding agent comprises two polypeptide chains that have the amino acid sequence set forth in SEQ ID NO:77.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:78. In some embodiments, the binding agent comprises one polypeptide chain that has the amino acid sequence set forth in SEQ ID NO:78. In other embodiments, the binding agent comprises two polypeptide chains, having an amino acid sequence at least 75%, 80% 85%, 90%, 95%, 99% or 100% identical to the amino acid sequence set forth in SEQ ID NO:78. In yet other embodiments, the binding agent comprises two polypeptide chains that have the amino acid sequence set forth in SEQ ID NO:78.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:79. In some embodiments, the binding agent comprises one polypeptide chain that has the amino acid sequence set forth in SEQ ID NO:79. In other embodiments, the binding agent comprises two polypeptide chains, having an amino acid sequence at least 75%, 80% 85%, 90%, 95%, 99% or 100% identical to the amino acid sequence set forth in SEQ ID NO:79. In yet other embodiments, the binding agent comprises two polypeptide chains that have the amino acid sequence set forth in SEQ ID NO:79.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:80. In some embodiments, the binding agent comprises one polypeptide chain that has the amino acid sequence set forth in SEQ ID NO:80. In other embodiments, the binding agent comprises two polypeptide chains, having an amino acid sequence at least 75%, 80% 85%, 90%, 95%, 99% or 100% identical to the amino acid sequence set forth in SEQ ID NO:80. In yet other embodiments, the binding agent comprises two polypeptide chains that have the amino acid sequence set forth in SEQ ID NO:80.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:81. In some embodiments, the binding agent comprises one polypeptide chain that has the amino acid sequence set forth in SEQ ID NO:81. In other embodiments, the binding agent comprises two polypeptide chains, having an amino acid sequence at least 75%, 80% 85%, 90%, 95%, 99% or 100% identical to the amino acid sequence set forth in SEQ ID NO:81. In yet other embodiments, the binding agent comprises two polypeptide chains that have the amino acid sequence set forth in SEQ ID NO:81.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:82. In some embodiments, the binding agent comprises one polypeptide chain that has the amino acid sequence set forth in SEQ ID NO:82. In other embodiments, the binding agent comprises two polypeptide chains, having an amino acid sequence at least 75%, 80% 85%, 90%, 95%, 99% or 100% identical to the amino acid sequence set forth in SEQ ID NO:82. In yet other embodiments, the binding agent comprises two polypeptide chains that have the amino acid sequence set forth in SEQ ID NO:82.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:83. In some embodiments, the binding agent comprises one polypeptide chain that has the amino acid sequence set forth in SEQ ID NO:83. In other embodiments, the binding agent comprises two polypeptide chains, having an amino acid sequence at least 75%, 80% 85%, 90%, 95%, 99% or 100% identical to the amino acid sequence set forth in SEQ ID NO:83. In yet other embodiments, the binding agent comprises two polypeptide chains that have the amino acid sequence set forth in SEQ ID NO:83.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:85. In some embodiments, the binding agent comprises one polypeptide chain that has the amino acid sequence set forth in SEQ ID NO:85. In other embodiments, the binding agent comprises two polypeptide chains, having an amino acid sequence at least 75%, 80% 85%, 90%, 95%, 99% or 100% identical to the amino acid sequence set forth in SEQ ID NO:85. In yet other embodiments, the binding agent comprises two polypeptide chains that have the amino acid sequence set forth in SEQ ID NO:85.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:86. In some embodiments, the binding agent comprises one polypeptide chain that has the amino acid sequence set forth in SEQ ID NO:86. In other embodiments, the binding agent comprises two polypeptide chains, having an amino acid sequence at least 75%, 80% 85%, 90%, 95%, 99% or 100% identical to the amino acid sequence set forth in SEQ ID NO:86. In yet other embodiments, the binding agent comprises two polypeptide chains that have the amino acid sequence set forth in SEQ ID NO:86.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:87. In some embodiments, the binding agent comprises one polypeptide chain that has the amino acid sequence set forth in SEQ ID NO:87. In other embodiments, the binding agent comprises two polypeptide chains, having an amino acid sequence at least 75%, 80% 85%, 90%, 95%, 99% or 100% identical to the amino acid sequence set forth in SEQ ID NO:87. In yet other embodiments, the binding agent comprises two polypeptide chains that have the amino acid sequence set forth in SEQ ID NO:87.

In some embodiments, the binding agent comprises one or more polypeptide chains, wherein at least one of the polypeptide chains has an amino acid sequence at least 75%, 80% 85%, 90%, 95%, 99% or 100% identical to the amino acid sequence set forth in SEQ ID NO:88. In some embodiments, the binding agent comprises one polypeptide chain that has the amino acid sequence set forth in SEQ ID NO:88. In other embodiments, the binding agent comprises two polypeptide chains, having an amino acid sequence at least 75%, 80% 85%, 90%, 95%, 99% or 100% identical to the amino acid sequence set forth in SEQ ID NO:88. In yet other embodiments, the binding agent comprises two polypeptide chains that have the amino acid sequence set forth in SEQ ID NO:88.

Other exemplary embodiments of multispecific binding agents are provided herein including in Table 7.

In some embodiments, the binding agent of the present disclosure comprises an antigen binding domain that binds DR2, an antigen binding domain that binds PD1 and an antigen binding domain that binds to CD47. In some embodiments, the binding agent of the present disclosure may be capable of bringing T cells in proximity to DR2-expressing tumor cells, may be capable of restoring T cell function and/or may be capable of enhancing macrophage function via blocking of SIRPα/CD47 interaction. In some embodiments of the present disclosure, the binding agent may exert its anti-tumor activity via antibody-dependent cell-mediated cellular cytotoxicity (ADCC).

Variants

Variants of the sequences disclosed herein are also encompassed by the present disclosure.

Variants encompassed by the present disclosure include those which may comprise an insertion of one or more amino acid residues at one or more position, a deletion of one or more amino acid residues at one or more position or a substitution of one or more amino acid residues at one or more position (conservative or non-conservative substitutions).

For example, naturally occurring residues are divided into groups based on common side chain properties. Conservative substitutions may be made by exchanging an amino acid from one of the groups listed below (group 1 to 6) for another amino acid of the same group. Non-conservative substitutions will entail exchanging a member of one of these groups for another.

(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr), Asparagine (Asn), Glutamine (Gln),
(group 3) acidic: Aspartic acid (Asp), Glutamic acid (Glu)
(group 4) basic: Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Other exemplary embodiments of conservative substitutions are shown in Table 2 under the heading of "preferred substitutions". If such substitutions result in an undesired property, then more substantial changes, denominated "exemplary substitutions" in Table 2, or as further described below in reference to amino acid classes, may be introduced and the products screened.

One of skill in the art will recognize that certain amino acids are less positively charged, are neutral, are negatively charged or have a reduced charge in comparison to other amino acids. Amino acids can be categorized based on net charge as indicated by an amino acid's isoelectric point. The isoelectric point is the pH at which the average net charge of the amino acid molecule is zero. When pH>pI, an amino acid has a net negative charge, and when the pH<pI, an amino acid has a net positive charge. In some embodiments, the measured pI value for an antibody is between about 3 and 9 (e.g. 3.0, 3.5, 4.0, 4.5, 5.0, 5.5, 6.0, 6.5, 7.0, 7.5, 8.0, 8.1, 8.2, 8.3, 8.4, 8.5, and 9) and any values in between. In some embodiments, the measured pI value for an antibody is between about 4 and 7 (e.g. 4.0, 4.5, 5.0, 5.5, 6.0, 6.5, 7.0), and any values in between. Exemplary isoelectric points of amino acids are shown in Table 2 below. Generally amino acids with positive electrically charged side chains include, for example, Arginine (R), Histidine (H), and Lysine (K). Amino acids with negative electrically charged side chains include, for example, Aspartic Acid (D) and Glutamic Acid (E). Amino acids with polar properties include, for example, Serine (S), Threonine (T), Asparagine (N), Glutamine (Q), and Cysteine (C), Tyrosine (Y) and Tryptophan (W). Non-polar amino acids include, for example, Alanine (A), Valine (V), Isoleucine (I), Leucine (L), Methionine (M), Phenylalanine (F), Glycine (G) and Proline (P).

In some embodiments, the isoelectric point of an antibody is modified via amino acid substitution. See, e.g. US20110076275. In some embodiments, modifying the isoelectric point of a polypeptide comprising an antibody results in a change in the antibody's half-life.

TABLE 2

Exemplary amino acid substitutions

| Original residue | Exemplary substitution | Conservative substitution | pI (isoelectric point) |
|---|---|---|---|
| Ala (A) | Val, Leu, Ile | Val | 6.0 |
| Arg (R) | Lys, Gln, Asn | Lys | 10.76 |
| Asn (N) | Gln, His, Lys, Arg, Asp | Gln | 5.41 |
| Asp (D) | Glu, Asn | Glu | 2.77 |
| Cys (C) | Ser, Ala | Ser | 5.07 |
| Gln (Q) | Asn; Glu | Asn | 5.65 |
| Glu (E) | Asp, Gln | Asp | 3.22 |
| Gly (G) | Ala | Ala | 5.97 |
| His (H) | Asn, Gln, Lys, Arg, | Arg | 7.59 |
| Ile (I) | Leu, Val, Met, Ala, Phe, norleucine | Leu | 6.02 |
| Leu (L) | Norleucine, Ile, Val, Met, Ala, Phe | Ile | 5.98 |
| Lys (K) | Arg, Gln, Asn | Arg | 9.74 |
| Met (M) | Leu, Phe, Ile | Leu | 5.74 |
| Phe (F) | Leu, Val, Ile, Ala, Tyr | Tyr | 5.48 |
| Pro (P) | Ala | Ala | 6.30 |
| Ser (S) | Thr | Thr | 5.58 |
| Thr (T) | Ser | Ser | 5.60 |
| Trp (W) | Tyr, Phe | Tyr | 5.89 |
| Tyr (Y) | Trp, Phe, Thr, Ser | Phe | 5.66 |
| Val (V) | Ile, Leu, Met, Phe, Ala, norleucine | Leu | 5.96 |

Generally, the degree of similarity and identity between variable chains is determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position.

Percent similarity will be indicative of amino acids which are identical and those which are replaced with conservative amino acid substitution in comparison with the original peptide at the same or similar position.

Variants of the present disclosure may therefore comprise a sequence that is at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% identical with that of an original or reference sequence or a portion of an original sequence.

In some embodiments, polypeptide chains having an amino acid sequence which is at least 75%, 80% 85%, 90%, 95%, 99% identical or less than 100% identical to a given amino acid sequence, may have amino acid substitutions, additions or deletions that are generally located outside of the complementarity determining regions.

In some embodiments, a variant may have at least 80% sequence identity with a sequence disclosed herein. In other embodiments, a variant may have at least 85% sequence identity with a sequence disclosed herein. In yet embodiments, a variant may have at least 90% sequence identity with a sequence disclosed herein. In further embodiments, a variant may have at least 95% sequence identity with a sequence disclosed herein. In other embodiments, a variant may have at least 99% sequence identity with a sequence disclosed herein.

Exemplary embodiments of variants include polypeptide chains or binding agents that comprise a hinge, Fc, CH3, CH2/CH3 region that is derived from a natural antibody but that comprise one, two, three, four, five, six, seven, eight, nine, ten or more amino acid difference (including amino acid substitutions, insertions or deletions).

In some embodiments, the polypeptide chain of the present disclosure may thus comprise a mutated hinge region that is at least 80% identical, at least 85% identical, at least 90% identical, at least 95% identical, at least 99% identical to a hinge region of a natural antibody.

In some embodiments, the polypeptide chain of the present disclosure may thus comprise a mutated Fc portion that is at least 80% identical to a Fc of a natural antibody.

In some embodiments, the polypeptide chain of the present disclosure may thus comprise a mutated CH2 domain that is at least 80% identical, at least 85% identical, at least 90% identical, at least 95% identical, at least 99% identical to the CH2 domain of a natural antibody.

In some embodiments, the polypeptide chain of the present disclosure may thus comprise a mutated CH3 domain that is at least 80% identical, at least 85% identical, at least 90% identical, at least 95% identical, at least 99% identical to the CH3 domain of a natural antibody.

In some embodiments, the polypeptide chain of the present disclosure may thus comprise a mutated CH2/CH3 domain that is at least 80% identical, at least 85% identical, at least 90% identical, at least 95% identical, at least 99% identical to the CH2/CH3 domain of a natural antibody.

Nucleic Acids, Vectors, Kits, Cells and Method of Making Polypeptides Chains

Nucleic acid molecules of the present disclosure may be single-stranded or double-stranded. The nucleic acid molecules disclosed herein may comprises deoxyribonucleotides, ribonucleotides, modified deoxyribonucleotides or modified ribonucleotides. The nucleic acid molecules of the present disclosure may comprise for example DNA.

DNA segments and vectors encoding one or more modules or entire polypeptide chains are particularly provided.

The DNA segments and/or vectors may be provided in separate vials and sold as a kit.

Particularly contemplated are sets of DNA segments that comprise sequence allowing directional assembly of the modules and cloning vectors that incorporate the DNA segments or entire polypeptide chains.

The DNA segments and vectors may be provided as part of a kit for assembling DNA constructs capable of expressing the polypeptide chains or binding agents disclosed herein.

The kit may at least comprise one or more DNA segment or vectors that allow a user to generate a polypeptide chain comprising the mutated dimerization domain having amino acid substitutions at position 356, 357, 370, 399 and/or 439 (in accordance with EU numbering system) as disclosed herein.

Due to the inherent degeneracy of the genetic code, DNA sequences that encode the same, substantially the same or a functionally equivalent amino acid sequence may be produced and used. The nucleotide sequences of the present disclosure may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth. Codon-optimized nucleic acids encoding the polypeptide chains described herein are encompassed by the present disclosure.

The polypeptide chains and binding agents disclosed herein may be made by a variety of methods familiar to those skilled in the art, including by recombinant DNA methods or by in vitro transcription/translation.

Generally, the polypeptide chains described herein are expressed from nucleic acid sequences inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions.

A variety of expression vector/host cell systems known to those of skill in the art may be used to express the polypeptide chains described herein. In the event, that the binding agent is composed of distinct polypeptide chains, each of such polypeptide chain may be provided by separate expression vectors or by a unique expression vector. In accordance with the present disclosure, the two chains of a binding agent may be encoded by a single vector or by separate vectors (vector set).

Polypeptides are often expressed in mammalian cells. For long-term production of recombinant proteins, a stable expression system may be used in which the DNA segment is incorporated into the host cell genome or maintained in an episomal form by the use of selectable markers. A host cell type may be chosen for its ability to modulate expression of the inserted sequences or to process the expressed polypeptide in the desired fashion. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Other types of expression system can be used. These include, for example, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems.

The present disclosure therefore relates to isolated cells transformed or transfected with a vector, nucleic acid, sets of vectors or sets of nucleic acids encoding at least one of the polypeptide chains described herein. The present disclosure therefore also relates to isolated cells capable or expressing the polypeptide chains or binding agents disclosed herein.

The present disclosure also relates to a method of making binding agents. The method may comprise providing a cell (e.g., a mammalian cell) with a vector or sets of vectors encoding one or more of the polypeptide chains disclosed herein and allowing expression.

The method may also comprises purifying the binding agent from cells or cell debris.

In some embodiments, the method of manufacture allows to reach a purity level of at least 80%, of at least 85%, at least 90%, at least 99% (of dimers).

In some embodiments, the purity level of the binding agent is between 80.0% to 99.9%.

In some embodiments, the purity level of the binding agent is between 95.0% to 99.9%.

In some embodiments, the purity level of the binding agent is at least 90.0+/−5.0%.

In some embodiments, the purity level of the binding agent is at least 95.0+/−5.0%.

In some embodiments, the purity level of the binding agent equal to or higher than 95%.

In some embodiments, the purity level of the binding agent is 97.0+/−1.0%.

In some embodiments, the purity level of the binding agent equal to or higher than 97%.

In some embodiments, the purity level of the binding agent is 99.0+/−1.0%.

In some embodiments, the purity level of the binding agent equal to or higher than 99%.

In some embodiments, the titer of the binding agents produced by cells may be 0.1 g/L or more. In some instances, the titer of the binding agents produced by cells may be 0.5 g/L or more.

In some instances, the titer of the binding agent produced by cells may be 1 g/L or more. In some instances, the titer of the binding agent produced by cells may be 2 g/L or more. In some instances, the titer of the binding agent produced by cells may be 3 g/L or more. In some instances, the titer of the binding agent produced by cells may be 4 g/L or more. In some instances, the titer of the binding agent produced by cells may be 5 g/L or more. In some instances, the titer of the binding agent produced by cells may be 6 g/L or more. Usually, homodimers are made by transfection of cells with a vector comprising a nucleic acid sequence encoding one of the polypeptide chains disclosed herein. The collected supernatant may contain homodimers or a mixture of monomers and/or homodimers.

Generally, heterodimers are made by co-transfection of cells with at least two types of vectors (a vector set) each comprising a nucleic acid sequence encoding two distinct polypeptide chains. The proper ratio of Chain A over Chain B is generally dependent on the level of protein expression obtained from each individual plasmid and may vary for example from about 1:10 to about 10:1. A DNA ratio of approximately 1:1 is particularly preferred for some of the constructs disclosed herein.

Heterodimers can also be made by transfecting cells with a single vector encoding both polypeptide chains. The collected supernatant may contain heterodimers or a mixture of monomers, heterodimers and/or homodimers.

The method of making polypeptide chains of the present disclosure may further comprise a step of separating or isolating monomers, homodimers and heterodimers from a mixture that comprises. Homodimers or heterodimers may be purified and isolated, for example, by size exclusion chromatography or with the help of tags or by other methods known to a person of skill in the art.

The method may also comprise a step of isolating and/or purifying the binding agent from impurities.

The method of the present disclosure will therefore result in compositions comprising homodimers, heterodimers or a mixture of monomers heterodimers and/or homodimers.

In some exemplary embodiments, the composition may mainly comprise homodimers. In an exemplary embodiment, the composition may comprise a proportion of at least about 80%, at least 85%, at least 90%, at least 99% or 100% of homodimers.

In other exemplary embodiments, the composition may mainly comprise heterodimers. In an exemplary embodiment, the composition may comprise a proportion of at least about 80%, at least 85%, at least 90%, at least 99% or 100% of heterodimers.

Conjugates

The polypeptide chain or binding agent of the present disclosure may be conjugated, for example, with a therapeutic moiety (for therapeutic purposes) or with a detectable moiety (i.e., for detection or diagnostic purposes) or to a protein allowing an extended half-life or is attached to nanoparticle. In some instances, therapeutic or detectable moieties may be linked to at least one amino acid residues of the polypeptide chain.

In an exemplary embodiment, the polypeptide chain or binding agent of the present disclosure is conjugated with a therapeutic moiety such as for example and without limitation, a chemotherapeutic, a cytokine, a cytotoxic agent, an anti-cancer drug (e.g., small molecule), and the like.

Therapeutic moiety may include, for example and without limitation, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)), 5-fluorouracil, adriamycin, irinotecan, taxanes, pseudomonas endotoxin, ricin, auristatins (e.g., monomethyl auristatin E, monomethyl auristatin F), maytansinoids (e.g., mertansine) and other toxins.

In another exemplary embodiment, the polypeptide chain or binding agent of the present disclosure is conjugated with a detectable moiety including for example and without limitation, a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to the polypeptide chain or binding agent using methods well known in the art. A wide variety of detectable moieties may be used, with the choice depending on the sensitivity required, ease of conjugation, stability requirements and available instrumentation. A suitable detectable moiety includes, but is not limited to, a fluorescent label, a radioactive label (for example, without limitation, $^{125}$, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

Pharmaceutical Compositions

Pharmaceutical compositions comprising the polypeptide chains or binding agents of the present disclosure are also encompassed by the present disclosure. The pharmaceutical composition may also comprise a pharmaceutically acceptable carrier.

In some embodiments, the pharmaceutical composition comprises conjugated polypeptide chains or conjugated binding agent as disclosed herein. In some embodiments, the pharmaceutical composition comprises polypeptide chains or binding agents conjugated with a therapeutic moiety. In some embodiments, the pharmaceutical composition comprises polypeptide chains or binding agent is conjugated with a detectable label.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also encompassed by the disclosure are particulate compositions coated with polymers (e.g., poloxamers or poloxamines). Other embodiments of the compositions of the disclosure incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the pharmaceutical compositions described above may be applied to any subject in need of therapy, including, but not limited to, mammals such as dogs, cats, cows, horses, rabbits, monkeys, and especially humans.

The pharmaceutical compositions described herein may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In some embodiments, the pharmaceutical composition is made of binding agents that have a purity level of between 80.0% to 99.9%. Accordingly, in some embodiments the pharmaceutical composition comprises binding agents that are substantially free of impurities. For example, pharmaceutical composition comprises binding agents that are at least 90.0+/−5.0% pure. In other examples, the pharmaceutical composition comprises binding agents that are at least 95.0+/−5.0% pure. In other embodiments the pharmaceutical composition comprises binding agent that are at least 99.0+/−1.0% pure.

In some embodiments, the pharmaceutical composition comprises binding agents that are stable in solution under one or more stress conditions as described herein.

Method of Use

The polypeptide chains and binding agents of the present disclosure may be used for treatment of disorders or diseases.

In some embodiments, the polypeptide chains and binding agents may be used to target therapeutics and/or diagnostics to a target cell, circulating protein or tissue.

In some embodiments, the polypeptide chains and binding agents may be conjugated with a therapeutic moiety and used for therapeutic methods.

In some embodiments, the polypeptide chains and binding agents may be conjugated with a detectable moiety and used for detection or diagnostic methods.

In some embodiments, the polypeptide chains and binding agents of the present disclosure may be used for targeting tumors in vivo.

In some embodiments, the polypeptide chains and binding agents are used for promoting tumor regression and/or reducing tumor volume in vivo.

The polypeptide chains and binding agents of the present disclosure may thus be used for cancer treatment.

The method of the present disclosure may comprise a step of administering the polypeptide chains, binding agents or mixture disclosed herein or a pharmaceutical composition comprising the polypeptide chains, binding agents or mixture to an individual in need.

In some embodiments, the polypeptide chains and binding agents are administered in combination with a chemotherapeutic.

In accordance with the present disclosure, the individual in need may be a human. Further in accordance with the present disclosure, the individual in need may be an animal.

In some embodiment, treatment of disorders or diseases that are caused or associated with expression of a neo-antigen are particularly contemplated.

In some embodiment, treatment of disorders or diseases that are caused or associated with expression over expression of an antigen are particularly contemplated.

In some embodiments, the disorder or disease may be cancer.

In other embodiments, the disorder or disease may be an infection.

In other embodiments, the disorder or disease may be an immune dysregulation.

In other embodiments, the disorder or disease may be a metabolic dysregulation.

In some embodiment, the binding agent is administered intravenously.

In some embodiment, the binding agent is administered by infusion.

The polypeptide chains and binding agents of the present disclosure may be used for detection purposes.

Detection of a particular target may be performed in vitro by contacting a sample, containing or suspected of containing the target with a polypeptide chain or binding agent comprising an antigen binding domain for such target and quantifying a signal associated with positive or negative binding using a detection apparatus.

The sample may originate from a mammal (e.g., a human). The sample may be a tissue sample obtained from the mammal or a cell culture supernatant.

In some embodiments, the sample may be a serum sample, a plasma sample, a blood sample, semen or ascitic fluid obtained from the mammal.

Detection of a particular target may be performed in vivo by administering a polypeptide chain or binding agent comprising an antigen binding domain for such target to an individual and quantifying a signal associated with positive or negative binding using a detection apparatus.

Upon detecting the presence of the target in the sample or in the individual, a drug (e.g., antibody, small molecule, a polypeptide chain or binding agent disclosed herein) may be administered to the individual.

In addition to the embodiments described and provided in this disclosure, the following non-limiting embodiments are particularly contemplated.

Table 3, Table 4, Table 5 and Table 6 illustrate VHHs having biological activity on their own (e.g., as fusion with dimerization domain) and as part of the multimeric, multivalent and/or multispecific binding agents as exemplified in Table 7.

EXAMPLES

Example 1—Animal Immunization and Immune Library Construction

Single domain antibodies were generated by immunizing alpacas (*Vicugna pacos*) or llamas (*Llama glama*) with human antigens, cDNA plasmid encoding the human antigens and/or cells overexpressing the human antigens.

For example, anti-DR2 single domain antibodies were generated by immunizing alpacas (*Vicugna pacos*) with DR2 antigens including the human DR2 protein, human DR2 cDNA plasmid, and human DR2 overexpressing cell line; SH-SY5Y-D2 cells. Anti-PD-1 single domain antibodies were generated by immunizing alpacas (*Vicugna pacos*) with PD-1 antigens including the human PD-1 protein, human PD-1 cDNA plasmid and a human PD-1 overexpressing cell line; CHO-PD1 cells. In the case of anti-CD47, single domain antibodies were generated by immunizing llamas (*Llama glama*) with CD47 antigens including the human CD47 protein, human CD47 cDNA, and human PBMCs (activated).

Sequences of single-domain antibodies were uncovered from clone picking after phage display panning of reconstituted immune libraries against the antigens.

DNA fragments encoding VHHs were generally subcloned into constructs for expression of polypeptide chains (e.g., see Table 6 or Table 7) and in vitro and in vivo testing.

Controls were also generated by substitution of one or more VHH with HEWL-specific VHH.

Example 2—Transfection, Expression, and Purification of Binding Agents

Transfection and Expression of Polypeptide Chains in ExpiCHO or in Expi293 Cells Protein dimers (e.g., homodimers or heterodimers) were expressed in 2.5 mL or 400 mL culture volume from the DNA construct using the ExpiCHO™ Expression System (Thermo Fisher, Cat. No. A29133) or the Expi293™ Expression System (Thermo Fisher, Cat. No. A14635).

Briefly, freshly thawed CHO cells were allowed to recover in culture for two or more passages before transfection. Cells were then passaged every 3-4 days until they reach $4\times10^6$-$6\times10^6$ cells/mL at which time they were diluted to $2\times10^5$-$3\times10^5$ cells/mL in ExpiCHO™ Expression Medium pre-warmed to 37° C. The day prior to transfection, cells were diluted to $3\times10^6$-$4\times10^6$ cells/mL, and on the day of transfection, cells were further diluted to $6.\times10^6$ cells/mL. 1 μg of DNA/mL of culture volume was diluted with cold OptiPRO™ medium (100 μL for 2.5 mL of culture volume; 16 mL for 400 mL of culture volume). ExpiFectamine™ CHO Reagent (8 μL for 2.5 mL of culture volume; 1280 μL for 400 mL of culture volume) was added to the medium containing DNA and incubated with ExpiFectamine™/DNA complexes at room temperature for 1-5 minutes. Then the DNA complex was transferred to culture (at $6\times10^6$ cells/mL) while swirling. The cells were incubated at 37° C. under 8% $CO_2$ and 80% humidity with shaking (INFORS HT shaker, 125 rpm). 18-22 h after onset of transfection, ExpiCHO™ feed (0.6 mL for 2.5 mL of culture volume; 96 mL for 400 mL of culture volume) and ExpiCHO™ enhancer (15 μL for 2.5 mL of culture volume; 2.4 mL for 400 mL of culture volume) were added to the cells. The cells were returned to INFORS HT incubator set at 37° C. under 8% $CO_2$ and 80% humidity with shaking at 125 rpm (25 mm orbit). 8 days post-transfection, supernatants were clarified by centrifugation at 4000×g for 30 minutes. Supernatants were filter-sterilized using a Nalgene™ Rapid-Flow™ Sterile Disposable Filter Units 1000 mL filter unit (Thermo Scientific, Cat. No. 567-0020) and were stored at 4° C. or frozen for later analysis.

Freshly thawed HEK293 cells were allowed to recover in culture for two or more passages before transfection. Cells were then passaged every 3-4 days until they reach $3\times10^6$-$5\times10^6$ cells/mL at which time they were diluted to $3\times10^5$-$5\times10^5$ cells/mL in Expi293™ Expression Medium pre-warmed to 37° C. The day prior to transfection, cells were diluted to $2.5\times10^6$-$3\times10^6$ and on the day of transfection, cells were further diluted to $3\times10^6$ viable cells/mL. 1 μg of DNA/mL of culture volume was diluted with Opti-MEM™ I Reduced Serum medium to get a final volume of 150 μL for 2.5 mL of culture volume and 24 mL for 400 mL of culture volume. ExpiFectamine™ 293 Reagent (8 μL for 2.5 mL of culture volume; 1.3 mL for 400 mL of culture volume) was added to medium Opti-MEM™ I reduced serum medium (140 μL for 2.5 mL of culture volume; 22.5 mL for 400 mL of culture volume) to incubate at room temperature for 5 minutes. Diluted ExpiFectamine™ was added to diluted DNA and incubate for 15 minutes at room temperature. ExpiFectamine™/DNA solution was transferred to culture drop by drop (at $3\times10^6$ cells/mL) while swirling. The cells were incubated at 37° C. under 8% $CO_2$ and 80% humidity with overnight shaking (INFORS HT shaker, 125 rpm). 18-22 h after onset of transfection, ExpiFectamine™

293 Transfection Enhancer 1 (15 μL for 2.5 mL of culture volume; 2.4 mL for 400 mL of culture volume) and Expi-Fectamine™ 293 Transfection Enhancer 2 (50 μL for 2.5 mL of culture volume; 24 mL for 400 mL of culture volume) were added to the cells. The cells were returned to INFORS HT incubator set at 37° C. under 8% $CO_2$ and 80% humidity with shaking at 125 rpm (25 mm orbit). 5 days post-transfection, supernatants were clarified by centrifugation at 4000×g for 30 minutes. Supernatants were filter-sterilized using a Nalgene™ Rapid-Flow™ Sterile Disposable Filter Units 1000 mL filter unit (Thermo Scientific, Cat. No. 567-0020) and were stored at 4° C. or frozen for later analysis.

Purification

Proteins are purified using 3-mL MabSelect™ SuRe™ resin (GE Healthcare, Cat. No. 17-5438-02) with gravity columns or 40-mL MabSelect™ SuRe™ resin with AKTA PURE (GE Healthcare, Piscataway, NJ) depending on the supernatant volume. Resin was incubated with 0.5 M NaOH overnight and equilibrated with Tris-base buffer pH 7.4 (50 mM Tris-HCl, 150 mM NaCl, pH 7.4) prior to injection. Supernatant was applied on gravity columns or the at 5 mL/min on 40-mL column. Resin column was washed with 3 CV (column volume) with Tris-base buffer pH 7.4 at a flow rate of 10 mL/min. Protein was eluted with 3 CV of 0.1 M citrate acid pH 3 at 10 mL/min. Fractions identified with protein from the visual output of the chromatogram (absorbance at 280 nm) were pooled together. Pooled fractions were neutralized with 1 M Tris-HCl pH 9.0 to achieve the pH~5-6 before transferring into phosphate-buffered saline (PBS) pH 6.0 buffer prepared from PBS 10×pH 7.2 (15 mM Potassium Phosphate monobasic, 1552 mM Sodium Chloride, 27 mM Sodium Phosphate dibasic, ThermoFisher, Cat. No. 70013073).

Buffer exchange was carried out by sample concentrators for proteins purified from gravity columns or either by dialysis or by desalting column for proteins purified from AKTA PURE. Proteins purified from gravity columns were concentrated with sample concentrator VivaSpin 2, 50 kDa MWCO (GE Healthcare, Cat. No. 28932257) by centrifugation at 3,500-4,000×g at 4° C. then, diluted with PBS pH 6 to achieve 4-fold and repeated until sample reached 200-fold. Dialysis was carried out in 4 L of PBS pH 6 overnight at 4° C. using 7 kDa molecular weight cut-off dialysis tubing (ThermoFisher, Cat. No. 68799). On the other hand, the desalting column was incubated with 0.5 M NaOH overnight and equilibrated with PBS pH 6. Volume of 15 mL of neutralized protein sample was loaded into the HiPrep 26/10 desalting column (GE Healthcare, Cat. No. 17-5087-02) at 0.5 mL/min then, protein was eluted with 2 CV of PBS pH 6. Loading and elution steps were repeated until no neutralized protein sample from elution of affinity column is left. Fractions identified with protein from the visual output of the chromatogram (absorbance at 280 nm) were pooled together.

Sample was filter-sterilized using a Nalgene™ Rapid-Flow™ sterile disposable filter units 150 mL filter unit (Thermo Scientific, Cat. No. 565-0010). The final protein sample was quantified by Pierce™ bicinchoninic acid protein assay kit (ThermoFisher, Cat. No. 23227) and tested for endotoxin level with Endosafe® LAL reagent cartridges (Charles River Cat. No. PTS2005). The final protein sample was analyzed on SDS-PAGE gels under reducing or non-reducing conditions.

Production of binding agents in CHO cells followed by conventional two-step purification with protein A affinity chromatography followed by size-exclusion chromatography (SEC) resulted in purities ranging from 95.5% to 99.5% (of dimers).

The purity of KC020 was found to be above 97% after size exclusion chromatography (SEC) and SDS caliper. The DNA sequence of the top three clones were verified; the charge profile and glycosylation profile of KC020 were found to be similar to that of monoclonal antibodies. The table below represents the titer KC020 after 14 days from three representative clones selected for the cell line development.

| Clone ID | Day 14 titer (g/L) | Purity >97% (by SEC) | Purity >97% (by SDS_Caliper_nR) |
|---|---|---|---|
| 22 | 5.13 | ✓ | ✓ |
| 6 | 6.45 | ✓ | ✓ |
| 21 | 6.59 | ✓ | ✓ |

SDS-PAGE and Western Blotting

Samples were prepared for SDS-PAGE analysis under reducing or non-reducing conditions with NuPAGE™ LDS sample buffer (ThermoFisher Cat. No NP0007) with NuPAGE™ sample reducing agent (ThermoFisher Cat. No. NP0004) or without reducing agent. Samples under reducing conditions were denatured by heating at 70° C. for 10 minutes. Samples (16 μL) were loaded onto 3-8% Tris-Acetate mini-gels (1.5 mm, 15 wells) alongside a BSA standard. Electrophoresis was conducted using a X-Cell SureLock™ mini-gel device at 125 volts for approximately 1 hour. Gels were stained using GelCode™ staining reagent (Thermo Fisher, Cat. No. 24594).

For western blots analysis, proteins were transferred to nitrocellulose membranes using the iBlot™ system (Thermo Fisher, Cat. No. 1B301031) according to the manufacturer's instructions.

Detection of the His tag was carried out with the Anti-Penta His-HRP antibody. Briefly, membranes were blocked by incubation in 20 mL in Qiagen blocking buffer (Qiagen, Cat. No. 1018862) for 1 hour at room temperature with shaking, followed by incubation in 20 mL in Starting Blocking™ T20 (PBS) Blocking (Thermo Fisher, Cat. No. 37528) for 1 hour at room temperature with shaking. Membranes were washed three times for 10 minutes with 1×TBS Tween™_20. Membranes were incubated with Anti-Penta His-HRP (Qiagen, Cat. No. 1014992) previously diluted 1:2000 in blocking buffer for 1 hour at room temperature with shaking. Membranes were washed three times for 10 minutes with 1×TBS Tween™-20. The signal was visualized using of Super Signal™ West Pico PLUS (Thermo Fisher, Cat. No. 34080) according to the manufacturer's instructions. Images were recorded using the Azure Biosystem imaging system.

The results of these experiments indicate that the binding agents (homodimers or heterodimers) of the present disclosure are efficiently expressed in cells, purified and that the format of the polypeptide chains disclosed herein allows to achieve yields of binding agents (homodimers or heterodimers) in the range of gram(s)/L (data not shown).

Example 3—In Vitro and In Vivo Testing of Binding Agents Comprising Anti-D2 Antigen Binding Domain(s)

Cell Lines

OCI-AML3 cells are acute myeloid leukemia cells of human origin that are used as target cells in PBMC-dependent cytotoxicity assays. THP-1 is a monocytic cell line derived from acute monocytic leukemia patient. THP-1 cells are used as the target cells in the PBMC-dependent cytotoxicity assay.

NCI-H82, NCI-H69 and NCI-H510A are human small cell lung cancer (SCLC) cell lines that are used in SCLC xenograft tumor model in the immunodeficient mice. NCI-H82, NCI-H69 and NCI-H510A overexpress the dopamine receptor D2 and are used herein, amongst other things, as a models for D2 targeting studies.

NCI-H727 cells are human non-small cell lung cancer (NSCLC) cells that are used for NSCLC xenograft tumor model in immunodeficient mice model. D2 has been shown to be upregulated in the NCI-H727 cells.

PANC1 is a human pancreatic cell line that is used for the xenograft tumor model in the immunodeficient mice model.

Proteoliposome Production

To determine the binding specificity of anti-D2 binding agents, human D2 presenting proteoliposomes were produced with ProteoLiposome BD kit from CellFree Science (CellFree Science, Cat. No. CFS-CPLE-BD) following the supplemented protocol.

In brief, a transcription reaction was set up by mixing required volumes of nuclease-free water, 5× Transcription buffer, NTP mix, RNase inhibitor, SP6 RNA polymerase and plasmid DNA, in a 1.5 mL tube with six-hour incubation at 37° C. To set up the translation reaction, a mixture of mRNA mixture, feeding buffer, WEPRO7240, creatine kinase and asolectin liposome was prepared as instructed. The translation reaction was set up by adding the translation reaction mixture to a slide-A-Lyzer Mini Dialysis device (Thermo Scientific, Cat. No. 69570) with 72-hour incubation at 15° C.

Proteoliposomes were purified by washing with PBS and centrifuge at 15000 rpm, 4° C. for 10 minutes. After repeating the washing steps for 3 times, the harvested proteoliposomes were resuspended in the appropriate amount of PBS and stored at −80° C.

The binding of anti-D2 binding agents (e.g., Table 6) to human D2 presenting proteoliposomes (FIG. 1, FIG. 25, FIG. 26) was assessed by ELISA. Briefly, proteoliposomes containing the target protein or empty liposomes were coated on 96-well plates. Plates were covered and left at 4° C. overnight. The next day, plates were washed once with PBS and blocked with blocking buffer for 1 hour at room temperature. Binding agents were tested at the indicated concentration, diluted in the blocking buffer, and incubate for 1 hour at 37° C. After incubation, plates were washed three times with washing buffer. Plates were incubated with anti-human-Fc-HRP (Sigma-Aldrich, Cat. No. AP113P) diluted at 1:5000 for 1 hour at room temperature, then washed three times with PBS-T washing buffer. The signal was developed with SuperSignal™ ELISA Pico Chemiluminescent Substrate (Thermofisher, Cat. No. 37069). The plates were read on a SpectraMax™ i3x Multi-Mode Microplate Reader (Molecular Devices).

A representative result of such experiment is presented in FIG. 1 which demonstrate that the tested anti-D2 binding agent binds specifically to D2 proteoliposomes (with an EC50 of 0.1488 nM) and has a very high-affinity.

GPCR BRET Assay

The effect of various anti-D2 binding agents on D2 downstream signaling was evaluated (FIG. 2). Before transfection, HEK293 cells were maintained in Dulbecco's Modified Eagle Medium (DMEM) supplemented with 1% penicillin/streptomycin and 10% fetal bovine serum. Polyethylenimine (PEI) transfection reagent was used for all transfection. HEK293 cells were co-transfected with hDR2 and one of the biosensors. The total amount of transfected DNA was kept constant at 1 μg per mL of cell culture to be transfected. The PEI to DNA ratio (μg:μg) was fixed at 3:1. DNA and PEI were first diluted separately in 150 mM NaCl. The volume of the diluent in each tube corresponds to 5% of the cell culture volume to be transfected. Once DNA and PEI were diluted, the PEI-containing solution was added to the DNA solution and the DNA/PEI mixture immediately vortexed for 5 seconds. The DNA/PEI mixture was incubated for at least 20 minutes at room temperature to allow for the formation of DNA/PEI complexes. During the incubation, HEK293 cells were detached, counted and re-suspended in culture medium. At the end of the incubation period, the DNA/PEI mixture was added to the cells. Cells were finally distributed in 96-well plates at a density of 35000.

At 48 hours post-transfection, BRET experiments were performed to detect the D2 downstream signaling in the agonist testing mode. Culture medium was aspirated and replaced with 50 μl of Hank's Balanced Salt Solution buffer from the 96-well plates. 10 μl of 10 μM e-Coelenterazine Prolume Purple was added to each well for a final concentration of 1 μM for assays performed in HEK239 cells. Dopamine was added to each well using the HP D300 digital dispenser as the positive control. Dopamine was assayed at 16 concentrations with each biosensor. Antibodies were added to each well manually (final concentration of 1 μM by well). The anti-D2 binding agents were assayed at 8 concentrations with each biosensor in duplicates. Cells were incubated with the dopamine at room temperature for 10 minutes and antibodies at room temperature for 60 minutes. BRET signals were collected with a 0.4 sec integration time on a Synergy NEO plate reader.

The EC50s of various anti-D2 binding agents in the GPCR BRET assays transfected with various G protein sensors are presented in FIG. 2. Dopamine was used as a positive control to show the GPCR response with G proteins including Gαz, Gαi2, GαoA, and Barr2. Unexpectedly, all the anti-D2 binding agents including KC011, KC012, KC013, and KC014 showed specific GPCR signaling through Gαz. The result indicates that the anti-D2 binding agents bind to unique epitopes on D2 and initiate a highly specific signaling pathway.

RNAseq and qRT-PCR Validation

The mechanism of action of KC013 was investigated in NCI-H69 cells in vitro, through the use of next-generation sequencing technology assessing global transcriptional profiles post-treatment. Suspension NCI-H69 cells were collected and resuspended at a concentration of $5\times10^6$ cells/mL. Ten million cells per 2 mL of complete medium were transferred to the wells of a 6-well plate. KC013 and negative control KC018 (in which the VHH portion is replaced with the anti-4HEM VHH set forth in SEQ ID NO:114) were added to the appropriate wells at a final concentration of 1.0 μM. Cells were returned to a 37° C., 5% CO2 incubator and treated for 3 hours. After the incubation period, cells were homogenized using the QiaShredder column, and RNeasy RNA Isolation Kit was used to isolate total RNA from the disrupted cell lysates, as per the manufacturer's protocol. A total of 500 ng of total RNA was snap-frozen and transferred to Genome Quebec for analysis.

Figure 3:
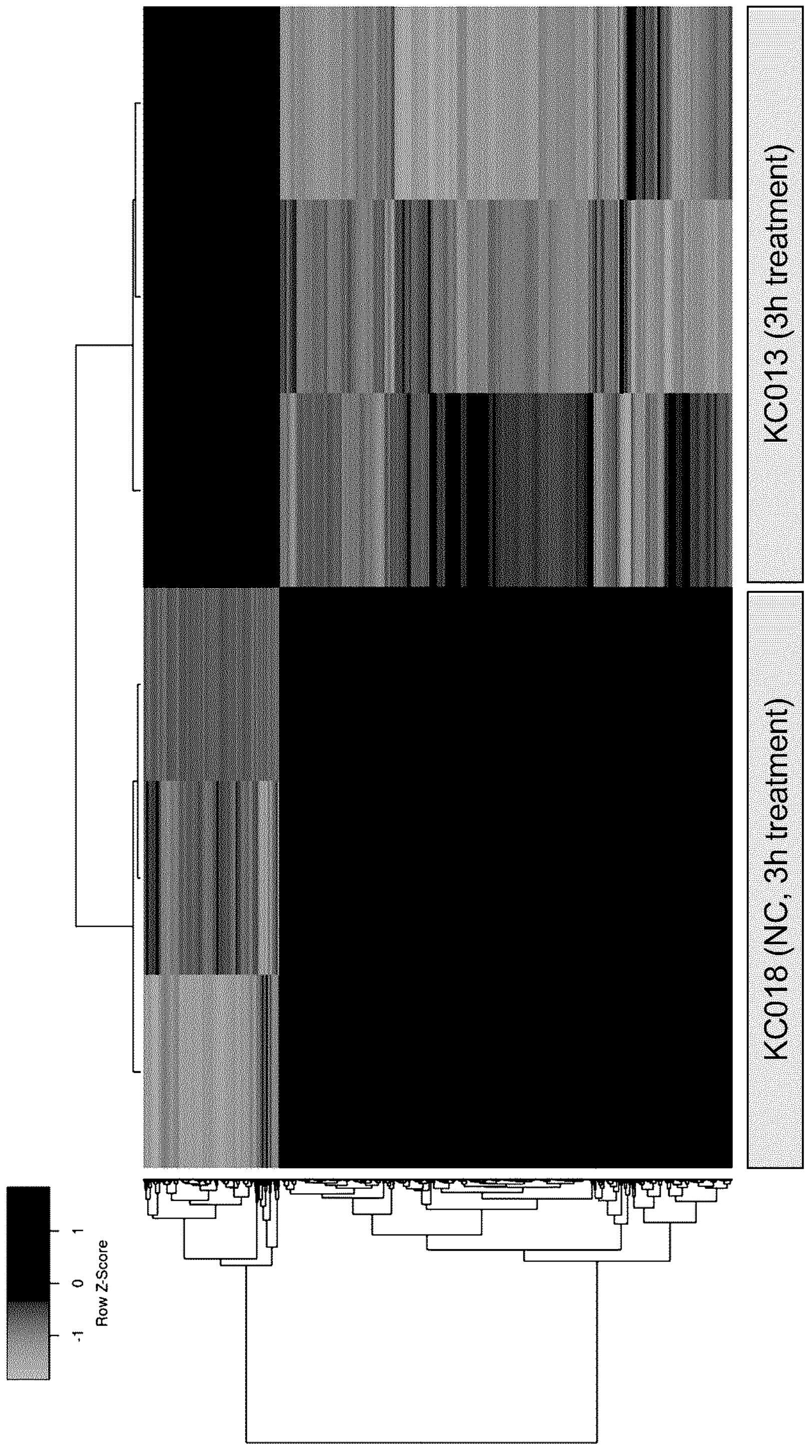
FIG. 3: Heat map displaying the changes of gene expression in NCI-H69 cells upon treatment with binding agent comprising D2-specific antigen binding domain (VHH-hinge-CH2-CH3) (KC013; SEQ ID NO:73). Negative control is 4HEM-specific binding agent (VHH-hinge-CH2-CH3) comprising the antigen binding domain set forth in SEQ ID NO:114 (KC018).

RNA integrity was assessed using an Agilent bioanalyzer. Libraries were prepared using the NEB mRNA stranded NEBNext Ultra II kit (NEB, Cat. No. E7645S), incorporating mRNA enrichment steps followed by Illumina library QC assessment. Samples were sequenced on a NovaSeq 6000 PE100 instrument (Illumina) at 25 million reads per sample. Reads were mapped to the ENSEMBL GRCh38 (*Homo sapien*) release 86 human reference genome sequence and annotations. This resulted in count data for 58,051 genes. Genes that do not exceed 1 count per million (CPM) in at least 3 samples (i.e. the smallest group size) were filtered out, leaving 14,983 genes for downstream analysis Gene lists were constructed by using a maximum False Discovery Rate (FDR) of 0.05 between KC013 treatment relative to the KC018 negative control. Enrichment analysis was conducted using Enrichr (Icahn School of Medicine, Mount Sinai; http://amp.pharm.mssm.edu/Enrichr/). Over-representation analysis was conducted using the PANTHER database (University of Southern California; http://pantherdb.org) using Fischer's exact test with FDR multiple test correction and focusing on Gene Ontology (GO) biological pathways and protein classes. Gene lists used consist of the 191 up-regulated and 634 downregulated genes, combined for a total count of 825 significantly altered genes (FDR<0.05) (FIG. 3). Pathway analysis was conducted using Ingenuity Pathway Analysis (IPA, Qiagen) (FIGS. 4A&B). Heat maps were constructed using Log 2 transformed transcript read counts (FDR<0.05, 825 genes), with complete linkage clustering and Pearson distance measurement.

Pathway analysis of RNA-Seq data revealed down-regulation of several cancer-associated pathways, including CREB, Wnt, and mTOR signaling pathways relative to the negative control (KC018) treated cells including NCI-H69 and NCI-H82 SCLC, and activation of p53 through multiple signaling pathways.

Figure 5:
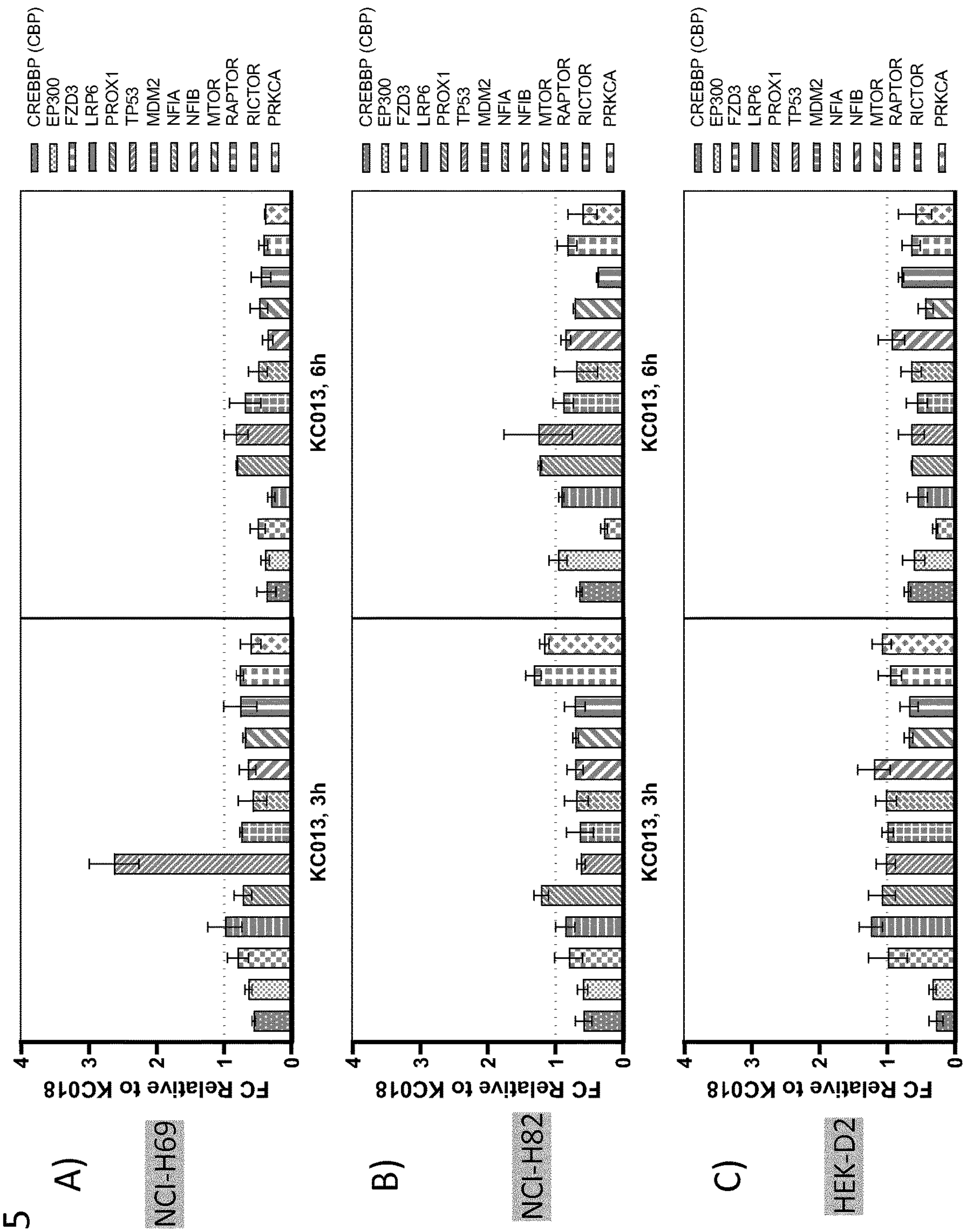
FIGS. 5A-5C: graph representing the downregulated genes verified by qRT-PCR NCI-H69 (FIG. 5A), NCI-H82 (FIG. 5B), and HEK-D2 (FIG. 5C) upon treatment with binding agent comprising D2-specific antigen binding domain (VHH-hinge-CH2-CH3) (KC013; SEQ ID NO:73).

Pathway analysis of RNA-Seq data was validated by quantitative reverse transcriptase-PCR (qRT-PCR) using three different cell lines including NCI-H69 (FIG. 5A), NCI-H82 (FIG. 5B), and HEK-D2 (FIG. 5C). Briefly, suspension cells were grown in T175 flasks in complete medium. Cells were seeded in three 6-well plates at $5\times10^6$ cells/mL per well and were treated with 1.0 μM KC013 or 1.0 μM of KC018 in triplicates for 3 hours and 6 hours. After the specified incubation period, replicates were scraped and transferred into 15 mL falcon tubes for each time point. Cells were washed twice with 1×PBS and cell pellets were flash-frozen in liquid nitrogen and stored at −80° C. for downstream analysis. Total RNA was extracted using the Quick-RNA Miniprep Plus kit (Cedarlane, Cat. No. R1057), according to the manufacturer's instructions. The amount of RNA recovered for each sample was quantified by measuring absorbance at 260 and 280 nm using NanoPhotometer. 1 μg of RNA was used for reverse transcription with the iScript™ Reverse Transcription Supermix, according to manufacturer's instructions. The resulting cDNAs were then diluted 1:20 using ddH2O containing 40 ng/mL glycogen.

Gene expression analysis was performed using SsoAdvanced Universal IT SYBR Green in iQTM5 Real-Time PCR System using the relative standard curve method. Final reaction volume were 10 μl per well of a 96-well plate containing 1×SYBR green mix, 200 nM final primer concentration, 2 μl cDNA and ddH2O. Raw Data of qRT-PCR for target genes were collected as the number of cycles required for the fluorescent signal to cross background levels (i.e. threshold). These values are known as the Cycle Threshold values or Ct values. To determine the relative gene expression levels of target genes following treatment with KC013 vs KC018, the geometric mean of multiple internal control genes method was used, followed by the ΔΔCt calculation method described below. This approach is described in detail by Vandesompele J. et al. Genome Biology 2002 and Hellemans et al. Genome Biology, 2007. The final data was presented as the fold-change in gene expression normalized to the selected common endogenous reference genes and relative to the control binding agents. Data were presented as the average of 3 biological replicates performed in 3 technical replicates. Results were representative data from the assay performed in triplicate at least 3 times.

Changes in gene expression in NCI-H69 cells upon treatment with KC013 is illustrated by heat map (FIG. 3) with color and intensity variation representing changes in individual gene expression. Results of this experiment indicate that a total count of 825 significantly altered genes (FDR<0.05) were observed after treatment with KC013, with 634 genes downregulated.

FIG. 4 represents the downregulated signaling pathways and protein classes from the PANTHER analysis of the RNAseq result. The top downregulated signaling pathways include Wnt pathway, Gonadotropin-releasing hormone (GnRH) pathway and the Cadherin signaling pathways (FIG. 4A). The most downregulated protein classes by PANTHER analysis are gene-specific transcriptional regulators (FIG. 4B). Wnt pathway and Cadherin signaling pathway has been suggested to played important roles in tumor cell survival, proliferation, tumor formation, and progression. Aberrant Wnt signaling pathway has been shown to play a key role in the initiation of many cancer cells by regulating Cancer Stem Cells (CSCs). Downregulation of these pathways and transcriptional regulators suggests the anti-tumor mechanism of KC013.

Consistent with the RNAseq profile, specific signaling components in the Wnt pathway, mTOR pathway and cAMP pathway showed downregulation in the NCI-H69 cells (FIG. 5A), NCI-H82 cells (FIG. 5B), and HEK-D2 cells (FIG. 5C) upon treatment with KC013.

Single Dose PK in CB-17 Fox Chase SCID Mice

CB-17 Fox Chase SCID mice (6-8 weeks old, female), purchased from University Health Network (UHN, Toronto, ON) were used for the PK studies. Mice were housed in a pathogen-free environment at the animal facility in UHN. The animal work was conducted according to the guidelines of the Canadian Council on Animal Care (CCAC) and the Animal Use Protocol approved by the Animal Care Committee at UHN. In brief, mice were divided into 2 experimental groups (6 mice/group), and each group of the mice received a 30 mg/kg single dose of Trastuzumab (UHN pharmacy store) or KC013 by either intravenous injection (FIG. 6A) or intraperitoneal injection (FIG. 6B). For each study, blood samples were collected at 0.083 hour (for PK iv study only), 1 hour (for PK ip study only), 3 hours, 6 hours, 1 day, 3 days, 7 days, 10 days, 15 days, 21 days and 28 days post-injection. The blood samples were centrifuged, the serum samples were collected and stored at −80° C. until the time they were analyzed. Concentrations of Trastuzumab and KC013 in mouse serum were measured by a quantitative enzyme-linked immunosorbent assay (ELISA) as described below. Pharmacokinetic data analysis was performed by the non-compartmental method using Phoenix WinNonlin software (Certara).

Antibodies in the mice serum were quantified by quantitative ELISA (FIG. 6). In brief, mouse anti-human IgG antibody (Bio-rad, Cat. No. MCA878G, using 1/200 dilution) was used to coat the 96-well plate overnight at 4° C. The next day, plate was washed three times and blocked with 2% BSA for 1 hour at room temperature. Meanwhile, standard (STD, Bio-rad, Cat. No. MCA6092), quality control (QC), and each serum sample were diluted in the washing buffer containing 1% mouse serum. 100 μl of STD, QC, and diluted serum sample were added into the 96-well plates and incubated for 2 hours at room temperature. After washing three times, plates were incubated with the secondary antibody (goat anti-human Fc antibody, 1/5000 dilution, Cedarlane, Cat. No. 109-035-098) for 1 hour at room temperature. Plates were washed three times before adding 100 μl of detection substrate for each well. When the highest STD reading reached 0.9-1.1 at 650 nm wavelength, 50 μl of stopping solution was added to each well to stop the reaction. Plates were read at 450 nm wavelength for antibody measurement.

Result of these experiments indicates that IV injection of KC013 (FIG. 6A) showed a T1/2 of 214 hours and IP injection (FIG. 6B) showed a T1/2 of 159 hours. The Cmax achieved for KC013 is similar to the full-size human antibody Trastuzumab. This data demonstrated a long half-life of anti-D2 binding agents in the SCID mice.

Tumor Prevention Model in CB-17 Fox Chase SCID Mice

CB-17 Fox Chase SCID mice (6-8 weeks old, female) were purchased either from Charles River Laboratories (St. Constant, QC) or from UHN (Toronto, ON). The animal husbandry and the guidelines of animal work are the same as those described above.

The efficacy of anti-D2 binding agents was assessed in various tumor prevention models, NCI-H510A (FIG. 7C, FIG. 8), NCI-H727 (FIG. 7A, FIG. 8), PANC1 (FIG. 8), and NCI-H69 (FIG. 7B, FIG. 8). For each model, tumor cells (8 million cells/mouse for NCI-H510A, 6 million/mouse for NCI-H727, 5 million/mouse for PANC1, or 3 million/mouse for NCI-H69) in DPBS were injected subcutaneously (s.c.) into the right flank of mice. One day after the cell inoculations, mice inoculated with each cell line were randomly divided into 2 experimental groups (10 or 5 mice/group), and each group of mice received 16 mg/kg ip. either KC018 (negative control) or KC013, twice weekly, for a total of eight weeks. Tumor volumes were measured using vernier calipers and the mice were weighed one or two times weekly. Tumor volume was calculated using the formula: 12 (Length×Width$^2$). For calculation of percentage tumor growth inhibition (TGI), KC013 treated group was compared with its respective negative control. TGI was calculated by the following formula:

$$TGI[\%] = 100 - \frac{\text{mean}\left(TV(\text{treated})_{day\,z} - TV(\text{treated})_{day\,x}\right)}{\text{mean}\left(TV(resp.\ control)_{day\,z} - TV(resp.\ control)_{day\,x}\right)} \times 100$$

TV day z represents the tumor volume of an individual animal at a defined study day (day z) and TV day x represents the tumor volume of an individual animal at the staging day (day x).

Statistical tests were performed by a student t-test (two-tailed).

Figure 7:
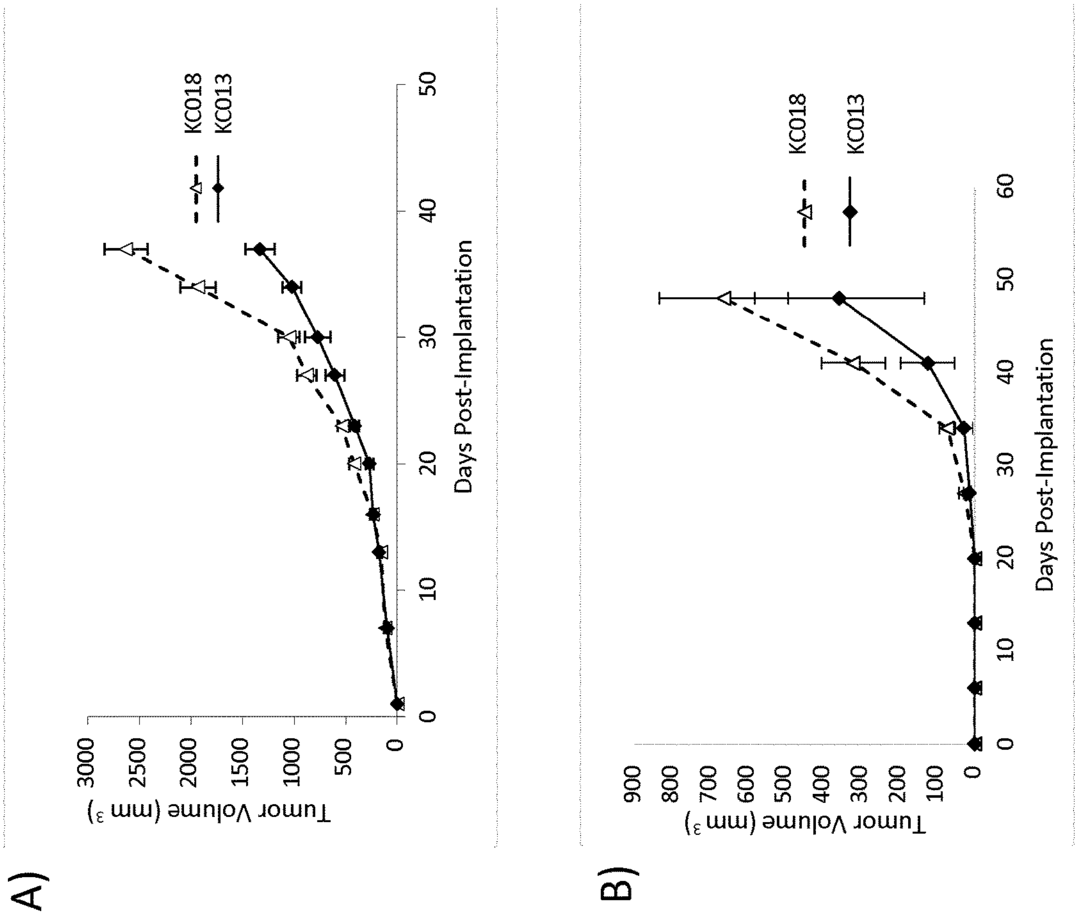
FIGS. 7A-7C: graph showing the tumor kinetics and in vivo efficacy of binding agent comprising D2-specific antigen binding domain (VHH-hinge-CH2-CH3, solid line) (KC013; SEQ ID NO:73) in NCG mice with small cell lung cancer (SCLC) xenograft models compared to isotype control (dashed line) in the NCI-H727 tumor prevention model (FIG. 7A), in the NCI-H69 tumor prevention model (FIG. 7B) or in the NCI-H510A tumor prevention model (FIG. 7C). Negative control is 4HEM-specific binding agent (VHH-hinge-CH2-CH3) comprising the antigen binding domain set forth in SEQ ID NO:114 (KC018).
Figure 7:
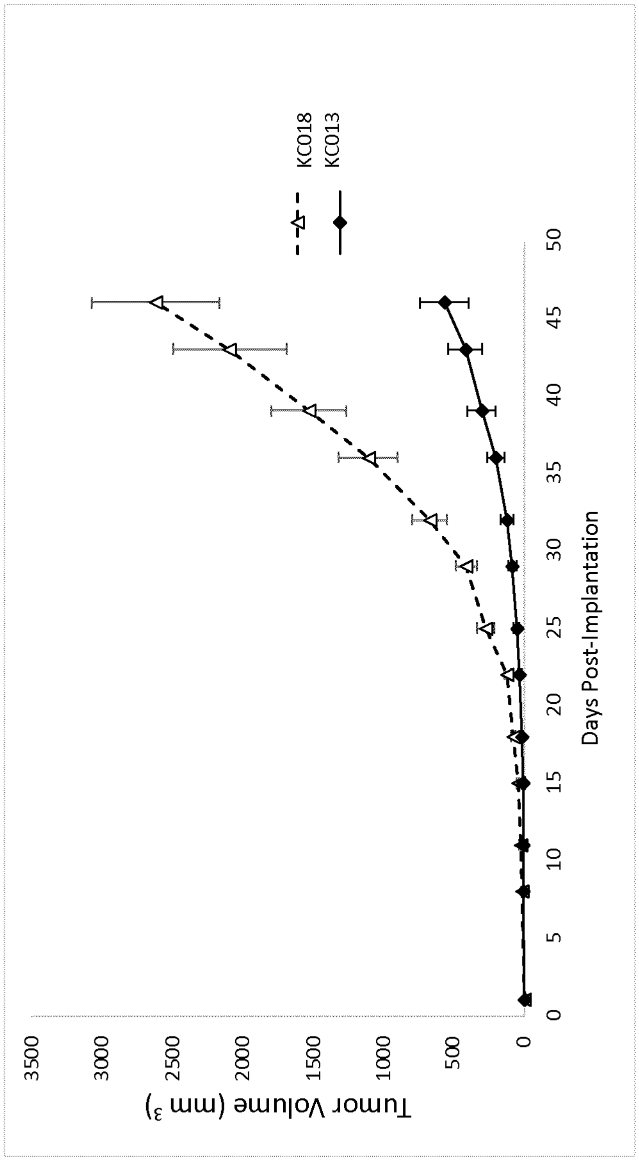

As illustrated in FIG. 7, KC013 showed 49% tumor growth inhibition in the NCI-H727 tumor prevention model (FIG. 7A), 46% tumor growth inhibition in the NCI-H69 tumor prevention model (FIG. 7B) and 77% tumor growth inhibition in the NCI-H510A tumor prevention model (FIG. 7C) in comparison with isotype control.

As illustrated in FIG. 8, KC013, KC012, and KC014 demonstrated a universal tumor growth inhibition in all of the tumor prevention SCLC tumor models, with KC013 obtaining the best in vivo efficacy than other anti-D2 binding agents. As all of these anti-D2 binding agents initiated the unique Gαz signals in the BRET assays, the in vivo efficacy achieved in SCLC tumor models may be relevant with the specific Gαz signals in the tumor cells. The in vivo efficacy is also explained by the downregulated signaling pathways which are important for tumor progression.

Example 4—In Vitro and In Vivo Testing of Binding Agents Comprising Anti-PD1 and Anti-CD47 Antigen Binding Domain(s)

ELISA Binding Assays

The binding of binding agents comprising anti-PD-1 and -CD47 antigen binding domain to recombinant human or cynomolgous PD-1 (Cedarlane, Cat. No. HPLC-10377-H08H-100) or recombinant human or cynomolgous CD47 (Cedarlane, Cat. No. 12283-H08H-200 and 90869-C08H) was assessed by ELISA (FIG. 9A, FIG. 9B, FIG. 9C, FIG. 9D, FIG. 22, FIG. 23). Pembrolizumab was used as a positive control in PD1 binding assays. The monoclonal anti-CD47 antibody (clone B6H12) was used as a positive control in CD47 binding assays (Biolegend, Cat. No. 401401).

Briefly, recombinant proteins were coated on 96-well plates. Plates were covered and left at 4° C. overnight. The next day, plates were washed once with PBS and blocked with blocking buffer for 1 hour at room temperature. Binding agents were tested at the indicated concentration, diluted in the blocking buffer, and incubated for 1 hour at 37° C. After incubation, plates were washed three times with washing buffer. Plates were incubated with anti-human-Fc-HRP (Sigma-Aldrich, Cat. No. AP113P) diluted at 1:5000 for 1 hour at room temperature, then washed three times with PBS-T washing buffer. The signal was developed with SuperSignal™ ELISA Pico Chemiluminescent Substrate (Thermofisher, Cat. No. 37069). The plates were read on a SpectraMax™ i3x Multi-Mode Microplate Reader (Molecular Devices).

Figure 9:
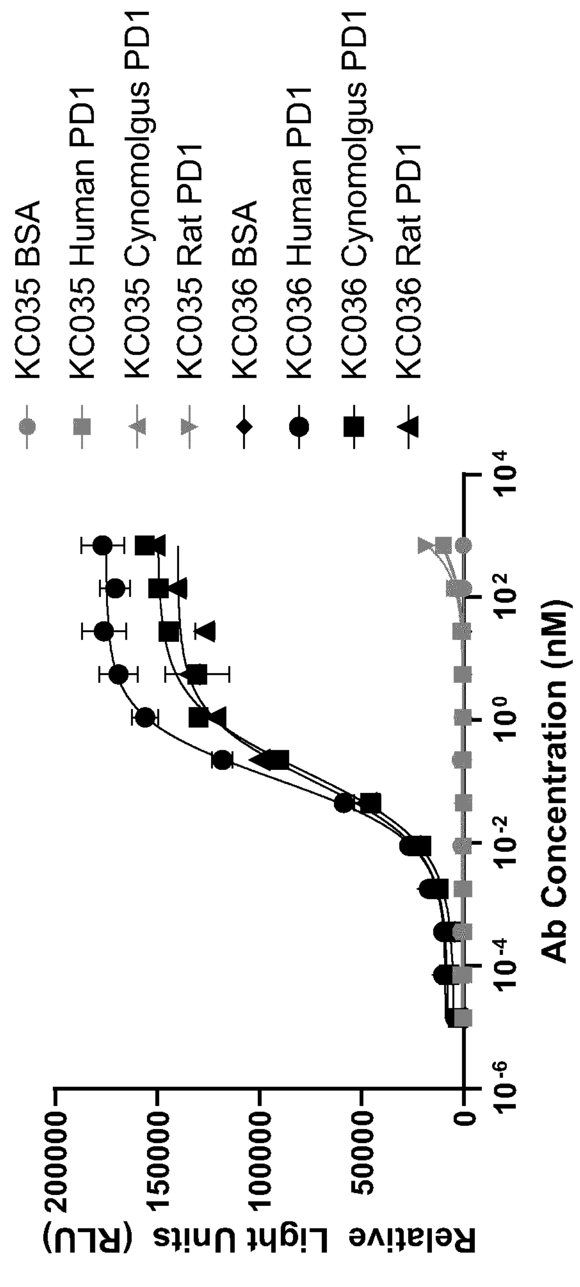
FIG. 9A: graph displaying the binding curve of PD-1-specific binding agent (KC036; SEQ ID NO:94) on human, cynomolgus monkey, and rat recombinant PD1 protein or on control protein (BSA). Negative control is a binding agent that comprises HEWL-specific antigen binding domains (KC035: SEQ ID NO:93).
FIG. 9B: graph displaying the binding curve of PD-1-specific binding agent (KC036; SEQ ID NO:94) on human recombinant PD1 protein in comparison with the anti-PD-1 antibody Pembrolizumab (positive control). Negative control is a binding agent that comprises HEWL-specific antigen binding domains (KC035: SEQ ID NO:93).
FIG. 9C: graph displaying the binding curve of CD47-specific binding agent (KC015; SEQ ID NO:75) on human recombinant CD47 protein. Negative control for KC015 is a binding agent that comprises HEWL-specific antigen binding domains (KC016: SEQ ID NO:76). The positive control is monoclonal antibody clone B6H12. The isotype control for clone B6H12 is used as mouse IgG isotype control antibody.
FIG. 9D: graph displaying the binding curve of CD47-specific binding agent KC015 on cynomolgus CD47 protein. Negative control KC016 is a binding agent that comprises HEWL-specific antigen binding domains. The positive control is monoclonal antibody clone B6H12. The isotype control for clone B6H12 is used as mouse IgG isotype control antibody.
FIG. 9E: graph representing the binding curve of CD47-specific binding agent KC015 on various blood cell subtypes including the T cells, monocytes, granulocytes, red blood cells (RBCs), and platelets.
Figure 9:
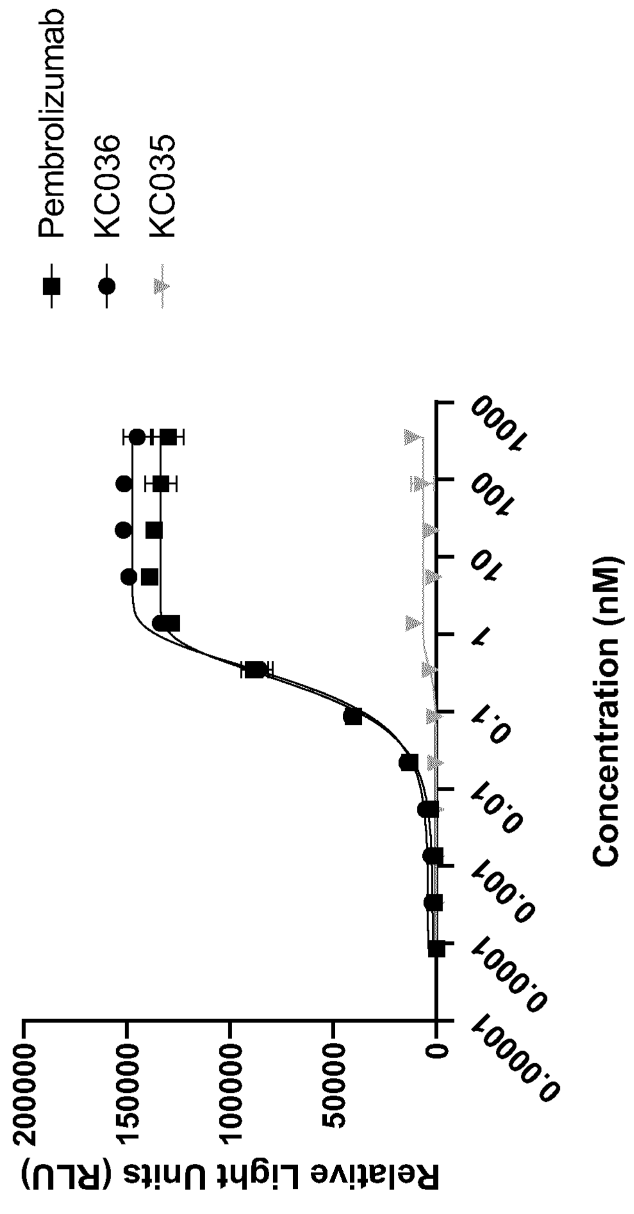
Figure 9:
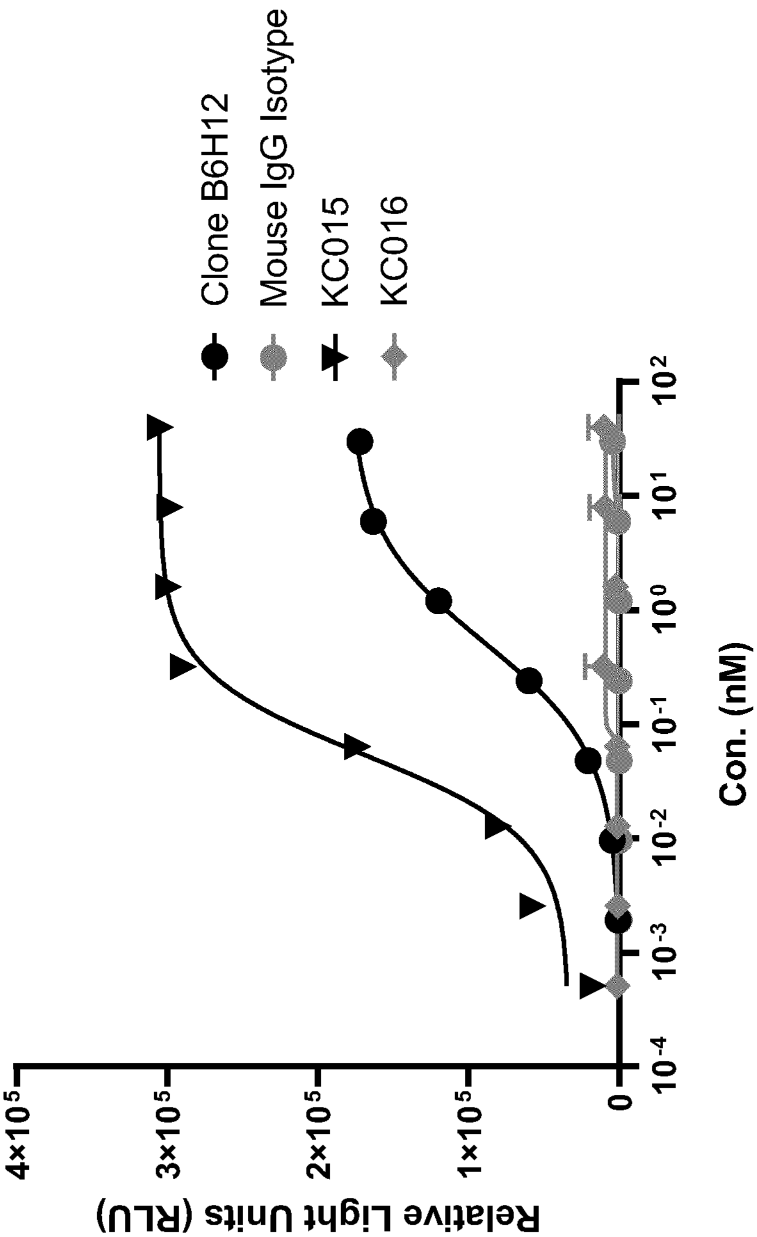
Figure 9:
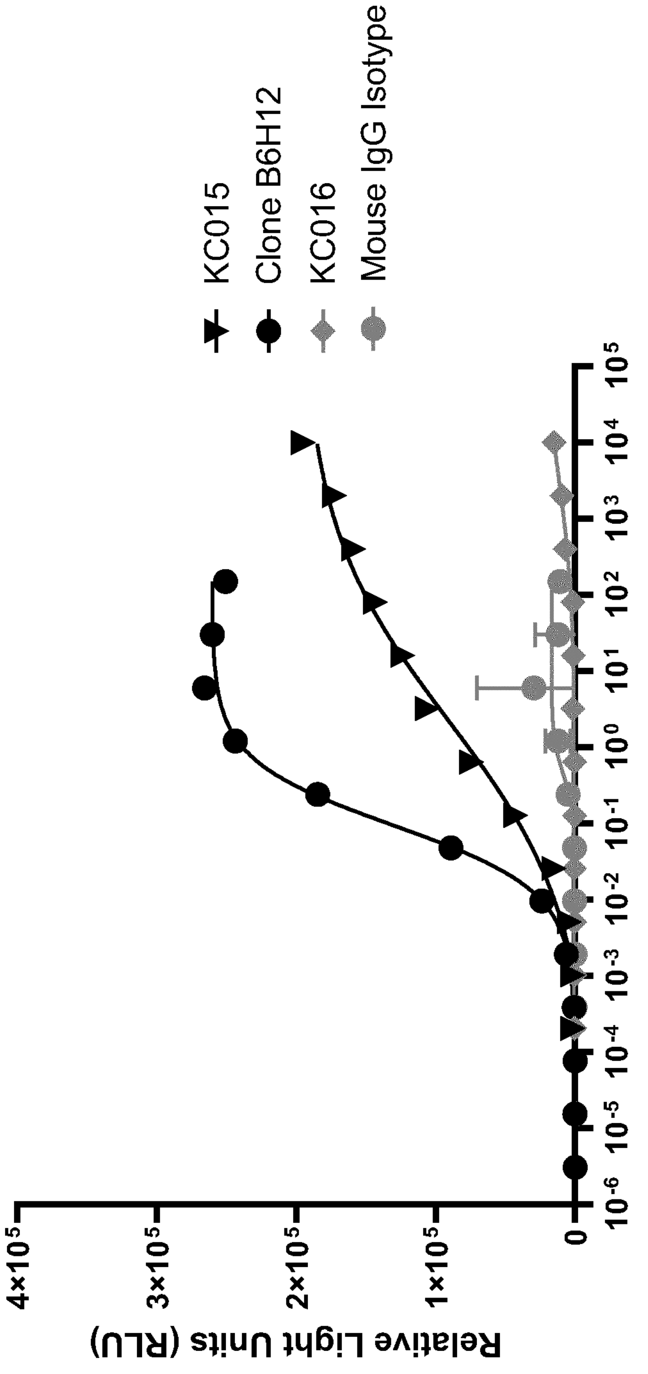
Figure 9:
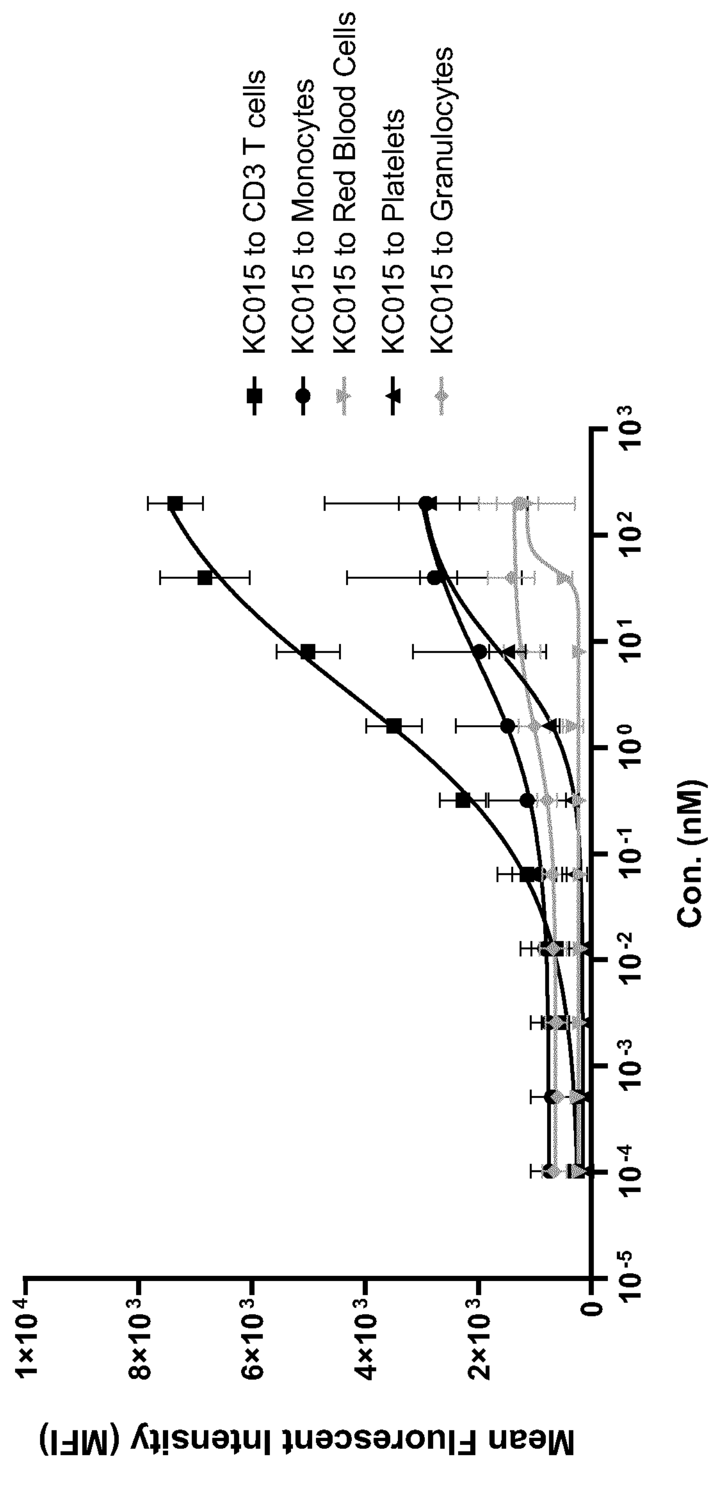

As illustrated in FIG. 9A, the anti-PD1 binding agent KC009 efficiently binds to human, cynomolgus monkey, and rat recombinant PD1 proteins. The cross-species binding activity of KC009 implies the feasibility of using cynomolgus monkey and rat as the toxicity model for KC009.

The binding of KC036 was compared with Pembrolizumab. Both KC036 and Pembrolizumab were diluted 1/5, starting from 500 nM. As illustrated in FIG. 9B, KC036 binds similarly to Pembrolizumab by ELISA. The negative control KC036 did not bind to the PD-1 recombinant protein.

The binding of KC015 was compared with the anti-CD47 antibody B6H12 (ThermoFisher, Cat. No. 14-0479-82). Both KC015 and B6H12 antibodies were diluted 1/5, starting from 50 nM.

As illustrated in FIG. 9C, KC015 showed higher binding affinity than clone B6H12 by ELISA. The negative control KC016 did not bind to the CD47 recombinant protein.

As illustrated in FIGS. 9C and 9D, the anti-CD47 binding agent efficiently binds to human and cynomolgus monkey CD47 recombinant protein, whereas the negative control showed no binding to both of the CD47 recombinant protein.

Blood Cell Binding of the Binding Agent by Flow Cytometry

To evaluate the binding activity of KC015 on various blood cell subtypes, fresh blood was collected from two healthy donors into the Becton Dicinson Vacutainer. For white cell preparation, add 10 mL of 1× red blood cell lysis buffer (eBiosceince, 00-4300-54) into each 1 mL fresh blood and incubate at RT for 15 mins. The cell suspension was then centrifuged at 300 g for 5 minutes at room temperature, followed by washing one more time with PBMC medium ((RPMI+10% heat-inactivated FBS). The white blood cell number was counted before staining with the binding agents.

For red blood cell (RBC) preparation and staining, fresh blood was transferred to a 15 mL conical bottom polypropylene tube and mixed with the PBS washing buffer (PBS+ 2% heat-inactivated FBS). Tubes were centrifuged at 800 g for 10 minutes at room temperature with the brake off. Red blood cells were collected from the bottom of the tube, resuspended into the PBS washing buffer (PBS+2% heat-inactivated FBS), and counted the cell number before staining with the binding agents.

For platelet cell preparation, fresh blood was transferred to a 15 mL conical bottom polypropylene tube and mixed with the PBS washing buffer (PBS+2% heat-inactivated FBS). Tubes were centrifuged at 800 g for 10 minutes at room temperature with the brake off. The platelet-rich plasma was collected from the top of the tube (2/3 of plasma volume). The platelet-rich plasma was transferred to 9 mL of PBS washing buffer and centrifuged at 1250 g for 15 minutes at room temperature with the brake off Platelet cell number was counted before staining with the binding agents.

Fc receptor blocking antibody was added into cell suspension at the 1/100 dilution and incubated on ice for 10 minutes. Primary binding agents were added into the cell suspension at a serial of antibody concentrations and incubated on ice for 30 minutes. Cells were washed once with PBS washing buffer before staining with the secondary detection antibody. T cells were also stained with the CD3 marker antibody (Biolegend, 557705). Monocytes were stained with CD14 antibody (Biolegend, 301814). Granulocyte populations were gated based on FSC and SSC. The red blood cells were stained with CD235ab antibody (Biolegend, 306620). Platelets were stained with CD41 antibody (Biolegend, 303704). All cells were stained with 7-AAD (BD, 559925) with 1/100 dilution before analysis by the cytometer FACSCantoII.

As illustrated in FIG. 9E, KC015 efficiently binds to human T-cells but with less efficiency to RBCs and platelets.

FACS Binding Assays Cells

Figure 10:
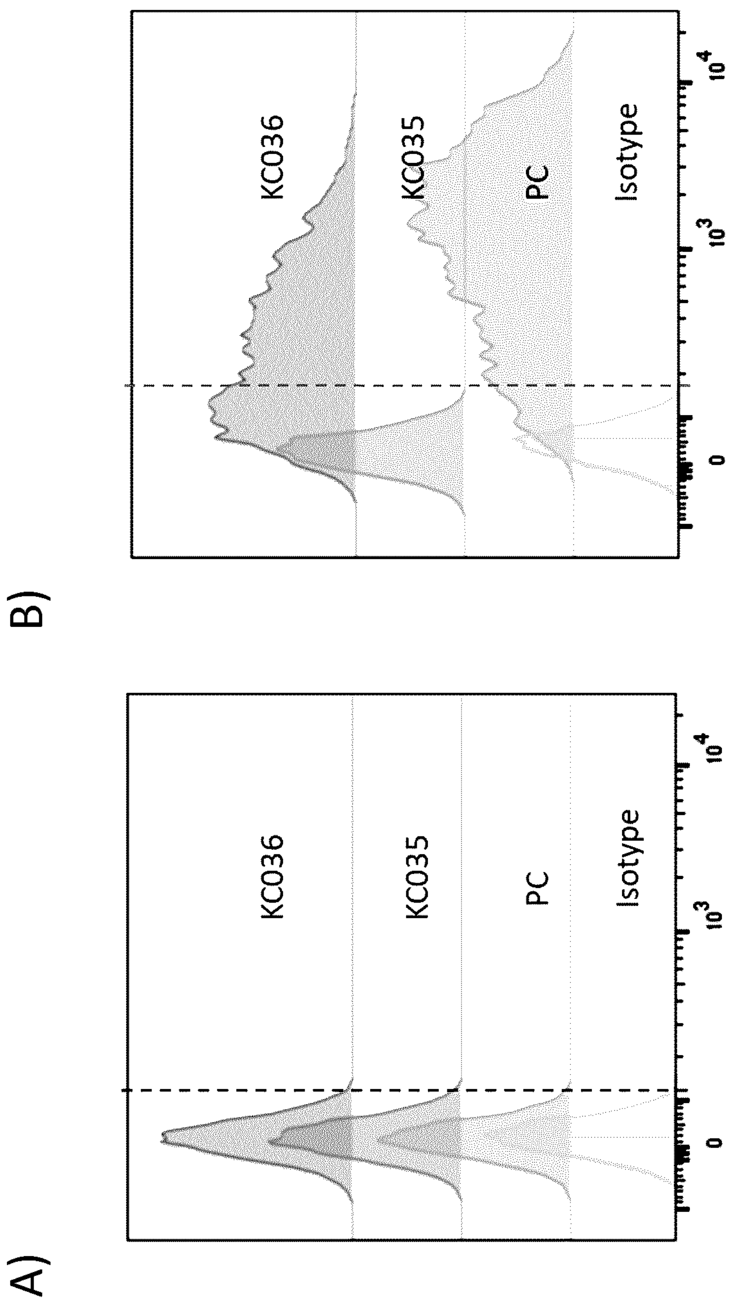
FIG. 10: graph representing the cell-binding activity of PD-1-specific binding agent (KC036; SEQ ID NO:94) on CHO-PD1 cells (FIG. 10B) and CHO parental cells (FIG. 10A) obtained by flow cytometry. A commercially available PD-1 antibody is used as positive control. Negative control is a binding agent that comprises HEWL-specific antigen binding domains (KC035: SEQ ID NO:93).

The binding of binding agents to cells was assessed by flow cytometry. To determine the binding specificity of binding agents comprising anti-PD-1 antigen binding domain, CHO parental and CHO-PD-1 cell lines were used in the binding assay (FIG. 10). In brief, $1\times10^5$ cells were incubated with Fc receptor blocking antibody (1/100 dilution, Cedarlane, Cat. No. 422302) for 10 minutes at room temperature. Binding agents comprising anti-PD-1 antigen binding domain, were diluted in FACS staining buffer to 20 μg/mL and added and incubated with cells for 30 minutes on ice. The PD-1 antibody (clone EH12.2H7, Biolegend) was used as a positive control. After washing three times with FACS staining buffer, APC-conjugated secondary antibodies recognizing human Fc region ((Cedarlane, Cat. No. 409306) were mixed with cells. After staining for 30 minutes, cells were washed three times, followed by resuspension into 100 μl of 7-Amino-Actinomycin D (7-AAD) solution (1/500 dilution, BD Bioscience, Cat. No. 559925). Cells were analyzed by BD FACSCanto™ II Flow cytometer (BD Bioscience). Data were analyzed with FlowJo via gating on single cells and live cells.

As illustrated in FIG. 10 KC036 only bound to the CHO-PD1 cells and not to non-PD1 expressing cells (CHO parental cells), evidencing the high specificity of the anti-PD-1 module KC009.

PBMC-Mediated Cytotoxicity Assay

PBMC-mediated cellular cytotoxicity was evaluated by flow cytometry. Briefly, tumor cells (THP-1 or OCI-AML3) were stained with CellTrace violet for 10 minutes at 37° C. Cells were washed and mixed with human PBMC (Cedarlane, Cat. No. 70025.1) at the ratio of 5:1. Anti-CD3 antibodies or the CD33 Bi-specific T-cell engager (BiTE, G&P Bioscience, Cat. No. FLC2032) were added to activate T cells. Binding agents were added into the corresponding wells at the indicated concentrations to determine the effect of anti-PD-1 module on the cytotoxicity. After incubation for 48 or 72 hours, cells were washed three times, followed by resuspension in 100 μl of 7-AAD solution (1/100 dilution, BD Bioscience, Cat. No. 559925). Cells were analyzed by BD FACSCanto™ II Flow cytometer (BD Bioscience). Data were analyzed with FlowJo by gating only on single cells and live cells.

Figure 11:
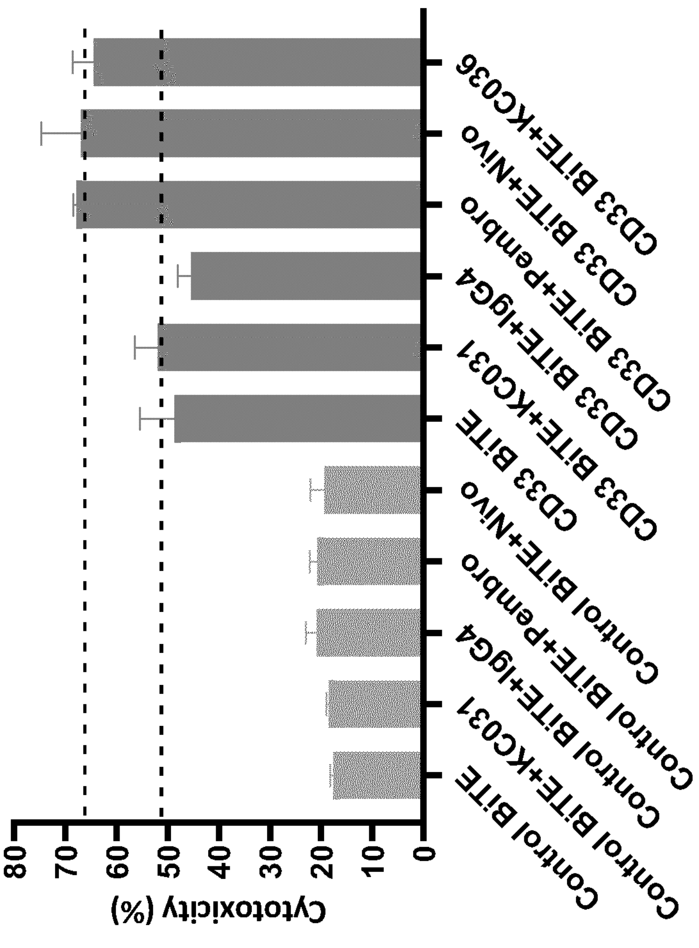
FIG. 11: graph representing the cytotoxicity data of PBMC-mediated THP-1 death induced by PD-1-specific binding agent (KC036; SEQ ID NO:94) in the presence CD33 BiTE 48 hours after incubation which was used to activate T cells via CD3 subunits or in the presence of control BiTE. Negative control is a binding agent that comprises HEWL-specific antigen binding domains (KC031: SEQ ID NO:89). Positive controls include Pembrolizumab and Nivolumab.

As illustrated in FIG. 11 KC036 (SEQ ID NO:94) showed checkpoint inhibition (CPI) activity by increasing the T cell-dependent cytotoxicity, to a similar level of positive controls Pembrolizumab and Nivolumab.

PD-1/PD-L1 Blockade Bioassay

The blockade activity of binding agent comprising anti-PD-1 antigen binding domains was assessed using a PD-1/PD-L1 blockade assay (Promega, Cat. No. J1255) within a luminescent NFAT-RE reporter system, and compared to positive control. PD-L1 aAPC/CHO-K1 (target) cells were thawed and seeded into 96-well plate at the recommended density, and allowed to adhere to the plate overnight. The following day, the binding agents were diluted to 350 nM in assay buffer (Ham's F12 media with 10% low IgG FBS), and eight 2.5× serial dilutions were conducted. Media from the 96-well plate was decanted, and 40 μl of diluted binding agents and 40 μl Jurkat (effector) cells were added to the plate. Plates were incubated at 37° C. for 6 hours. Bio-Glo luciferase assay buffer and substrate were combined, and 80 μl of the solution was transferred to each well. The plate was incubated at room temperature for 5 minutes, and the luminescence was measured using a plate reader.

Figure 12:
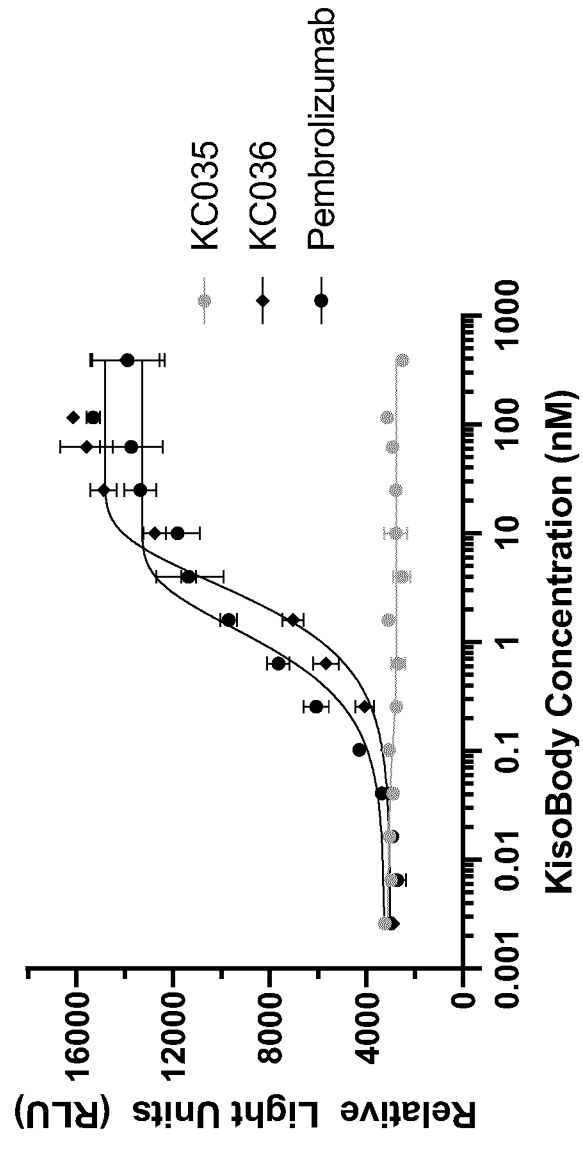
FIG. 12: graph displaying the checkpoint inhibition activity of PD-1-specific binding agent (KC036; SEQ ID NO:94) using PD-1/PD-L1 blockade bioassay system. This system is an engineered Jurkat cell line expressing luciferase reporter under the NFAT promoter. The negative control is a binding agent that comprises HEWL-specific antigen binding domains (KC035: SEQ ID NO:93). The anti-PD-1 antibody Pembrolizumab is used as a positive control.

Result of these experiments shows that KC036 achieved a similar in vitro CPI activity to Pembrolizumab, suggesting that the binding agent can induce anti-tumor activity by restoring T-cell function in "exhausted" T cells (FIG. 12).

The anti-PD1 antigen binding domain of KC036 is substituted for other anti-PD-1 antigen binding domains listed in Table 4 and in a manner similar to what is described herein.

Example 5—In Vitro and In Vivo Testing of Binding Agents Comprising Anti-CD47 Antigen Binding Domain(s)

Figure 13:
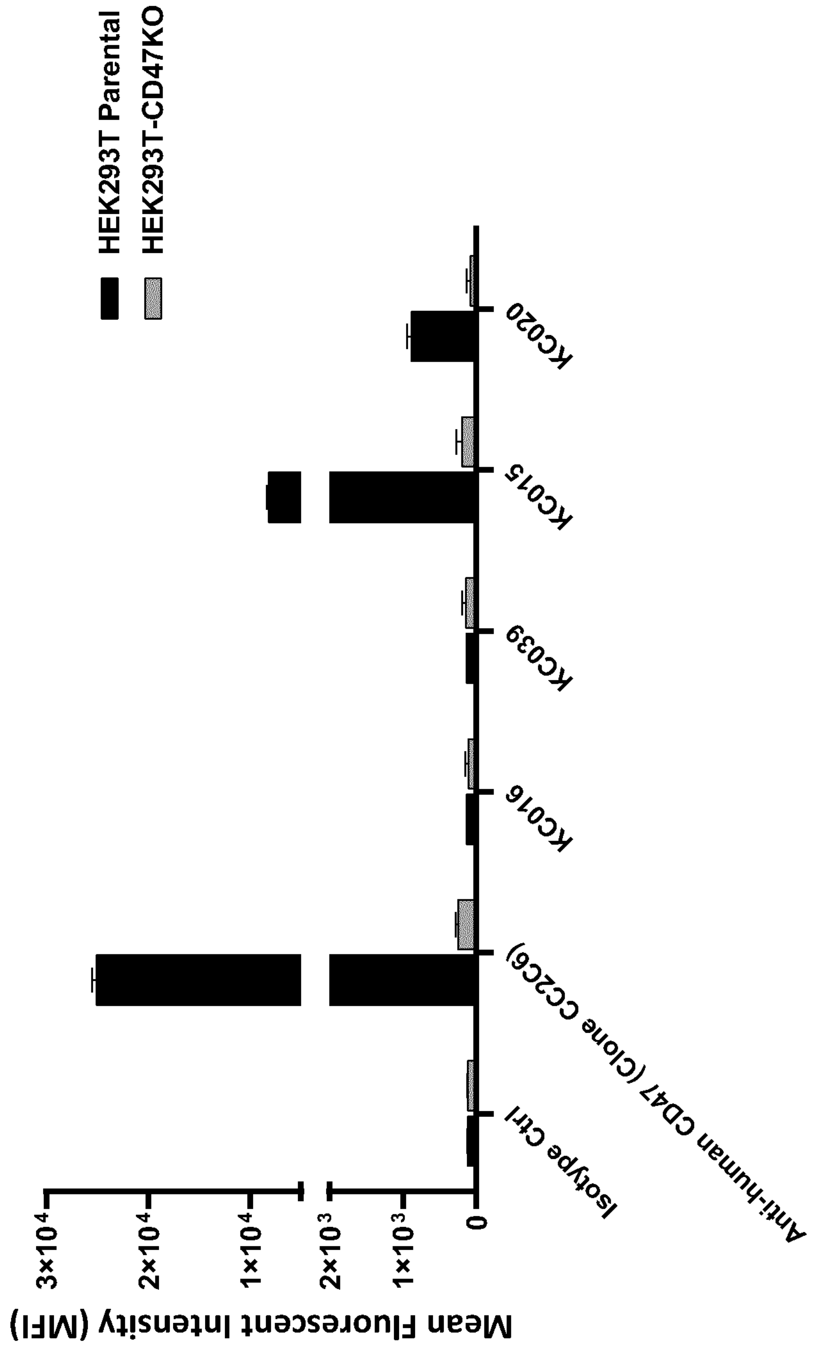
FIG. 13: graph representing the binding data of a trispecific binding agent comprising anti-D2-, anti-PD-1 and anti-CD47 antigen binding domains to HEK293T cells and HEK293T-CD47 KO cells (CD47 knock-out cells) (KC020; SEQ ID NO:77) as well as a monospecific binding agent comprising the same anti-CD47 antigen binding domains (KC015: SEQ ID NO:75 VHH-hinge-CH2-CH3). Negative controls include corresponding formats comprising anti-HEWL antigen binding domains (KC016 (SEQ ID NO:76) and KC039 (SEQ ID NO:97)). A commercially available anti-human CD47 antibody (Clone CC2C6) is used as positive control.
Figure 14:
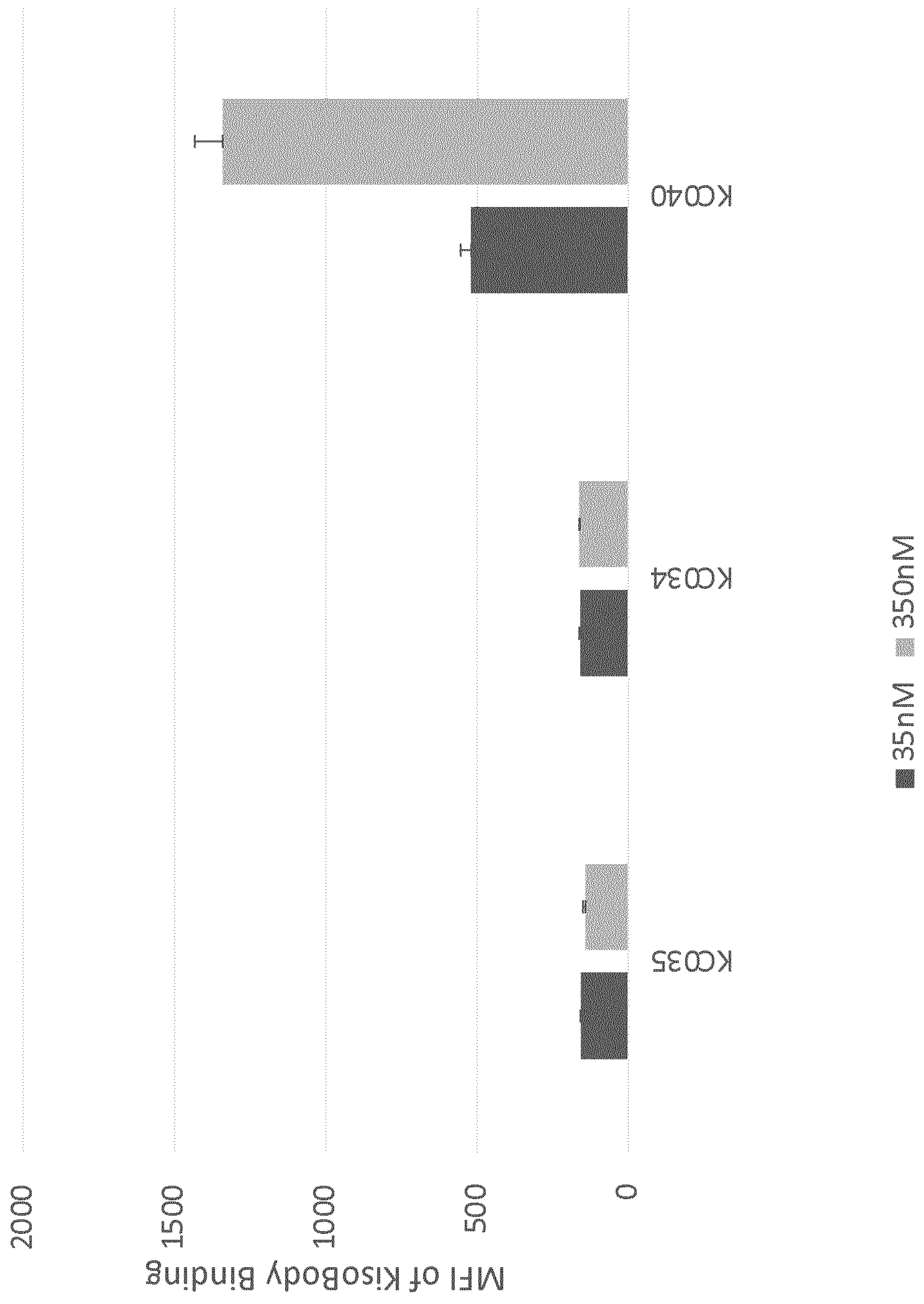
FIG. 14: graph representing binding of binding agent comprising anti-D2-, and anti-CD47 antigen binding domains on human T cells (KC040: SEQ ID NO:84) compared to control binding agents comprising anti-HEWL antigen binding domains (KC035: SEQ ID NO:93) or anti-CD3 and anti-HEWL antigen binding domains (KC034; SEQ ID NO:92).

Binding agents comprising anti-D2 and anti-CD47 antigen binding domains (KC040) or anti-D2-, anti-PD-1- and anti-CD47 antigen binding domains (SEQ ID NO:70) were tested for binding on HEK293T or HEK293T-CD47KO cells (CD47 knock-out) (FIG. 13) or in primary human T cells (PBMC, StemCell) (FIG. 14).

As illustrated in FIG. 13 the binding agents that comprise an anti-CD47 module binds to the parental HEK293T cells and not on the CD47 knock-out cells (HEK293T-CD47KO).

As illustrated in FIG. 14 the binding agents that comprise an anti-CD47 module binds to primary human T cells.

T Cell Activation Assay

The ability of binding agents that comprise an anti-CD47 module to induce polyclonal T cell activation was performed in the presence (FIG. 16) or absence of concanavalin A (ConA, Cedarlane, 14951-250) (FIG. 15A). Briefly, PBMC were incubated for 24 hours with binding agents at the indicated concentration in the presence or absence of 10 μg/mL ConA. Plates were spun down and cells were incubated with Fc receptor blocking antibody (Biolegend, 1/200 dilution) for 10 minutes on ice. Plates were spun down again and cells were stained with APC-conjugated anti-CD3 (Cedarlane, Cat. No. 300312) and FITC-conjugated anti-CD69 antibodies (Biolegend, Cat. No. 310904, 1/500 dilution) for 30 minutes on ice. Cells were washed three times, followed by resuspension in 100 μl of 7-AAD solution (BD Bioscience, 1/100 dilution). Cells were analyzed by BD FACSCanto™ II Flow cytometer (BD Bioscience). Data were analyzed with FlowJo by gating only on single cells and live cells.

PBMC-Mediated Cytotoxicity Assay

PBMC-mediated cellular cytotoxicity was evaluated by flow cytometry (FIG. 15B). Briefly, tumor cells (THP-1 or OCI-AML3) were stained with CellTrace violet for 10 minutes at 37° C. Cells were washed and mixed with PBMC at the ratio of 5:1. Anti-CD3 antibodies or the CD33 Bi-specific T-cell engager (BiTE, G&P Bioscience, Cat. No. FLC2032) were added to activate T cells. Binding agents were added into the corresponding wells at the indicated concentrations to determine the effect of CD47 on the cytotoxicity. After incubation for 48 or 72 hours, cells were washed three times, followed by resuspension in 100 μl of 7-AAD solution (1/100 dilution, BD Bioscience, Cat. No. 559925). Cells were analyzed by BD FACSCanto™ II Flow cytometer (BD Bioscience). Data were analyzed with FlowJo by gating only on single cells and live cells.

As illustrated in FIG. 15 the binding agents comprising an anti-CD47 module did not activate T cells (FIG. 15A) and did not mediate T cell-dependent cytotoxicity against THP-1 tumor cells (FIG. 15B). Although the binding agent showed binding to HEK293T and primary T cells, it did not activate T cells in vitro, which may result in better safety for immune cell redirection without activating T cells.

Figure 16:
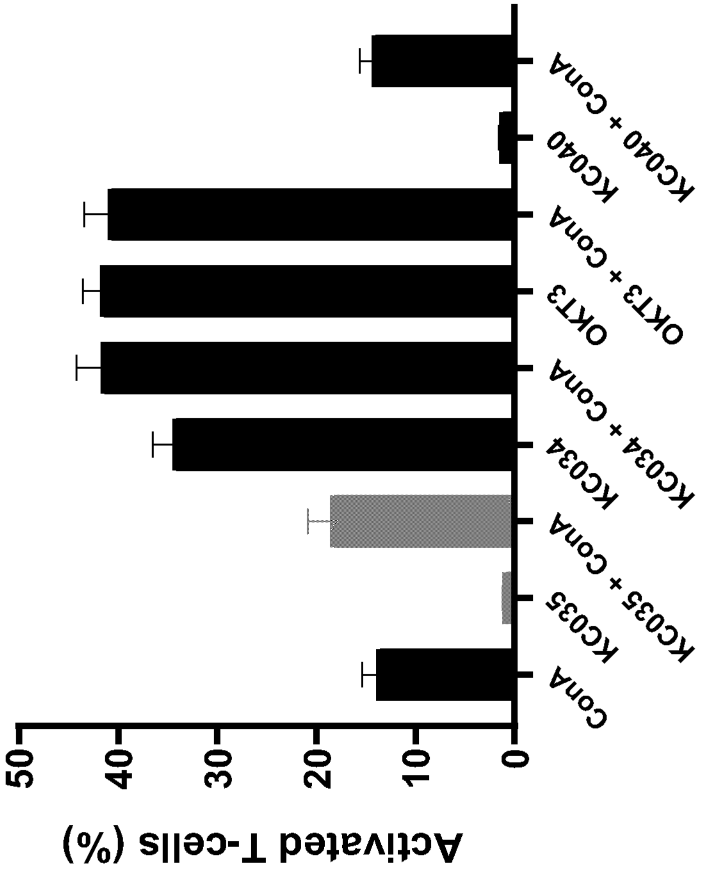
FIG. 16: graph illustrating T cell activation upon treatment with binding agent comprising D2- and CD47-specific antigen binding domains (KC040: SEQ ID NO:84) in the presence or absence of Concanavalin A. Controls include binding agent comprising HEWL-specific antigen binding domains (KC035: SEQ ID NO:93) or anti-CD3 and anti-HEWL antigen binding domains (positive control KC034; SEQ ID NO:92) or OKT3 (positive control).

As illustrated in FIG. 16 concanavalin A-mediated T cell activation is not affected by the binding agent comprising the anti-CD47 module. Concanavalin A, a superantigen, leads to T cell activation through the TCR-MHC complex. These results suggest that the anti-CD47 module did not interfere with T cell activation induced through the TCR-MHC complex.

CD47/SIRPα Blockade Bioassay

The blocking activity of binding agents comprising anti-CD47 antigen binding domains was assessed using a CD47/SIRPα blockade assay in a luminescent reporter system and compared to the B6H12 antibody as positive control (Promega, Cat. No. CS316013). CD47 CHO-K1 target cells were thawed and resuspended in Ham's F12 media containing 10% FBS. Cells suspensions were dispensed at 100 μL of CD47 CHO-K1 cells per well of a 96 well plate, and incubated overnight at 37° C., 5% $CO_2$. On the next day, 1.5× serial dilutions of test molecules were prepared in assay buffer (RMPI-1640 media containing 2% FBS). Cell media was removed and 50 μL of serially diluted antibodies were added to corresponding wells. SIRPα effector cells were thawed and resuspended in assay buffer. Cells suspensions were dispensed at 75 μL of SIRPα cell suspension per well. Plates were incubated for four hours at 37° C., 5% $CO_2$. At the end of the 4-hour incubation, 75 μL of Bio-Glo-NL Luciferase Assay Reagent was added per well, and 5-10 minutes later luminescence was measured using a Spectra Max ix3 Plate Reader.

Figure 17:
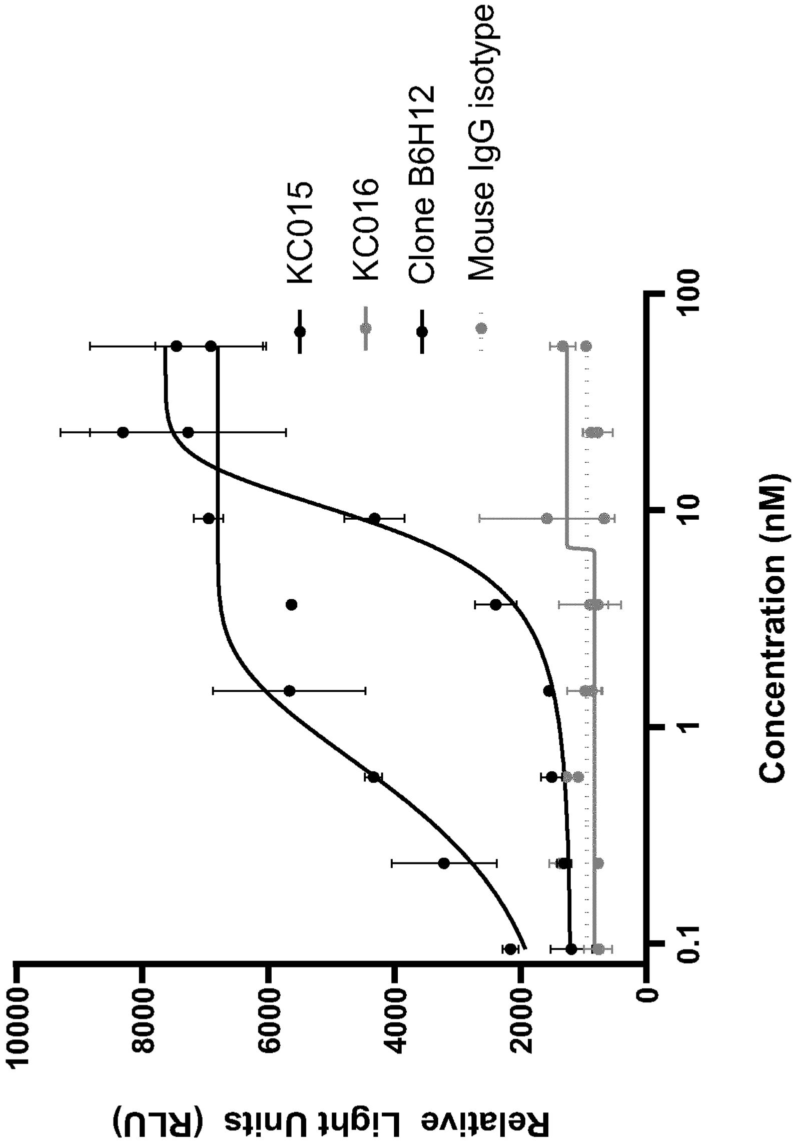
FIG. 17: graph displaying the checkpoint inhibition activity of CD47 specific binding agent (KC015; SEQ ID NO:75) using the Promega CD47/SIRPα blockade bioassay system. This system is an engineered THP-1 cell line expressing luciferase reporter induced by FcTR protein that engages FcTRs. Negative control is a binding agent that comprises HEWL-specific antigen binding domains (KC016: SEQ ID NO:76) The positive control is monoclonal antibody clone B6H12. The isotype control for clone B6H12 is the mouse IgG isotype control antibody.

As illustrated in FIG. 17, KC015 (SEQ ID NO:75) exhibited checkpoint inhibition (CPI) activity by blocking the interaction between CD47 and SIRPα. The negative control (KC016: SEQ ID NO:76) did not show any CPI activity.

Figure 18:
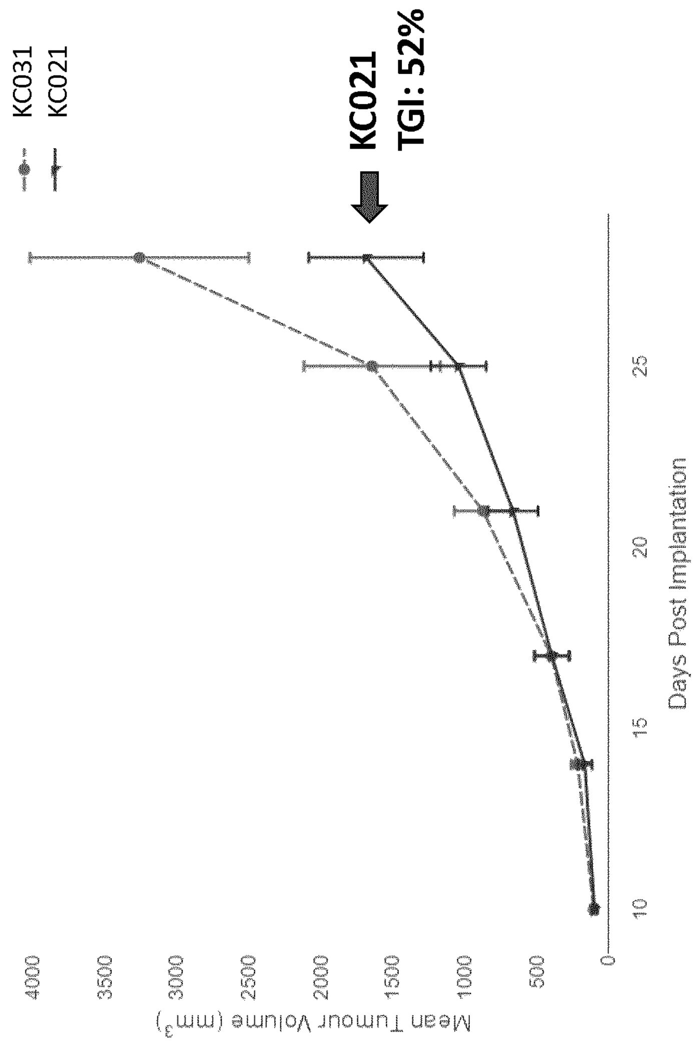
FIG. 18: graph representing tumor volume upon treatment with trispecific binding agent comprising anti-D2-, anti-PD-1 and anti-CD47 antigen binding domains (KC021: SEQ ID NO:78) in established NCI-H82 xenograft model in NCG mice. Negative control includes binding agent comprising HEWL-specific antigen binding domains (KC031: SEQ ID NO:89).
Figure 22:
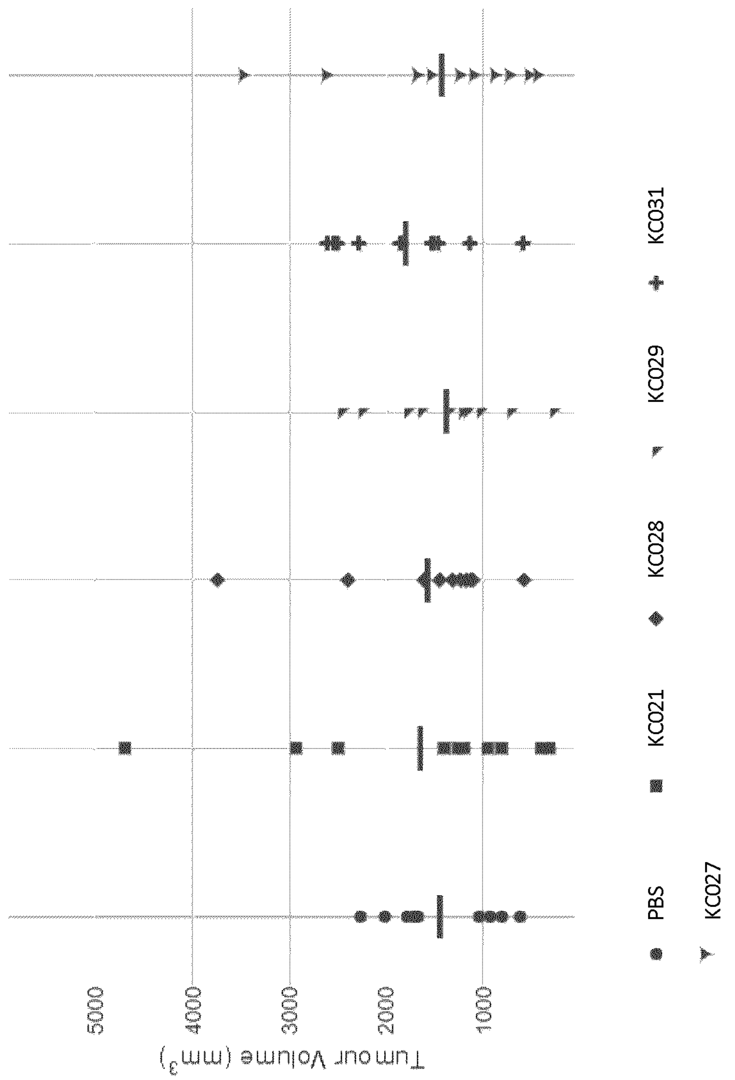
FIG. 22: graph representing tumor volume upon treatment with IgG1 or IgG4 isoforms of binding agent comprising anti-D2-, anti-PD-1- and anti-CD47 antigen binding domains (KC028; SEQ ID NO:86; KC029; SEQ ID NO:87, KC027: SEQ ID NO:85). Control includes binding agent comprising anti-HEWL antigen binding domains (KC031: SEQ ID NO: 89).

Example 6—In Vitro and In Vivo Testing of Binding Agents that Comprises Anti-DR2, Pd-1 and CD47 Antigen Binding Domains Established Tumor Model in NCG Mice To determine the anti-tumor efficacy of multivalent and multispecific binding agents, an established tumor model in humanized NCG mice was used in the study (FIG. 18, FIG. 22). In brief, NCG mice (5-6 weeks old, female) were purchased from Charles River Laboratories (St. Constant, QC). Tumor cells (8 million cells/mouse for NCI-H82) in DPBS were injected subcutaneously (s.c.) into the right flank of mice. Once tumors grew to 100 $mm^3$, mice were randomly divided into experimental groups (10 or 9 mice/group). Human PBMC (10 million cells) were injected intravenously (i.v.). The next day, each group of mice received the binding agents (28 mg/kg) treatment by intraperitoneal (i.p.), twice a week, for a total of eight doses. Tumor volumes were measured using Vernier calipers and the mice were weighed twice a week. Tumor volume and tumor growth inhibition were calculated in the same way as described above ("Tumor prevention tumor model in CB-17 Fox Chase SCID mice" in the method section). Statistical tests were performed by a student t-test (two-tailed).

As illustrated in FIG. 18 binding agents comprising anti-D2, anti-PD-1 and anti-CD47 antigen binding domains displayed a TGI of 52%. The result implied that the trispecific binding agent can suppress tumor growth in vivo. The binding agents comprising the anti-CD47 antigen binding domain disclosed herein is expected to provide better safety than other activating antibodies for immune cell redirection.

In Vitro T Cell Recruitment Assay

To test if the binding agent targeting tumor antigen (D2) and T cells could recruit T cells and bridge T cells with tumor cells, T cells were co-cultured with NCI-H69 cell clusters in the presence of the binding agents.

Figure 19:
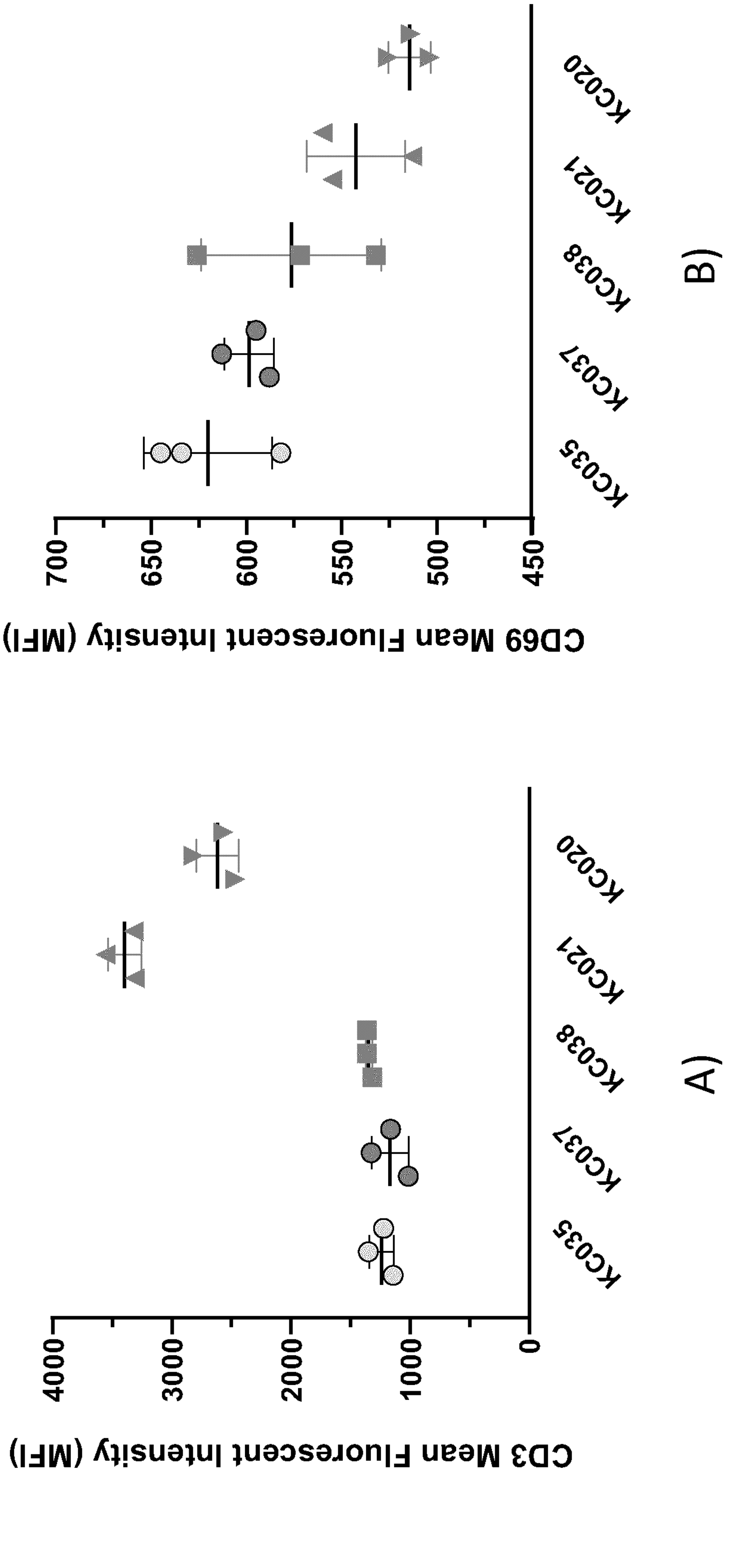
FIGS. 19A-19B: Plots representing T cell infiltration into NCI-H69 cell clusters upon treatment with binding agent comprising anti-D2 and anti-PD-1 antigen binding domains (KC037; SEQ ID NO:95), anti-PD-1 and anti-CD47 antigen binding domains (KC038; SEQ ID NO:96) or trispecific binding agents comprising same anti-D2, anti-PD1- and anti-CD47 antigen binding domains (KC020; SEQ ID NO:77 and KC021: SEQ ID NO:78) (FIG. 19A) or T cell activation with the same agents (FIG. 19B). Controls include binding agent comprising HEWL-specific antigen binding domains (KC035: SEQ ID NO:93).

Briefly, the levels of T cell recruitment into NCI-H69 SCLC cell clusters were quantified, for various binding agents containing anti-D2-, anti-PD1- and/or anti-CD47 modules, and variations of this module combination (FIG. 19). Suspension NCI-H69 cells were collected and transferred to a 12-well plate, and returned to a 37° C., 5% $CO_2$ incubator for 72 hours in order to grow larger cell clusters. After 72 hours, $5.0\times10^5$ PBMC and binding agents (final concentration of 25 μg/mL) were added to the NCI-H69 cells. Plates were returned to a 37° C., 5% $CO_2$ incubator for 24 hours to allow for T cell recruitments into NCI-H69 cell clusters.

After 24 hours, the media from each well was transferred to a microcentrifuge tube, and each tube was briefly centrifuged using a benchtop mini centrifuge for a 5 second pulse spin. The supernatant was separated, and the pellets were resuspended in 150 μL flow buffer (PBS with 5 mM EDTA).

The pellet and supernatant fractions were assessed using a brightfield microscope in order to ensure efficient separation of large cell clusters. The resuspended pellets from the microcentrifuge tubes were transferred to a 96-well plate. The plate was centrifuged at 1200 RPM to pellet cells, plates were inverted to remove supernatant, and Human TruStain FcX Block (BD Bioscience, Cat. No. 559925) was added at 2 μL per 100 μL flow buffer per well and incubated on ice for 10 minutes. The plate was centrifuged at 1200 RPM to pellet cells, and APC conjugated anti-human CD3 (Cedarlane, Cat. No. 300312) and FITC conjugated anti-human CD69 antibodies (Cedarlane, Cat. No. 310904) were added at 0.5 μL each per 100 μL flow buffer per well, including the appropriate isotype controls in separate wells. Following the addition of fluorescently-conjugated antibodies, plates were covered and incubated on ice for 30 minutes. After the incubation period, the plates were centrifuged at 1200 RPM to pellet cells and washed with 150 μl flow buffer. Plates were centrifuged at 1200 RPM to pellet cells, and resuspended in 7-AAD solution containing 1.0 μL 7-AAD per 100 μL flow buffer per well.

Cell populations were analyzed by flow cytometry. Raw reads were collected on a BD FACSCanto II machine. A total of 100,000 events were collected for data analysis. The total live cell population was assessed by gating for 7-AAD negative cells (PerCP-Cy5.5). Total T cell populations were assessed by gating for CD3 positive cells (APC), and activated T cell populations were assessed by gating for dual CD3 (APC) and CD69 (FITC) positive cells. The CD3 (APC) and CD69 (FITC) mean fluorescent intensity (MFI) was quantified and compared between treatment groups. All samples described in this report were tested in triplicate. Results represented the mean+/−standard deviation.

As illustrated in FIG. 19, it was found that the binding agents effectively recruit T cells into the NCI-H69 cell clusters in vitro.

Tumor Prevention Tumor Model in CB-17 Fox Chase SCID Mice

Binding agents comprising an anti-D2 module were tested in tumor prevention model as described in Example 3.

Figure 24:
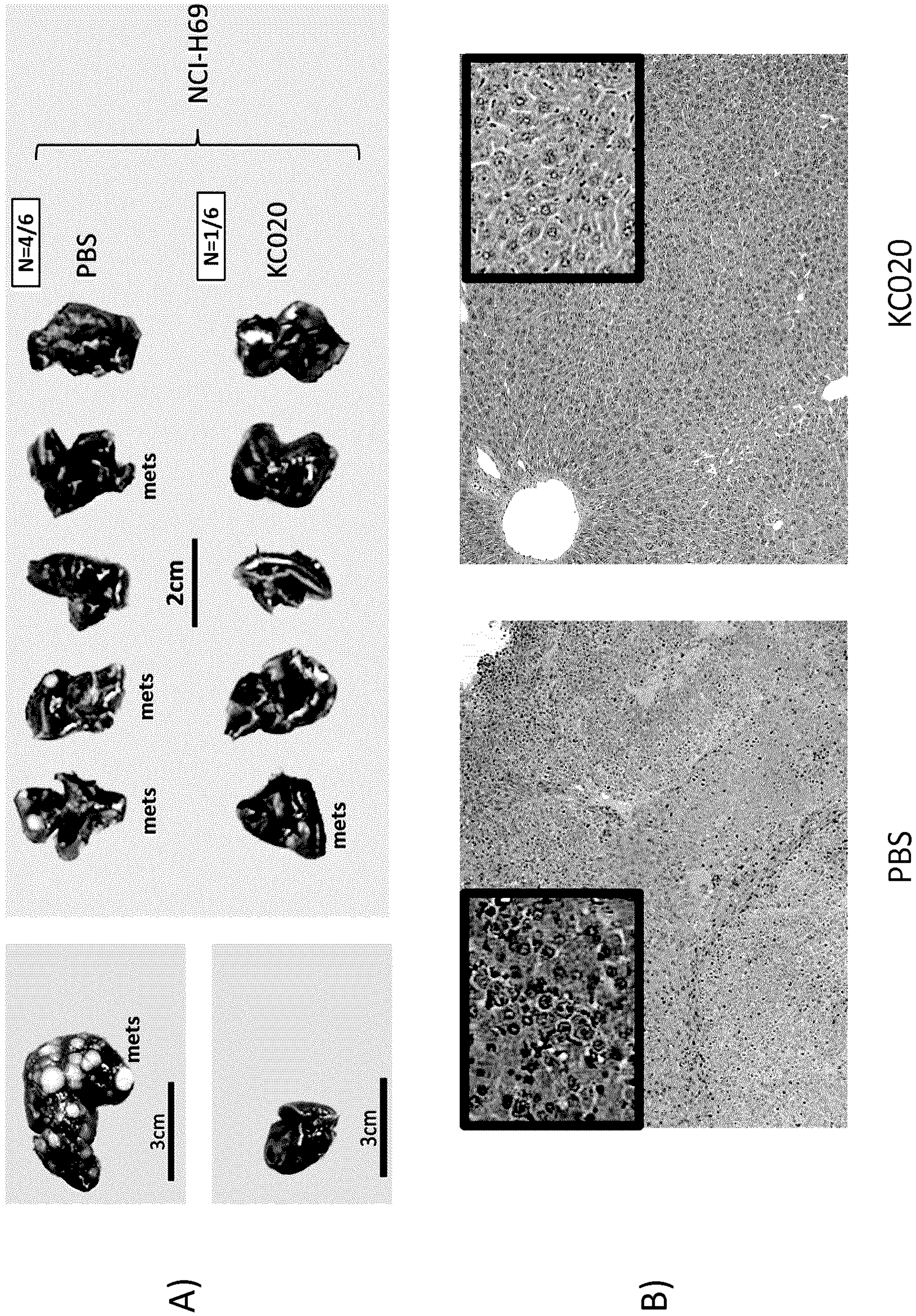
FIGS. 24A-24B: graph representing the metastasis of livers from hCD34+ humanized NCG mice bearing established NCI-H69 tumors treated with either PBS or KC020 (SEQ ID NO:77) (FIG. 24A) and H&E staining pictures of tumors indicating the disseminated tumor cells from PBS group but not KC020 (SEQ ID NO:77) group as shown in the black box (FIG. 24B).
FIG. 24C: graph representing tumor kinetics and in vivo efficacy of KC020 in the NCI-H82/PBMC co-engraftment models at an E:T ratio of 1:5 in NCG mice.
Figure 24:
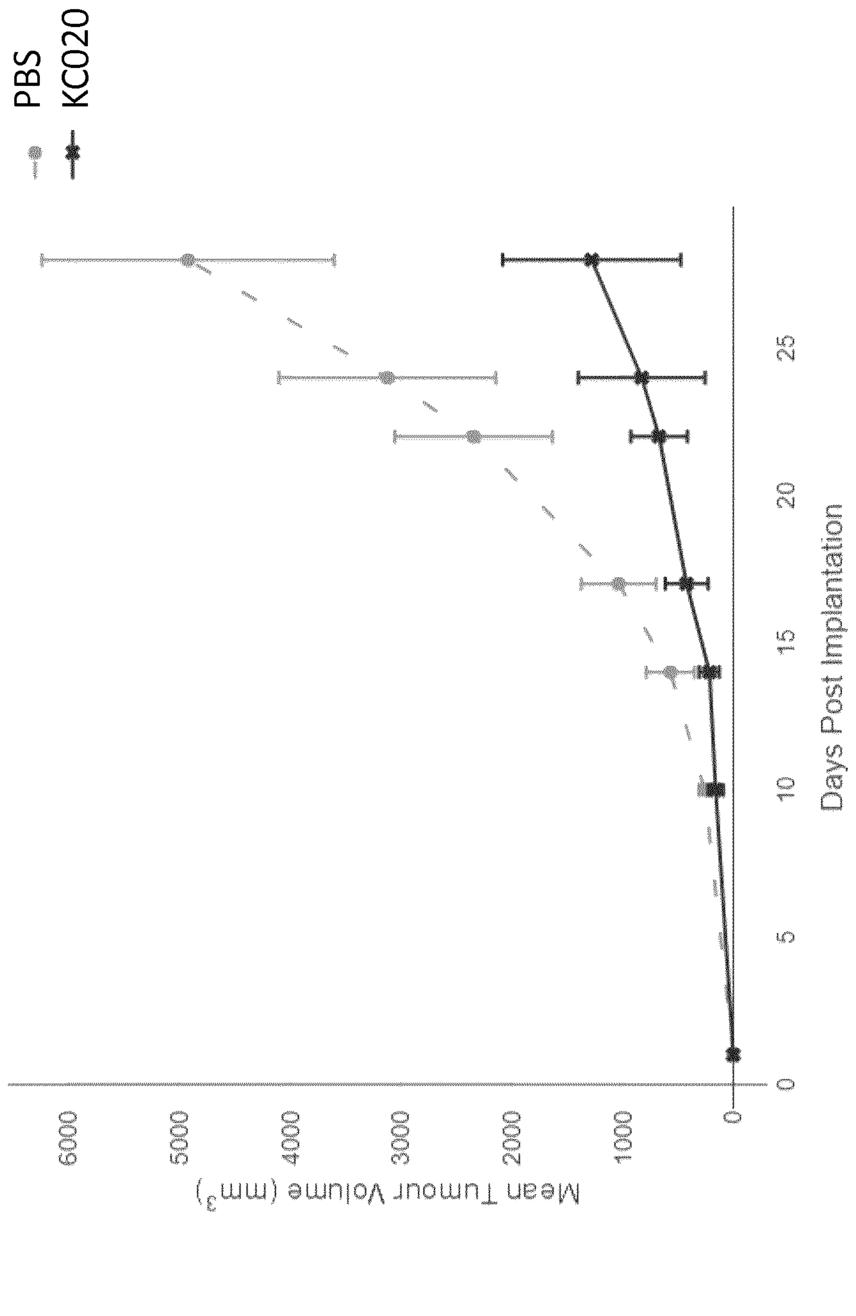

Briefly, the binding agents (KC020; SEQ ID NO:77, KC022; SEQ ID NO:79, KC023; SEQ ID NO:80, KC024; SEQ ID NO:81, KC025; SEQ ID NO:82, KC026; SEQ ID NO:83) were tested in tumor prevention model inoculated with NCI-H82 cells similarly in NCG mice, except human PBMC and NCI-H82 cells were co-engrafted with a ratio of 1:5 (FIG. 20A-B and FIG. 24C).

Figure 20:
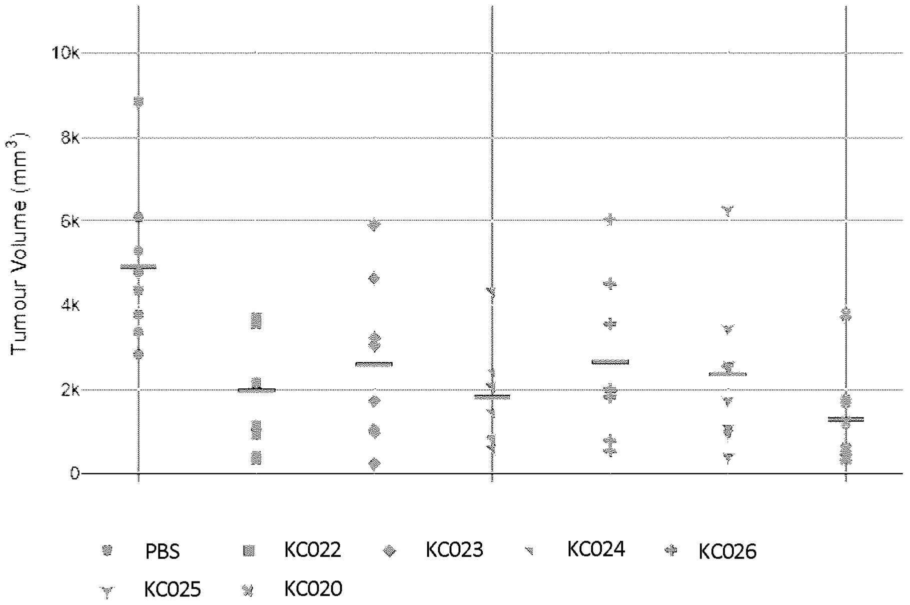
FIGS. 20A-20B: graph representing tumor volume (FIG. 20A) and table representing tumor growth inhibition (FIG. 20B) upon treatment with trispecific binding agent comprising varying anti-D2, and same anti-PD-1 and anti-CD47 antigen binding domains (KC020; SEQ ID NO:77, KC022; SEQ ID NO:79, KC023; SEQ ID NO:80, KC024; SEQ ID NO:81, KC025; SEQ ID NO:82, KC026; SEQ ID NO:83).

As illustrated in FIG. 20B the binding agent containing KC001, KC009 and KC010 (SEQ ID NO:77) showed the best efficacy of 74% compared to other D2 modules with KC009 and KC010 (FIGS. 20A&B). The superiority of KC001 efficacy data is also consistent with the D2 efficacy data as VHH-hinge-CH2-CH3 (FIG. 20), in which KC001 (KC013; SEQ ID NO:73) showed the best efficacy in several tumor models including NCI-H69, NCI-H510A, and NCI-H727.

In Vivo Efficacy of KC015 in the PBMC Pre-Engrafted Model

Figure 21:
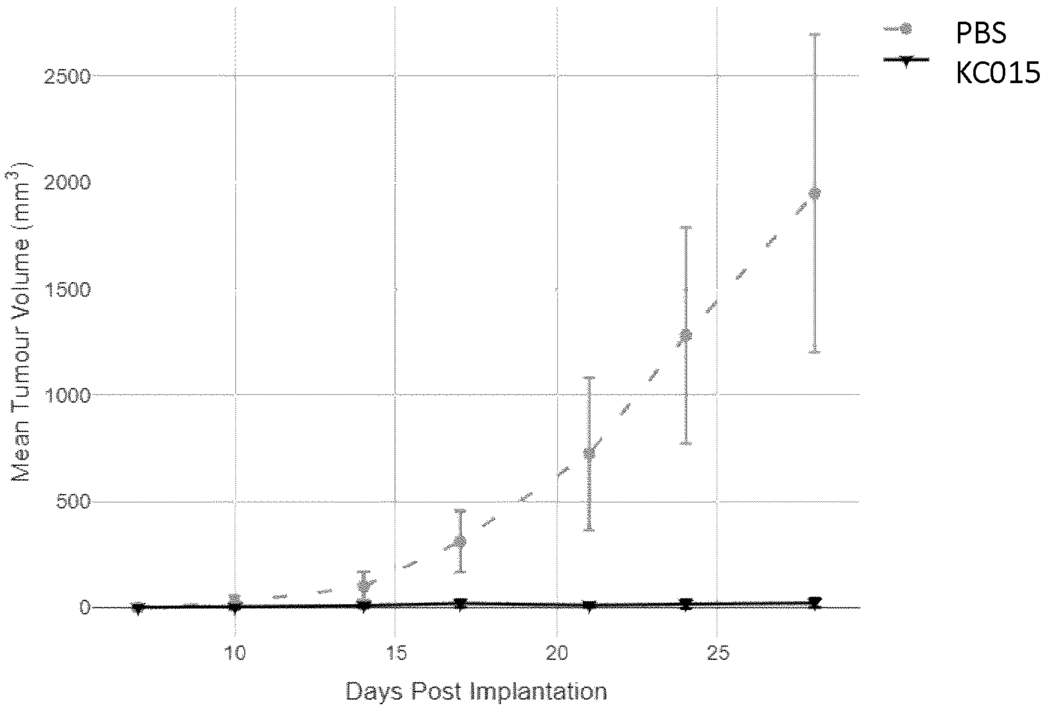
FIG. 21A: graph representing tumor volume upon treatment with CD47 specific binding agent (KC015; SEQ ID NO:75) in PBMC pre-engrafted NCI-H82 xenograft model in NCG mice. 10 million PBMC were engrafted into NCG mice 3 days before tumor cell implantation. Treatment started 10 days after PBMC engraftment, twice per week for a total of 8 doses. Negative control used in the study was PBS.
FIG. 21B: Table showing the in vivo efficacy of KC020 (SEQ ID NO:77) using various tumor cells including NCI-H69, NCI-H82, SCLC-21H and RKO in different models.
FIG. 21C: graph representing tumor volume upon treatment with anti-CD47 specific binding agent KC015 in the established MDA-MB-231 xenograft model in SCID mice. The negative control used in the study was PBS. 5 million MDA-MB-231 cells were subcutaneously (s.c.) into the right flank of mice injected into SCID. Mice received the binding agents (8 mg/kg) treatment by intraperitoneal (i.p.), once a week, for a total of eight doses.
Figure 21:
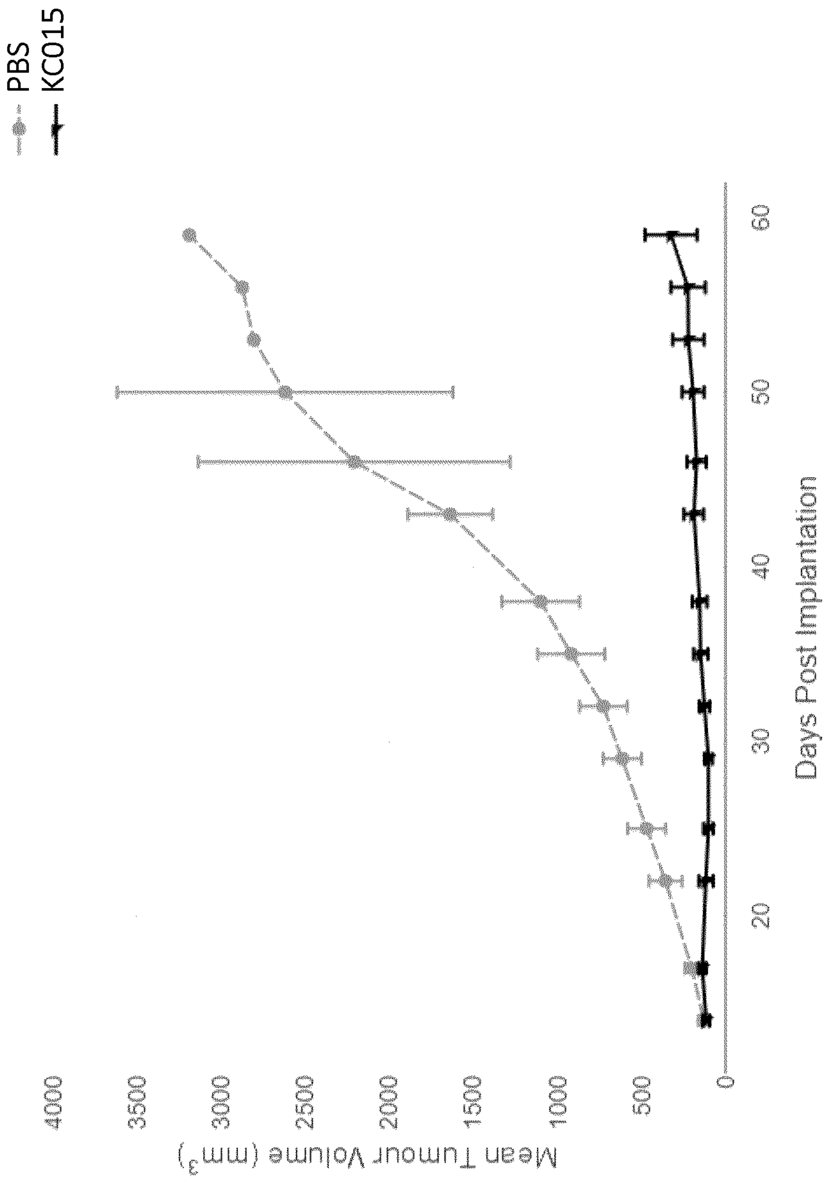

The anti-tumor activity of KC015 was evaluated in NCG mice using PBMC pre-engrafted NCI-H82 xenograph tumor model (FIG. 21A). The anti-tumor activity of KC020 was also studied in the PBMC pre-engrafted NCI-H69, RKO, and SCLC-21H xenograft tumor models (FIG. 21B) In brief, NCG mice (5-6 weeks old, female) were purchased from Charles River Laboratories (St. Constant, QC). 10 million PBMC were engrafted into NCG mice 3 days before tumor cell implantation. Treatment started 10 days after PBMC engraftment, twice per week for a total of 8 doses. Negative control used in the study was PBS. Tumor volume was calculated using the formula: ½ (Length×Width$^2$). For calculation of percentage tumor growth inhibition (TGI), the treated group was compared with its respective negative control. TGI was calculated as described herein. Statistical tests were performed by a student t-test (two-tailed).

At the end of the study, animals were sacrificed and tumor and livers were collected for metastasis analysis.

Results of these experiments showed that KC015 (SEQ ID NO:75) suppressed NCI-H82 tumor growth in the PBMC pre-engrafted model. KC020 (SEQ ID NO:77) suppressed NCI-H69, RKO and SCLC-21H xenograft tumor growth in human PBMC pre-engrafted models of cancer.

In Vivo Efficacy of KC015 in Established Tumor Model in SCID Mice

The anti-tumor efficacy of the KC015 binding agent was evaluated in an established MDA-MB-231 tumor model in SCID mice (FIG. 21C). Tumor cells (5 million cells/mouse) in PBS were injected subcutaneously (s.c.) into the right flank of SCID mice (5-6 weeks old, female; Charles River Laboratories (St. Constant, QC). Once tumors grew to 100 mm$^3$, mice were randomly divided into experimental groups (9 mice/group). The next day, each group of mice received the binding agents (8 mg/kg) treatment by intraperitoneal (i.p.), once a week, for a total of eight doses. Tumor volumes were measured using Vernier calipers and the mice were weighed twice a week. Tumor volume and tumor growth inhibition were calculated in the same way as described above. Statistical tests were performed by a student t-test (two-tailed).

As illustrated in FIG. 21C, the established MDA-MB-231 tumor model did not grow upon treatment with KC015 indicating a potent anti-tumor activity in this tumor model.

In Vivo Efficacy of IgG4 Versus IG1 Version of Binding Agents.

IgG4 is commonly used for therapeutic antibodies to avoid the ADCC effect, which in this case may lead to T cell killing, and cytokine release storm. To determine the anti-tumor efficacy of binding agents comprising an IgG4 CH3 domain, established tumor model in humanized NCG mice was used as described above.

As illustrated in FIG. 22 there no significant difference was observed between IgG4 and IgG1 versions of the binding agents (compare KC021 (SEQ ID NO:78) and KC027: SEQ ID NO:85).

Figure 23:
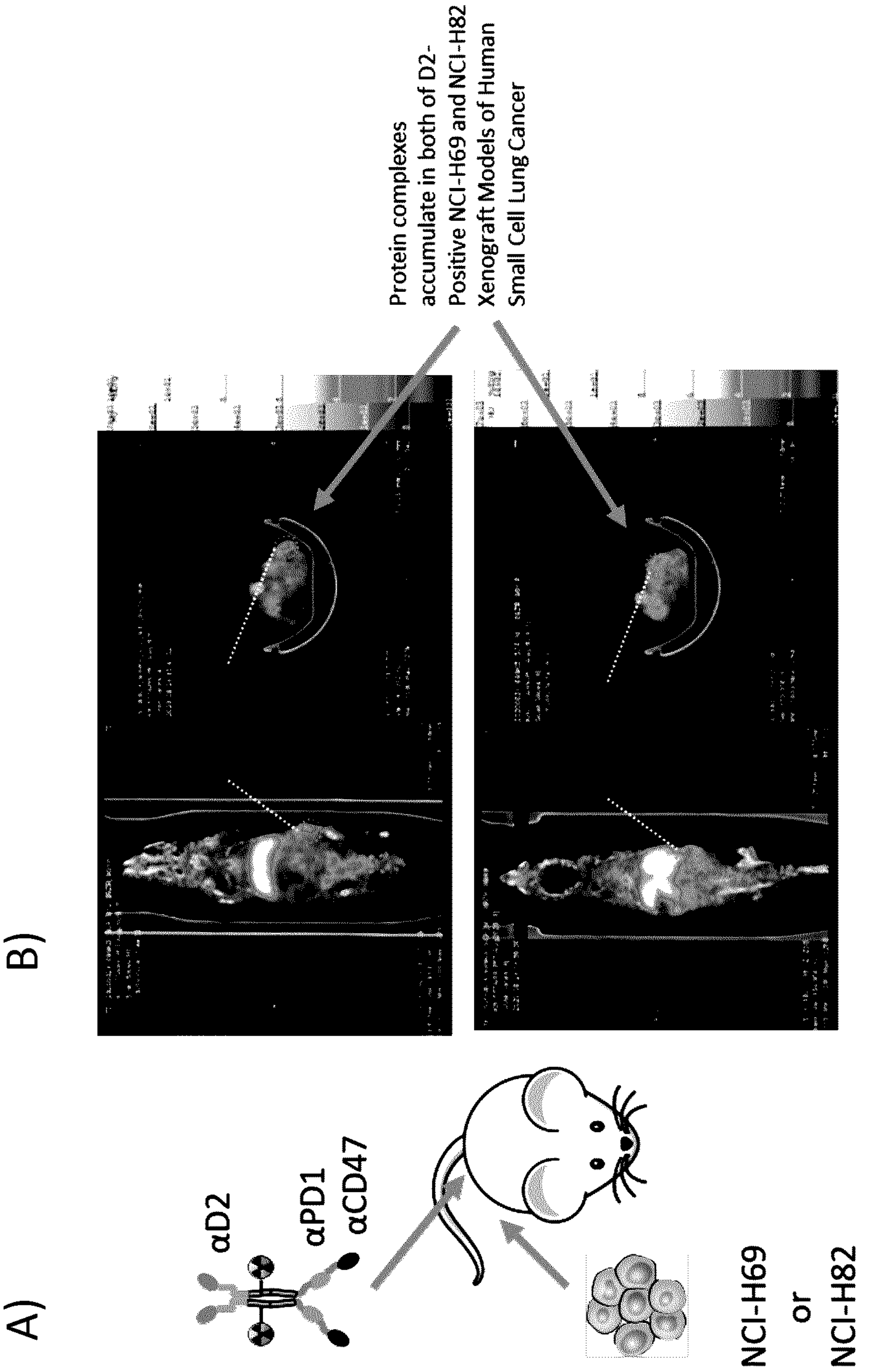
FIGS. 23A-23B: illustration of the biodistribution experiment (FIG. 23A) and pictures (FIG. 23B) displaying the accumulation of trispecific binding agent comprising anti-D2, anti-PD-1 and anti-CD47 antigen binding domains (KC021; SEQ ID NO:78) in the NCI-H82 (top panel) and NCI-H69 (bottom panel) xenograft models in NCG mice.

Micro-PET/CT Imaging of Binding Agents Biodistribution in Tumor Bearing Mouse Models The radiolabeling of binding agents and micro-PET/CT imaging of its biodistribution were performed (FIG. 23). A preparation of binding agent was first buffer exchanged with 0.1 M Sodium carbonate, pH 9.0, using Amicon® Ultra-4 Centrifugal Filter (MWCO 30 kDa, UFC803008). The binding agent was then modified with desferrioxamine (DFO) by a reaction with a 14-fold molar excess of p-isothiocyanatobenzyl desferrioxamine (p-NCS-Bz-DFO, Macrocyclics). Briefly, 20-40 μL of a 20 mM (15 μg/L) solution of p-NCS-Bz-DFO in anhydrous DMSO was reacted with 4-7 mg of binding agent (3-4 mg/mL in 0.1 M $NaHCO_3$ buffer, pH 9.0) for 30 minutes at 37° C. with mixing at 300 rpm on an Excella E24 mixer (New Brunswick Scientific). The reaction was split into small aliquots to avoid cross linking and aggregation of the antibody. After 30 minutes reaction, excess p-NCS-Bz-DFO was removed by ultrafiltration, repeated 4 times on an Amicon Ultra-4 centrifugal filter device (Millipore, 30 kDa cutoff) centrifuged at 5000×g for 5 minutes using excess 0.25 M Na acetate buffer, pH 5.5.

The purity and homogeneity of the DFO-binding agent were assessed by sodium dodecyl sulfate polyacrylamide gel electrophoresis (SDS-PAGE) on a 4-20% Tris-HCl gel (Bio-Rad) under reducing (2-mercaptoethanol) and non-reducing conditions.

After DFO conjugation, the binding agent was radiolabeled with $^{89}$Zr by the following protocol. $^{89}$Zr as the oxalate salt was purchased from Washington University (St. Louis, MO) and was incubated for 3 minutes with 2 M $NaCO_3$, pH 10.0, to neutralize the solution. Then, 0.25 M Na acetate buffer containing 32 mM gentisic acid (5 mg/mL) and 0.5 M of 4-(2-hydroxyethyl)-1-piperazineethanesulfonic acid (HEPES buffer), pH 7.0, were added followed by binding agent comprising D2-, PD-1- and CD47-specific antigen binding domains (KC020; SEQ ID NO:77) (1-5.0 mg/mL). Radiolabeling was performed at room temperature for 60-90 minutes at a specific activity of 0.28 mCi/mg. Radiochemical purity was measured by instant thin layer-silica gel chromatography (ITLC-SG) developed in 22 mM citric acid in 20 mM $Na_2CO_3$, pH 5.0.

After radiolabeling, [$^{89}$Zr]-DFO-binding agent was injected into mice with 2 different types of xenografts (NCI-H69 and NCI-H82). Mice were anesthetized using isoflurane (Fresenius Kabi Canada Ltd.) anesthesia (5% induction, 1.5-2% maintenance), followed by i.v. injection with [$^{89}$Zr]-DFO-binding agent and received 200 μL, 2.86±0.2 MBq, and 30 mg/Kg. Animals were imaged using Mediso nanoScan® SPECT/CT/PET 82S system at 24 hours, 96 hours, and 144 hours post injection.

As illustrated in FIG. 23A and FIG. 23B, it was found that the radiolabeled binding agent showed accumulation in the tumors in both NCI-H69 and NCI-H82 xenograft models, suggesting the recruitment of binding agent via the tumor antigen.

Example 7—In Vivo Testing of Binding Agents in the hCD34+ Humanized NCG Mice Model The hCD34+ humanized NCG mice were purchased from the Charles River Laboratories. HSC engraftment level was assessed by flow cytometry one day before tumor implantation. The mice were randomized into 2 groups and NCI-H69 cells were implanted subcutaneously (s.c) on the right flank of each animal (8 million cells per animal). Once tumors reached an average of 100 mm$^3$ in volume, negative control and test article were administered by IP injection twice per week. Tumor volume, percentage tumor growth inhibition (TGI) and statistical analysis are performed as described in Example 3.

At the end of the study, animals were sacrificed and tumor and livers were collected for metastasis analysis.

Results of these experiments presented in FIG. 24A-B showed that KC020 (SEQ ID NO:77) reduced metastasis of NCI-H69 cells to the liver in hCD34+ humanized NCG mice model. Results of FIG. 24C also showed the efficacy of KC020 (SEQ ID NO:77) in the NCI-H82/PBMC co-engraftment model.

Example 8—Testing Binding Agents in Other Solid Tumors

To determine the anti-tumor efficacy of anti-D2 binding agent including KC013, KC011, KC012, and KC014 in in the NCI-H510A and NCI-H727 s.c. preventative xenograft model of human Small Cell Lung Cancer, female SCID mice were purchased from Charle River Laboratories and were used for the studies when 4-6-weeks old. For NCI-H510a cells, cells were implanted subcutaneously (s.c) on the right flank of each animal, 8 million cells per mice. For NCI-H727 cells, cells were implanted subcutaneously (s.c) on the right flank of each animal, 1 and 6 million cells per mice. The next day, vehicle control and test articles were administered by i.p injection once a week. Tumor volume, percentage tumor growth inhibition (TGI) and statistical analysis are performed as described in Example 3.

To evaluate the efficacy of anti-D2 binding agent in the PANC1 s.c. preventative xenograft model of human pancreas cancer, female SCID mice were purchased from Charles River Laboratories and were used for the studies when 4-6-week old. Cells were implanted subcutaneously (s.c.) on the right flank of each animal, 5 million each. Treatment was initiated one day after cell implantation. Negative control antibody and test articles were administered by i.p. injection once weekly. Tumor volume, percentage tumor growth inhibition (TGI) and statistical analysis are performed as described in Example 3.

Example 9—Stability Studies

Solutions of purified binding agents at a concentration of 20 mg/mL (+/−0.5) were prepared and separated in two batches. One batch was stored at −80° C. (not stressed conditions) and the other batch was submitted to various stress conditions including agitation for three days (25° C.), freeze and thaw for five cycles, 40° C. storage for two weeks, or low pH (3.5) treatment for 4 hours and 48 hours. Both batches were tested for binding to D2-containing proteoliposomes (FIG. 25A and FIG. 26A), to recombinant PD-1 (Cedarlane, Cat. No. 10377-H08H-50) (FIG. 25B and FIG. 26B) or to recombinant CD47 (Cedarlane. Cat. No. 12283-H08H-200) (FIG. 25C and FIG. 26C) as described in Examples 3 and 4.

Figure 25:
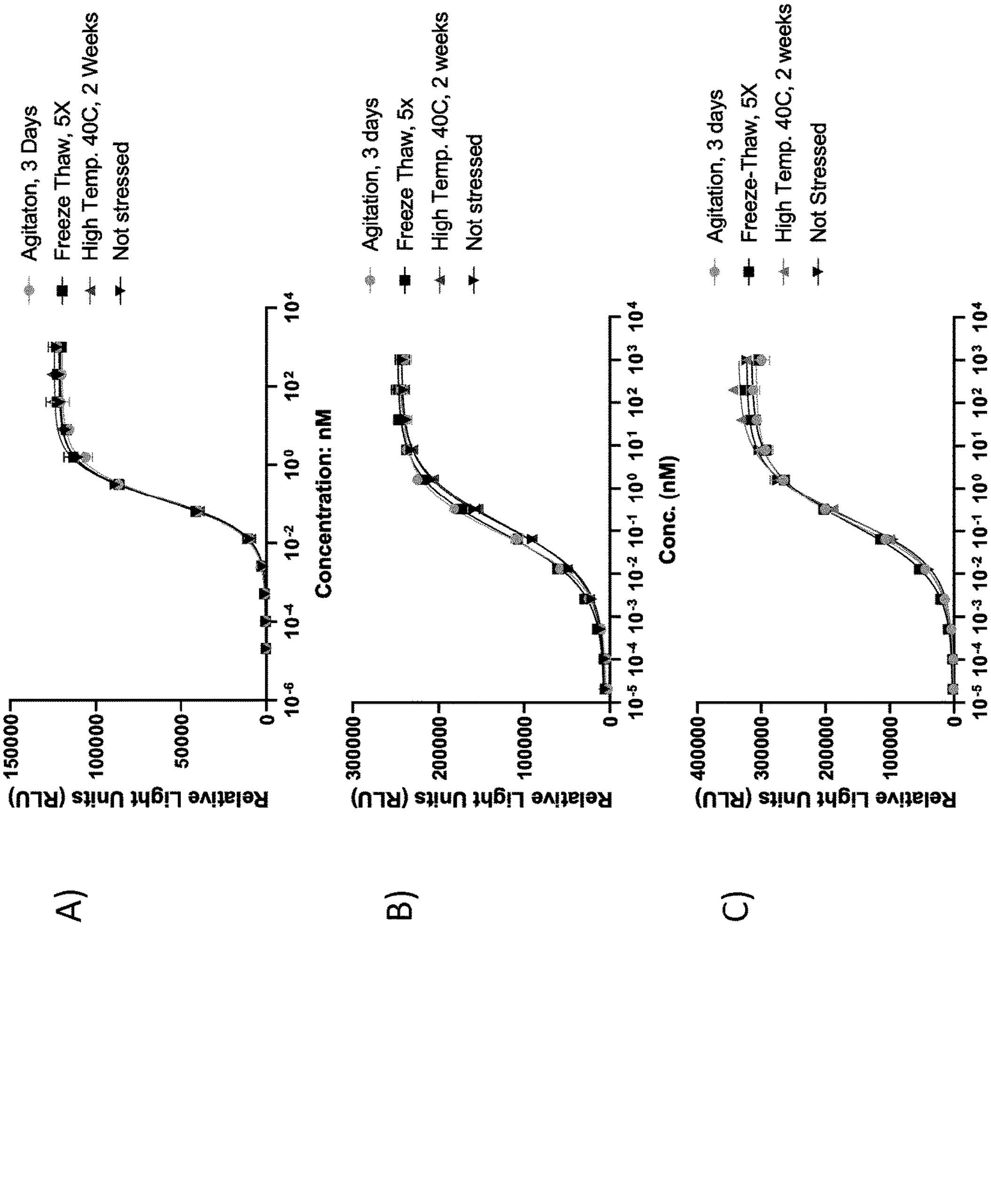
FIGS. 25A-25C: graph representing binding of KC020 (SEQ ID NO:77) submitted to stress conditions on D2 proteoliposome (FIG. 25A), human recombinant PD-1 protein (FIG. 25B), and human recombinant CD47 protein (FIG. 25C) as measured by ELISA assay. The stressed conditions include agitation for 3 days, freeze and thaw for five times, and storage at 40° C. for two weeks.
Figure 26:
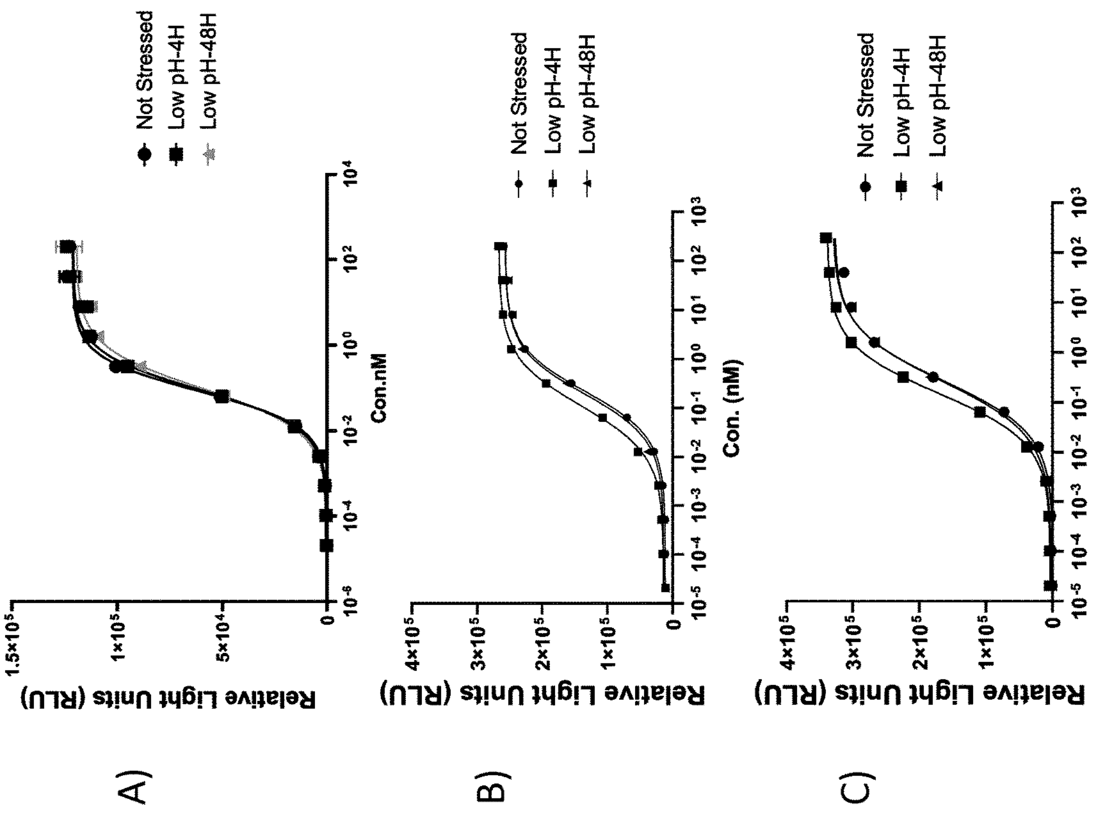
FIGS. 26A-26C: graph representing binding of KC020 (SEQ ID NO:77) submitted to low pH stress on D2 proteoliposome (FIG. 26A), human recombinant PD-1 protein (FIG. 26B), and human recombinant CD47 protein (FIG. 26C) as measured by ELISA assay. The stressed conditions include treatment at pH 3.5 for 4 hours and 48 hours.

Results presented in FIG. 25 and FIG. 26 indicate that the binding of KC020 to its targets is not affected by the tested stress conditions.

In addition the biophysical characteristics (solubility and aggregation) of the solution did not significantly change under these conditions.

Similar results were obtained for several other binding agents (data not shown).

Figure 27:
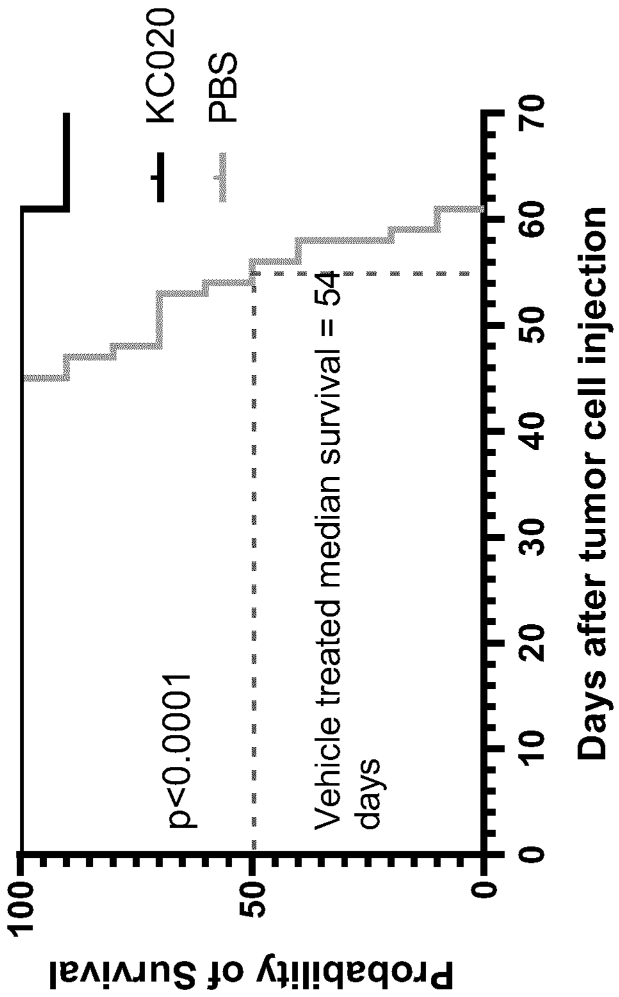
FIG. 27: graph representing the survival curves of KC020 treated animals implanted with the NCI-H82 SCLC tail vein metastatic model. NCG mice were inoculated with 50,000 NCI-H82 cells, followed by KC020 treatment the next day. KC020 was treated biweekly. Negative control used in the study was PBS.

Example 10—Testing Binding Agents in a NCI-H82 Tail Vein Metastatic Model of SCLC NCG mice (5-6 weeks old, female) were purchased from Charles River Laboratories (St. Constant, QC). NCG mice were inoculated with 50,000 NCI-H82 cells through tail vein injection. Mice received the KC020 treatment 24 hours before tumor cell injection by intraperitoneal injection. KC020 was administered biweekly for a total of 8 doses. Animals were monitored for body weight loss and overall health for the entire duration of the study. Overall, KC020 treatment significantly prolonged survival in mice transplanted i.v. with the NCI-H82 SCLC compared to the vehicle-treated negative control group (FIG. 27).

For the in vivo bioluminescence imaging study, a total of 20 NCG mice were randomly distributed into 4 groups, including PBS group, KC020 3 mg/kg group, KC020 10 mg/kg group and KC020 30 mg/kg group. At Day 0, all mice received one treatment of KC020 or PBS. For the KC020 3 mg/kg group, mice received one treatment of human IgG at 10 mg/kg one day before KC020 treatment. The NCI-H82-luciferase cells were inoculated into the NCG mice through tail vein injection, 100,000 cells per mouse. All mice were treated twice a week with either PBS or KC020, for a total of 8 doses. Bioluminescence imaging were performed three weeks after tumor cell inoculation, once per week. Before imaging, mice were dosed with firefly luciferase substrate at 15 mg/mL in DPBS, with the administration volume of 200 μL through intraperitoneal injection. The result of this experiment shows that KC020 treatment prevented the tumor development even at all doses tested including the lowest dose of 3 mg/kg.

The results presented herein indicates, amongst other things, that the binding agents of the present disclosure bind to each of its target and exhibit in vitro CPI activity, display in vivo tumor suppression efficacy in both preventative and established xenograft models of human cancers, prevent metastasis development and extend mice survival in the tail vein model of human cancers. In addition, the binding agents of the present disclosures are produced in very high yield in a manufacturing cell line and exhibits favorable stability under accelerated stability testing.

The embodiments and examples described herein are illustrative and are not meant to limit the scope of the claims. Variations of the foregoing embodiments, including alternatives, modifications and equivalents, are intended by the inventors to be encompassed by the claims. Citations listed in the present application are incorporated herein by reference.

REFERENCES

All patents, patent applications and publications referred to throughout the application are incorporated herein by reference.

Angal, S. et al., A Single Amino Acid Substitution Abolishes the Heterogeneity of Chimeric Mouse/human IgG4 Antibody, Mol Immunol 30, 105-108, 1993

Chen X et al., Fusion Protein Linkers: Properties, Design and Functionality, Adv Drug Deliv Rev. 2013; 65(10): 1357-1369.

Conrath, K. E. et al., Camel Single-Domain Antibodies as Modular Building Units in Bispecific and Bivalent Antibody Constructs. J. Biol. Chem. 2001, 276, 7346-7350.

Coppieters, K. et al., Formatted Anti-Tumor Necrosis Factor alpha VHH Proteins Derived from Camelids Show Superior Potency and Targeting to Inflamed Joints in a Murine Model of Collagen-induced Arthritis. Arthritis Rheum. 2006, 54, 1856-1866.

Detallea L, et al., Generation and Characterisation of ALX-0171, a Potent Novel Therapeutic Nanobody for the Treatment of Respiratory Syncytial Virus infection. Antimicrobial Agents and Chemotherapy 60(1) 2015

De Vlieger et al., Single-domain Antibodies and their Formatting to Combat Viral Infections, Antibodies 8(1), 1-22, 2019

Duggan S. Caplacizumab: First Global Approval. Drugs (2018) 78:1639-1642

Fleischmann R, et al., A Novel Individualized Treatment Approach in Open-Label Extension Study of Ozoralizumab (ATN-103) in Subjects with Rheumatoid Arthritis on a Background of Methotrexate. Abstract 1311, ACR/ARHP Annual Meeting (2012).

Fridy P C, et al., A Robust Pipeline for Rapid Production of Versatile Nanobody Repertoires. Nat Methods. 2014 December; 11(12): 1253-1260.

Godar M et al. Therapeutic Bispecific Antibody Formats: a Patent Applications Review (1994-2017) Expert Opinion on Therapeutic patents, 2018; 28(3):251-276

Ha, J-H et al. Immunoglobulin Fc Heterodimer Platform Technology: From Design to Applications in Therapeutic Antibodies and Proteins, Front Immunol, 2016; 7:394.

Hamers-Casterman C, et al., Naturally-occurring Antibodies Devoid of Light-chains. Nature 1993, 363:446-448.

Hmila, I. et al., VHH, Bivalent Domains and Chimeric Heavy Chain-only Antibodies with High Neutralizing Efficacy for Scorpion Toxin AahI'. Mol. Immunol. 2008, 45, 3847-3856.

Hultberg, A et al., Llama-derived Single Domain Antibodies to Build Multivalent, Super Potent and Broadened Neutralizing Anti-viral Molecules. PLoS One 2011, doi: 10.1371/journal.pone.0017665.

Jähnichen S, et al, CXCR4 Nanobodies (VHH-based single variable domains) Potently Inhibit Chemotaxis and HIV-1 Replication and Mobilize Stem Cells. Proc Natl Acad Sci USA. (2010) 107: 20565-20570.

Kovalenko O V et al. Atypical Antigen Recognition Mode of a Shark Immunoglobulin New Antigen Receptor (IgNAR) Variable Domain Characterized by Humanization and Structural Analysis, J Biol Chem. 2013, 288:17408-17419

Muyldermans, S and Smider, 2016. Distinct Antibody Species: Structural Differences Creating Therapeutic Opportunities. Current Opinion in Immunology 2016, 40:7-13

Muyldermans, S et al., 1994. Sequence and Structure of VH Domain From Naturally Occurring Camel Heavy Chain Immunoglobulins Lacking Light Chains. Protein Eng. 7: 1129-1135.

Saunders K. O., Conceptual Approach to Modulating Antibody Effector Functions and Circulation Half-Life, Front. Immunol. 10:1296, 2019.

Schoen P, et al., Anti-RANKL Nanobody® ALX-0141 Shows Sustained Biomarker Inhibition in a Phase I Study in Healthy Postmenopausal Women. DOI: 10.1530/boneabs.1.PP135 (2013)

Simmons, D. P et al., Dimerisation Strategies for Shark IgNAR Single Domain Antibody Fragments. J. Immunol. Methods 2006, 315, 171-184.

Svecova D, et al., A Randomized, Double-Blind, Placebo-Controlled Phase 1 Study of Multiple Ascending Doses of Subcutaneous M1095, an Anti-Interleukin-17A/F Nanobody®, in Moderate-to-Severe Psoriasis. J Am Acad Dermatol. 2019 Mar. 26.

Tatusova, T. A, et al. (1999), BLAST 2 Sequences, a New Tool for Comparing Protein and Nucleotide Sequences, FEMS Microbiol Lett. 174:247-250)

Van Roy M, et al., The Preclinical Pharmacology of the High Affinity Anti-IL-6R Nanobody® ALX-0061 Supports its Clinical Development in Rheumatoid Arthritis. Arthritis Research & Therapy (2015) 17:135

Vincke C. et al. General Strategy to Humanize a Camelid Single-Domain Antibody and Identification of a Universal Humanized Nanobody Scaffold, J. Biol Chem. 2009, 284(5):3273-3284

Vu, K. B., et al., 1997. Comparison of Llama VH Sequences from Conventional and Heavy Chain Antibodies. Mol. Immunol. 34: 1121-1131.

Sequence Tables

TABLE 3 anti-D2 VHHs sequences

| Anti-DR2 VHHs | CDR1 | CDR2 | CDR3 |
|---|---|---|---|
| KC001 (Kabat CDRs) | ITAMN (SEQ ID NO: 1) | GISSSGKITYQDSVKG (SEQ ID NO: 2) | WAGARDAI (SEQ ID NO: 3) |
| KC001 (IMGT CDRs) | EIIFSITA (SEQ ID NO: 4) | ISSSGKI (SEQ ID NO: 5) | NTWAGARDAI (SEQ ID NO: 6) |
| KC001 (VHH) (SEQ ID NO: 7) | QVQLQESGGGLVQAGGSLRLSCAASEIIFSITAMNWYRQAPGKQRELVAGISSSGKITYQDSVKGRFTISKDNAKNTLYLQMNSLKPEDTAVYYCNTWAGARDAIWGQGTQVTVSS | | |
| KC002 (Kabat CDRs) | NKDMG (SEQ ID NO: 8) | AIAKNNGSTYYADSVKG (SEQ ID NO: 9) | LTHRGASKFNY (SEQ ID NO: 10) |
| KC002 (IMGT CDRs) | GDRITNKD (SEQ ID NO: 11) | IAKNNGST (SEQ ID NO: 12) | AGLTHRGASKFNY (SEQ ID NO: 13) |
| KC002 (VHH) (SEQ ID NO: 14) | QVQLLESGGGLVQPGGSLRLSCAASGDRITNKDMGWVRQAPGKGLEWVSAIAKNNGSTYYADSVKGRFTISRDNSKNTLYLQMNSLRAEDTAVYYCAGLTHRGASKFNYWGQGTLVTVSS | | |
| KC003 (Kabat CDRs) | RHAMS (SEQ ID NO: 15) | DIRSGDGGDGGTSYADSVKG (SEQ ID NO: 16) | GLWKILPST (SEQ ID NO: 17) |
| KC003 (IMGT CDRs) | GFTFSRHA (SEQ ID NO: 18) | IRSGDGGDGGT (SEQ ID NO: 19) | ALGLWKILPST (SEQ ID NO: 20) |
| KC003 (VHH) (SEQ ID NO: 21) | QVQLQESGGGLAPPGGSLRLSCAASGFTFSRHAMSWVRQAPGKGLEWVSDIRSGDGGDGGTSYADSVKGRFTISRDNAKNTLYLQMNSLKPEDTAVYYCALGLWKILPSTRGRGTQVTVSS | | |
| KC004 (Kabat CDRs) | QRAMS (SEQ ID NO: 22) | DIKSTGETSYADSVKG (SEQ ID NO: 23) | GLWKILPSV (SEQ ID NO: 24) |
| KC004 (IMGT CDRs) | GLTFSQRA (SEQ ID NO: 25) | IKSTGET (SEQ ID NO: 26) | ALGLWKILPSV (SEQ ID NO: 27) |
| KC004 (VHH) (SEQ ID NO: 28) | QVQLQESGGGLVHPGGSLRLSCAASGLTFSQRAMSWVRQAPGKGLEWISDIKSTGETSYADSVKGRFTISRDNARNTVYLQMNSLKPEDTAVYYCALGLWKILPSVRGRGTQVTVSS | | |
| KC005 (Kabat CDRs) | LRSMG (SEQ ID NO: 29) | VITSSAASTNYADSVKG (SEQ ID NO: 30) | RGASRWYGTPSDY (SEQ ID NO: 31) |
| KC005 (IMGT CDRs) | GSSLSLRS (SEQ ID NO: 32) | ITSSAAST (SEQ ID NO: 33) | NFRGASRWYGTPSDY (SEQ ID NO: 34) |
| KC005 (VHH) (SEQ ID NO: 35) | QVQLQESGGGLVQPGGSLRLSCAASGSSLSLRSMGWYRQGPGKMRELVAVITSSAASTNYADSVKGRFTISFDNAKNTMYLQMNSLTPEDTAVYYCNFRGASRWYGTPSDYWGQGTQVTVSS | | |
| KC006 (Kabat CDRs) | LRSMG (SEQ ID NO: 36) | VITSSAASTNYADSVKG (SEQ ID NO: 37) | RGASRWYGTPSDY (SEQ ID NO: 38) |
| KC006 (IMGT CDRs) | GSSLSLRS (SEQ ID NO: 39) | ITSSAAST (SEQ ID NO: 40) | NFRGASRWYGTPSDY (SEQ ID NO: 41) |
| KC006 (VHH) (SEQ ID NO: 42) | QVQLQESGGGLVQAGGSLRLSCAASGSSLSLRSMGWYRQGPGKMRELVAVITSSAASTNYADSVKGRFTISFDNAKNTMYLQMNSLTPEDTAVYYCNFRGASRWYGTPSDYWGQGTQVTVSS | | |
| KC007 (Kabat CDRs) | QRAMS (SEQ ID NO: 43) | DIRSTGDTSYADSVKG (SEQ ID NO: 44) | GLWKILPSA (SEQ ID NO: 45) |

TABLE 3-continued

| anti-D2 VHHs sequences | | | |
|---|---|---|---|
| Anti-DR2 VHHs | CDR1 | CDR2 | CDR3 |
| KC007 (IMGT CDRs) | GFAFSQRA (SEQ ID NO: 46) | IRSTGDT (SEQ ID NO: 47) | ALGLWKILPSA (SEQ ID NO: 48) |
| KC007 (VHH) (SEQ ID NO: 49) | QVQLQESGGGLVQPGGSLLLSCAASGFAFSQRAMSWVRQAPGKG LEWVSDIRSTGDTSYADSVKGRFTISRDNAKNTLYLQMNSLKPED TAVYYCALGLWKILPSARGRGTQVTVSS | | |
| KC008 (Kabat CDRs) | QRAMS (SEQ ID NO: 50) | DIRSTGDTSYA DSVKG (SEQ ID NO: 51) | GLWKILPSA (SEQ ID NO: 52) |
| AKC008 (IMGT CDRs) | GFTFSQRA (SEQ ID NO: 53) | IRSTGDT (SEQ ID NO: 54) | ALGLWKILPSA (SEQ ID NO: 55) |
| KC008 (VHH) (SEQ ID NO: 56) | QVQLQESGGGLVQPGGSLLLSCAASGFTFSQRAMSWVRQAPGKG LEWVSDIRSTGDTSYADSVKGRFTISRDNAKNTLYLQMNSLKPED TAVYYCALGLWKILPSARGRGTQVTVSS | | |

TABLE 4

| anti-PD-1 VHHs | | | |
|---|---|---|---|
| Anti-PD-1 VHHs | CDR1 | CDR2 | CDR3 |
| KC009 (Kabat CDRs) | RSSMS (SEQ ID NO: 57) | IISSSGIITHYSDSVK G (SEQ ID NO: 58) | VLDDDSGDY (SEQ ID NO: 59) |
| KC009 (IMGT CDRs) | GFTFSRSS (SEQ ID NO: 60) | ISSSGIIT (SEQ ID NO: 61) | NAVLDDDSGDY (SEQ ID NO: 62) |
| KC009 (VHH) (SEQ ID NO: 63) | QVQLQESGGGWVQPGGSLRLSCVASGFTFSRSSMSWHRQAPGKE RDLVAIISSSGIITHYSDSVKGRFTISRDNAKDTVYLQMNSLKPEDT AVYVCNAVLDDDSGDYWGQGTQVTVSS | | |

TABLE 5

| anti-CD47 VHHs | | | |
|---|---|---|---|
| Anti-CD47 VHHs | CDR1 | CDR2 | CDR3 |
| KC010 (Kabat CDRs) | VNDIR (SEQ ID NO: 64) | RITGGGRTDYADSV KG (SEQ ID NO: 65) | WGRGY (SEQ ID NO: 66) |
| KC010 (IMGT CDRs) | RFDFSVND (SEQ ID NO: 67) | ITGGGRT (SEQ ID NO: 68) | WGRGY (SEQ ID NO: 69) |
| KC010 (VHH) (SEQ ID NO: 70) | QVQLQESGGGLVQPGGSLRLSCAASRFDFSVNDIRWYRQAPGNE RELVARITGGGRTDYADSVKGRFTISRDNAKNTVYLQMNNLKPE DTAVYYCWGRGYWGQGTQVTVSS | | |

TABLE 6

Exemplary embodiments of polypeptide chains comprising one antigen binding domain (VHH-hinge-CH2-CH3) (may comprise a His-tag or not)

| SEQ ID NO: (specificity) | SEQUENCE |
|---|---|
| KC011 (DR2) (SEQ ID NO: 71) | QVQLQESGGGLAPPGGSLRLSCAASGFTFSRHAMSWVRQAPGKGL EWVSDIRSGDGGDGGTSYADSVKGRFTISRDNAKNTLYLQMNSLK PEDTAVYYCALGLWKILPSTRGRGTQVTVSSEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK |
| KC012 (DR2) (SEQ ID NO: 72) | QVQLQESGGGLVHPGGSLRLSCAASGLTFSQRAMSWVRQAPGKGL EWISDIKSTGETSYADSVKGRFTISRDNARNTVYLQMNSLKPEDTA VYYCALGLWKILPSVRGRGTQVTVSSEPKSCDKTHTCPPCPAPELL GGPSVFLFPPKPKDTLMISRTPEVTCVVVDVSHEDPEVKFNWYVDG VEVHNAKTKPREEQYNSTYRVVSVLTVLHQDWLNGKEYKCKVSN KALPAPIEKTISKAKGQPREPQVYTLPPSREEMTKNQVSLTCLVKGF YPSDIAVEWESNGQPENNYKTTPPVLDSDGSFFLYSKLTVDKSRWQ QGNVFSCSVMHEALHNHYTQKSLSLSPGK |
| KC013 (DR2) (SEQ ID NO: 73) | QVQLQESGGGLVQAGGSLRLSCAASEIIFSITAMNWYRQAPGKQRE LVAGISSSGKITYQDSVKGRFTISKDNAKNTLYLQMNSLKPEDTAV YYCNTWAGARDAIWGQGTQVTVSSEPKSCDKTHTCPPCPAPELLG GPSVFLFPPKPKDTLMISRTPEVTCVVVDVSHEDPEVKFNWYVDGV EVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQ GNVFSCSVMHEALHNHYTQKSLSLSPGK |
| KC014 (DR2) (SEQ ID NO: 74) | QVQLLESGGGLVQPGGSLRLSCAASGDRITNKDMGWVRQAPGKGL EWVSAIAKNNGSTYYADSVKGRFTISRDNSKNTLYLQMNSLRAED TAVYYCAGLTHRGASKFNYWGQGTLVTVSSEPKSCDKTHTCPPCP APELLGGPSVFLFPPKPKDTLMISRTPEVTCVVVDVSHEDPEVKFN WYVDGVEVHNAKTKPREEQYNSTYRVVSVLTVLHQDWLNGKEY KCKVSNKALPAPIEKTISKAKGQPREPQVYTLPPSREEMTKNQVSLT CLVKGFYPSDIAVEWESNGQPENNYKTTPPVLDSDGSFFLYSKLTV DKSRWQQGNVFSCSVMHEALHNHYTQKSLSLSPGK |
| KC015 (CD47) SEQ ID NO: 75 | QVQLQESGGGLVQPGGSLRLSCAASRFDFSVNDIRWYRQAPGNER ELVARITGGGRTDYADSVKGRFTISRDNAKNTVYLQMNNLKPEDT AVYYCWGRGYWGQGTQVTVSSEPKSCDKTHTCPPCPAPELLGGPS VFLFPPKPKDTLMISRTPEVTCVVVDVSHEDPEVKFNWYVDGVEV HNAKTKPREEQYNSTYRVVSVLTVLHQDWLNGKEYKCKVSNKAL PAPIEKTISKAKGQPREPQVYTLPPSREEMTKNQVSLTCLVKGFYPS DIAVEWESNGQPENNYKTTPPVLDSDGSFFLYSKLTVDKSRWQQG NVFSCSVMHEALHNHYTQKSLSLSPGK |
| KC016 (HEWL) SEQ ID NO: 76 | DVQLVESGGGSVQAGGSLRLSCAASGSTDSIEYMTWFRQAPGKAR EGVAALYTHTGNTYYTDSVKGRFTISQDKAKNMAYLRMDSVKSE DTAIYTCGATRKYVPVRFALDQSSYDYWGQGTQVTVSSEPKSCDK THTCPPCPAPELLGGPSVFLFPPKPKDTLMISRTPEVTCVVVDVSHE DPEVKFNWYVDGVEVHNAKTKPREEQYNSTYRVVSVLTVLHQDW LNGKEYKCKVSNKALPAPIEKTISKAKGQPREPQVYTLPPSREEMT KNQVSLTCLVKGFYPSDIAVEWESNGQPENNYKTTPPVLDSDGSFF LYSKLTVDKSRWQQGNVFSCSVMHEALHNHYTQKSLSLSPGK |

TABLE 7

Exemplary embodiments of polypeptide chains comprising three antigen binding domains (may comprise a His-tag or not)

| SEQ ID NO: (specificity) | SEQUENCE |
|---|---|
| KC020 SEQ ID NO: 77 (DR2; PD1; CD47) | QVQLQESGGGLVQAGGSLRLSCAASEIIFSITAMNWYRQAPGKQR ELVAGISSSGKITYQDSVKGRFTISKDNAKNTLYLQMNSLKPEDTA VYYCNTWAGARDAIWGQGTQVTVSSEPKSCDKTHTCPPCPAPEL LGGPSVFLFPPKPKDTLMISRTPEVTCVVVDVSHEDPEVKFNWYV DGVEVHNAKTKPREEQYNSTYRVVSVLTVLHQDWLNGKEYKCK VSNKALPAPIEKTISKAKGQPREPQVYTLPPSREEMTKNQVSLTCL VKGFYPSDIAVEWESNGQPENNYKTTPPVLDSDGSFFLYSKLTVD KSRWQQGNVFSCSVMHEALHNHYTQKSLSLSPGKAPAPAPAPAP KAQVQLQESGGGWVQPGGSLRLSCVASGFTFSRSSMSWHRQAPG |

TABLE 7-continued

| Exemplary embodiments of polypeptide chains comprising three antigen binding domains (may comprise a His-tag or not) | |
|---|---|
| SEQ ID NO: (specificity) | SEQUENCE |
| | KERDLVAIISSSGIITHYSDSVKGRFTISRDNAKDTVYLQMNSLKPE DTAVYVCNAVLDDDSGDYWGQGTQVTVSSGGGGSGGGGSGGG GSQVQLQESGGGLVQPGGSLRLSCAASRFDFSVNDIRWYRQAPG NERELVARITGGGRTDYADSVKGRFTISRDNAKNTVYLQMNNLK PEDTAVYYCWGRGYWGQGTQVTVSS |
| KC021 SEQ ID NO: 78 (DR2; PD1; CD47) | QVQLQESGGGLVQAGGSLRLSCAASEIIFSITAMNWYRQAPGKQR ELVAGISSSGKITYQDSVKGRFTISKDNAKNTLYLQMNSLKPEDTA VYYCNTWAGARDAIWGQGTQVTVSSEPKSCDKTHTCPPCPAPEL LGGPSVFLFPPKPKDTLMISRTPEVTCVVVDVSHEDPEVKFNWYV DGVEVHNAKTKPREEQYNSTYRVVSVLTVLHQDWLNGKEYKCK VSNKALPAPIEKTISKAKGQPREPQVYTLPPSREQMTKNQVSLTCL VKGFYPSDIAVEWESNGQPENNYKTTPPVLNSDGSFFLYSKLTVD KSRWQQGNVFSCSVMHEALHNHYTQESLSLSPGKAPAPAPAPAP KAQVQLQESGGGWVQPGGSLRLSCVASGFTFSRSSMSWHRQAPG KERDLVAIISSSGIITHYSDSVKGRFTISRDNAKDTVYLQMNSLKPE DTAVYVCNAVLDDDSGDYWGQGTQVTVSSGGGGSGGGGSGGG GSQVQLQESGGGLVQPGGSLRLSCAASRFDFSVNDIRWYRQAPG NERELVARITGGGRTDYADSVKGRFTISRDNAKNTVYLQMNNLK PEDTAVYYCWGRGYWGQGTQVTVSS |
| KC022 SEQ ID NO: 79 (DR2; PD1; CD47) | QVQLQESGGGLVQPGGSLRLSCAASGSSLSLRSMGWYRQGPGKM RELVAVITSSAASTNYADSVKGRFTISFDNAKNTMYLQMNSLTPE DTAVYYCNFRGASRWYGTPSDYWGQGTQVTVSSEPKSCDKTHT CPPCPAPELLGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGKAP APAPAPAPKAQVQLQESGGGWVQPGGSLRLSCVASGFTFSRSSMS WHRQAPGKERDLVAIISSSGIITHYSDSVKGRFTISRDNAKDTVYL QMNSLKPEDTAVYVCNAVLDDDSGDYWGQGTQVTVSSGGGGSG GGGSGGGGSQVQLQESGGGLVQPGGSLRLSCAASRFDFSVNDIR WYRQAPGNERELVARITGGGRTDYADSVKGRFTISRDNAKNTVY LQMNNLKPEDTAVYYCWGRGYWGQGTQVTVSS |
| KC023 SEQ ID NO: 80 (DR2; PD1; CD47) | QVQLQESGGGLVQAGGSLRLSCAASGSSLSLRSMGWYRQGPGK MRELVAVITSSAASTNYADSVKGRFTISFDNAKNTMYLQMNSLTP EDTAVYYCNFRGASRWYGTPSDYWGQGTQVTVSSEPKSCDKTHT CPPCPAPELLGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGKAP APAPAPAPKAQVQLQESGGGWVQPGGSLRLSCVASGFTFSRSSMS WHRQAPGKERDLVAIISSSGIITHYSDSVKGRFTISRDNAKDTVYL QMNSLKPEDTAVYVCNAVLDDDSGDYWGQGTQVTVSSGGGGSG GGGSGGGGSQVQLQESGGGLVQPGGSLRLSCAASRFDFSVNDIR WYRQAPGNERELVARITGGGRTDYADSVKGRFTISRDNAKNTVY LQMNNLKPEDTAVYYCWGRGYWGQGTQVTVSS |
| KC024 SEQ ID NO: 81 (DR2; PD1; CD47) | QVQLQESGGGLVQPGGSLLLSCAASGFTFSQRAMSWVRQAPGKG LEWVSDIRSTGDTSYADSVKGRFTISRDNAKNTLYLQMNSLKPED TAVYYCALGLWKILPSARGRGTQVTVSSEPKSCDKTHTCPPCPAP ELLGGPSVFLFPPKPKDTLMISRTPEVTCVVVDVSHEDPEVKFNW YVDGVEVHNAKTKPREEQYNSTYRVVSVLTVLHQDWLNGKEYK CKVSNKALPAPIEKTISKAKGQPREPQVYTLPPSREEMTKNQVSLT CLVKGFYPSDIAVEWESNGQPENNYKTTPPVLDSDGSFFLYSKLT VDKSRWQQGNVFSCSVMHEALHNHYTQKSLSLSPGKAPAPAPAP APKAQVQLQESGGGWVQPGGSLRLSCVASGFTFSRSSMSWHRQA PGKERDLVAIISSSGIITHYSDSVKGRFTISRDNAKDTVYLQMNSLK PEDTAVYVCNAVLDDDSGDYWGQGTQVTVSSGGGGSGGGGSGG GGSQVQLQESGGGLVQPGGSLRLSCAASRFDFSVNDIRWYRQAP GNERELVARITGGGRTDYADSVKGRFTISRDNAKNTVYLQMNNL KPEDTAVYYCWGRGYWGQGTQVTVSS |
| KC025 SEQ ID NO: 82 (DR2; PD1; CD47) | QVQLQESGGGLAPPGGSLRLSCAASGFTFSRHAMSWVRQAPGKG LEWVSDIRSGDGGDGGTSYADSVKGRFTISRDNAKNTLYLQMNS LKPEDTAVYYCALGLWKILPSTRGRGTQVTVSSEPKSCDKTHTCP PCPAPELLGGPSVFLFPPKPKDTLMISRTPEVTCVVVDVSHEDPEV KFNWYVDGVEVHNAKTKPREEQYNSTYRVVSVLTVLHQDWLNG KEYKCKVSNKALPAPIEKTISKAKGQPREPQVYTLPPSREEMTKN QVSLTCLVKGFYPSDIAVEWESNGQPENNYKTTPPVLDSDGSFFL YSKLTVDKSRWQQGNVFSCSVMHEALHNHYTQKSLSLSPGKAPA |

TABLE 7-continued

Exemplary embodiments of polypeptide chains comprising three antigen binding domains (may comprise a His-tag or not)

| SEQ ID NO: (specificity) | SEQUENCE |
|---|---|
| | PAPAPAPKAQVQLQESGGGWVQPGGSLRLSCVASGFTFSRSSMS<br>WHRQAPGKERDLVAIISSSGIITHYSDSVKGRFTISRDNAKDTVYL<br>QMNSLKPEDTAVYVCNAVLDDDSGDYWGQGTQVTVSSGGGGSG<br>GGGSGGGGSQVQLQESGGGLVQPGGSLRLSCAASRFDFSVNDIR<br>WYRQAPGNERELVARITGGGRTDYADSVKGRFTISRDNAKNTVY<br>LQMNNLKPEDTAVYYCWGRGYWGQGTQVTVSS |
| KC026<br>SEQ ID NO: 83<br>(DR2; PD1; CD47) | QVQLQESGGGLVHPGGSLRLSCAASGLTFSQRAMSWVRQAPGKG<br>LEWISDIKSTGETSYADSVKGRFTISRDNARNTVYLQMNSLKPEDT<br>AVYYCALGLWKILPSVRGRGTQVTVSSEPKSCDKTHTCPPCPAPE<br>LLGGPSVFLFPPKPKDTLMISRTPEVTCVVVDVSHEDPEVKFNWY<br>VDGVEVHNAKTKPREEQYNSTYRVVSVLTVLHQDWLNGKEYKC<br>KVSNKALPAPIEKTISKAKGQPREPQVYTLPPSREEMTKNQVSLTC<br>LVKGFYPSDIAVEWESNGQPENNYKTTPPVLDSDGSFFLYSKLTV<br>DKSRWQQGNVFSCSVMHEALHNHYTQKSLSLSPGKAPAPAPAPA<br>PKAQVQLQESGGGWVQPGGSLRLSCVASGFTFSRSSMSWHRQAP<br>GKERDLVAIISSSGIITHYSDSVKGRFTISRDNAKDTVYLQMNSLKP<br>EDTAVYVCNAVLDDDSGDYWGQGTQVTVSSGGGGSGGGGSGG<br>GGSQVQLQESGGGLVQPGGSLRLSCAASRFDFSVNDIRWYRQAP<br>GNERELVARITGGGRTDYADSVKGRFTISRDNAKNTVYLQMNNL<br>KPEDTAVYYCWGRGYWGQGTQVTVSS |
| KC040<br>SEQ ID NO: 84<br>(DR2; HEWL;<br>CD47) | QVQLQESGGGLVQAGGSLRLSCAASEIIFSITAMNWYRQAPGKQR<br>ELVAGISSSGKITYQDSVKGRFTISKDNAKNTLYLQMNSLKPEDTA<br>VYYCNTWAGARDAIWGQGTQVTVSSEPKSCDKTHTCPPCPAPEL<br>LGGPSVFLFPPKPKDTLMISRTPEVTCVVVDVSHEDPEVKFNWYV<br>DGVEVHNAKTKPREEQYNSTYRVVSVLTVLHQDWLNGKEYKCK<br>VSNKALPAPIEKTISKAKGQPREPQVYTLPPSREEMTKNQVSLTCL<br>VKGFYPSDIAVEWESNGQPENNYKTTPPVLDSDGSFFLYSKLTVD<br>KSRWQQGNVFSCSVMHEALHNHYTQKSLSLSPGKAPAPAPAPAP<br>KADVQLVESGGGSVQAGGSLRLSCAASGSTDSIEYMTWFRQAPG<br>KAREGVAALYTHTGNTYYTDSVKGRFTISQDKAKNMAYLRMDS<br>VKSEDTAIYTCGATRKYVPVRFALDQSSYDYWGQGTQVTVSSGG<br>GGSGGGGSGGGGSQVQLQESGGGLVQPGGSLRLSCAASRFDFSV<br>NDIRWYRQAPGNERELVARITGGGRTDYADSVKGRFTISRDNAK<br>NTVYLQMNNLKPEDTAVYYCWGRGYWGQGTQVTVSS |
| KC027<br>SEQ ID NO: 85<br>(D2; PD1; CD47)<br>(IgG4) | QVQLQESGGGLVQAGGSLRLSCAASEIIFSITAMNWYRQAPGKQR<br>ELVAGISSSGKITYQDSVKGRFTISKDNAKNTLYLQMNSLKPEDTA<br>VYYCNTWAGARDAIWGQGTQVTVSSESKYGPPCPPCPAPEAAGG<br>PSVFLFPPKPKDTLMISRTPEVTCVVVDVSQEDPEVQFNWYVDGV<br>EVHNAKTKPREEQFNSTYRVVSVLTVLHQDWLNGKEYKCKVSN<br>KGLPSSIEKTISKAKGQPREPQVYTLPPSQEEMTKNQVSLTCLVKG<br>FYPSDIAVEWESNGQPENNYKTTPPVLDSDGSFFLYSRLTVDKSR<br>WQEGNVFSCSVMHEALHNHYTQKSLSLSLGKAPAPAPAPAPKAQ<br>VQLQESGGGWVQPGGSLRLSCVASGFTFSRSSMSWHRQAPGKER<br>DLVAIISSSGIITHYSDSVKGRFTISRDNAKDTVYLQMNSLKPEDTA<br>VYVCNAVLDDDSGDYWGQGTQVTVSSGGGGSGGGGSGGGGSQ<br>VQLQESGGGLVQPGGSLRLSCAASRFDFSVNDIRWYRQAPGNERE<br>LVARITGGGRTDYADSVKGRFTISRDNAKNTVYLQMNNLKPEDT<br>AVYYCWGRGYWGQGTQVTVSS |
| KC028<br>SEQ ID NO: 86<br>(D2; PD1; CD47)<br>(IgG4) | QVQLQESGGGLVQPGGSLRLSCAASGSSLSLRSMGWYRQGPGKM<br>RELVAVITSSAASTNYADSVKGRFTISFDNAKNTMYLQMNSLTPE<br>DTAVYYCNFRGASRWYGTPSDYWGQGTQVTVSSESKYGPPCPPC<br>PAPEAAGGPSVFLFPPKPKDTLMISRTPEVTCVVVDVSQEDPEVQF<br>NWYVDGVEVHNAKTKPREEQFNSTYRVVSVLTVLHQDWLNGKE<br>YKCKVSNKGLPSSIEKTISKAKGQPREPQVYTLPPSQEEMTKNQVS<br>LTCLVKGFYPSDIAVEWESNGQPENNYKTTPPVLDSDGSFFLYSRL<br>TVDKSRWQEGNVFSCSVMHEALHNHYTQKSLSLSLGKAPAPAPA<br>PAPKAQVQLQESGGGWVQPGGSLRLSCVASGFTFSRSSMSWHRQ<br>APGKERDLVAIISSSGIITHYSDSVKGRFTISRDNAKDTVYLQMNSL<br>KPEDTAVYVCNAVLDDDSGDYWGQGTQVTVSSGGGGSGGGGSG<br>GGGSQVQLQESGGGLVQPGGSLRLSCAASRFDFSVNDIRWYRQA<br>PGNERELVARITGGGRTDYADSVKGRFTISRDNAKNTVYLQMNN<br>LKPEDTAVYYCWGRGYWGQGTQVTVSS |
| KC029<br>SEQ ID NO: 87<br>(D2; PD1; CD3) | QVQLQESGGGLVQPGGSLRLSCAASGSSLSLRSMGWYRQGPGKM<br>RELVAVITSSAASTNYADSVKGRFTISFDNAKNTMYLQMNSLTPE<br>DTAVYYCNFRGASRWYGTPSDYWGQGTQVTVSSEPKSCDKTHT<br>CPPCPAPELLGGPSVFLFPPKPKDTLMISRTPEVTCVVVDVSHEDPE<br>VKFNWYVDGVEVHNAKTKPREEQYNSTYRVVSVLTVLHQDWLN<br>GKEYKCKVSNKALPAPIEKTISKAKGQPREPQVYTLPPSREEMTK<br>NQVSLTCLVKGFYPSDIAVEWESNGQPENNYKTTPPVLDSDGSFF |

TABLE 7-continued

Exemplary embodiments of polypeptide chains comprising three antigen binding domains (may comprise a His-tag or not)

| SEQ ID NO: (specificity) | SEQUENCE |
|---|---|
| | LYSKLTVDKSRWQQGNVFSCSVMHEALHNHYTQKSLSLSPGKAP APAPAPAPKAQVQLQESGGGWVQPGGSLRLSCVASGFTFSRSSMS WHRQAPGKERDLVAIISSSGIITHYSDSVKGRFTISRDNAKDTVYL QMNSLKPEDTAVYVCNAVLDDDSGDYWGQGTQVTVSSGGGGSG GGGSGGGGSEVQLVESGGGLVQPGGSLRLSCAASGDIYKSFDMG WYRQAPGKQRDLVAVIGSRGNNRGRTNYADSVKGRFTISRDGTG NTVYLLMNKLRPEDTAIYYCNTAPLVAGRPWGRGTLVTVSS |
| KC030 SEQ ID NO: 88 (D2; PD1; CD3) | QVQLQESGGGLVQPGGSLRLSCAASGSSLSLRSMGWYRQGPGKM RELVAVITSSAASTNYADSVKGRFTISFDNAKNTMYLQMNSLTPE DTAVYYCNFRGASRWYGTPSDYWGQGTQVTVSSEPKSCDKTHT CPPCPAPELLGGPSVFLFPPKPKDTLMISRTPEVTCVVVDVSHEDPE VKFNWYVDGVEVHNAKTKPREEQYNSTYRVVSVLTVLHQDWLN GKEYKCKVSNKALPAPIEKTISKAKGQPREPQVYTLPPSREEMTK NQVSLTCLVKGFYPSDIAVEWESNGQPENNYKTTPPVLDSDGSFF LYSKLTVDKSRWQQGNVFSCSVMHEALHNHYTQKSLSLSPGKAP APAPAPAPKAQVQLQESGGGWVQPGGSLRLSCVASGFTFSRSSMS WHRQAPGKERDLVAIISSSGIITHYSDSVKGRFTISRDNAKDTVYL QMNSLKPEDTAVYVCNAVLDDDSGDYWGQGTQVTVSSGGGGSG GGGSGGGGSEVQLVESGGGLVQPGGSLRLSCAASGDIYKSFDMG WYRQAPGKQRDLVAVIGSRGNNRGRTNYADSVKGRFTISRDGTG NTVYLLMNKLRPEDTAIYYCNTAPLVAGRPWGRGTLVTVSS |
| KC031 SEQ ID NO: 89 (HEWL-HEWL-HEWL) | QVQLVESGGGSVQAGGSLRLSCAASGSTDSIEYMTWFRQAPGKA REGVAALYTHTGNTYYTDSVKGRFTISQDKAKNMAYLRMDSVK SEDTAIYTCGATRKYVPVRFALDQSSYDYWGQGTQVTVSSEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSR EEMTKNQVSLTCLVKGFYPSDIAVEWESNGQPENNYKTTPPVLDS DGSFFLYSKLTVDKSRWQQGNVFSCSVMHEALHNHYTQKSLSLS PGKEPKIPQPQPKPQPQPQPGGSGSAEAAAKAPKAPEVOLVESGG GSVQAGGSLRLSCAASGSTDSIEYMTWFRQAPGKAREGVAALYT HTGNTYYTDSVKGRFTISQDKAKNMAYLRMDSVKSEDTAIYTCG ATRKYVPVRFALDQSSYDYWGQGTQVTVSSGGGGSGGGGSGGG GSQVQLVESGGGSVQAGGSLRLSCAASGSTDSIEYMTWFRQAPG KAREGVAALYTHTGNTYYTDSVKGRFTISQDKAKNMAYLRMDS VKSEDTAIYTCGATRKYVPVRFALDQSSYDYWGQGTQVTVSS |
| KC032 SEQ ID NO: 90 (D2; HEWL; HEWL) | QVQLQESGGGLVQAGGSLRLSCAASEIIFSITAMNWYRQAPGKQR ELVAGISSSGKITYQDSVKGRFTISKDNAKNTLYLQMNSLKPEDTA VYYCNTWAGARDAIWGQGTQVTVSSEPKSCDKTHTCPPCPAPEL LGGPSVFLFPPKPKDTLMISRTPEVTCVVVDVSHEDPEVKFNWYV DGVEVHNAKTKPREEQYNSTYRVVSVLTVLHQDWLNGKEYKCK VSNKALPAPIEKTISKAKGQPREPQVYTLPPSREQMTKNQVSLTCL VKGFYPSDIAVEWESNGQPENNYKTTPPVLNSDGSFFLYSKLTVD KSRWQQGNVFSCSVMHEALHNHYTQESLSLSPGKEPKIPQPQPKP QPQPQPGGSGSAEAAAKAPKAPEVQLVESGGGSVQAGGSLRLSC AASGSTDSIEYMTWFRQAPGKAREGVAALYTHTGNTYYTDSVKG RFTISQDKAKNMAYLRMDSVKSEDTAIYTCGATRKYVPVRFALD QSSYDYWGQGTQVTVSSGGGGSGGGGSGGGGSQVQLVESGGGS VQAGGSLRLSCAASGSTDSIEYMTWFRQAPGKAREGVAALYTHT GNTYYTDSVKGRFTISQDKAKNMAYLRMDSVKSEDTAIYTCGAT RKYVPVRFALDQSSYDYWGQGTQVTVSS |
| KC033 SEQ ID NO: 91 (D2; HEWL; CD3) | QVQLQESGGGLVQAGGSLRLSCAASEIIFSITAMNWYRQAPGKQR ELVAGISSSGKITYQDSVKGRFTISKDNAKNTLYLQMNSLKPEDTA VYYCNTWAGARDAIWGQGTQVTVSSEPKSCDKTHTCPPCPAPEL LGGPSVFLFPPKPKDTLMISRTPEVTCVVVDVSHEDPEVKFNWYV DGVEVHNAKTKPREEQYNSTYRVVSVLTVLHQDWLNGKEYKCK VSNKALPAPIEKTISKAKGQPREPQVYTLPPSREQMTKNQVSLTCL VKGFYPSDIAVEWESNGQPENNYKTTPPVLNSDGSFFLYSKLTVD KSRWQQGNVFSCSVMHEALHNHYTQESLSLSPGKAPAPAPAPAP KAQVQLVESGGGSVQAGGSLRLSCAASGSTDSIEYMTWFRQAPG KAREGVAALYTHTGNTYYTDSVKGRFTISQDKAKNMAYLRMDS VKSEDTAIYTCGATRKYVPVRFALDQSSYDYWGQGTQVTVSSGG GGSGGGGSGGGGSEVQLVESGGGLVQPGGSLRLSCAASGDIYKSF DMGWYRQAPGKQRDLVAVIGSRGNNRGRTNYADSVKGRFTISR DGTGNTVYLLMNKLRPEDTAIYYCNTAPLVAGRPWGRGTLVTVS S |
| KC034 SEQ ID NO: 92 (HEWL; HEWL; CD3) | QVQLVESGGGSVQAGGSLRLSCAASGSTDSIEYMTWFRQAPGKA REGVAALYTHTGNTYYTDSVKGRFTISQDKAKNMAYLRMDSVK SEDTAIYTCGATRKYVPVRFALDQSSYDYWGQGTQVTVSSEPKSC |

TABLE 7-continued

Exemplary embodiments of polypeptide chains comprising three antigen binding domains (may comprise a His-tag or not)

| SEQ ID NO:<br>(specificity) | SEQUENCE |
|---|---|
| | DKTHTCPPCPAPELLGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPAPIEKTISKAKGQPREPQVYTLPPSR<br>EQMTKNQVSLTCLVKGFYPSDIAVEWESNGQPENNYKTTPPVLNS<br>DGSFFLYSKLTVDKSRWQQGNVFSCSVMHEALHNHYTQESLSLSP<br>GKAPAPAPAPAPKAQVQLVESGGGSVQAGGSLRLSCAASGSTDSI<br>EYMTWFRQAPGKAREGVAALYTHTGNTYYTDSVKGRFTISQDKA<br>KNMAYLRMDSVKSEDTAIYTCGATRKYVPVRFALDQSSYDYWG<br>QGTQVTVSSGGGGSGGGGSGGGGSEVQLVESGGGLVQPGGSLRL<br>SCAASGDIYKSFDMGWYRQAPGKQRDLVAVIGSRGNNRGRTNY<br>ADSVKGRFTISRDGTGNTVYLLMNKLRPEDTAIYYCNTAPLVAGR<br>PWGRGTLVTVSS |
| KC035<br>SEQ ID NO: 93<br>(HEWL; HEWL; HEWL) | QVQLVESGGGSVQAGGSLRLSCAASGSTDSIEYMTWFRQAPGKA<br>REGVAALYTHTGNTYYTDSVKGRFTISQDKAKNMAYLRMDSVK<br>SEDTAIYTCGATRKYVPVRFALDQSSYDYWGQGTQVTVSSEPKSC<br>DKTHTCPPCPAPELLGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPAPIEKTISKAKGQPREPQVYTLPPSR<br>EQMTKNQVSLTCLVKGFYPSDIAVEWESNGQPENNYKTTPPVLNS<br>DGSFFLYSKLTVDKSRWQQGNVFSCSVMHEALHNHYTQESLSLSP<br>GKAPAPAPAPAPKAQVQLVESGGGSVQAGGSLRLSCAASGSTDSI<br>EYMTWFRQAPGKAREGVAALYTHTGNTYYTDSVKGRFTISQDKA<br>KNMAYLRMDSVKSEDTAIYTCGATRKYVPVRFALDQSSYDYWG<br>QGTQVTVSSGGGGSGGGGSGGGGSQVQLVESGGGSVQAGGSLRL<br>SCAASGSTDSIEYMTWFRQAPGKAREGVAALYTHTGNTYYTDSV<br>KGRFTISQDKAKNMAYLRMDSVKSEDTAIYTCGATRKYVPVRFA<br>LDQSSYDYWGQGTQVTVSS |
| KC036<br>SEQ ID NO: 94<br>(HEWL; PD1; HEWL) | QVQLVESGGGSVQAGGSLRLSCAASGSTDSIEYMTWFRQAPGKA<br>REGVAALYTHTGNTYYTDSVKGRFTISQDKAKNMAYLRMDSVK<br>SEDTAIYTCGATRKYVPVRFALDQSSYDYWGQGTQVTVSSEPKSC<br>DKTHTCPPCPAPELLGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPAPIEKTISKAKGQPREPQVYTLPPSR<br>EQMTKNQVSLTCLVKGFYPSDIAVEWESNGQPENNYKTTPPVLNS<br>DGSFFLYSKLTVDKSRWQQGNVFSCSVMHEALHNHYTQESLSLSP<br>GKAPAPAPAPAPKAQVQLQESGGGWVQPGGSLRLSCVASGFTFS<br>RSSMSWHRQAPGKERDLVAIISSSGIITHYSDSVKGRFTISRDNAK<br>DTVYLQMNSLKPEDTAVYVCNAVLDDDSGDYWGQGTQVTVSSG<br>GGGSGGGGSGGGGSQVQLVESGGGSVQAGGSLRLSCAASGSTDSI<br>EYMTWFRQAPGKAREGVAALYTHTGNTYYTDSVKGRFTISQDKA<br>KNMAYLRMDSVKSEDTAIYTCGATRKYVPVRFALDQSSYDYWG<br>QGTQVTVSS |
| KC037<br>(D2; PD1: HEWL)<br>SEQ ID NO: 95 | QVQLQESGGGLVQAGGSLRLSCAASEIIFSITAMNWYRQAPGKQR<br>ELVAGISSSGKITYQDSVKGRFTISKDNAKNTLYLQMNSLKPEDTA<br>VYYCNTWAGARDAIWGQGTQVTVSSEPKSCDKTHTCPPCPAPEL<br>LGGPSVFLFPPKPKDTLMISRTPEVTCVVVDVSHEDPEVKFNWYV<br>DGVEVHNAKTKPREEQYNSTYRVVSVLTVLHQDWLNGKEYKCK<br>VSNKALPAPIEKTISKAKGQPREPQVYTLPPSREQMTKNQVSLTCL<br>VKGFYPSDIAVEWESNGQPENNYKTTPPVLNSDGSFFLYSKLTVD<br>KSRWQQGNVFSCSVMHEALHNHYTQESLSLSPGKAPAPAPAPAP<br>KAQVQLQESGGGWVQPGGSLRLSCVASGFTFSRSSMSWHRQAPG<br>KERDLVAIISSSGIITHYSDSVKGRFTISRDNAKDTVYLQMNSLKPE<br>DTAVYVCNAVLDDDSGDYWGQGTQVTVSSGGGGSGGGGSGGG<br>GSQVQLVESGGGSVQAGGSLRLSCAASGSTDSIEYMTWFRQAPG<br>KAREGVAALYTHTGNTYYTDSVKGRFTISQDKAKNMAYLRMDS<br>VKSEDTAIYTCGATRKYVPVRFALDQSSYDYWGQGTQVTVSS |
| KC038<br>SEQ ID NO: 96<br>(HEWL; PD1: CD47) | QVQLVESGGGSVQAGGSLRLSCAASGSTDSIEYMTWFRQAPGKA<br>REGVAALYTHTGNTYYTDSVKGRFTISQDKAKNMAYLRMDSVK<br>SEDTAIYTCGATRKYVPVRFALDQSSYDYWGQGTQVTVSSEPKSC<br>DKTHTCPPCPAPELLGGPSVFLFPPKPKDTLMISRTPEVTCVVVDV<br>SHEDPEVKFNWYVDGVEVHNAKTKPREEQYNSTYRVVSVLTVLH<br>QDWLNGKEYKCKVSNKALPAPIEKTISKAKGQPREPQVYTLPPSR<br>EQMTKNQVSLTCLVKGFYPSDIAVEWESNGQPENNYKTTPPVLNS<br>DGSFFLYSKLTVDKSRWQQGNVFSCSVMHEALHNHYTQESLSLSP<br>GKAPAPAPAPAPKAQVQLQESGGGWVQPGGSLRLSCVASGFTFS<br>RSSMSWHRQAPGKERDLVAIISSSGIITHYSDSVKGRFTISRDNAK<br>DTVYLQMNSLKPEDTAVYVCNAVLDDDSGDYWGQGTQVTVSSG<br>GGGSGGGGSGGGGSQVQLQESGGGLVQPGGSLRLSCAASRFDFS<br>VNDIRWYRQAPGNERELVARITGGGRTDYADSVKGRFTISRDNA<br>KNTVYLQMNNLKPEDTAVYYCWGRGYWGQGTQVTVSS |

TABLE 7-continued

| Exemplary embodiments of polypeptide chains comprising three antigen binding domains (may comprise a His-tag or not) | |
|---|---|
| SEQ ID NO: (specificity) | SEQUENCE |
| KC039 SEQ ID NO: 97 (HEWL; HEWL; HEWL) | QVQLVESGGGSVQAGGSLRLSCAASGSTDSIEYMTWFRQAPGKA REGVAALYTHTGNTYYTDSVKGRFTISQDKAKNMAYLRMDSVK SEDTAIYTCGATRKYVPVRFALDQSSYDYWGQGTQVTVSSEPKSC DKTHTCPPCPAPELLGGPSVFLFPPKPKDTLMISRTPEVTCVVVDV SHEDPEVKFNWYVDGVEVHNAKTKPREEQYNSTYRVVSVLTVLH QDWLNGKEYKCKVSNKALPAPIEKTISKAKGQPREPQVYTLPPSR EEMTKNQVSLTCLVKGFYPSDIAVEWESNGQPENNYKTTPPVLDS DGSFFLYSKLTVDKSRWQQGNVFSCSVMHEALHNHYTQKSLSLS PGKAPAPAPAPAPKAQVQLVESGGGSVQAGGSLRLSCAASGSTDS IEYMTWFRQAPGKAREGVAALYTHTGNTYYTDSVKGRFTISQDK AKNMAYLRMDSVKSEDTAIYTCGATRKYVPVRFALDQSSYDYW GQGTQVTVSSGGGGSGGGGSGGGGSQVQLVESGGGSVQAGGSL RLSCAASGSTDSIEYMTWFRQAPGKAREGVAALYTHTGNTYYTD SVKGRFTISQDKAKNMAYLRMDSVKSEDTAIYTCGATRKYVPVR FALDQSSYDYWGQGTQVTVSS |

(natural human IgG1 hinge region)
SEQ ID NO: 98
EPKSCDKTHTCPPCP (Linker-HL1)
SEQ ID NO: 99
EPKIPQPQPKPQPQPQPGGSGSAEAAAKAPKAP (flexible linker-FL2)
SEQ ID NO: 100
GGGGSGGGGS (flexible linker-FL18)
SEQ ID NO: 101
GGGGSGGGGSGGGGS (flexible linker-FL4)
SEQ ID NO: 102
GGGGSGGGGSGGGGSGGGGSGGGGS (flexible linker- FL5)
SEQ ID NO: 103
GGGGSGGGGSGGGGSGGGGSGGGGSGGGGS (flexible linker)
SEQ ID NO: 104
$(GGGGS)_n$ wherein n is an integer selected from 1 to 10

(rigid linker-RL5)
SEQ ID NO: 105
PAPAPKA (rigid linker-RL7)
SEQ ID NO: 106
APAPAPAPAPKA (rigid linker-RL12)
SEQ ID NO: 107
APAPAPAPAPAPAPAPAPAPKA (rigid linker)
SEQ ID NO: 108
$(X(PAPAP))_n$KA wherein n is an integer selected from 1 to 10, wherein X is present or absent and is A (helical linker-RL1)
SEQ ID NO: 109
AEAAAKEAAAKA (helical linker-RL2)
SEQ ID NO: 110
AEAAAKEAAAKEAAAKA -continued (helical linker-RL4)

SEQ ID NO: 111

AEAAAKEAAAKEAAAKEAAAKEAAAKA (helical linker

SEQ ID NO: 112

X(EAAAK)$_n$ Y wherein n is an integer selected from 1 to 10, more preferably 2-5 wherein X and Y are independently present or absent and is preferably A

Anti-HEWL VHH (KC017)

SEQ ID NO: 113

XVQLVESGGGSVQAGGSLRLSCAASGSTDSIEYMTWFRQAPGKAREGVAALYTHTGNT
YYTDSVKGRFTISQDKAKNMAYLRMDSVKSEDTAIYTCGATRKYVPVRFALDQSSYDY
WGQGTQVTVSS

Wherein X is E or Q

Anti-4HEM VHH (VHH portion of KC018)

SEQ ID NO: 114

XVQLVESGGGLVQAGGSLRLSCAASESTFSNYAMGWFRQAPGPEREFVATISQTGSHTY
YRNSVKGRFTISRDNAKNTVYLQMNNMKPEDTAVYYCAAGDNYYYTRTYEYDYWGQ
GTQVTVSS

Wherein X is E or Q

Anti-CD3 VHH (KC019)

SEQ ID NO: 115

XVQLVESGGGLVQPGGSLRLSCAASGDIYKSFDMGWYRQAPGKQRDLVAVIGSRGNN
RGRTNYADSVKGRFTISRDGTGNTVYLLMNKLRPEDTAIYYCNTAPLVAGRPWGRGTL
VTVSS

Wherein X is E or D natural human IgG1 CH3

SEQ ID NO: 116

GQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGK natural human IgG1 CH2

SEQ ID NO: 117

APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAK mutated human IgG1 hinge region

SEQ ID NO: 118

EPKSSDKTHTCPPCP mutated human IgGI hinge region

SEQ ID NO: 119

EPKSSDKTHTSPPSP mutated human IgG1 hinge region

SEQ ID NO: 120

DKTHTCPPC natural human IgG2 hinge region

SEQ ID NO: 121

ERKCCVECPPCP mutated human IgG2 hinge region

SEQ ID NO: 122

ERKSSVECPPCP mutated human IgG2 hinge region

SEQ ID NO: 123

ERKSSVESPPCP mutated human IgG2 hinge region

SEQ ID NO: 124

ERKSSVESPPSP

-continued natural human IgG3 hinge region
SEQ ID NO: 125
ELKTPLGDTTHTCPRCPEPKSCDTPPPCPRCPEPKSCDTPPPCPRCPEPKSCDTPPPCPRCP mutated human IgG3 hinge region
SEQ ID NO: 126
EPKSSDTPPPCPRCP mutated human IgG3 hinge region
SEQ ID NO: 127
EPKSSDTPPPSPRCP mutated human IgG3 hinge region
SEQ ID NO: 128
EPKSSDTPPPSPRSP natural human IgG4 hinge region
SEQ ID NO: 129
ESKYGPPCPSCP mutated human IgG4 hinge region
SEQ ID NO: 130
ESKYGPPCPPCP mutated human IgG4 hinge region
SEQ ID NO: 131
ESKYGPPSPSCP mutated human IgG4 hinge region)
SEQ ID NO: 132
ESKYGPPSPSSP Signal Peptide
SEQ ID NO: 133
MEWSWVFLFFLSVTTGVHS Epitope Tag
SEQ ID NO: 134
HHHHHH Natural human IgG1 constant region
SEQ ID NO: 135
APELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPGK

Mutated CH3 domain (Chain A- mutations D399N; K370E; E356Q)
SEQ ID NO: 136
GQPREPQVYTLPPSRQEMTKNQVSLTCLVEGFYPSDIAVEWESNGQPENNYKTTPPVLN

SDGSFFLYSKLTVDKSRWQQGNVFSCSVMHEALHNHYTQKSLSLSPGK

Mutated CH3 domain (Chain B- mutations D399N; K439E; E357Q)
SEQ ID NO: 137
GQPREPQVYTLPPSREQMTKNQVSLTCLVKGFYPSDIAVEWESNGQPENNYKTTPPVLN

SDGSFFLYSKLTVDKSRWQQGNVFSCSVMHEALHNHYTQESLSLSPGK

Mutated human IgG1 constant region (Chain A- mutations D399N; K370E; E356Q)
SEQ ID NO: 138
APELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSRQEMTKNQVSLTCLVEGFYPSDIAVEWESNGQPENNYKTTPPVLNSDGSFFL

YSKLTVDKSRWQQGNVFSCSVMHEALHNHYTQKSLSLSPGK

Mutated human IgG1 constant region (Chain B- mutations D399N; K439E; E357Q)
SEQ ID NO: 139
APELLGGPSVFLFPPKPKDTLMISRTPEVTCVVVDVSHEDPEVKFNWYVDGVEVHNAKT

KPREEQYNSTYRVVSVLTVLHQDWLNGKEYKCKVSNKALPAPIEKTISKAKGQPREPQ

VYTLPPSREQMTKNQVSLTCLVKGFYPSDIAVEWESNGQPENNYKTTPPVLNSDGSFFL

YSKLTVDKSRWQQGNVFSCSVMHEALHNHYTQESLSLSPGK

-continued

Mutated human IgG4 constant region

SEQ ID NO: 140

APEAAGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPVLDSDGSFFL

YSRLTVDKSRWQEGNVFSCSVMHEALHNHYTQKSLSLSLGK

The invention claimed is:

1. A binding agent that comprises one or more antigen binding domains, wherein at least one of the antigen binding domains is an antigen binding domain 1 (ABD1) of a heavy chain only antibody that is capable of binding to dopamine receptor D2, wherein the ABD1 comprises:

a. a heavy chain complementarity determining region 1 (CDRH1) having the amino acid sequence set forth in SEQ ID NO:1, a heavy chain complementarity determining region 2 (CDRH2) having the amino acid sequence set forth in SEQ ID NO: 2 and a heavy chain complementarity determining region 3 (CDRH3) having the amino acid sequence set forth in SEQ ID NO:3, or b. a CDRH1 having the amino acid sequence set forth in SEQ ID NO:4, a CDRH2 having the amino acid sequence set forth in SEQ ID NO:5 and a CDRH3 having the amino acid sequence set forth in SEQ ID NO:6

CDRH2.

2. The binding agent of claim 1, wherein at least one of the antigen binding domains is an antigen binding domain 2 (ABD2) of a heavy chain only antibody that is capable of binding to PD-1 and comprises:

a. a heavy chain complementarity determining region 1 (CDRH1) having the amino acid sequence set forth in SEQ ID NO:57, a heavy chain complementarity determining region 2 (CDRH2) having the amino acid sequence set forth in SEQ ID NO: 58 and a heavy chain complementarity determining region 3 (CDRH3) having the amino acid sequence set forth in SEQ ID NO:59 or;

b. a CDRH1 having the amino acid sequence set forth in SEQ ID NO:60, a CDRH2 having the amino acid sequence set forth in SEQ ID NO:61 and a CDRH3 having the amino acid sequence set forth in SEQ ID NO:62.

3. The binding agent of claim 2, wherein at least one of the antigen binding domains is an antigen binding domain 3 (ABD3) of a heavy chain only antibody that is capable of binding to CD47 and comprises:

a. a heavy chain complementarity determining region 1 (CDRH1) having the amino acid sequence set forth in SEQ ID NO:64, a heavy chain complementarity determining region 2 (CDRH2) having the amino acid sequence set forth in SEQ ID NO: 65 and a heavy chain complementarity determining region 3 (CDRH3) having the amino acid sequence set forth in SEQ ID NO:66; or b. a CDRH1 having the amino acid sequence set forth in SEQ ID NO:67, a CDRH2 having the amino acid sequence set forth in SEQ ID NO:68 and a CDRH3 having the amino acid sequence set forth in SEQ ID NO:69.

4. The binding agent of claim 1, wherein at least one of the antigen binding domains is an antigen binding domain capable of binding to an immunomodulator.

5. The binding agent of claim 4, wherein the immunomodulator is an immune checkpoint protein.

6. The binding agent of claim 3, wherein the binding agent comprises:

a. three or more antigen binding domains, wherein the ABD1 comprises an amino acid sequence as set forth in SEQ ID NO:7; the ABD2 comprises an amino acid sequence as set forth in SEQ ID NO:63; and the ABD3 comprises a heavy chain having an amino acid sequence as set forth in SEQ ID NO:70; or b. three or more antigen binding domains, wherein the ABD1 comprises an amino acid sequence at least 80% identical to the amino acid sequence set forth in SEQ ID NO:7; the ABD2 comprises an amino acid sequence at least 80% identical to the amino acid sequence set forth in SEQ ID NO:63; and the ABD3 comprises a heavy chain having an amino acid sequence at least 80% identical to the amino acid sequence set forth in SEQ ID NO: 70.

7. The binding agent of claim 1, wherein the binding agent comprises two polypeptide chains and wherein each of the polypeptide chain comprises in a N- to C-terminal fashion a) an amino acid sequence as set forth in SEQ ID NO:7, b) a hinge and c) CH2-CH3 domain.

8. The binding agent of claim 3, wherein the binding agent comprises two polypeptide chains that are capable of assembling to form a dimer and wherein each polypeptide chain is different or identical and comprises the antigen binding domains.

9. The binding agent of claim 8, wherein each of the polypeptide chains independently comprises in a N- to C-terminal fashion an amino acid sequence of formula I:

$$X\text{-}[(Ab_a)\text{-}(L_b)]_m\text{-}(DD)\text{-}[(L_c)\text{-}(Ab_d)]_n\text{-}Y$$

wherein m is 0, 1, 2 or an integer greater than 2;
wherein n is 0, 1, 2 or an integer greater than 2;

wherein m and n are not 0 simultaneously;

wherein $Ab_a$, $Ab_d$, each represents an antigen binding domain wherein at least one of the antigen binding domains is an antigen binding domain 1 (ABD1), at least one of the antigen binding domains is an antigen binding domain 2 (ABD2) and, at least one of the antigen binding domains is an antigen binding domain 3 (ABD3);

wherein X or Y are independently present or absent and comprises an amino acid sequence;

wherein $L_b$, $L_c$, each independently comprises one or more linkers; and wherein DD represents the dimerization domain.

10. The binding agent of claim 9, wherein m is 2, 3, 4, 5 or an integer greater than 5 and/or wherein n is 3, 4, 5 or an integer greater than 5.

11. The binding agent of claim 8, wherein each of the polypeptide chains independently comprises in a N- to C-terminal fashion an amino acid sequence of any one of the following:

X-($Ab_{a1}$)-($L_{b1}$)-(DD)-($L_{c1}$)-($Ab_{d1}$)-Y (formula II);

X-($Ab_{a1}$)-($L_{b1}$)-(DD)-($L_{c1}$)-($Ab_{d1}$)-($L_{c2}$)-($Ab_{d2}$)-Y (formula III);

X-($Ab_{a1}$)-($L_{b2}$)-($Ab_{a2}$)-($L_{b1}$)-(DD)-($L_{c1}$)-($Ab_{d1}$)-Y (formula IV);

X-($Ab_{a1}$)-($L_{b2}$)-($Ab_{a2}$)-($L_{b1}$)-(DD)-($L_{c1}$)-($Ab_{d1}$)-($L_{c2}$)-($Ab_{d2}$)-Y (formula V)

X-($Ab_{a1}$)-($L_{b2}$)-($Ab_{a2}$)-($L_{b1}$)-(DD)-($L_{c1}$)-($Ab_{d1}$)-($L_{c2}$)-($Ab_{d2}$)-($L_{c3}$)-($Ab_{d3}$)-Y (formula VI);

X-($Ab_{a1}$)-($L_{b3}$)-($Ab_{a2}$)-($L_{b2}$)-($Ab_{a3}$)-($L_{b1}$)-(DD)-($L_{c1}$)-($Ab_{d1}$)-($L_{c2}$)-($Ab_{d2}$)-Y (formula VII); and X-($Ab_{a1}$)-($L_{b3}$)-($Ab_{a2}$)-($L_{b2}$)-($Ab_{a3}$)-($L_{b1}$)-(DD)-($L_{c1}$)-($Ab_{d1}$)-($L_{c2}$)-($Ab_{d2}$)-($L_{c3}$)-($Ab_{d3}$)-Y (formula VIII)

wherein $Ab_{a1}$, $Ab_{a2}$, $Ab_{a3}$, $Ab_{d1}$, $Ab_{d2}$, $Ab_{d3}$, each represents an antigen binding domain, wherein at least one of the antigen binding domains is an antigen binding domain 1 (ABD1), at least one of the antigen binding domains is an antigen binding domain 2 (ABD2) and, at least one of the antigen binding domains is an antigen binding domain 3 (ABD3)

wherein $L_{b1}$ comprises a linker or linkers and/or a hinge region of an antibody or antigen binding fragment thereof;

wherein $L_{b2}$, $L_{b3}$ $L_{c1}$, $L_{c2}$, and $L_{c3}$ each independently comprise a linker or linkers; and wherein DD represents a dimerization domain.

12. The binding agent of claim 8, wherein each of the polypeptide chains independently comprises in a N- to C-terminal fashion:

a. an amino acid sequence of formula III

X-($Ab_{a1}$)-($L_{b1}$)-(DD)-($L_{c1}$)-($Ab_{d1}$)-($L_{c2}$)-($Ab_{d2}$)-Y (formula III);

wherein one of $Ab_{a1}$, $Ab_{d1}$ or $Ab_{d2}$ represents the antigen binding domain 1 (ABD1); one of $Ab_{a1}$, $Ab_{d1}$ or $Ab_{d2}$ represents the antigen binding domain 2 (ABD2) and, one of $Ab_{a1}$, $Ab_{d1}$ or $Ab_{d2}$ represents the antigen binding domain 3 (ABD3);

b. an amino acid sequence of formula IIIa:

X-(ABD1)-(Lb1)-(DD)-(Lc1)-(ABD2)-(Lc2)-(ABD3)-Y (formula IIIa), or c. an amino acid sequence of formula IIIb:

X-(ABD1)-(Lb1)-(DD)-(Lc1)-(ABD3)-(Lc2)-(ABD2)-Y (formula IIIb), wherein X or Y are independently present or absent and comprises an amino acid sequence;

wherein DD comprises a dimerization domain;

wherein $L_{b1}$ comprises a linker or linkers and/or a hinge region of an antibody or antigen binding fragment thereof; and wherein $L_{c1}$, and $L_{c2}$, each independently comprise a linker or linkers.

13. The binding agent of claim 12, wherein the dimerization domain comprises a constant region of an antibody or a portion thereof, a CH3 domain or a CH2-CH3 domain, wherein the CH3 domain is a natural CH3 domain or a mutated CH3 domain and wherein the CH2 domain is a natural CH2 domain or a mutated CH2 domain.

14. The binding agent of claim 13, wherein the mutated CH3 domain comprises mutations in comparison with a natural human IgG1 CH3 domain amino acid sequence set forth in SEQ ID NO: 116, wherein the mutations are selected from:

a. mutations D399N, D/E356Q, K370E;
b. mutations D399N, K439E, E357Q;
c. mutations D399Q, D/E356Q, K370E, Y349K and S354K;
d. mutations D399N, D/E356Q, K370E and L351W;
e. mutations D399N, D/E356Q, K370E and S354M;
f. mutations D399N, D/E356Q, K370E and T350I;
g. mutations D399N, D/E356Q, K370E and T350V;
h. mutations D399N, D/E356Q, K370E and P352R;
i. mutations D399N, D/E356Q, K370E and P352E;
j. mutations D399Q, D/E356Q and K370E;
k. mutations D399N, D/E356Q, K370E and L351Y;
l. Mutations D399N, D/E356Q, K370E, and L351H;
m. mutations D399N, D/E356Q, K370E, and R355K;
n. mutations D399N, D/E356Q, K370E, and Q355K;
o. mutations D399N, D/E356Q, K370E and S354K;
p. mutations D399N, D/E356Q, K370E and T350L;
q. mutations D399N, D/E356Q, K370E and T394N;
r. mutations D399N, D/E356Q, K370E and P352Y;
s. mutations D399N, D/E356Q, K370E and P352V;
t. mutations D399N, D/E356Q, K370E and P352T;
u. mutations D399N, D/E356Q, K370E and P352L;
v. mutations D399N, D/E356Q, K370E and P352G;
x. mutations D399N, D/E356Q, K370E and P352C;
y. mutations D399N, D/E356Q, K370E and L351T;
z. mutations D399N, D/E356Q, K370E and L351A;
aa. mutations D399Q, E357Q, K439E, Y349D and S354D;
bb. mutations D399N, E357Q, K439E and L351R;
cc. mutations In D399N, E357Q, K439E and L351Y;
dd. mutations D399N, E357Q, K439E and T350I;
ee. mutations D399N, E357Q, K439E and T350V;
ff. mutations D399Q, K439E, E357Q;
gg. mutations D399N, K439E, E357Q, S354K;
hh. mutations D399N, K439E, E357Q, S354W;
ii. mutations D399N, K439E, E357Q, Y349R;
jj. mutations D399N, K439E, E357Q, T350L;
kk. mutations D399N, K439E, E357Q, R355W;
ll. mutations D399N, K439E, E357Q, Q355W;
mm. mutations D399N, K439E, E357Q, P395I;
nn. mutations D399N, K439E, E357Q, P395G;
oo. mutations D399N, K439E, E357Q, P395E;
pp. mutations D399N, K439E, E357Q, P352K;
qq. mutations D399N, K439E, E357Q, P352D and;
rr. mutations D399N, K439E, E357Q, L351D and, wherein the mutations are in accordance with the EU numbering system.

15. The binding agent of claim 9, wherein each of the one or more linkers independently has at least 5, 10, 15, 20, 25, 30, 35, 40, 45 or 50 amino acid residues in length and is independently a flexible linker, a helical linker, a rigid linker or a hinge region of an antibody or antigen binding fragment thereof.

16. The binding agent of claim 8, wherein the antigen binding domain comprises the variable region of the heavy chain only antibody.

17. The binding agent of claim 1, wherein the binding agent is an antibody or an antigen binding fragment thereof, an antibody-like molecule, a protein scaffold or comprises an immune cell modulating agent.

18. The binding agent of claim 3, wherein the binding agent comprises one or more polypeptide chains, wherein at least one of the polypeptide chains comprises an amino acid sequence at least 80% identical to the amino acid sequence set forth in any one of SEQ ID NO: 73, 77, or 78.

19. A binding agent selected from:

a. a binding agent comprising two polypeptide chains each having an amino acid sequence as set forth in SEQ ID NO:77;

b. a binding agent comprising two polypeptide chains each having an amino acid sequence as set forth in SEQ ID NO:78; and c. a binding agent comprising two polypeptide chains each having an amino acid sequence as set forth in SEQ ID NO:73.

20. The binding agent of claim 19, wherein the binding agent is conjugated to a therapeutic moiety, to a detectable moiety, to a protein allowing an extended half-life or to a nanoparticle.

21. A composition or pharmaceutical composition comprising the binding agent of claim 19.

22. A nucleic acid or set of nucleic acids encoding the binding agent of claim 19.

23. A vector comprising the nucleic acid of claim 22.

24. A cell expressing the binding agent of claim 19.

25. A kit comprising the binding agent of claim 19.

26. A method of treating a disorder or disease associated with dopamine receptor D2 expression, the method comprising administering the pharmaceutical composition of claim 21.

27. The method of claim 26, wherein the disorder or disease is cancer, solid tumor, advanced metastatic solid cancer, hematogenous cancer, lung cancer, small cell lung cancer, non-small cell lung cancer, metastatic lung cancer, metastatic small cell lung cancer, metastatic non-small cell lung cancer, myeloma, prostate cancer, breast cancer, rectal cancer, pancreatic cancer, glioblastoma, an infection or an immune dysregulation.

28. A method of making the binding agent, the method comprising transforming cells with one or more vectors comprising the nucleic acid or set of nucleic acids of claim 22.

29. A binding agent that comprises one or more antigen binding domains, wherein at least one of the antigen binding domains is an antigen binding domain 2 (ABD2) that is capable of binding to PD-1 and comprises:

a. a heavy chain complementarity determining region 1 (CDRH1) having the amino acid sequence set forth in SEQ ID NO:57, a heavy chain complementarity determining region 2 (CDRH2) having the amino acid sequence set forth in SEQ ID NO:58 and a heavy chain complementarity determining region 3 (CDRH3) having the amino acid sequence set forth in SEQ ID NO:59; or a CDRH1 having the amino acid sequence set forth in SEQ ID NO:60, a CDRH2 having the amino acid sequence set forth in SEQ ID NO:61 and a CDRH3 having the amino acid sequence set forth in SEQ ID NO:62.

30. A binding agent that comprises one or more antigen binding domains, wherein at least one of the antigen binding domains is an antigen binding domain 3 (ABD3) that is capable of binding to CD47 and comprises:

a. a heavy chain complementarity determining region 1 (CDRH1) having the amino acid sequence set forth in SEQ ID NO:64, a heavy chain complementarity determining region 2 (CDRH2) having the amino acid sequence set forth in SEQ ID NO:65 and a heavy chain complementarity determining region 3 (CDRH3) having the amino acid sequence set forth in SEQ ID NO:66; or a CDRH1 having the amino acid sequence set forth in SEQ ID NO:67, a CDRH2 having the amino acid sequence set forth in SEQ ID NO:68 and a CDRH3 having the amino acid sequence set forth in SEQ ID NO:69.

31. A composition or pharmaceutical composition comprising the binding agent of claim 1.

32. A method of treating a disorder or disease associated with dopamine receptor D2 expression, the method comprising administering the pharmaceutical composition of claim 31.

* * * * *

SEQUENCE LISTING

<160> NUMBER OF SEQ ID NOS: 151

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Ile Thr Ala Met Asn
1 5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

Gly Ile Ser Ser Ser Gly Lys Ile Thr Tyr Gln Asp Ser Val Lys Gly
1 5 10 15

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Trp Ala Gly Ala Arg Asp Ala Ile
1 5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Glu Ile Ile Phe Ser Ile Thr Ala
1 5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

Ile Ser Ser Ser Gly Lys Ile
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Thr Trp Ala Gly Ala Arg Asp Ala Ile
1               5                   10

<210> SEQ ID NO 7
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser
        115

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asn Lys Asp Met Gly
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ile Ala Lys Asn Asn Gly Ser Thr Tyr Tyr Ala Asp Ser Val Lys
1 5 10 15

Gly

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Leu Thr His Arg Gly Ala Ser Lys Phe Asn Tyr
1 5 10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Asp Arg Ile Thr Asn Lys Asp
1 5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ile Ala Lys Asn Asn Gly Ser Thr
1 5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Ala Gly Leu Thr His Arg Gly Ala Ser Lys Phe Asn Tyr
1 5 10

<210> SEQ ID NO 14
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

Gln Val Gln Leu Leu Glu Ser Gly Gly Gly Leu Val Gln Pro Gly Gly
1 5 10 15

Ser Leu Arg Leu Ser Cys Ala Ala Ser Gly Asp Arg Ile Thr Asn Lys
20 25 30

```
Asp Met Gly Trp Val Arg Gln Ala Pro Gly Lys Gly Leu Glu Trp Val
        35                  40                  45

Ser Ala Ile Ala Lys Asn Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Leu Thr His Arg Gly Ala Ser Lys Phe Asn Tyr Trp Gly Gln
            100                 105                 110

Gly Thr Leu Val Thr Val Ser Ser
        115                 120


<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg His Ala Met Ser
1               5


<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asp Ile Arg Ser Gly Asp Gly Gly Asp Gly Gly Thr Ser Tyr Ala Asp
1               5                   10                  15

Ser Val Lys Gly
            20


<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Leu Trp Lys Ile Leu Pro Ser Thr
1               5


<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Thr Phe Ser Arg His Ala
1               5
```

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 19

Ile Arg Ser Gly Asp Gly Gly Asp Gly Gly Thr
1 5 10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Ala Leu Gly Leu Trp Lys Ile Leu Pro Ser Thr
1 5 10

<210> SEQ ID NO 21
<211> LENGTH: 121
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 21

Gln Val Gln Leu Gln Glu Ser Gly Gly Gly Leu Ala Pro Pro Gly Gly
1 5 10 15

Ser Leu Arg Leu Ser Cys Ala Ala Ser Gly Phe Thr Phe Ser Arg His
20 25 30

Ala Met Ser Trp Val Arg Gln Ala Pro Gly Lys Gly Leu Glu Trp Val
35 40 45

Ser Asp Ile Arg Ser Gly Asp Gly Gly Asp Gly Gly Thr Ser Tyr Ala
50 55 60

Asp Ser Val Lys Gly Arg Phe Thr Ile Ser Arg Asp Asn Ala Lys Asn
65 70 75 80

Thr Leu Tyr Leu Gln Met Asn Ser Leu Lys Pro Glu Asp Thr Ala Val
85 90 95

Tyr Tyr Cys Ala Leu Gly Leu Trp Lys Ile Leu Pro Ser Thr Arg Gly
100 105 110

Arg Gly Thr Gln Val Thr Val Ser Ser
115 120

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gln Arg Ala Met Ser
1 5

<210> SEQ ID NO 23
<211> LENGTH: 16

<212> TYPE: PRT
<213> ORGANISM: Artificial Sequence
<220> FEATURE:
<223> OTHER INFORMATION: Description of Artificial Sequence: Synthetic peptide

<400> SEQUENCE: 23

Asp Ile Lys Ser Thr Gly Glu Thr Ser Tyr Ala Asp Ser Val Lys Gly
1 5 10 15

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Gly Leu Trp Lys Ile Leu Pro Ser Val
1 5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

Gly Leu Thr Phe Ser Gln Arg Ala
1 5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ile Lys Ser Thr Gly Glu Thr
1 5

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Ala Leu Gly Leu Trp Lys Ile Leu Pro Ser Val
1 5 10

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

Gln Val Gln Leu Gln Glu Ser Gly Gly Gly Leu Val His Pro Gly Gly

```
1               5                   10                  15

Ser Leu Arg Leu Ser Cys Ala Ala Ser Gly Leu Thr Phe Ser Gln Arg
            20                  25                  30

Ala Met Ser Trp Val Arg Gln Ala Pro Gly Lys Gly Leu Glu Trp Ile
        35                  40                  45

Ser Asp Ile Lys Ser Thr Gly Glu Thr Ser Tyr Ala Asp Ser Val Lys
    50                  55                  60

Gly Arg Phe Thr Ile Ser Arg Asp Asn Ala Arg Asn Thr Val Tyr Leu
65                  70                  75                  80

Gln Met Asn Ser Leu Lys Pro Glu Asp Thr Ala Val Tyr Tyr Cys Ala
                85                  90                  95

Leu Gly Leu Trp Lys Ile Leu Pro Ser Val Arg Gly Arg Gly Thr Gln
            100                 105                 110

Val Thr Val Ser Ser
        115


<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Arg Ser Met Gly
1               5


<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Ile Thr Ser Ser Ala Ala Ser Thr Asn Tyr Ala Asp Ser Val Lys
1               5                   10                  15

Gly


<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Gly Ala Ser Arg Trp Tyr Gly Thr Pro Ser Asp Tyr
1               5                   10


<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Ser Leu Ser Leu Arg Ser
```

1 5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Ile Thr Ser Ser Ala Ala Ser Thr
1 5

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Asn Phe Arg Gly Ala Ser Arg Trp Tyr Gly Thr Pro Ser Asp Tyr
1 5 10 15

<210> SEQ ID NO 35
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Gln Val Gln Leu Gln Glu Ser Gly Gly Gly Leu Val Gln Pro Gly Gly
1 5 10 15

Ser Leu Arg Leu Ser Cys Ala Ala Ser Gly Ser Ser Leu Ser Leu Arg
20 25 30

Ser Met Gly Trp Tyr Arg Gln Gly Pro Gly Lys Met Arg Glu Leu Val
35 40 45

Ala Val Ile Thr Ser Ser Ala Ala Ser Thr Asn Tyr Ala Asp Ser Val
50 55 60

Lys Gly Arg Phe Thr Ile Ser Phe Asp Asn Ala Lys Asn Thr Met Tyr
65 70 75 80

Leu Gln Met Asn Ser Leu Thr Pro Glu Asp Thr Ala Val Tyr Tyr Cys
85 90 95

Asn Phe Arg Gly Ala Ser Arg Trp Tyr Gly Thr Pro Ser Asp Tyr Trp
100 105 110

Gly Gln Gly Thr Gln Val Thr Val Ser Ser
115 120

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Leu Arg Ser Met Gly
1 5

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Val Ile Thr Ser Ser Ala Ala Ser Thr Asn Tyr Ala Asp Ser Val Lys
1 5 10 15

Gly

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Arg Gly Ala Ser Arg Trp Tyr Gly Thr Pro Ser Asp Tyr
1 5 10

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Gly Ser Ser Leu Ser Leu Arg Ser
1 5

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Ile Thr Ser Ser Ala Ala Ser Thr
1 5

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Asn Phe Arg Gly Ala Ser Arg Trp Tyr Gly Thr Pro Ser Asp Tyr
1 5 10 15

<210> SEQ ID NO 42
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 42

Gln Val Gln Leu Gln Glu Ser Gly Gly Gly Leu Val Gln Ala Gly Gly
1 5 10 15

Ser Leu Arg Leu Ser Cys Ala Ala Ser Gly Ser Ser Leu Ser Leu Arg
20 25 30

Ser Met Gly Trp Tyr Arg Gln Gly Pro Gly Lys Met Arg Glu Leu Val
35 40 45

Ala Val Ile Thr Ser Ser Ala Ala Ser Thr Asn Tyr Ala Asp Ser Val
50 55 60

Lys Gly Arg Phe Thr Ile Ser Phe Asp Asn Ala Lys Asn Thr Met Tyr
65 70 75 80

Leu Gln Met Asn Ser Leu Thr Pro Glu Asp Thr Ala Val Tyr Tyr Cys
85 90 95

Asn Phe Arg Gly Ala Ser Arg Trp Tyr Gly Thr Pro Ser Asp Tyr Trp
100 105 110

Gly Gln Gly Thr Gln Val Thr Val Ser Ser
115 120

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Gln Arg Ala Met Ser
1 5

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Asp Ile Arg Ser Thr Gly Asp Thr Ser Tyr Ala Asp Ser Val Lys Gly
1 5 10 15

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Gly Leu Trp Lys Ile Leu Pro Ser Ala
1 5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Gly Phe Ala Phe Ser Gln Arg Ala
1 5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Ile Arg Ser Thr Gly Asp Thr
1 5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ala Leu Gly Leu Trp Lys Ile Leu Pro Ser Ala
1 5 10

<210> SEQ ID NO 49
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Gln Val Gln Leu Gln Glu Ser Gly Gly Gly Leu Val Gln Pro Gly Gly
1 5 10 15

Ser Leu Leu Leu Ser Cys Ala Ala Ser Gly Phe Ala Phe Ser Gln Arg
20 25 30

Ala Met Ser Trp Val Arg Gln Ala Pro Gly Lys Gly Leu Glu Trp Val
35 40 45

Ser Asp Ile Arg Ser Thr Gly Asp Thr Ser Tyr Ala Asp Ser Val Lys
50 55 60

Gly Arg Phe Thr Ile Ser Arg Asp Asn Ala Lys Asn Thr Leu Tyr Leu
65 70 75 80

Gln Met Asn Ser Leu Lys Pro Glu Asp Thr Ala Val Tyr Tyr Cys Ala
85 90 95

Leu Gly Leu Trp Lys Ile Leu Pro Ser Ala Arg Gly Arg Gly Thr Gln
100 105 110

Val Thr Val Ser Ser
115

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Gln Arg Ala Met Ser
1 5

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Asp Ile Arg Ser Thr Gly Asp Thr Ser Tyr Ala Asp Ser Val Lys Gly
1 5 10 15

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Gly Leu Trp Lys Ile Leu Pro Ser Ala
1 5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Gly Phe Thr Phe Ser Gln Arg Ala
1 5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

Ile Arg Ser Thr Gly Asp Thr
1 5

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

Ala Leu Gly Leu Trp Lys Ile Leu Pro Ser Ala
1 5 10

<210> SEQ ID NO 56
<211> LENGTH: 117
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 56

Gln Val Gln Leu Gln Glu Ser Gly Gly Gly Leu Val Gln Pro Gly Gly
1               5                   10                  15

Ser Leu Leu Leu Ser Cys Ala Ala Ser Gly Phe Thr Phe Ser Gln Arg
            20                  25                  30

Ala Met Ser Trp Val Arg Gln Ala Pro Gly Lys Gly Leu Glu Trp Val
        35                  40                  45

Ser Asp Ile Arg Ser Thr Gly Asp Thr Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Ala
                85                  90                  95

Leu Gly Leu Trp Lys Ile Leu Pro Ser Ala Arg Gly Arg Gly Thr Gln
            100                 105                 110

Val Thr Val Ser Ser
        115

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

Arg Ser Ser Met Ser
1               5

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

Ile Ile Ser Ser Ser Gly Ile Ile Thr His Tyr Ser Asp Ser Val Lys
1               5                   10                  15

Gly

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Val Leu Asp Asp Asp Ser Gly Asp Tyr
1               5

<210> SEQ ID NO 60
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 60

Gly Phe Thr Phe Ser Arg Ser Ser
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Ser Ser Ser Gly Ile Ile Thr
1               5

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asn Ala Val Leu Asp Asp Asp Ser Gly Asp Tyr
1               5                   10

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Gly Gly Trp Val Gln Pro Gly Gly
1               5                   10                  15

Ser Leu Arg Leu Ser Cys Val Ala Ser Gly Phe Thr Phe Ser Arg Ser
            20                  25                  30

Ser Met Ser Trp His Arg Gln Ala Pro Gly Lys Glu Arg Asp Leu Val
        35                  40                  45

Ala Ile Ile Ser Ser Ser Gly Ile Ile Thr His Tyr Ser Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Val Tyr Val Cys
                85                  90                  95

Asn Ala Val Leu Asp Asp Asp Ser Gly Asp Tyr Trp Gly Gln Gly Thr
            100                 105                 110

Gln Val Thr Val Ser Ser
        115

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Val Asn Asp Ile Arg
1 5

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Arg Ile Thr Gly Gly Gly Arg Thr Asp Tyr Ala Asp Ser Val Lys Gly
1 5 10 15

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Trp Gly Arg Gly Tyr
1 5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Arg Phe Asp Phe Ser Val Asn Asp
1 5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ile Thr Gly Gly Gly Arg Thr
1 5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Trp Gly Arg Gly Tyr
1 5

<210> SEQ ID NO 70
<211> LENGTH: 111

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 70

Gln Val Gln Leu Gln Glu Ser Gly Gly Gly Leu Val Gln Pro Gly Gly
1 5 10 15

Ser Leu Arg Leu Ser Cys Ala Ala Ser Arg Phe Asp Phe Ser Val Asn
20 25 30

Asp Ile Arg Trp Tyr Arg Gln Ala Pro Gly Asn Glu Arg Glu Leu Val
35 40 45

Ala Arg Ile Thr Gly Gly Gly Arg Thr Asp Tyr Ala Asp Ser Val Lys
50 55 60

Gly Arg Phe Thr Ile Ser Arg Asp Asn Ala Lys Asn Thr Val Tyr Leu
65 70 75 80

Gln Met Asn Asn Leu Lys Pro Glu Asp Thr Ala Val Tyr Tyr Cys Trp
85 90 95

Gly Arg Gly Tyr Trp Gly Gln Gly Thr Gln Val Thr Val Ser Ser
100 105 110

<210> SEQ ID NO 71
<211> LENGTH: 353
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 71

Gln Val Gln Leu Gln Glu Ser Gly Gly Gly Leu Ala Pro Pro Gly Gly
1 5 10 15

Ser Leu Arg Leu Ser Cys Ala Ala Ser Gly Phe Thr Phe Ser Arg His
20 25 30

Ala Met Ser Trp Val Arg Gln Ala Pro Gly Lys Gly Leu Glu Trp Val
35 40 45

Ser Asp Ile Arg Ser Gly Asp Gly Gly Asp Gly Gly Thr Ser Tyr Ala
50 55 60

Asp Ser Val Lys Gly Arg Phe Thr Ile Ser Arg Asp Asn Ala Lys Asn
65 70 75 80

Thr Leu Tyr Leu Gln Met Asn Ser Leu Lys Pro Glu Asp Thr Ala Val
85 90 95

Tyr Tyr Cys Ala Leu Gly Leu Trp Lys Ile Leu Pro Ser Thr Arg Gly
100 105 110

Arg Gly Thr Gln Val Thr Val Ser Ser Glu Pro Lys Ser Cys Asp Lys
115 120 125

Thr His Thr Cys Pro Pro Cys Pro Ala Pro Glu Leu Leu Gly Gly Pro
130 135 140

Ser Val Phe Leu Phe Pro Pro Lys Pro Lys Asp Thr Leu Met Ile Ser
145 150 155 160

Arg Thr Pro Glu Val Thr Cys Val Val Val Asp Val Ser His Glu Asp
165 170 175

Pro Glu Val Lys Phe Asn Trp Tyr Val Asp Gly Val Glu Val His Asn
180 185 190

Ala Lys Thr Lys Pro Arg Glu Glu Gln Tyr Asn Ser Thr Tyr Arg Val
195 200 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 72
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Gln Glu Ser Gly Gly Gly Leu Val His Pro Gly Gly
1               5                   10                  15

Ser Leu Arg Leu Ser Cys Ala Ala Ser Gly Leu Thr Phe Ser Gln Arg
            20                  25                  30

Ala Met Ser Trp Val Arg Gln Ala Pro Gly Lys Gly Leu Glu Trp Ile
        35                  40                  45

Ser Asp Ile Lys Ser Thr Gly Glu Thr Ser Tyr Ala Asp Ser Val Lys
    50                  55                  60

Gly Arg Phe Thr Ile Ser Arg Asp Asn Ala Arg Asn Thr Val Tyr Leu
65                  70                  75                  80

Gln Met Asn Ser Leu Lys Pro Glu Asp Thr Ala Val Tyr Tyr Cys Ala
                85                  90                  95

Leu Gly Leu Trp Lys Ile Leu Pro Ser Val Arg Gly Arg Gly Thr Gln
            100                 105                 110

Val Thr Val Ser Ser Glu Pro Lys Ser Cys Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

```
Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys
            340                 345


<210> SEQ ID NO 73
<211> LENGTH: 348
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220
```

Ser Asn Lys Ala Leu Pro Ala Pro Ile Glu Lys Thr Ile Ser Lys Ala
225 230 235 240

Lys Gly Gln Pro Arg Glu Pro Gln Val Tyr Thr Leu Pro Pro Ser Arg
245 250 255

Glu Glu Met Thr Lys Asn Gln Val Ser Leu Thr Cys Leu Val Lys Gly
260 265 270

Phe Tyr Pro Ser Asp Ile Ala Val Glu Trp Glu Ser Asn Gly Gln Pro
275 280 285

Glu Asn Asn Tyr Lys Thr Thr Pro Pro Val Leu Asp Ser Asp Gly Ser
290 295 300

Phe Phe Leu Tyr Ser Lys Leu Thr Val Asp Lys Ser Arg Trp Gln Gln
305 310 315 320

Gly Asn Val Phe Ser Cys Ser Val Met His Glu Ala Leu His Asn His
325 330 335

Tyr Thr Gln Lys Ser Leu Ser Leu Ser Pro Gly Lys
340 345

<210> SEQ ID NO 74
<211> LENGTH: 352
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

Gln Val Gln Leu Leu Glu Ser Gly Gly Gly Leu Val Gln Pro Gly Gly
1 5 10 15

Ser Leu Arg Leu Ser Cys Ala Ala Ser Gly Asp Arg Ile Thr Asn Lys
20 25 30

Asp Met Gly Trp Val Arg Gln Ala Pro Gly Lys Gly Leu Glu Trp Val
35 40 45

Ser Ala Ile Ala Lys Asn Asn Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gly Leu Thr His Arg Gly Ala Ser Lys Phe Asn Tyr Trp Gly Gln
100 105 110

Gly Thr Leu Val Thr Val Ser Ser Glu Pro Lys Ser Cys Asp Lys Thr
115 120 125

His Thr Cys Pro Pro Cys Pro Ala Pro Glu Leu Leu Gly Gly Pro Ser
130 135 140

Val Phe Leu Phe Pro Pro Lys Pro Lys Asp Thr Leu Met Ile Ser Arg
145 150 155 160

Thr Pro Glu Val Thr Cys Val Val Val Asp Val Ser His Glu Asp Pro
165 170 175

Glu Val Lys Phe Asn Trp Tyr Val Asp Gly Val Glu Val His Asn Ala
180 185 190

Lys Thr Lys Pro Arg Glu Glu Gln Tyr Asn Ser Thr Tyr Arg Val Val
195 200 205

Ser Val Leu Thr Val Leu His Gln Asp Trp Leu Asn Gly Lys Glu Tyr
210 215 220

Lys Cys Lys Val Ser Asn Lys Ala Leu Pro Ala Pro Ile Glu Lys Thr

```
225                 230                 235                 240

Ile Ser Lys Ala Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350


<210> SEQ ID NO 75
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Gln Glu Ser Gly Gly Gly Leu Val Gln Pro Gly Gly
1               5                   10                  15

Ser Leu Arg Leu Ser Cys Ala Ala Ser Arg Phe Asp Phe Ser Val Asn
            20                  25                  30

Asp Ile Arg Trp Tyr Arg Gln Ala Pro Gly Asn Glu Arg Glu Leu Val
        35                  40                  45

Ala Arg Ile Thr Gly Gly Gly Arg Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Trp
                85                  90                  95

Gly Arg Gly Tyr Trp Gly Gln Gly Thr Gln Val Thr Val Ser Ser Glu
            100                 105                 110

Pro Lys Ser Cys Asp Lys Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240
```

```
Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340


<210> SEQ ID NO 76
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255
```

```
Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys
        355


<210> SEQ ID NO 77
<211> LENGTH: 604
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
```

```
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys Ala Pro Ala Pro
            340                 345                 350

Ala Pro Ala Pro Ala Pro Lys Ala Gln Val Gln Leu Gln Glu Ser Gly
        355                 360                 365

Gly Gly Trp Val Gln Pro Gly Gly Ser Leu Arg Leu Ser Cys Val Ala
    370                 375                 380

Ser Gly Phe Thr Phe Ser Arg Ser Ser Met Ser Trp His Arg Gln Ala
385                 390                 395                 400

Pro Gly Lys Glu Arg Asp Leu Val Ala Ile Ile Ser Ser Ser Gly Ile
                405                 410                 415

Ile Thr His Tyr Ser Asp Ser Val Lys Gly Arg Phe Thr Ile Ser Arg
            420                 425                 430

Asp Asn Ala Lys Asp Thr Val Tyr Leu Gln Met Asn Ser Leu Lys Pro
        435                 440                 445

Glu Asp Thr Ala Val Tyr Val Cys Asn Ala Val Leu Asp Asp Asp Ser
    450                 455                 460

Gly Asp Tyr Trp Gly Gln Gly Thr Gln Val Thr Val Ser Ser Gly Gly
465                 470                 475                 480

Gly Gly Ser Gly Gly Gly Gly Ser Gly Gly Gly Gly Ser Gln Val Gln
                485                 490                 495

Leu Gln Glu Ser Gly Gly Gly Leu Val Gln Pro Gly Gly Ser Leu Arg
            500                 505                 510

Leu Ser Cys Ala Ala Ser Arg Phe Asp Phe Ser Val Asn Asp Ile Arg
        515                 520                 525

Trp Tyr Arg Gln Ala Pro Gly Asn Glu Arg Glu Leu Val Ala Arg Ile
    530                 535                 540

Thr Gly Gly Gly Arg Thr Asp Tyr Ala Asp Ser Val Lys Gly Arg Phe
545                 550                 555                 560

Thr Ile Ser Arg Asp Asn Ala Lys Asn Thr Val Tyr Leu Gln Met Asn
                565                 570                 575

Asn Leu Lys Pro Glu Asp Thr Ala Val Tyr Tyr Cys Trp Gly Arg Gly
            580                 585                 590

Tyr Trp Gly Gln Gly Thr Gln Val Thr Val Ser Ser
        595                 600


<210> SEQ ID NO 78
<211> LENGTH: 604
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78
```

```
Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Gln Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asn Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Glu Ser Leu Ser Leu Ser Pro Gly Lys Ala Pro Ala Pro
            340                 345                 350

Ala Pro Ala Pro Ala Pro Lys Ala Gln Val Gln Leu Gln Glu Ser Gly
        355                 360                 365

Gly Gly Trp Val Gln Pro Gly Gly Ser Leu Arg Leu Ser Cys Val Ala
    370                 375                 380

Ser Gly Phe Thr Phe Ser Arg Ser Ser Met Ser Trp His Arg Gln Ala
385                 390                 395                 400

Pro Gly Lys Glu Arg Asp Leu Val Ala Ile Ile Ser Ser Ser Gly Ile
                405                 410                 415

Ile Thr His Tyr Ser Asp Ser Val Lys Gly Arg Phe Thr Ile Ser Arg
```

```
            420                 425                 430

Asp Asn Ala Lys Asp Thr Val Tyr Leu Gln Met Asn Ser Leu Lys Pro
        435                 440                 445

Glu Asp Thr Ala Val Tyr Val Cys Asn Ala Val Leu Asp Asp Asp Ser
    450                 455                 460

Gly Asp Tyr Trp Gly Gln Gly Thr Gln Val Thr Val Ser Ser Gly Gly
465                 470                 475                 480

Gly Gly Ser Gly Gly Gly Gly Ser Gly Gly Gly Gly Ser Gln Val Gln
                485                 490                 495

Leu Gln Glu Ser Gly Gly Gly Leu Val Gln Pro Gly Gly Ser Leu Arg
            500                 505                 510

Leu Ser Cys Ala Ala Ser Arg Phe Asp Phe Ser Val Asn Asp Ile Arg
        515                 520                 525

Trp Tyr Arg Gln Ala Pro Gly Asn Glu Arg Glu Leu Val Ala Arg Ile
    530                 535                 540

Thr Gly Gly Gly Arg Thr Asp Tyr Ala Asp Ser Val Lys Gly Arg Phe
545                 550                 555                 560

Thr Ile Ser Arg Asp Asn Ala Lys Asn Thr Val Tyr Leu Gln Met Asn
                565                 570                 575

Asn Leu Lys Pro Glu Asp Thr Ala Val Tyr Tyr Cys Trp Gly Arg Gly
            580                 585                 590

Tyr Trp Gly Gln Gly Thr Gln Val Thr Val Ser Ser
        595                 600


<210> SEQ ID NO 79
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ser Leu Ser Leu Arg
            20                  25                  30

Ser Met Gly Trp Tyr Arg Gln Gly Pro Gly Lys Met Arg Glu Leu Val
        35                  40                  45

Ala Val Ile Thr Ser Ser Ala Ala Ser Thr Asn Tyr Ala Asp Ser Val
    50                  55                  60

Lys Gly Arg Phe Thr Ile Ser Phe Asp Asn Ala Lys Asn Thr Met Tyr
65                  70                  75                  80

Leu Gln Met Asn Ser Leu Thr Pro Glu Asp Thr Ala Val Tyr Tyr Cys
                85                  90                  95

Asn Phe Arg Gly Ala Ser Arg Trp Tyr Gly Thr Pro Ser Asp Tyr Trp
            100                 105                 110

Gly Gln Gly Thr Gln Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175
```

```
Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Ala Pro Ala Pro Ala Pro Ala Pro Ala Pro Lys Ala Gln Val
        355                 360                 365

Gln Leu Gln Glu Ser Gly Gly Gly Trp Val Gln Pro Gly Gly Ser Leu
    370                 375                 380

Arg Leu Ser Cys Val Ala Ser Gly Phe Thr Phe Ser Arg Ser Ser Met
385                 390                 395                 400

Ser Trp His Arg Gln Ala Pro Gly Lys Glu Arg Asp Leu Val Ala Ile
                405                 410                 415

Ile Ser Ser Ser Gly Ile Ile Thr His Tyr Ser Asp Ser Val Lys Gly
            420                 425                 430

Arg Phe Thr Ile Ser Arg Asp Asn Ala Lys Asp Thr Val Tyr Leu Gln
        435                 440                 445

Met Asn Ser Leu Lys Pro Glu Asp Thr Ala Val Tyr Val Cys Asn Ala
    450                 455                 460

Val Leu Asp Asp Asp Ser Gly Asp Tyr Trp Gly Gln Gly Thr Gln Val
465                 470                 475                 480

Thr Val Ser Ser Gly Gly Gly Gly Ser Gly Gly Gly Gly Ser Gly Gly
                485                 490                 495

Gly Gly Ser Gln Val Gln Leu Gln Glu Ser Gly Gly Gly Leu Val Gln
            500                 505                 510

Pro Gly Gly Ser Leu Arg Leu Ser Cys Ala Ala Ser Arg Phe Asp Phe
        515                 520                 525

Ser Val Asn Asp Ile Arg Trp Tyr Arg Gln Ala Pro Gly Asn Glu Arg
    530                 535                 540

Glu Leu Val Ala Arg Ile Thr Gly Gly Gly Arg Thr Asp Tyr Ala Asp
545                 550                 555                 560

Ser Val Lys Gly Arg Phe Thr Ile Ser Arg Asp Asn Ala Lys Asn Thr
                565                 570                 575

Val Tyr Leu Gln Met Asn Asn Leu Lys Pro Glu Asp Thr Ala Val Tyr
            580                 585                 590

Tyr Cys Trp Gly Arg Gly Tyr Trp Gly Gln Gly Thr Gln Val Thr Val
```

```
        595                 600                 605

Ser Ser
    610


<210> SEQ ID NO 80
<211> LENGTH: 610
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ser Leu Ser Leu Arg
            20                  25                  30

Ser Met Gly Trp Tyr Arg Gln Gly Pro Gly Lys Met Arg Glu Leu Val
        35                  40                  45

Ala Val Ile Thr Ser Ser Ala Ala Ser Thr Asn Tyr Ala Asp Ser Val
    50                  55                  60

Lys Gly Arg Phe Thr Ile Ser Phe Asp Asn Ala Lys Asn Thr Met Tyr
65                  70                  75                  80

Leu Gln Met Asn Ser Leu Thr Pro Glu Asp Thr Ala Val Tyr Tyr Cys
                85                  90                  95

Asn Phe Arg Gly Ala Ser Arg Trp Tyr Gly Thr Pro Ser Asp Tyr Trp
            100                 105                 110

Gly Gln Gly Thr Gln Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335
```

Glu Ala Leu His Asn His Tyr Thr Gln Lys Ser Leu Ser Leu Ser Pro
340 345 350

Gly Lys Ala Pro Ala Pro Ala Pro Ala Pro Ala Pro Lys Ala Gln Val
355 360 365

Gln Leu Gln Glu Ser Gly Gly Gly Trp Val Gln Pro Gly Gly Ser Leu
370 375 380

Arg Leu Ser Cys Val Ala Ser Gly Phe Thr Phe Ser Arg Ser Ser Met
385 390 395 400

Ser Trp His Arg Gln Ala Pro Gly Lys Glu Arg Asp Leu Val Ala Ile
405 410 415

Ile Ser Ser Ser Gly Ile Ile Thr His Tyr Ser Asp Ser Val Lys Gly
420 425 430

Arg Phe Thr Ile Ser Arg Asp Asn Ala Lys Asp Thr Val Tyr Leu Gln
435 440 445

Met Asn Ser Leu Lys Pro Glu Asp Thr Ala Val Tyr Val Cys Asn Ala
450 455 460

Val Leu Asp Asp Asp Ser Gly Asp Tyr Trp Gly Gln Gly Thr Gln Val
465 470 475 480

Thr Val Ser Ser Gly Gly Gly Gly Ser Gly Gly Gly Gly Ser Gly Gly
485 490 495

Gly Gly Ser Gln Val Gln Leu Gln Glu Ser Gly Gly Gly Leu Val Gln
500 505 510

Pro Gly Gly Ser Leu Arg Leu Ser Cys Ala Ala Ser Arg Phe Asp Phe
515 520 525

Ser Val Asn Asp Ile Arg Trp Tyr Arg Gln Ala Pro Gly Asn Glu Arg
530 535 540

Glu Leu Val Ala Arg Ile Thr Gly Gly Gly Arg Thr Asp Tyr Ala Asp
545 550 555 560

Ser Val Lys Gly Arg Phe Thr Ile Ser Arg Asp Asn Ala Lys Asn Thr
565 570 575

Val Tyr Leu Gln Met Asn Asn Leu Lys Pro Glu Asp Thr Ala Val Tyr
580 585 590

Tyr Cys Trp Gly Arg Gly Tyr Trp Gly Gln Gly Thr Gln Val Thr Val
595 600 605

Ser Ser
610

<210> SEQ ID NO 81
<211> LENGTH: 605
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 81

Gln Val Gln Leu Gln Glu Ser Gly Gly Gly Leu Val Gln Pro Gly Gly
1 5 10 15

Ser Leu Leu Leu Ser Cys Ala Ala Ser Gly Phe Thr Phe Ser Gln Arg
20 25 30

Ala Met Ser Trp Val Arg Gln Ala Pro Gly Lys Gly Leu Glu Trp Val
35 40 45

Ser Asp Ile Arg Ser Thr Gly Asp Thr Ser Tyr Ala Asp Ser Val Lys
50 55 60

Gly Arg Phe Thr Ile Ser Arg Asp Asn Ala Lys Asn Thr Leu Tyr Leu
65 70 75 80

```
Gln Met Asn Ser Leu Lys Pro Glu Asp Thr Ala Val Tyr Tyr Cys Ala
                85                  90                  95

Leu Gly Leu Trp Lys Ile Leu Pro Ser Ala Arg Gly Arg Gly Thr Gln
            100                 105                 110

Val Thr Val Ser Ser Glu Pro Lys Ser Cys Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Ala Pro Ala
            340                 345                 350

Pro Ala Pro Ala Pro Ala Pro Lys Ala Gln Val Gln Leu Gln Glu Ser
        355                 360                 365

Gly Gly Gly Trp Val Gln Pro Gly Gly Ser Leu Arg Leu Ser Cys Val
    370                 375                 380

Ala Ser Gly Phe Thr Phe Ser Arg Ser Ser Met Ser Trp His Arg Gln
385                 390                 395                 400

Ala Pro Gly Lys Glu Arg Asp Leu Val Ala Ile Ile Ser Ser Ser Gly
                405                 410                 415

Ile Ile Thr His Tyr Ser Asp Ser Val Lys Gly Arg Phe Thr Ile Ser
            420                 425                 430

Arg Asp Asn Ala Lys Asp Thr Val Tyr Leu Gln Met Asn Ser Leu Lys
        435                 440                 445

Pro Glu Asp Thr Ala Val Tyr Val Cys Asn Ala Val Leu Asp Asp Asp
    450                 455                 460

Ser Gly Asp Tyr Trp Gly Gln Gly Thr Gln Val Thr Val Ser Ser Gly
465                 470                 475                 480

Gly Gly Gly Ser Gly Gly Gly Gly Ser Gly Gly Gly Gly Ser Gln Val
                485                 490                 495
```

```
Gln Leu Gln Glu Ser Gly Gly Gly Leu Val Gln Pro Gly Gly Ser Leu
            500                 505                 510

Arg Leu Ser Cys Ala Ala Ser Arg Phe Asp Phe Ser Val Asn Asp Ile
        515                 520                 525

Arg Trp Tyr Arg Gln Ala Pro Gly Asn Glu Arg Glu Leu Val Ala Arg
    530                 535                 540

Ile Thr Gly Gly Gly Arg Thr Asp Tyr Ala Asp Ser Val Lys Gly Arg
545                 550                 555                 560

Phe Thr Ile Ser Arg Asp Asn Ala Lys Asn Thr Val Tyr Leu Gln Met
                565                 570                 575

Asn Asn Leu Lys Pro Glu Asp Thr Ala Val Tyr Tyr Cys Trp Gly Arg
            580                 585                 590

Gly Tyr Trp Gly Gln Gly Thr Gln Val Thr Val Ser Ser
        595                 600                 605


<210> SEQ ID NO 82
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Gln Glu Ser Gly Gly Gly Leu Ala Pro Pro Gly Gly
1               5                   10                  15

Ser Leu Arg Leu Ser Cys Ala Ala Ser Gly Phe Thr Phe Ser Arg His
            20                  25                  30

Ala Met Ser Trp Val Arg Gln Ala Pro Gly Lys Gly Leu Glu Trp Val
        35                  40                  45

Ser Asp Ile Arg Ser Gly Asp Gly Gly Asp Gly Gly Thr Ser Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Lys Pro Glu Asp Thr Ala Val
                85                  90                  95

Tyr Tyr Cys Ala Leu Gly Leu Trp Lys Ile Leu Pro Ser Thr Arg Gly
            100                 105                 110

Arg Gly Thr Gln Val Thr Val Ser Ser Glu Pro Lys Ser Cys Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255
```

```
Leu Pro Pro Ser Arg Glu Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
            325                 330                 335

Ala Leu His Asn His Tyr Thr Gln Lys Ser Leu Ser Leu Ser Pro Gly
            340                 345                 350

Lys Ala Pro Ala Pro Ala Pro Ala Pro Ala Pro Lys Ala Gln Val Gln
        355                 360                 365

Leu Gln Glu Ser Gly Gly Gly Trp Val Gln Pro Gly Gly Ser Leu Arg
    370                 375                 380

Leu Ser Cys Val Ala Ser Gly Phe Thr Phe Ser Arg Ser Ser Met Ser
385                 390                 395                 400

Trp His Arg Gln Ala Pro Gly Lys Glu Arg Asp Leu Val Ala Ile Ile
            405                 410                 415

Ser Ser Ser Gly Ile Ile Thr His Tyr Ser Asp Ser Val Lys Gly Arg
            420                 425                 430

Phe Thr Ile Ser Arg Asp Asn Ala Lys Asp Thr Val Tyr Leu Gln Met
        435                 440                 445

Asn Ser Leu Lys Pro Glu Asp Thr Ala Val Tyr Val Cys Asn Ala Val
    450                 455                 460

Leu Asp Asp Asp Ser Gly Asp Tyr Trp Gly Gln Gly Thr Gln Val Thr
465                 470                 475                 480

Val Ser Ser Gly Gly Gly Gly Ser Gly Gly Gly Gly Ser Gly Gly Gly
            485                 490                 495

Gly Ser Gln Val Gln Leu Gln Glu Ser Gly Gly Gly Leu Val Gln Pro
            500                 505                 510

Gly Gly Ser Leu Arg Leu Ser Cys Ala Ala Ser Arg Phe Asp Phe Ser
        515                 520                 525

Val Asn Asp Ile Arg Trp Tyr Arg Gln Ala Pro Gly Asn Glu Arg Glu
    530                 535                 540

Leu Val Ala Arg Ile Thr Gly Gly Gly Arg Thr Asp Tyr Ala Asp Ser
545                 550                 555                 560

Val Lys Gly Arg Phe Thr Ile Ser Arg Asp Asn Ala Lys Asn Thr Val
                565                 570                 575

Tyr Leu Gln Met Asn Asn Leu Lys Pro Glu Asp Thr Ala Val Tyr Tyr
            580                 585                 590

Cys Trp Gly Arg Gly Tyr Trp Gly Gln Gly Thr Gln Val Thr Val Ser
        595                 600                 605

Ser
```

<210> SEQ ID NO 83
<211> LENGTH: 605
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

```
Gln Val Gln Leu Gln Glu Ser Gly Gly Gly Leu Val His Pro Gly Gly
1               5                   10                  15

Ser Leu Arg Leu Ser Cys Ala Ala Ser Gly Leu Thr Phe Ser Gln Arg
            20                  25                  30

Ala Met Ser Trp Val Arg Gln Ala Pro Gly Lys Gly Leu Glu Trp Ile
        35                  40                  45

Ser Asp Ile Lys Ser Thr Gly Glu Thr Ser Tyr Ala Asp Ser Val Lys
    50                  55                  60

Gly Arg Phe Thr Ile Ser Arg Asp Asn Ala Arg Asn Thr Val Tyr Leu
65                  70                  75                  80

Gln Met Asn Ser Leu Lys Pro Glu Asp Thr Ala Val Tyr Tyr Cys Ala
                85                  90                  95

Leu Gly Leu Trp Lys Ile Leu Pro Ser Val Arg Gly Arg Gly Thr Gln
            100                 105                 110

Val Thr Val Ser Ser Glu Pro Lys Ser Cys Asp Lys Thr His Thr Cys
        115                 120                 125

Pro Pro Cys Pro Ala Pro Glu Leu Leu Gly Gly Pro Ser Val Phe Leu
    130                 135                 140

Phe Pro Pro Lys Pro Lys Asp Thr Leu Met Ile Ser Arg Thr Pro Glu
145                 150                 155                 160

Val Thr Cys Val Val Val Asp Val Ser His Glu Asp Pro Glu Val Lys
                165                 170                 175

Phe Asn Trp Tyr Val Asp Gly Val Glu Val His Asn Ala Lys Thr Lys
            180                 185                 190

Pro Arg Glu Glu Gln Tyr Asn Ser Thr Tyr Arg Val Val Ser Val Leu
        195                 200                 205

Thr Val Leu His Gln Asp Trp Leu Asn Gly Lys Glu Tyr Lys Cys Lys
    210                 215                 220

Val Ser Asn Lys Ala Leu Pro Ala Pro Ile Glu Lys Thr Ile Ser Lys
225                 230                 235                 240

Ala Lys Gly Gln Pro Arg Glu Pro Gln Val Tyr Thr Leu Pro Pro Ser
                245                 250                 255

Arg Glu Glu Met Thr Lys Asn Gln Val Ser Leu Thr Cys Leu Val Lys
            260                 265                 270

Gly Phe Tyr Pro Ser Asp Ile Ala Val Glu Trp Glu Ser Asn Gly Gln
        275                 280                 285

Pro Glu Asn Asn Tyr Lys Thr Thr Pro Pro Val Leu Asp Ser Asp Gly
    290                 295                 300

Ser Phe Phe Leu Tyr Ser Lys Leu Thr Val Asp Lys Ser Arg Trp Gln
305                 310                 315                 320

Gln Gly Asn Val Phe Ser Cys Ser Val Met His Glu Ala Leu His Asn
                325                 330                 335

His Tyr Thr Gln Lys Ser Leu Ser Leu Ser Pro Gly Lys Ala Pro Ala
            340                 345                 350

Pro Ala Pro Ala Pro Ala Pro Lys Ala Gln Val Gln Leu Gln Glu Ser
        355                 360                 365

Gly Gly Gly Trp Val Gln Pro Gly Gly Ser Leu Arg Leu Ser Cys Val
    370                 375                 380

Ala Ser Gly Phe Thr Phe Ser Arg Ser Ser Met Ser Trp His Arg Gln
385                 390                 395                 400

Ala Pro Gly Lys Glu Arg Asp Leu Val Ala Ile Ile Ser Ser Ser Gly
                405                 410                 415
```

```
Ile Ile Thr His Tyr Ser Asp Ser Val Lys Gly Arg Phe Thr Ile Ser
            420                 425                 430

Arg Asp Asn Ala Lys Asp Thr Val Tyr Leu Gln Met Asn Ser Leu Lys
        435                 440                 445

Pro Glu Asp Thr Ala Val Tyr Val Cys Asn Ala Val Leu Asp Asp Asp
    450                 455                 460

Ser Gly Asp Tyr Trp Gly Gln Gly Thr Gln Val Thr Val Ser Ser Gly
465                 470                 475                 480

Gly Gly Gly Ser Gly Gly Gly Gly Ser Gly Gly Gly Gly Ser Gln Val
                485                 490                 495

Gln Leu Gln Glu Ser Gly Gly Gly Leu Val Gln Pro Gly Gly Ser Leu
            500                 505                 510

Arg Leu Ser Cys Ala Ala Ser Arg Phe Asp Phe Ser Val Asn Asp Ile
        515                 520                 525

Arg Trp Tyr Arg Gln Ala Pro Gly Asn Glu Arg Glu Leu Val Ala Arg
    530                 535                 540

Ile Thr Gly Gly Gly Arg Thr Asp Tyr Ala Asp Ser Val Lys Gly Arg
545                 550                 555                 560

Phe Thr Ile Ser Arg Asp Asn Ala Lys Asn Thr Val Tyr Leu Gln Met
                565                 570                 575

Asn Asn Leu Lys Pro Glu Asp Thr Ala Val Tyr Tyr Cys Trp Gly Arg
            580                 585                 590

Gly Tyr Trp Gly Gln Gly Thr Gln Val Thr Val Ser Ser
        595                 600                 605
```

<210> SEQ ID NO 84
<211> LENGTH: 613
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

```
Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175
```

```
Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Pro Gly Lys Ala Pro Ala Pro
            340                 345                 350

Ala Pro Ala Pro Ala Pro Lys Ala Asp Val Gln Leu Val Glu Ser Gly
        355                 360                 365

Gly Gly Ser Val Gln Ala Gly Gly Ser Leu Arg Leu Ser Cys Ala Ala
    370                 375                 380

Ser Gly Ser Thr Asp Ser Ile Glu Tyr Met Thr Trp Phe Arg Gln Ala
385                 390                 395                 400

Pro Gly Lys Ala Arg Glu Gly Val Ala Ala Leu Tyr Thr His Thr Gly
                405                 410                 415

Asn Thr Tyr Tyr Thr Asp Ser Val Lys Gly Arg Phe Thr Ile Ser Gln
            420                 425                 430

Asp Lys Ala Lys Asn Met Ala Tyr Leu Arg Met Asp Ser Val Lys Ser
        435                 440                 445

Glu Asp Thr Ala Ile Tyr Thr Cys Gly Ala Thr Arg Lys Tyr Val Pro
    450                 455                 460

Val Arg Phe Ala Leu Asp Gln Ser Ser Tyr Asp Tyr Trp Gly Gln Gly
465                 470                 475                 480

Thr Gln Val Thr Val Ser Ser Gly Gly Gly Gly Ser Gly Gly Gly Gly
                485                 490                 495

Ser Gly Gly Gly Gly Ser Gln Val Gln Leu Gln Glu Ser Gly Gly Gly
            500                 505                 510

Leu Val Gln Pro Gly Gly Ser Leu Arg Leu Ser Cys Ala Ala Ser Arg
        515                 520                 525

Phe Asp Phe Ser Val Asn Asp Ile Arg Trp Tyr Arg Gln Ala Pro Gly
    530                 535                 540

Asn Glu Arg Glu Leu Val Ala Arg Ile Thr Gly Gly Gly Arg Thr Asp
545                 550                 555                 560

Tyr Ala Asp Ser Val Lys Gly Arg Phe Thr Ile Ser Arg Asp Asn Ala
                565                 570                 575

Lys Asn Thr Val Tyr Leu Gln Met Asn Asn Leu Lys Pro Glu Asp Thr
            580                 585                 590
```

```
Ala Val Tyr Tyr Cys Trp Gly Arg Gly Tyr Trp Gly Gln Gly Thr Gln
        595                 600                 605

Val Thr Val Ser Ser
    610


<210> SEQ ID NO 85
<211> LENGTH: 601
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Ser Lys Tyr Gly Pro Pro Cys Pro Pro Cys Pro
        115                 120                 125

Ala Pro Glu Ala Ala Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335
```

Lys Ser Leu Ser Leu Ser Leu Gly Lys Ala Pro Ala Pro Ala Pro Ala
340 345 350

Pro Ala Pro Lys Ala Gln Val Gln Leu Gln Glu Ser Gly Gly Gly Trp
355 360 365

Val Gln Pro Gly Gly Ser Leu Arg Leu Ser Cys Val Ala Ser Gly Phe
370 375 380

Thr Phe Ser Arg Ser Ser Met Ser Trp His Arg Gln Ala Pro Gly Lys
385 390 395 400

Glu Arg Asp Leu Val Ala Ile Ile Ser Ser Ser Gly Ile Ile Thr His
405 410 415

Tyr Ser Asp Ser Val Lys Gly Arg Phe Thr Ile Ser Arg Asp Asn Ala
420 425 430

Lys Asp Thr Val Tyr Leu Gln Met Asn Ser Leu Lys Pro Glu Asp Thr
435 440 445

Ala Val Tyr Val Cys Asn Ala Val Leu Asp Asp Asp Ser Gly Asp Tyr
450 455 460

Trp Gly Gln Gly Thr Gln Val Thr Val Ser Ser Gly Gly Gly Gly Ser
465 470 475 480

Gly Gly Gly Gly Ser Gly Gly Gly Gly Ser Gln Val Gln Leu Gln Glu
485 490 495

Ser Gly Gly Gly Leu Val Gln Pro Gly Gly Ser Leu Arg Leu Ser Cys
500 505 510

Ala Ala Ser Arg Phe Asp Phe Ser Val Asn Asp Ile Arg Trp Tyr Arg
515 520 525

Gln Ala Pro Gly Asn Glu Arg Glu Leu Val Ala Arg Ile Thr Gly Gly
530 535 540

Gly Arg Thr Asp Tyr Ala Asp Ser Val Lys Gly Arg Phe Thr Ile Ser
545 550 555 560

Arg Asp Asn Ala Lys Asn Thr Val Tyr Leu Gln Met Asn Asn Leu Lys
565 570 575

Pro Glu Asp Thr Ala Val Tyr Tyr Cys Trp Gly Arg Gly Tyr Trp Gly
580 585 590

Gln Gly Thr Gln Val Thr Val Ser Ser
595 600

<210> SEQ ID NO 86
<211> LENGTH: 607
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

Gln Val Gln Leu Gln Glu Ser Gly Gly Gly Leu Val Gln Pro Gly Gly
1 5 10 15

Ser Leu Arg Leu Ser Cys Ala Ala Ser Gly Ser Ser Leu Ser Leu Arg
20 25 30

Ser Met Gly Trp Tyr Arg Gln Gly Pro Gly Lys Met Arg Glu Leu Val
35 40 45

Ala Val Ile Thr Ser Ser Ala Ala Ser Thr Asn Tyr Ala Asp Ser Val
50 55 60

Lys Gly Arg Phe Thr Ile Ser Phe Asp Asn Ala Lys Asn Thr Met Tyr
65 70 75 80

Leu Gln Met Asn Ser Leu Thr Pro Glu Asp Thr Ala Val Tyr Tyr Cys

```
                85                  90                  95

Asn Phe Arg Gly Ala Ser Arg Trp Tyr Gly Thr Pro Ser Asp Tyr Trp
            100                 105                 110

Gly Gln Gly Thr Gln Val Thr Val Ser Ser Glu Ser Lys Tyr Gly Pro
        115                 120                 125

Pro Cys Pro Pro Cys Pro Ala Pro Glu Ala Ala Gly Gly Pro Ser Val
    130                 135                 140

Phe Leu Phe Pro Pro Lys Pro Lys Asp Thr Leu Met Ile Ser Arg Thr
145                 150                 155                 160

Pro Glu Val Thr Cys Val Val Val Asp Val Ser Gln Glu Asp Pro Glu
                165                 170                 175

Val Gln Phe Asn Trp Tyr Val Asp Gly Val Glu Val His Asn Ala Lys
            180                 185                 190

Thr Lys Pro Arg Glu Glu Gln Phe Asn Ser Thr Tyr Arg Val Val Ser
        195                 200                 205

Val Leu Thr Val Leu His Gln Asp Trp Leu Asn Gly Lys Glu Tyr Lys
    210                 215                 220

Cys Lys Val Ser Asn Lys Gly Leu Pro Ser Ser Ile Glu Lys Thr Ile
225                 230                 235                 240

Ser Lys Ala Lys Gly Gln Pro Arg Glu Pro Gln Val Tyr Thr Leu Pro
                245                 250                 255

Pro Ser Gln Glu Glu Met Thr Lys Asn Gln Val Ser Leu Thr Cys Leu
            260                 265                 270

Val Lys Gly Phe Tyr Pro Ser Asp Ile Ala Val Glu Trp Glu Ser Asn
        275                 280                 285

Gly Gln Pro Glu Asn Asn Tyr Lys Thr Thr Pro Pro Val Leu Asp Ser
    290                 295                 300

Asp Gly Ser Phe Phe Leu Tyr Ser Arg Leu Thr Val Asp Lys Ser Arg
305                 310                 315                 320

Trp Gln Glu Gly Asn Val Phe Ser Cys Ser Val Met His Glu Ala Leu
                325                 330                 335

His Asn His Tyr Thr Gln Lys Ser Leu Ser Leu Ser Leu Gly Lys Ala
            340                 345                 350

Pro Ala Pro Ala Pro Ala Pro Ala Pro Lys Ala Gln Val Gln Leu Gln
        355                 360                 365

Glu Ser Gly Gly Gly Trp Val Gln Pro Gly Gly Ser Leu Arg Leu Ser
    370                 375                 380

Cys Val Ala Ser Gly Phe Thr Phe Ser Arg Ser Ser Met Ser Trp His
385                 390                 395                 400

Arg Gln Ala Pro Gly Lys Glu Arg Asp Leu Val Ala Ile Ile Ser Ser
                405                 410                 415

Ser Gly Ile Ile Thr His Tyr Ser Asp Ser Val Lys Gly Arg Phe Thr
            420                 425                 430

Ile Ser Arg Asp Asn Ala Lys Asp Thr Val Tyr Leu Gln Met Asn Ser
        435                 440                 445

Leu Lys Pro Glu Asp Thr Ala Val Tyr Val Cys Asn Ala Val Leu Asp
    450                 455                 460

Asp Asp Ser Gly Asp Tyr Trp Gly Gln Gly Thr Gln Val Thr Val Ser
465                 470                 475                 480

Ser Gly Gly Gly Gly Ser Gly Gly Gly Gly Ser Gly Gly Gly Gly Ser
                485                 490                 495

Gln Val Gln Leu Gln Glu Ser Gly Gly Gly Leu Val Gln Pro Gly Gly
            500                 505                 510
```

```
Ser Leu Arg Leu Ser Cys Ala Ala Ser Arg Phe Asp Phe Ser Val Asn
        515                 520                 525

Asp Ile Arg Trp Tyr Arg Gln Ala Pro Gly Asn Glu Arg Glu Leu Val
    530                 535                 540

Ala Arg Ile Thr Gly Gly Gly Arg Thr Asp Tyr Ala Asp Ser Val Lys
545                 550                 555                 560

Gly Arg Phe Thr Ile Ser Arg Asp Asn Ala Lys Asn Thr Val Tyr Leu
                565                 570                 575

Gln Met Asn Asn Leu Lys Pro Glu Asp Thr Ala Val Tyr Tyr Cys Trp
            580                 585                 590

Gly Arg Gly Tyr Trp Gly Gln Gly Thr Gln Val Thr Val Ser Ser
        595                 600                 605


<210> SEQ ID NO 87
<211> LENGTH: 619
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ser Leu Ser Leu Arg
            20                  25                  30

Ser Met Gly Trp Tyr Arg Gln Gly Pro Gly Lys Met Arg Glu Leu Val
        35                  40                  45

Ala Val Ile Thr Ser Ser Ala Ala Ser Thr Asn Tyr Ala Asp Ser Val
    50                  55                  60

Lys Gly Arg Phe Thr Ile Ser Phe Asp Asn Ala Lys Asn Thr Met Tyr
65                  70                  75                  80

Leu Gln Met Asn Ser Leu Thr Pro Glu Asp Thr Ala Val Tyr Tyr Cys
                85                  90                  95

Asn Phe Arg Gly Ala Ser Arg Trp Tyr Gly Thr Pro Ser Asp Tyr Trp
            100                 105                 110

Gly Gln Gly Thr Gln Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
```

```
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Ala Pro Ala Pro Ala Pro Ala Pro Ala Pro Lys Ala Gln Val
        355                 360                 365

Gln Leu Gln Glu Ser Gly Gly Gly Trp Val Gln Pro Gly Gly Ser Leu
    370                 375                 380

Arg Leu Ser Cys Val Ala Ser Gly Phe Thr Phe Ser Arg Ser Ser Met
385                 390                 395                 400

Ser Trp His Arg Gln Ala Pro Gly Lys Glu Arg Asp Leu Val Ala Ile
                405                 410                 415

Ile Ser Ser Ser Gly Ile Ile Thr His Tyr Ser Asp Ser Val Lys Gly
            420                 425                 430

Arg Phe Thr Ile Ser Arg Asp Asn Ala Lys Asp Thr Val Tyr Leu Gln
        435                 440                 445

Met Asn Ser Leu Lys Pro Glu Asp Thr Ala Val Tyr Val Cys Asn Ala
    450                 455                 460

Val Leu Asp Asp Asp Ser Gly Asp Tyr Trp Gly Gln Gly Thr Gln Val
465                 470                 475                 480

Thr Val Ser Ser Gly Gly Gly Gly Ser Gly Gly Gly Gly Ser Gly Gly
                485                 490                 495

Gly Gly Ser Glu Val Gln Leu Val Glu Ser Gly Gly Gly Leu Val Gln
            500                 505                 510

Pro Gly Gly Ser Leu Arg Leu Ser Cys Ala Ala Ser Gly Asp Ile Tyr
        515                 520                 525

Lys Ser Phe Asp Met Gly Trp Tyr Arg Gln Ala Pro Gly Lys Gln Arg
    530                 535                 540

Asp Leu Val Ala Val Ile Gly Ser Arg Gly Asn Asn Arg Gly Arg Thr
545                 550                 555                 560

Asn Tyr Ala Asp Ser Val Lys Gly Arg Phe Thr Ile Ser Arg Asp Gly
                565                 570                 575

Thr Gly Asn Thr Val Tyr Leu Leu Met Asn Lys Leu Arg Pro Glu Asp
            580                 585                 590

Thr Ala Ile Tyr Tyr Cys Asn Thr Ala Pro Leu Val Ala Gly Arg Pro
        595                 600                 605

Trp Gly Arg Gly Thr Leu Val Thr Val Ser Ser
    610                 615
```

<210> SEQ ID NO 88
<211> LENGTH: 619
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ser Leu Ser Leu Arg
            20                  25                  30

Ser Met Gly Trp Tyr Arg Gln Gly Pro Gly Lys Met Arg Glu Leu Val
        35                  40                  45

Ala Val Ile Thr Ser Ser Ala Ala Ser Thr Asn Tyr Ala Asp Ser Val
    50                  55                  60

Lys Gly Arg Phe Thr Ile Ser Phe Asp Asn Ala Lys Asn Thr Met Tyr
65                  70                  75                  80

Leu Gln Met Asn Ser Leu Thr Pro Glu Asp Thr Ala Val Tyr Tyr Cys
                85                  90                  95

Asn Phe Arg Gly Ala Ser Arg Trp Tyr Gly Thr Pro Ser Asp Tyr Trp
            100                 105                 110

Gly Gln Gly Thr Gln Val Thr Val Ser Ser Glu Pro Lys Ser Cys Asp
        115                 120                 125

Lys Thr His Thr Cys Pro Pro Cys Pro Ala Pro Glu Leu Leu Gly Gly
    130                 135                 140

Pro Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205

Val Val Ser Val Leu Thr Val Leu His Gln Asp Trp Leu Asn Gly Lys
    210                 215                 220

Glu Tyr Lys Cys Lys Val Ser Asn Lys Ala Leu Pro Ala Pro Ile Glu
225                 230                 235                 240

Lys Thr Ile Ser Lys Ala Lys Gly Gln Pro Arg Glu Pro Gln Val Tyr
                245                 250                 255

Thr Leu Pro Pro Ser Arg Glu Glu Met Thr Lys Asn Gln Val Ser Leu
            260                 265                 270

Thr Cys Leu Val Lys Gly Phe Tyr Pro Ser Asp Ile Ala Val Glu Trp
        275                 280                 285

Glu Ser Asn Gly Gln Pro Glu Asn Asn Tyr Lys Thr Thr Pro Pro Val
    290                 295                 300

Leu Asp Ser Asp Gly Ser Phe Phe Leu Tyr Ser Lys Leu Thr Val Asp
305                 310                 315                 320

Lys Ser Arg Trp Gln Gln Gly Asn Val Phe Ser Cys Ser Val Met His
                325                 330                 335

Glu Ala Leu His Asn His Tyr Thr Gln Lys Ser Leu Ser Leu Ser Pro
            340                 345                 350

Gly Lys Ala Pro Ala Pro Ala Pro Ala Pro Ala Pro Lys Ala Gln Val
        355                 360                 365

Gln Leu Gln Glu Ser Gly Gly Gly Trp Val Gln Pro Gly Gly Ser Leu
    370                 375                 380

Arg Leu Ser Cys Val Ala Ser Gly Phe Thr Phe Ser Arg Ser Ser Met
385                 390                 395                 400

Ser Trp His Arg Gln Ala Pro Gly Lys Glu Arg Asp Leu Val Ala Ile
                405                 410                 415

Ile Ser Ser Ser Gly Ile Ile Thr His Tyr Ser Asp Ser Val Lys Gly
```

```
            420                 425                 430

Arg Phe Thr Ile Ser Arg Asp Asn Ala Lys Asp Thr Val Tyr Leu Gln
        435                 440                 445

Met Asn Ser Leu Lys Pro Glu Asp Thr Ala Val Tyr Val Cys Asn Ala
    450                 455                 460

Val Leu Asp Asp Asp Ser Gly Asp Tyr Trp Gly Gln Gly Thr Gln Val
465                 470                 475                 480

Thr Val Ser Ser Gly Gly Gly Gly Ser Gly Gly Gly Gly Ser Gly Gly
                485                 490                 495

Gly Gly Ser Glu Val Gln Leu Val Glu Ser Gly Gly Gly Leu Val Gln
            500                 505                 510

Pro Gly Gly Ser Leu Arg Leu Ser Cys Ala Ala Ser Gly Asp Ile Tyr
        515                 520                 525

Lys Ser Phe Asp Met Gly Trp Tyr Arg Gln Ala Pro Gly Lys Gln Arg
    530                 535                 540

Asp Leu Val Ala Val Ile Gly Ser Arg Gly Asn Asn Arg Gly Arg Thr
545                 550                 555                 560

Asn Tyr Ala Asp Ser Val Lys Gly Arg Phe Thr Ile Ser Arg Asp Gly
                565                 570                 575

Thr Gly Asn Thr Val Tyr Leu Leu Met Asn Lys Leu Arg Pro Glu Asp
            580                 585                 590

Thr Ala Ile Tyr Tyr Cys Asn Thr Ala Pro Leu Val Ala Gly Arg Pro
        595                 600                 605

Trp Gly Arg Gly Thr Leu Val Thr Val Ser Ser
    610                 615


<210> SEQ ID NO 89
<211> LENGTH: 661
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160
```

Asp Thr Leu Met Ile Ser Arg Thr Pro Glu Val Thr Cys Val Val Val
165 170 175

Asp Val Ser His Glu Asp Pro Glu Val Lys Phe Asn Trp Tyr Val Asp
180 185 190

Gly Val Glu Val His Asn Ala Lys Thr Lys Pro Arg Glu Glu Gln Tyr
195 200 205

Asn Ser Thr Tyr Arg Val Val Ser Val Leu Thr Val Leu His Gln Asp
210 215 220

Trp Leu Asn Gly Lys Glu Tyr Lys Cys Lys Val Ser Asn Lys Ala Leu
225 230 235 240

Pro Ala Pro Ile Glu Lys Thr Ile Ser Lys Ala Lys Gly Gln Pro Arg
245 250 255

Glu Pro Gln Val Tyr Thr Leu Pro Pro Ser Arg Glu Glu Met Thr Lys
260 265 270

Asn Gln Val Ser Leu Thr Cys Leu Val Lys Gly Phe Tyr Pro Ser Asp
275 280 285

Ile Ala Val Glu Trp Glu Ser Asn Gly Gln Pro Glu Asn Asn Tyr Lys
290 295 300

Thr Thr Pro Pro Val Leu Asp Ser Asp Gly Ser Phe Phe Leu Tyr Ser
305 310 315 320

Lys Leu Thr Val Asp Lys Ser Arg Trp Gln Gln Gly Asn Val Phe Ser
325 330 335

Cys Ser Val Met His Glu Ala Leu His Asn His Tyr Thr Gln Lys Ser
340 345 350

Leu Ser Leu Ser Pro Gly Lys Glu Pro Lys Ile Pro Gln Pro Gln Pro
355 360 365

Lys Pro Gln Pro Gln Pro Gln Pro Gly Gly Ser Gly Ser Ala Glu Ala
370 375 380

Ala Ala Lys Ala Pro Lys Ala Pro Glu Val Gln Leu Val Glu Ser Gly
385 390 395 400

Gly Gly Ser Val Gln Ala Gly Gly Ser Leu Arg Leu Ser Cys Ala Ala
405 410 415

Ser Gly Ser Thr Asp Ser Ile Glu Tyr Met Thr Trp Phe Arg Gln Ala
420 425 430

Pro Gly Lys Ala Arg Glu Gly Val Ala Ala Leu Tyr Thr His Thr Gly
435 440 445

Asn Thr Tyr Tyr Thr Asp Ser Val Lys Gly Arg Phe Thr Ile Ser Gln
450 455 460

Asp Lys Ala Lys Asn Met Ala Tyr Leu Arg Met Asp Ser Val Lys Ser
465 470 475 480

Glu Asp Thr Ala Ile Tyr Thr Cys Gly Ala Thr Arg Lys Tyr Val Pro
485 490 495

Val Arg Phe Ala Leu Asp Gln Ser Ser Tyr Asp Tyr Trp Gly Gln Gly
500 505 510

Thr Gln Val Thr Val Ser Ser Gly Gly Gly Gly Ser Gly Gly Gly Gly
515 520 525

Ser Gly Gly Gly Gly Ser Gln Val Gln Leu Val Glu Ser Gly Gly Gly
530 535 540

Ser Val Gln Ala Gly Gly Ser Leu Arg Leu Ser Cys Ala Ala Ser Gly
545 550 555 560

Ser Thr Asp Ser Ile Glu Tyr Met Thr Trp Phe Arg Gln Ala Pro Gly
565 570 575

Lys Ala Arg Glu Gly Val Ala Ala Leu Tyr Thr His Thr Gly Asn Thr

```
            580                 585                 590

Tyr Tyr Thr Asp Ser Val Lys Gly Arg Phe Thr Ile Ser Gln Asp Lys
        595                 600                 605

Ala Lys Asn Met Ala Tyr Leu Arg Met Asp Ser Val Lys Ser Glu Asp
    610                 615                 620

Thr Ala Ile Tyr Thr Cys Gly Ala Thr Arg Lys Tyr Val Pro Val Arg
625                 630                 635                 640

Phe Ala Leu Asp Gln Ser Ser Tyr Asp Tyr Trp Gly Gln Gly Thr Gln
                645                 650                 655

Val Thr Val Ser Ser
            660


<210> SEQ ID NO 90
<211> LENGTH: 650
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Gln Met Thr Lys Asn Gln Val Ser Leu Thr Cys Leu Val Lys Gly
            260                 265                 270
```

```
Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asn Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Glu Ser Leu Ser Leu Ser Pro Gly Lys Glu Pro Lys Ile
            340                 345                 350

Pro Gln Pro Gln Pro Lys Pro Gln Pro Gln Pro Gln Pro Gly Gly Ser
        355                 360                 365

Gly Ser Ala Glu Ala Ala Ala Lys Ala Pro Lys Ala Pro Glu Val Gln
    370                 375                 380

Leu Val Glu Ser Gly Gly Gly Ser Val Gln Ala Gly Gly Ser Leu Arg
385                 390                 395                 400

Leu Ser Cys Ala Ala Ser Gly Ser Thr Asp Ser Ile Glu Tyr Met Thr
                405                 410                 415

Trp Phe Arg Gln Ala Pro Gly Lys Ala Arg Glu Gly Val Ala Ala Leu
            420                 425                 430

Tyr Thr His Thr Gly Asn Thr Tyr Tyr Thr Asp Ser Val Lys Gly Arg
        435                 440                 445

Phe Thr Ile Ser Gln Asp Lys Ala Lys Asn Met Ala Tyr Leu Arg Met
    450                 455                 460

Asp Ser Val Lys Ser Glu Asp Thr Ala Ile Tyr Thr Cys Gly Ala Thr
465                 470                 475                 480

Arg Lys Tyr Val Pro Val Arg Phe Ala Leu Asp Gln Ser Ser Tyr Asp
                485                 490                 495

Tyr Trp Gly Gln Gly Thr Gln Val Thr Val Ser Ser Gly Gly Gly Gly
            500                 505                 510

Ser Gly Gly Gly Gly Ser Gly Gly Gly Gly Ser Gln Val Gln Leu Val
        515                 520                 525

Glu Ser Gly Gly Gly Ser Val Gln Ala Gly Gly Ser Leu Arg Leu Ser
    530                 535                 540

Cys Ala Ala Ser Gly Ser Thr Asp Ser Ile Glu Tyr Met Thr Trp Phe
545                 550                 555                 560

Arg Gln Ala Pro Gly Lys Ala Arg Glu Gly Val Ala Ala Leu Tyr Thr
                565                 570                 575

His Thr Gly Asn Thr Tyr Tyr Thr Asp Ser Val Lys Gly Arg Phe Thr
            580                 585                 590

Ile Ser Gln Asp Lys Ala Lys Asn Met Ala Tyr Leu Arg Met Asp Ser
        595                 600                 605

Val Lys Ser Glu Asp Thr Ala Ile Tyr Thr Cys Gly Ala Thr Arg Lys
    610                 615                 620

Tyr Val Pro Val Arg Phe Ala Leu Asp Gln Ser Ser Tyr Asp Tyr Trp
625                 630                 635                 640

Gly Gln Gly Thr Gln Val Thr Val Ser Ser
                645                 650
```

<210> SEQ ID NO 91
<211> LENGTH: 622
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

Gln Val Gln Leu Gln Glu Ser Gly Gly Gly Leu Val Gln Ala Gly Gly
1               5                   10                  15

Ser Leu Arg Leu Ser Cys Ala Ala Ser Glu Ile Ile Phe Ser Ile Thr
            20                  25                  30

Ala Met Asn Trp Tyr Arg Gln Ala Pro Gly Lys Gln Arg Glu Leu Val
        35                  40                  45

Ala Gly Ile Ser Ser Ser Gly Lys Ile Thr Tyr Gln Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Thr Trp Ala Gly Ala Arg Asp Ala Ile Trp Gly Gln Gly Thr Gln Val
            100                 105                 110

Thr Val Ser Ser Glu Pro Lys Ser Cys Asp Lys Thr His Thr Cys Pro
        115                 120                 125

Pro Cys Pro Ala Pro Glu Leu Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Gln Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asn Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Glu Ser Leu Ser Leu Ser Pro Gly Lys Ala Pro Ala Pro
            340                 345                 350

Ala Pro Ala Pro Ala Pro Lys Ala Gln Val Gln Leu Val Glu Ser Gly
        355                 360                 365

Gly Gly Ser Val Gln Ala Gly Gly Ser Leu Arg Leu Ser Cys Ala Ala
    370                 375                 380

Ser Gly Ser Thr Asp Ser Ile Glu Tyr Met Thr Trp Phe Arg Gln Ala
385                 390                 395                 400

```
Pro Gly Lys Ala Arg Glu Gly Val Ala Ala Leu Tyr Thr His Thr Gly
                405                 410                 415

Asn Thr Tyr Tyr Thr Asp Ser Val Lys Gly Arg Phe Thr Ile Ser Gln
            420                 425                 430

Asp Lys Ala Lys Asn Met Ala Tyr Leu Arg Met Asp Ser Val Lys Ser
        435                 440                 445

Glu Asp Thr Ala Ile Tyr Thr Cys Gly Ala Thr Arg Lys Tyr Val Pro
    450                 455                 460

Val Arg Phe Ala Leu Asp Gln Ser Ser Tyr Asp Tyr Trp Gly Gln Gly
465                 470                 475                 480

Thr Gln Val Thr Val Ser Ser Gly Gly Gly Gly Ser Gly Gly Gly Gly
                485                 490                 495

Ser Gly Gly Gly Gly Ser Glu Val Gln Leu Val Glu Ser Gly Gly Gly
            500                 505                 510

Leu Val Gln Pro Gly Gly Ser Leu Arg Leu Ser Cys Ala Ala Ser Gly
        515                 520                 525

Asp Ile Tyr Lys Ser Phe Asp Met Gly Trp Tyr Arg Gln Ala Pro Gly
    530                 535                 540

Lys Gln Arg Asp Leu Val Ala Val Ile Gly Ser Arg Gly Asn Asn Arg
545                 550                 555                 560

Gly Arg Thr Asn Tyr Ala Asp Ser Val Lys Gly Arg Phe Thr Ile Ser
                565                 570                 575

Arg Asp Gly Thr Gly Asn Thr Val Tyr Leu Leu Met Asn Lys Leu Arg
            580                 585                 590

Pro Glu Asp Thr Ala Ile Tyr Tyr Cys Asn Thr Ala Pro Leu Val Ala
        595                 600                 605

Gly Arg Pro Trp Gly Arg Gly Thr Leu Val Thr Val Ser Ser
    610                 615                 620
```

<210> SEQ ID NO 92
<211> LENGTH: 633
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Gln Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140
```

Glu Leu Leu Gly Gly Pro Ser Val Phe Leu Phe Pro Pro Lys Pro Lys
145 150 155 160

Asp Thr Leu Met Ile Ser Arg Thr Pro Glu Val Thr Cys Val Val Val
165 170 175

Asp Val Ser His Glu Asp Pro Glu Val Lys Phe Asn Trp Tyr Val Asp
180 185 190

Gly Val Glu Val His Asn Ala Lys Thr Lys Pro Arg Glu Glu Gln Tyr
195 200 205

Asn Ser Thr Tyr Arg Val Val Ser Val Leu Thr Val Leu His Gln Asp
210 215 220

Trp Leu Asn Gly Lys Glu Tyr Lys Cys Lys Val Ser Asn Lys Ala Leu
225 230 235 240

Pro Ala Pro Ile Glu Lys Thr Ile Ser Lys Ala Lys Gly Gln Pro Arg
245 250 255

Glu Pro Gln Val Tyr Thr Leu Pro Pro Ser Arg Glu Gln Met Thr Lys
260 265 270

Asn Gln Val Ser Leu Thr Cys Leu Val Lys Gly Phe Tyr Pro Ser Asp
275 280 285

Ile Ala Val Glu Trp Glu Ser Asn Gly Gln Pro Glu Asn Asn Tyr Lys
290 295 300

Thr Thr Pro Pro Val Leu Asn Ser Asp Gly Ser Phe Phe Leu Tyr Ser
305 310 315 320

Lys Leu Thr Val Asp Lys Ser Arg Trp Gln Gln Gly Asn Val Phe Ser
325 330 335

Cys Ser Val Met His Glu Ala Leu His Asn His Tyr Thr Gln Glu Ser
340 345 350

Leu Ser Leu Ser Pro Gly Lys Ala Pro Ala Pro Ala Pro Ala Pro Ala
355 360 365

Pro Lys Ala Gln Val Gln Leu Val Glu Ser Gly Gly Gly Ser Val Gln
370 375 380

Ala Gly Gly Ser Leu Arg Leu Ser Cys Ala Ala Ser Gly Ser Thr Asp
385 390 395 400

Ser Ile Glu Tyr Met Thr Trp Phe Arg Gln Ala Pro Gly Lys Ala Arg
405 410 415

Glu Gly Val Ala Ala Leu Tyr Thr His Thr Gly Asn Thr Tyr Tyr Thr
420 425 430

Asp Ser Val Lys Gly Arg Phe Thr Ile Ser Gln Asp Lys Ala Lys Asn
435 440 445

Met Ala Tyr Leu Arg Met Asp Ser Val Lys Ser Glu Asp Thr Ala Ile
450 455 460

Tyr Thr Cys Gly Ala Thr Arg Lys Tyr Val Pro Val Arg Phe Ala Leu
465 470 475 480

Asp Gln Ser Ser Tyr Asp Tyr Trp Gly Gln Gly Thr Gln Val Thr Val
485 490 495

Ser Ser Gly Gly Gly Gly Ser Gly Gly Gly Gly Ser Gly Gly Gly Gly
500 505 510

Ser Glu Val Gln Leu Val Glu Ser Gly Gly Gly Leu Val Gln Pro Gly
515 520 525

Gly Ser Leu Arg Leu Ser Cys Ala Ala Ser Gly Asp Ile Tyr Lys Ser
530 535 540

Phe Asp Met Gly Trp Tyr Arg Gln Ala Pro Gly Lys Gln Arg Asp Leu
545 550 555 560

```
Val Ala Val Ile Gly Ser Arg Gly Asn Asn Arg Gly Arg Thr Asn Tyr
            565                 570                 575

Ala Asp Ser Val Lys Gly Arg Phe Thr Ile Ser Arg Asp Gly Thr Gly
            580                 585                 590

Asn Thr Val Tyr Leu Leu Met Asn Lys Leu Arg Pro Glu Asp Thr Ala
        595                 600                 605

Ile Tyr Tyr Cys Asn Thr Ala Pro Leu Val Ala Gly Arg Pro Trp Gly
    610                 615                 620

Arg Gly Thr Leu Val Thr Val Ser Ser
625                 630


<210> SEQ ID NO 93
<211> LENGTH: 640
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Gln Met Thr Lys
            260                 265                 270

Asn Gln Val Ser Leu Thr Cys Leu Val Lys Gly Phe Tyr Pro Ser Asp
        275                 280                 285
```

```
Ile Ala Val Glu Trp Glu Ser Asn Gly Gln Pro Glu Asn Asn Tyr Lys
    290                 295                 300

Thr Thr Pro Pro Val Leu Asn Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Glu Ser
            340                 345                 350

Leu Ser Leu Ser Pro Gly Lys Ala Pro Ala Pro Ala Pro Ala Pro Ala
        355                 360                 365

Pro Lys Ala Gln Val Gln Leu Val Glu Ser Gly Gly Gly Ser Val Gln
    370                 375                 380

Ala Gly Gly Ser Leu Arg Leu Ser Cys Ala Ala Ser Gly Ser Thr Asp
385                 390                 395                 400

Ser Ile Glu Tyr Met Thr Trp Phe Arg Gln Ala Pro Gly Lys Ala Arg
                405                 410                 415

Glu Gly Val Ala Ala Leu Tyr Thr His Thr Gly Asn Thr Tyr Tyr Thr
            420                 425                 430

Asp Ser Val Lys Gly Arg Phe Thr Ile Ser Gln Asp Lys Ala Lys Asn
        435                 440                 445

Met Ala Tyr Leu Arg Met Asp Ser Val Lys Ser Glu Asp Thr Ala Ile
    450                 455                 460

Tyr Thr Cys Gly Ala Thr Arg Lys Tyr Val Pro Val Arg Phe Ala Leu
465                 470                 475                 480

Asp Gln Ser Ser Tyr Asp Tyr Trp Gly Gln Gly Thr Gln Val Thr Val
                485                 490                 495

Ser Ser Gly Gly Gly Gly Ser Gly Gly Gly Gly Ser Gly Gly Gly Gly
            500                 505                 510

Ser Gln Val Gln Leu Val Glu Ser Gly Gly Gly Ser Val Gln Ala Gly
        515                 520                 525

Gly Ser Leu Arg Leu Ser Cys Ala Ala Ser Gly Ser Thr Asp Ser Ile
    530                 535                 540

Glu Tyr Met Thr Trp Phe Arg Gln Ala Pro Gly Lys Ala Arg Glu Gly
545                 550                 555                 560

Val Ala Ala Leu Tyr Thr His Thr Gly Asn Thr Tyr Tyr Thr Asp Ser
                565                 570                 575

Val Lys Gly Arg Phe Thr Ile Ser Gln Asp Lys Ala Lys Asn Met Ala
            580                 585                 590

Tyr Leu Arg Met Asp Ser Val Lys Ser Glu Asp Thr Ala Ile Tyr Thr
        595                 600                 605

Cys Gly Ala Thr Arg Lys Tyr Val Pro Val Arg Phe Ala Leu Asp Gln
    610                 615                 620

Ser Ser Tyr Asp Tyr Trp Gly Gln Gly Thr Gln Val Thr Val Ser Ser
625                 630                 635                 640
```

<210> SEQ ID NO 94
<211> LENGTH: 631
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gln Val Gln Leu Val Glu Ser Gly Gly Gly Ser Val Gln Ala Gly Gly
```

```
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45

Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Gln Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asn Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Glu Ser
            340                 345                 350

Leu Ser Leu Ser Pro Gly Lys Ala Pro Ala Pro Ala Pro Ala Pro Ala
        355                 360                 365

Pro Lys Ala Gln Val Gln Leu Gln Glu Ser Gly Gly Gly Trp Val Gln
    370                 375                 380

Pro Gly Gly Ser Leu Arg Leu Ser Cys Val Ala Ser Gly Phe Thr Phe
385                 390                 395                 400

Ser Arg Ser Ser Met Ser Trp His Arg Gln Ala Pro Gly Lys Glu Arg
                405                 410                 415

Asp Leu Val Ala Ile Ile Ser Ser Ser Gly Ile Ile Thr His Tyr Ser
            420                 425                 430
```

Asp Ser Val Lys Gly Arg Phe Thr Ile Ser Arg Asp Asn Ala Lys Asp
435 440 445

Thr Val Tyr Leu Gln Met Asn Ser Leu Lys Pro Glu Asp Thr Ala Val
450 455 460

Tyr Val Cys Asn Ala Val Leu Asp Asp Asp Ser Gly Asp Tyr Trp Gly
465 470 475 480

Gln Gly Thr Gln Val Thr Val Ser Ser Gly Gly Gly Gly Ser Gly Gly
485 490 495

Gly Gly Ser Gly Gly Gly Gly Ser Gln Val Gln Leu Val Glu Ser Gly
500 505 510

Gly Gly Ser Val Gln Ala Gly Gly Ser Leu Arg Leu Ser Cys Ala Ala
515 520 525

Ser Gly Ser Thr Asp Ser Ile Glu Tyr Met Thr Trp Phe Arg Gln Ala
530 535 540

Pro Gly Lys Ala Arg Glu Gly Val Ala Ala Leu Tyr Thr His Thr Gly
545 550 555 560

Asn Thr Tyr Tyr Thr Asp Ser Val Lys Gly Arg Phe Thr Ile Ser Gln
565 570 575

Asp Lys Ala Lys Asn Met Ala Tyr Leu Arg Met Asp Ser Val Lys Ser
580 585 590

Glu Asp Thr Ala Ile Tyr Thr Cys Gly Ala Thr Arg Lys Tyr Val Pro
595 600 605

Val Arg Phe Ala Leu Asp Gln Ser Ser Tyr Asp Tyr Trp Gly Gln Gly
610 615 620

Thr Gln Val Thr Val Ser Ser
625 630

<210> SEQ ID NO 95
<211> LENGTH: 620
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

Gln Val Gln Leu Gln Glu Ser Gly Gly Gly Leu Val Gln Ala Gly Gly
1 5 10 15

Ser Leu Arg Leu Ser Cys Ala Ala Ser Glu Ile Ile Phe Ser Ile Thr
20 25 30

Ala Met Asn Trp Tyr Arg Gln Ala Pro Gly Lys Gln Arg Glu Leu Val
35 40 45

Ala Gly Ile Ser Ser Ser Gly Lys Ile Thr Tyr Gln Asp Ser Val Lys
50 55 60

Gly Arg Phe Thr Ile Ser Lys Asp Asn Ala Lys Asn Thr Leu Tyr Leu
65 70 75 80

Gln Met Asn Ser Leu Lys Pro Glu Asp Thr Ala Val Tyr Tyr Cys Asn
85 90 95

Thr Trp Ala Gly Ala Arg Asp Ala Ile Trp Gly Gln Gly Thr Gln Val
100 105 110

Thr Val Ser Ser Glu Pro Lys Ser Cys Asp Lys Thr His Thr Cys Pro
115 120 125

Pro Cys Pro Ala Pro Glu Leu Leu Gly Gly Pro Ser Val Phe Leu Phe
130 135 140

Pro Pro Lys Pro Lys Asp Thr Leu Met Ile Ser Arg Thr Pro Glu Val

```
145                 150                 155                 160

Thr Cys Val Val Val Asp Val Ser His Glu Asp Pro Glu Val Lys Phe
                165                 170                 175

Asn Trp Tyr Val Asp Gly Val Glu Val His Asn Ala Lys Thr Lys Pro
            180                 185                 190

Arg Glu Glu Gln Tyr Asn Ser Thr Tyr Arg Val Val Ser Val Leu Thr
        195                 200                 205

Val Leu His Gln Asp Trp Leu Asn Gly Lys Glu Tyr Lys Cys Lys Val
    210                 215                 220

Ser Asn Lys Ala Leu Pro Ala Pro Ile Glu Lys Thr Ile Ser Lys Ala
225                 230                 235                 240

Lys Gly Gln Pro Arg Glu Pro Gln Val Tyr Thr Leu Pro Pro Ser Arg
                245                 250                 255

Glu Gln Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asn Ser Asp Gly Ser
    290                 295                 300

Phe Phe Leu Tyr Ser Lys Leu Thr Val Asp Lys Ser Arg Trp Gln Gln
305                 310                 315                 320

Gly Asn Val Phe Ser Cys Ser Val Met His Glu Ala Leu His Asn His
                325                 330                 335

Tyr Thr Gln Glu Ser Leu Ser Leu Ser Pro Gly Lys Ala Pro Ala Pro
            340                 345                 350

Ala Pro Ala Pro Ala Pro Lys Ala Gln Val Gln Leu Gln Glu Ser Gly
        355                 360                 365

Gly Gly Trp Val Gln Pro Gly Gly Ser Leu Arg Leu Ser Cys Val Ala
    370                 375                 380

Ser Gly Phe Thr Phe Ser Arg Ser Ser Met Ser Trp His Arg Gln Ala
385                 390                 395                 400

Pro Gly Lys Glu Arg Asp Leu Val Ala Ile Ile Ser Ser Ser Gly Ile
                405                 410                 415

Ile Thr His Tyr Ser Asp Ser Val Lys Gly Arg Phe Thr Ile Ser Arg
            420                 425                 430

Asp Asn Ala Lys Asp Thr Val Tyr Leu Gln Met Asn Ser Leu Lys Pro
        435                 440                 445

Glu Asp Thr Ala Val Tyr Val Cys Asn Ala Val Leu Asp Asp Asp Ser
    450                 455                 460

Gly Asp Tyr Trp Gly Gln Gly Thr Gln Val Thr Val Ser Ser Gly Gly
465                 470                 475                 480

Gly Gly Ser Gly Gly Gly Gly Ser Gly Gly Gly Gly Ser Gln Val Gln
                485                 490                 495

Leu Val Glu Ser Gly Gly Gly Ser Val Gln Ala Gly Gly Ser Leu Arg
            500                 505                 510

Leu Ser Cys Ala Ala Ser Gly Ser Thr Asp Ser Ile Glu Tyr Met Thr
        515                 520                 525

Trp Phe Arg Gln Ala Pro Gly Lys Ala Arg Glu Gly Val Ala Ala Leu
    530                 535                 540

Tyr Thr His Thr Gly Asn Thr Tyr Tyr Thr Asp Ser Val Lys Gly Arg
545                 550                 555                 560

Phe Thr Ile Ser Gln Asp Lys Ala Lys Asn Met Ala Tyr Leu Arg Met
                565                 570                 575
```

Asp Ser Val Lys Ser Glu Asp Thr Ala Ile Tyr Thr Cys Gly Ala Thr
580 585 590

Arg Lys Tyr Val Pro Val Arg Phe Ala Leu Asp Gln Ser Ser Tyr Asp
595 600 605

Tyr Trp Gly Gln Gly Thr Gln Val Thr Val Ser Ser
610 615 620

<210> SEQ ID NO 96
<211> LENGTH: 615
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Gln Val Gln Leu Val Glu Ser Gly Gly Gly Ser Val Gln Ala Gly Gly
1 5 10 15

Ser Leu Arg Leu Ser Cys Ala Ala Ser Gly Ser Thr Asp Ser Ile Glu
20 25 30

Tyr Met Thr Trp Phe Arg Gln Ala Pro Gly Lys Ala Arg Glu Gly Val
35 40 45

Ala Ala Leu Tyr Thr His Thr Gly Asn Thr Tyr Tyr Thr Asp Ser Val
50 55 60

Lys Gly Arg Phe Thr Ile Ser Gln Asp Lys Ala Lys Asn Met Ala Tyr
65 70 75 80

Leu Arg Met Asp Ser Val Lys Ser Glu Asp Thr Ala Ile Tyr Thr Cys
85 90 95

Gly Ala Thr Arg Lys Tyr Val Pro Val Arg Phe Ala Leu Asp Gln Ser
100 105 110

Ser Tyr Asp Tyr Trp Gly Gln Gly Thr Gln Val Thr Val Ser Ser Glu
115 120 125

Pro Lys Ser Cys Asp Lys Thr His Thr Cys Pro Pro Cys Pro Ala Pro
130 135 140

Glu Leu Leu Gly Gly Pro Ser Val Phe Leu Phe Pro Pro Lys Pro Lys
145 150 155 160

Asp Thr Leu Met Ile Ser Arg Thr Pro Glu Val Thr Cys Val Val Val
165 170 175

Asp Val Ser His Glu Asp Pro Glu Val Lys Phe Asn Trp Tyr Val Asp
180 185 190

Gly Val Glu Val His Asn Ala Lys Thr Lys Pro Arg Glu Glu Gln Tyr
195 200 205

Asn Ser Thr Tyr Arg Val Val Ser Val Leu Thr Val Leu His Gln Asp
210 215 220

Trp Leu Asn Gly Lys Glu Tyr Lys Cys Lys Val Ser Asn Lys Ala Leu
225 230 235 240

Pro Ala Pro Ile Glu Lys Thr Ile Ser Lys Ala Lys Gly Gln Pro Arg
245 250 255

Glu Pro Gln Val Tyr Thr Leu Pro Pro Ser Arg Glu Gln Met Thr Lys
260 265 270

Asn Gln Val Ser Leu Thr Cys Leu Val Lys Gly Phe Tyr Pro Ser Asp
275 280 285

Ile Ala Val Glu Trp Glu Ser Asn Gly Gln Pro Glu Asn Asn Tyr Lys
290 295 300

Thr Thr Pro Pro Val Leu Asn Ser Asp Gly Ser Phe Phe Leu Tyr Ser

```
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Glu Ser
            340                 345                 350

Leu Ser Leu Ser Pro Gly Lys Ala Pro Ala Pro Ala Pro Ala Pro Ala
        355                 360                 365

Pro Lys Ala Gln Val Gln Leu Gln Glu Ser Gly Gly Gly Trp Val Gln
    370                 375                 380

Pro Gly Gly Ser Leu Arg Leu Ser Cys Val Ala Ser Gly Phe Thr Phe
385                 390                 395                 400

Ser Arg Ser Ser Met Ser Trp His Arg Gln Ala Pro Gly Lys Glu Arg
                405                 410                 415

Asp Leu Val Ala Ile Ile Ser Ser Ser Gly Ile Ile Thr His Tyr Ser
            420                 425                 430

Asp Ser Val Lys Gly Arg Phe Thr Ile Ser Arg Asp Asn Ala Lys Asp
        435                 440                 445

Thr Val Tyr Leu Gln Met Asn Ser Leu Lys Pro Glu Asp Thr Ala Val
    450                 455                 460

Tyr Val Cys Asn Ala Val Leu Asp Asp Asp Ser Gly Asp Tyr Trp Gly
465                 470                 475                 480

Gln Gly Thr Gln Val Thr Val Ser Ser Gly Gly Gly Gly Ser Gly Gly
                485                 490                 495

Gly Gly Ser Gly Gly Gly Gly Ser Gln Val Gln Leu Gln Glu Ser Gly
            500                 505                 510

Gly Gly Leu Val Gln Pro Gly Gly Ser Leu Arg Leu Ser Cys Ala Ala
        515                 520                 525

Ser Arg Phe Asp Phe Ser Val Asn Asp Ile Arg Trp Tyr Arg Gln Ala
    530                 535                 540

Pro Gly Asn Glu Arg Glu Leu Val Ala Arg Ile Thr Gly Gly Gly Arg
545                 550                 555                 560

Thr Asp Tyr Ala Asp Ser Val Lys Gly Arg Phe Thr Ile Ser Arg Asp
                565                 570                 575

Asn Ala Lys Asn Thr Val Tyr Leu Gln Met Asn Asn Leu Lys Pro Glu
            580                 585                 590

Asp Thr Ala Val Tyr Tyr Cys Trp Gly Arg Gly Tyr Trp Gly Gln Gly
        595                 600                 605

Thr Gln Val Thr Val Ser Ser
    610                 615


<210> SEQ ID NO 97
<211> LENGTH: 640
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Glu Ser Gly Gly Gly Ser Val Gln Ala Gly Gly
1               5                   10                  15

Ser Leu Arg Leu Ser Cys Ala Ala Ser Gly Ser Thr Asp Ser Ile Glu
            20                  25                  30

Tyr Met Thr Trp Phe Arg Gln Ala Pro Gly Lys Ala Arg Glu Gly Val
        35                  40                  45
```

```
Ala Ala Leu Tyr Thr His Thr Gly Asn Thr Tyr Tyr Thr Asp Ser Val
    50                  55                  60

Lys Gly Arg Phe Thr Ile Ser Gln Asp Lys Ala Lys Asn Met Ala Tyr
65                  70                  75                  80

Leu Arg Met Asp Ser Val Lys Ser Glu Asp Thr Ala Ile Tyr Thr Cys
                85                  90                  95

Gly Ala Thr Arg Lys Tyr Val Pro Val Arg Phe Ala Leu Asp Gln Ser
            100                 105                 110

Ser Tyr Asp Tyr Trp Gly Gln Gly Thr Gln Val Thr Val Ser Ser Glu
        115                 120                 125

Pro Lys Ser Cys Asp Lys Thr His Thr Cys Pro Pro Cys Pro Ala Pro
    130                 135                 140

Glu Leu Leu Gly Gly Pro Ser Val Phe Leu Phe Pro Pro Lys Pro Lys
145                 150                 155                 160

Asp Thr Leu Met Ile Ser Arg Thr Pro Glu Val Thr Cys Val Val Val
                165                 170                 175

Asp Val Ser His Glu Asp Pro Glu Val Lys Phe Asn Trp Tyr Val Asp
            180                 185                 190

Gly Val Glu Val His Asn Ala Lys Thr Lys Pro Arg Glu Glu Gln Tyr
        195                 200                 205

Asn Ser Thr Tyr Arg Val Val Ser Val Leu Thr Val Leu His Gln Asp
    210                 215                 220

Trp Leu Asn Gly Lys Glu Tyr Lys Cys Lys Val Ser Asn Lys Ala Leu
225                 230                 235                 240

Pro Ala Pro Ile Glu Lys Thr Ile Ser Lys Ala Lys Gly Gln Pro Arg
                245                 250                 255

Glu Pro Gln Val Tyr Thr Leu Pro Pro Ser Arg Glu Glu Met Thr Lys
            260                 265                 270

Asn Gln Val Ser Leu Thr Cys Leu Val Lys Gly Phe Tyr Pro Ser Asp
        275                 280                 285

Ile Ala Val Glu Trp Glu Ser Asn Gly Gln Pro Glu Asn Asn Tyr Lys
    290                 295                 300

Thr Thr Pro Pro Val Leu Asp Ser Asp Gly Ser Phe Phe Leu Tyr Ser
305                 310                 315                 320

Lys Leu Thr Val Asp Lys Ser Arg Trp Gln Gln Gly Asn Val Phe Ser
                325                 330                 335

Cys Ser Val Met His Glu Ala Leu His Asn His Tyr Thr Gln Lys Ser
            340                 345                 350

Leu Ser Leu Ser Pro Gly Lys Ala Pro Ala Pro Ala Pro Ala Pro Ala
        355                 360                 365

Pro Lys Ala Gln Val Gln Leu Val Glu Ser Gly Gly Gly Ser Val Gln
    370                 375                 380

Ala Gly Gly Ser Leu Arg Leu Ser Cys Ala Ala Ser Gly Ser Thr Asp
385                 390                 395                 400

Ser Ile Glu Tyr Met Thr Trp Phe Arg Gln Ala Pro Gly Lys Ala Arg
                405                 410                 415

Glu Gly Val Ala Ala Leu Tyr Thr His Thr Gly Asn Thr Tyr Tyr Thr
            420                 425                 430

Asp Ser Val Lys Gly Arg Phe Thr Ile Ser Gln Asp Lys Ala Lys Asn
        435                 440                 445

Met Ala Tyr Leu Arg Met Asp Ser Val Lys Ser Glu Asp Thr Ala Ile
    450                 455                 460

Tyr Thr Cys Gly Ala Thr Arg Lys Tyr Val Pro Val Arg Phe Ala Leu
```

```
465                 470                 475                 480

Asp Gln Ser Ser Tyr Asp Tyr Trp Gly Gln Gly Thr Gln Val Thr Val
                485                 490                 495

Ser Ser Gly Gly Gly Gly Ser Gly Gly Gly Gly Ser Gly Gly Gly Gly
            500                 505                 510

Ser Gln Val Gln Leu Val Glu Ser Gly Gly Gly Ser Val Gln Ala Gly
        515                 520                 525

Gly Ser Leu Arg Leu Ser Cys Ala Ala Ser Gly Ser Thr Asp Ser Ile
    530                 535                 540

Glu Tyr Met Thr Trp Phe Arg Gln Ala Pro Gly Lys Ala Arg Glu Gly
545                 550                 555                 560

Val Ala Ala Leu Tyr Thr His Thr Gly Asn Thr Tyr Tyr Thr Asp Ser
                565                 570                 575

Val Lys Gly Arg Phe Thr Ile Ser Gln Asp Lys Ala Lys Asn Met Ala
            580                 585                 590

Tyr Leu Arg Met Asp Ser Val Lys Ser Glu Asp Thr Ala Ile Tyr Thr
        595                 600                 605

Cys Gly Ala Thr Arg Lys Tyr Val Pro Val Arg Phe Ala Leu Asp Gln
    610                 615                 620

Ser Ser Tyr Asp Tyr Trp Gly Gln Gly Thr Gln Val Thr Val Ser Ser
625                 630                 635                 640


<210> SEQ ID NO 98
<211> LENGTH: 15
<212> TYPE: PRT
<213> ORGANISM: Homo sapiens

<400> SEQUENCE: 98

Glu Pro Lys Ser Cys Asp Lys Thr His Thr Cys Pro Pro Cys Pro
1               5                   10                  15


<210> SEQ ID NO 99
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Pro Lys Ile Pro Gln Pro Gln Pro Lys Pro Gln Pro Gln Pro Gln
1               5                   10                  15

Pro Gly Gly Ser Gly Ser Ala Glu Ala Ala Ala Lys Ala Pro Lys Ala
            20                  25                  30

Pro


<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly Gly Gly Ser Gly Gly Gly Gly Ser
1               5                   10


<210> SEQ ID NO 101
<211> LENGTH: 15
```

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 101

Gly Gly Gly Gly Ser Gly Gly Gly Gly Ser Gly Gly Gly Gly Ser
1 5 10 15

<210> SEQ ID NO 102
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 102

Gly Gly Gly Gly Ser Gly Gly Gly Gly Ser Gly Gly Gly Gly Ser Gly
1 5 10 15

Gly Gly Gly Ser Gly Gly Gly Gly Ser
20 25

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 103

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser
20 25 30

<210> SEQ ID NO 104
<211> LENGTH: 50
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:

<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ser or absent
<220> FEATURE:
<221> NAME/KEY: MOD_RES
<222> LOCATION: (36)..(36)
<223> OTHER INFORMATION: Gly or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Ser or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Ser or absent
<220> FEATURE:
<221> NAME/KEY: SITE
<222> LOCATION: (6)..(50)
<223> OTHER INFORMATION: This region may encompass 1-9 “Gly Gly Gly Gly Ser" repeating units wherein some positions may be absent

<400> SEQUENCE: 104

Gly Gly Gly Gly Ser Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa
50

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Pro Ala Pro Ala Pro Lys Ala
1 5

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Ala Pro Ala Pro Ala Pro Ala Pro Ala Pro Lys Ala
1 5 10

<210> SEQ ID NO 107
<211> LENGTH: 22
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Ala Pro Ala Pro Ala Pro Ala Pro Ala Pro Ala Pro Ala Pro Ala Pro
1 5 10 15

Ala Pro Ala Pro Lys Ala
20

<210> SEQ ID NO 108
<211> LENGTH: 62
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ala or absent
<220> FEATURE:
<221> NAME/KEY: MOD_RES
<222> LOCATION: (7)..(7)
<223> OTHER INFORMATION: Ala or absent
<220> FEATURE:
<221> NAME/KEY: MOD_RES
<222> LOCATION: (8)..(8)
<223> OTHER INFORMATION: Pro or absent
<220> FEATURE:
<221> NAME/KEY: MOD_RES
<222> LOCATION: (9)..(9)
<223> OTHER INFORMATION: Ala or absent
<220> FEATURE:
<221> NAME/KEY: MOD_RES
<222> LOCATION: (10)..(10)
<223> OTHER INFORMATION: Pro or absent
<220> FEATURE:
<221> NAME/KEY: MOD_RES
<222> LOCATION: (11)..(11)
<223> OTHER INFORMATION: Ala or absent
<220> FEATURE:
<221> NAME/KEY: MOD_RES
<222> LOCATION: (12)..(12)
<223> OTHER INFORMATION: Pro or absent
<220> FEATURE:
<221> NAME/KEY: MOD_RES
<222> LOCATION: (13)..(13)
<223> OTHER INFORMATION: Ala or absent
<220> FEATURE:
<221> NAME/KEY: MOD_RES
<222> LOCATION: (14)..(14)
<223> OTHER INFORMATION: Pro or absent
<220> FEATURE:
<221> NAME/KEY: MOD_RES
<222> LOCATION: (15)..(15)
<223> OTHER INFORMATION: Ala or absent
<220> FEATURE:
<221> NAME/KEY: MOD_RES
<222> LOCATION: (16)..(16)
<223> OTHER INFORMATION: Pro or absent
<220> FEATURE:
<221> NAME/KEY: MOD_RES
<222> LOCATION: (17)..(17)
<223> OTHER INFORMATION: Ala or absent
<220> FEATURE:
<221> NAME/KEY: MOD_RES
<222> LOCATION: (18)..(18)
<223> OTHER INFORMATION: Pro or absent
<220> FEATURE:
<221> NAME/KEY: MOD_RES
<222> LOCATION: (19)..(19)
<223> OTHER INFORMATION: Ala or absent
<220> FEATURE:
<221> NAME/KEY: MOD_RES
<222> LOCATION: (20)..(20)
<223> OTHER INFORMATION: Pro or absent
<220> FEATURE:
<221> NAME/KEY: MOD_RES
<222> LOCATION: (21)..(21)
<223> OTHER INFORMATION: Ala or absent
<220> FEATURE:
<221> NAME/KEY: MOD_RES
<222> LOCATION: (22)..(22)
<223> OTHER INFORMATION: Pro or absent
<220> FEATURE:
<221> NAME/KEY: MOD_RES
<222> LOCATION: (23)..(23)
<223> OTHER INFORMATION: Ala or absent
<220> FEATURE:
<221> NAME/KEY: MOD_RES
<222> LOCATION: (24)..(24)
<223> OTHER INFORMATION: Pro or absent
<220> FEATURE:
<221> NAME/KEY: MOD_RES
<222> LOCATION: (25)..(25)
<223> OTHER INFORMATION: Ala or absent
<220> FEATURE:
<221> NAME/KEY: MOD_RES
<222> LOCATION: (26)..(26)
<223> OTHER INFORMATION: Pro or absent
<220> FEATURE:
<221> NAME/KEY: MOD_RES
<222> LOCATION: (27)..(27)
<223> OTHER INFORMATION: Ala or absent
<220> FEATURE:

<221> NAME/KEY: MOD_RES
<222> LOCATION: (28)..(28)
<223> OTHER INFORMATION: Pro or absent
<220> FEATURE:
<221> NAME/KEY: MOD_RES
<222> LOCATION: (29)..(29)
<223> OTHER INFORMATION: Ala or absent
<220> FEATURE:
<221> NAME/KEY: MOD_RES
<222> LOCATION: (30)..(30)
<223> OTHER INFORMATION: Pro or absent
<220> FEATURE:
<221> NAME/KEY: MOD_RES
<222> LOCATION: (31)..(31)
<223> OTHER INFORMATION: Ala or absent
<220> FEATURE:
<221> NAME/KEY: MOD_RES
<222> LOCATION: (32)..(32)
<223> OTHER INFORMATION: Pro or absent
<220> FEATURE:
<221> NAME/KEY: MOD_RES
<222> LOCATION: (33)..(33)
<223> OTHER INFORMATION: Ala or absent
<220> FEATURE:
<221> NAME/KEY: MOD_RES
<222> LOCATION: (34)..(34)
<223> OTHER INFORMATION: Pro or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(36)
<223> OTHER INFORMATION: Pro or absent
<220> FEATURE:
<221> NAME/KEY: MOD_RES
<222> LOCATION: (37)..(37)
<223> OTHER INFORMATION: Ala or absent
<220> FEATURE:
<221> NAME/KEY: MOD_RES
<222> LOCATION: (38)..(38)
<223> OTHER INFORMATION: Pro or absent
<220> FEATURE:
<221> NAME/KEY: MOD_RES
<222> LOCATION: (39)..(39)
<223> OTHER INFORMATION: Ala or absent
<220> FEATURE:
<221> NAME/KEY: MOD_RES
<222> LOCATION: (40)..(40)
<223> OTHER INFORMATION: Pro or absent
<220> FEATURE:
<221> NAME/KEY: MOD_RES
<222> LOCATION: (41)..(41)
<223> OTHER INFORMATION: Ala or absent
<220> FEATURE:
<221> NAME/KEY: MOD_RES
<222> LOCATION: (42)..(42)
<223> OTHER INFORMATION: Pro or absent
<220> FEATURE:
<221> NAME/KEY: MOD_RES
<222> LOCATION: (43)..(43)
<223> OTHER INFORMATION: Ala or absent
<220> FEATURE:
<221> NAME/KEY: MOD_RES
<222> LOCATION: (44)..(44)
<223> OTHER INFORMATION: Pro or absent
<220> FEATURE:
<221> NAME/KEY: MOD_RES
<222> LOCATION: (45)..(45)
<223> OTHER INFORMATION: Ala or absent
<220> FEATURE:
<221> NAME/KEY: MOD_RES
<222> LOCATION: (46)..(46)
<223> OTHER INFORMATION: Pro or absent
<220> FEATURE:
<221> NAME/KEY: MOD_RES
<222> LOCATION: (47)..(47)
<223> OTHER INFORMATION: Ala or absent
<220> FEATURE:
<221> NAME/KEY: MOD_RES
<222> LOCATION: (48)..(48)
<223> OTHER INFORMATION: Pro or absent
<220> FEATURE:
<221> NAME/KEY: MOD_RES
<222> LOCATION: (49)..(49)
<223> OTHER INFORMATION: Ala or absent
<220> FEATURE:
<221> NAME/KEY: MOD_RES
<222> LOCATION: (50)..(50)
<223> OTHER INFORMATION: Pro or absent
<220> FEATURE:
<221> NAME/KEY: MOD_RES
<222> LOCATION: (51)..(51)
<223> OTHER INFORMATION: Ala or absent
<220> FEATURE:
<221> NAME/KEY: MOD_RES
<222> LOCATION: (52)..(52)
<223> OTHER INFORMATION: Pro or absent
<220> FEATURE:
<221> NAME/KEY: MOD_RES
<222> LOCATION: (53)..(53)
<223> OTHER INFORMATION: Ala or absent
<220> FEATURE:
<221> NAME/KEY: MOD_RES
<222> LOCATION: (54)..(54)
<223> OTHER INFORMATION: Pro or absent
<220> FEATURE:
<221> NAME/KEY: MOD_RES
<222> LOCATION: (55)..(55)
<223> OTHER INFORMATION: Ala or absent
<220> FEATURE:
<221> NAME/KEY: MOD_RES
<222> LOCATION: (56)..(56)
<223> OTHER INFORMATION: Pro or absent
<220> FEATURE:
<221> NAME/KEY: MOD_RES
<222> LOCATION: (57)..(57)
<223> OTHER INFORMATION: Ala or absent
<220> FEATURE:
<221> NAME/KEY: MOD_RES
<222> LOCATION: (58)..(58)
<223> OTHER INFORMATION: Pro or absent
<220> FEATURE:
<221> NAME/KEY: MOD_RES
<222> LOCATION: (59)..(59)
<223> OTHER INFORMATION: Ala or absent
<220> FEATURE:
<221> NAME/KEY: MOD_RES
<222> LOCATION: (60)..(60)
<223> OTHER INFORMATION: Pro or absent
<220> FEATURE:
<221> NAME/KEY: SITE
<222> LOCATION: (7)..(60)
<223> OTHER INFORMATION: This region may encompass 1-9 “Xaa Pro Ala Pro Ala Pro” repeating units wherein some positions may be absent

<400> SEQUENCE: 108

```
Xaa Pro Ala Pro Ala Pro Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Lys Ala
    50                  55                  60
```

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Ala Glu Ala Ala Ala Lys Glu Ala Ala Ala Lys Ala
1 5 10

<210> SEQ ID NO 110
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Ala Glu Ala Ala Ala Lys Glu Ala Ala Ala Lys Glu Ala Ala Ala Lys
1 5 10 15

Ala

<210> SEQ ID NO 111
<211> LENGTH: 27
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Ala Glu Ala Ala Ala Lys Glu Ala Ala Ala Lys Glu Ala Ala Ala Lys
1 5 10 15

Glu Ala Ala Ala Lys Glu Ala Ala Ala Lys Ala
20 25

<210> SEQ ID NO 112
<211> LENGTH: 52
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Ala or absent
<220> FEATURE:
<221> NAME/KEY: MOD_RES
<222> LOCATION: (7)..(7)
<223> OTHER INFORMATION: Glu or absent
<220> FEATURE:
<221> NAME/KEY: MOD_RES
<222> LOCATION: (8)..(8)
<223> OTHER INFORMATION: Ala or absent
<220> FEATURE:
<221> NAME/KEY: MOD_RES
<222> LOCATION: (9)..(9)
<223> OTHER INFORMATION: Ala or absent
<220> FEATURE:
<221> NAME/KEY: MOD_RES
<222> LOCATION: (10)..(10)
<223> OTHER INFORMATION: Ala or absent
<220> FEATURE:
<221> NAME/KEY: MOD_RES
<222> LOCATION: (11)..(11)
<223> OTHER INFORMATION: Lys or absent
<220> FEATURE:
<221> NAME/KEY: MOD_RES
<222> LOCATION: (12)..(12)
<223> OTHER INFORMATION: Glu or absent
<220> FEATURE:
<221> NAME/KEY: MOD_RES
<222> LOCATION: (13)..(13)

<223> OTHER INFORMATION: Ala or absent
<220> FEATURE:
<221> NAME/KEY: MOD_RES
<222> LOCATION: (14)..(14)
<223> OTHER INFORMATION: Ala or absent
<220> FEATURE:
<221> NAME/KEY: MOD_RES
<222> LOCATION: (15)..(15)
<223> OTHER INFORMATION: Ala or absent
<220> FEATURE:
<221> NAME/KEY: MOD_RES
<222> LOCATION: (16)..(16)
<223> OTHER INFORMATION: Lys or absent
<220> FEATURE:
<221> NAME/KEY: MOD_RES
<222> LOCATION: (17)..(17)
<223> OTHER INFORMATION: Glu or absent
<220> FEATURE:
<221> NAME/KEY: MOD_RES
<222> LOCATION: (18)..(18)
<223> OTHER INFORMATION: Ala or absent
<220> FEATURE:
<221> NAME/KEY: MOD_RES
<222> LOCATION: (19)..(19)
<223> OTHER INFORMATION: Ala or absent
<220> FEATURE:
<221> NAME/KEY: MOD_RES
<222> LOCATION: (20)..(20)
<223> OTHER INFORMATION: Ala or absent
<220> FEATURE:
<221> NAME/KEY: MOD_RES
<222> LOCATION: (21)..(21)
<223> OTHER INFORMATION: Lys or absent
<220> FEATURE:
<221> NAME/KEY: MOD_RES
<222> LOCATION: (22)..(22)
<223> OTHER INFORMATION: Glu or absent
<220> FEATURE:
<221> NAME/KEY: MOD_RES
<222> LOCATION: (23)..(23)
<223> OTHER INFORMATION: Ala or absent
<220> FEATURE:
<221> NAME/KEY: MOD_RES
<222> LOCATION: (24)..(24)
<223> OTHER INFORMATION: Ala or absent
<220> FEATURE:
<221> NAME/KEY: MOD_RES
<222> LOCATION: (25)..(25)
<223> OTHER INFORMATION: Ala or absent
<220> FEATURE:
<221> NAME/KEY: MOD_RES
<222> LOCATION: (26)..(26)
<223> OTHER INFORMATION: Lys or absent
<220> FEATURE:
<221> NAME/KEY: MOD_RES
<222> LOCATION: (27)..(27)
<223> OTHER INFORMATION: Glu or absent
<220> FEATURE:
<221> NAME/KEY: MOD_RES
<222> LOCATION: (28)..(28)
<223> OTHER INFORMATION: Ala or absent
<220> FEATURE:
<221> NAME/KEY: MOD_RES
<222> LOCATION: (29)..(29)
<223> OTHER INFORMATION: Ala or absent
<220> FEATURE:
<221> NAME/KEY: MOD_RES
<222> LOCATION: (30)..(30)
<223> OTHER INFORMATION: Ala or absent
<220> FEATURE:
<221> NAME/KEY: MOD_RES
<222> LOCATION: (31)..(31)
<223> OTHER INFORMATION: Lys or absent
<220> FEATURE:
<221> NAME/KEY: MOD_RES
<222> LOCATION: (32)..(32)
<223> OTHER INFORMATION: Glu or absent
<220> FEATURE:
<221> NAME/KEY: MOD_RES
<222> LOCATION: (33)..(33)
<223> OTHER INFORMATION: Ala or absent
<220> FEATURE:
<221> NAME/KEY: MOD_RES
<222> LOCATION: (34)..(34)
<223> OTHER INFORMATION: Ala or absent
<220> FEATURE:
<221> NAME/KEY: MOD_RES
<222> LOCATION: (35)..(35)
<223> OTHER INFORMATION: Ala or absent
<220> FEATURE:
<221> NAME/KEY: MOD_RES
<222> LOCATION: (36)..(36)
<223> OTHER INFORMATION: Lys or absent
<220> FEATURE:
<221> NAME/KEY: MOD_RES
<222> LOCATION: (37)..(37)
<223> OTHER INFORMATION: Glu or absent
<220> FEATURE:
<221> NAME/KEY: MOD_RES
<222> LOCATION: (38)..(38)
<223> OTHER INFORMATION: Ala or absent
<220> FEATURE:
<221> NAME/KEY: MOD_RES
<222> LOCATION: (39)..(39)
<223> OTHER INFORMATION: Ala or absent
<220> FEATURE:
<221> NAME/KEY: MOD_RES
<222> LOCATION: (40)..(40)
<223> OTHER INFORMATION: Ala or absent
<220> FEATURE:
<221> NAME/KEY: MOD_RES
<222> LOCATION: (41)..(41)
<223> OTHER INFORMATION: Lys or absent
<220> FEATURE:
<221> NAME/KEY: MOD_RES
<222> LOCATION: (42)..(42)
<223> OTHER INFORMATION: Glu or absent
<220> FEATURE:
<221> NAME/KEY: MOD_RES
<222> LOCATION: (43)..(43)
<223> OTHER INFORMATION: Ala or absent
<220> FEATURE:
<221> NAME/KEY: MOD_RES
<222> LOCATION: (44)..(44)
<223> OTHER INFORMATION: Ala or absent
<220> FEATURE:
<221> NAME/KEY: MOD_RES
<222> LOCATION: (45)..(45)
<223> OTHER INFORMATION: Ala or absent
<220> FEATURE:
<221> NAME/KEY: MOD_RES
<222> LOCATION: (46)..(46)
<223> OTHER INFORMATION: Lys or absent
<220> FEATURE:
<221> NAME/KEY: MOD_RES
<222> LOCATION: (47)..(47)
<223> OTHER INFORMATION: Glu or absent
<220> FEATURE:
<221> NAME/KEY: MOD_RES
<222> LOCATION: (48)..(48)
<223> OTHER INFORMATION: Ala or absent
<220> FEATURE:
<221> NAME/KEY: MOD_RES
<222> LOCATION: (49)..(49)
<223> OTHER INFORMATION: Ala or absent
<220> FEATURE:
<221> NAME/KEY: MOD_RES
<222> LOCATION: (50)..(50)
<223> OTHER INFORMATION: Ala or absent
<220> FEATURE:
<221> NAME/KEY: MOD_RES
<222> LOCATION: (51)..(51)
<223> OTHER INFORMATION: Lys or absent
<220> FEATURE:
<221> NAME/KEY: SITE
<222> LOCATION: (7)..(51)
<223> OTHER INFORMATION: This region may encompass 1-9 “Glu Ala Ala Ala
Lys” repeating units wherein some positions may be absent <220> FEATURE:
<221> NAME/KEY: MOD_RES
<222> LOCATION: (52)..(52)
<223> OTHER INFORMATION: Ala or absent
<220> FEATURE:
<223> OTHER INFORMATION: See specification as filed for detailed
description of substitutions and preferred embodiments

<400> SEQUENCE: 112

Xaa Glu Ala Ala Ala Lys Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa
50

<210> SEQ ID NO 113
<211> LENGTH: 127
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: E or Q

<400> SEQUENCE: 113

Xaa Val Gln Leu Val Glu Ser Gly Gly Gly Ser Val Gln Ala Gly Gly
1 5 10 15

Ser Leu Arg Leu Ser Cys Ala Ala Ser Gly Ser Thr Asp Ser Ile Glu
20 25 30

Tyr Met Thr Trp Phe Arg Gln Ala Pro Gly Lys Ala Arg Glu Gly Val
35 40 45

Ala Ala Leu Tyr Thr His Thr Gly Asn Thr Tyr Tyr Thr Asp Ser Val
50 55 60

Lys Gly Arg Phe Thr Ile Ser Gln Asp Lys Ala Lys Asn Met Ala Tyr
65 70 75 80

Leu Arg Met Asp Ser Val Lys Ser Glu Asp Thr Ala Ile Tyr Thr Cys
85 90 95

Gly Ala Thr Arg Lys Tyr Val Pro Val Arg Phe Ala Leu Asp Gln Ser
100 105 110

Ser Tyr Asp Tyr Trp Gly Gln Gly Thr Gln Val Thr Val Ser Ser
115 120 125

<210> SEQ ID NO 114
<211> LENGTH: 123
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: E or Q

<400> SEQUENCE: 114

Xaa Val Gln Leu Val Glu Ser Gly Gly Gly Leu Val Gln Ala Gly Gly
1 5 10 15

```
Ser Leu Arg Leu Ser Cys Ala Ala Ser Glu Ser Thr Phe Ser Asn Tyr
            20                  25                  30

Ala Met Gly Trp Phe Arg Gln Ala Pro Gly Pro Glu Arg Glu Phe Val
        35                  40                  45

Ala Thr Ile Ser Gln Thr Gly Ser His Thr Tyr Tyr Arg Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Met Lys Pro Glu Asp Thr Ala Val Tyr Tyr Cys
                85                  90                  95

Ala Ala Gly Asp Asn Tyr Tyr Tyr Thr Arg Thr Tyr Glu Tyr Asp Tyr
            100                 105                 110

Trp Gly Gln Gly Thr Gln Val Thr Val Ser Ser
        115                 120


<210> SEQ ID NO 115
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: E or D

<400> SEQUENCE: 115

Xaa Val Gln Leu Val Glu Ser Gly Gly Gly Leu Val Gln Pro Gly Gly
1               5                   10                  15

Ser Leu Arg Leu Ser Cys Ala Ala Ser Gly Asp Ile Tyr Lys Ser Phe
            20                  25                  30

Asp Met Gly Trp Tyr Arg Gln Ala Pro Gly Lys Gln Arg Asp Leu Val
        35                  40                  45

Ala Val Ile Gly Ser Arg Gly Asn Asn Arg Gly Arg Thr Asn Tyr Ala
    50                  55                  60

Asp Ser Val Lys Gly Arg Phe Thr Ile Ser Arg Asp Gly Thr Gly Asn
65                  70                  75                  80

Thr Val Tyr Leu Leu Met Asn Lys Leu Arg Pro Glu Asp Thr Ala Ile
                85                  90                  95

Tyr Tyr Cys Asn Thr Ala Pro Leu Val Ala Gly Arg Pro Trp Gly Arg
            100                 105                 110

Gly Thr Leu Val Thr Val Ser Ser
        115                 120


<210> SEQ ID NO 116
<211> LENGTH: 107
<212> TYPE: PRT
<213> ORGANISM: Homo sapiens

<400> SEQUENCE: 116

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60
```

```
Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 117
<211> LENGTH: 110
<212> TYPE: PRT
<213> ORGANISM: Homo sapiens

<400> SEQUENCE: 117

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Glu Pro Lys Ser Ser Asp Lys Thr His Thr Cys Pro Pro Cys Pro
1               5                   10                  15


<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Glu Pro Lys Ser Ser Asp Lys Thr His Thr Ser Pro Pro Ser Pro
1               5                   10                  15


<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Asp Lys Thr His Thr Cys Pro Pro Cys
```

1 5

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Glu Arg Lys Cys Cys Val Glu Cys Pro Pro Cys Pro
1 5 10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Glu Arg Lys Ser Ser Val Glu Cys Pro Pro Cys Pro
1 5 10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Glu Arg Lys Ser Ser Val Glu Ser Pro Pro Cys Pro
1 5 10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Glu Arg Lys Ser Ser Val Glu Ser Pro Pro Ser Pro
1 5 10

<210> SEQ ID NO 125
<211> LENGTH: 62
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 125

Glu Leu Lys Thr Pro Leu Gly Asp Thr Thr His Thr Cys Pro Arg Cys
1 5 10 15

Pro Glu Pro Lys Ser Cys Asp Thr Pro Pro Pro Cys Pro Arg Cys Pro
20 25 30

Glu Pro Lys Ser Cys Asp Thr Pro Pro Pro Cys Pro Arg Cys Pro Glu
35 40 45

Pro Lys Ser Cys Asp Thr Pro Pro Pro Cys Pro Arg Cys Pro 50 55 60

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Glu Pro Lys Ser Ser Asp Thr Pro Pro Pro Cys Pro Arg Cys Pro
1 5 10 15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Glu Pro Lys Ser Ser Asp Thr Pro Pro Pro Ser Pro Arg Cys Pro
1 5 10 15

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Glu Pro Lys Ser Ser Asp Thr Pro Pro Pro Ser Pro Arg Ser Pro
1 5 10 15

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 129

Glu Ser Lys Tyr Gly Pro Pro Cys Pro Ser Cys Pro
1 5 10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 130

Glu Ser Lys Tyr Gly Pro Pro Cys Pro Pro Cys Pro
1 5 10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Glu Ser Lys Tyr Gly Pro Pro Ser Pro Ser Cys Pro
1 5 10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 132

Glu Ser Lys Tyr Gly Pro Pro Ser Pro Ser Ser Pro
1 5 10

<210> SEQ ID NO 133
<211> LENGTH: 19
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 133

Met Glu Trp Ser Trp Val Phe Leu Phe Phe Leu Ser Val Thr Thr Gly
1 5 10 15

Val His Ser

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
6xHis tag

<400> SEQUENCE: 134

His His His His His His
1 5

<210> SEQ ID NO 135
<211> LENGTH: 217
<212> TYPE: PRT
<213> ORGANISM: Homo sapiens

<400> SEQUENCE: 135

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Asp Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 136
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 136

Gly Gln Pro Arg Glu Pro Gln Val Tyr Thr Leu Pro Pro Ser Arg Gln
1 5 10 15

Glu Met Thr Lys Asn Gln Val Ser Leu Thr Cys Leu Val Glu Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asn Ser Asp Gly Ser Phe
50 55 60

Phe Leu Tyr Ser Lys Leu Thr Val Asp Lys Ser Arg Trp Gln Gln Gly
65 70 75 80

Asn Val Phe Ser Cys Ser Val Met His Glu Ala Leu His Asn His Tyr
85 90 95

Thr Gln Lys Ser Leu Ser Leu Ser Pro Gly Lys
100 105

<210> SEQ ID NO 137
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 137

Gly Gln Pro Arg Glu Pro Gln Val Tyr Thr Leu Pro Pro Ser Arg Glu
1 5 10 15

Gln Met Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asn Ser Asp Gly Ser Phe
50 55 60

Phe Leu Tyr Ser Lys Leu Thr Val Asp Lys Ser Arg Trp Gln Gln Gly
65 70 75 80

```
Asn Val Phe Ser Cys Ser Val Met His Glu Ala Leu His Asn His Tyr
                85                  90                  95

Thr Gln Glu Ser Leu Ser Leu Ser Pro Gly Lys
            100                 105


<210> SEQ ID NO 138
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Gln Glu Met
        115                 120                 125

Thr Lys Asn Gln Val Ser Leu Thr Cys Leu Val Glu Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asn Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 139
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45
```

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Gln Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asn Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Glu Ser Leu Ser Leu Ser Pro Gly Lys
    210                 215


<210> SEQ ID NO 140
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
```

180 185 190

Phe Ser Cys Ser Val Met His Glu Ala Leu His Asn His Tyr Thr Gln
195 200 205

Lys Ser Leu Ser Leu Ser Leu Gly Lys
210 215

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Gly Gly Gly Gly Ser
1 5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Glu Ala Ala Ala Lys
1 5

<210> SEQ ID NO 143
<211> LENGTH: 225
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (5)..(5)
<223> OTHER INFORMATION: Gly or absent
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Ser or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Gly or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Ser or absent
<220> FEATURE:
<221> NAME/KEY: MOD_RES
<222> LOCATION: (13)..(13)

<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Gly or absent
<220> FEATURE:
<221> NAME/KEY: MOD_RES
<222> LOCATION: (16)..(16)
<223> OTHER INFORMATION: Ser or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Ser or absent
<220> FEATURE:
<221> NAME/KEY: MOD_RES
<222> LOCATION: (25)..(25)
<223> OTHER INFORMATION: Gly or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Ser or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Ser or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Gly or absent
<220> FEATURE:
<221> NAME/KEY: MOD_RES
<222> LOCATION: (36)..(36)
<223> OTHER INFORMATION: Ser or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Ser or absent
<220> FEATURE:
<221> NAME/KEY: MOD_RES
<222> LOCATION: (45)..(45)
<223> OTHER INFORMATION: Gly or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Ser or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Gly or absent
<220> FEATURE:
<221> NAME/KEY: MOD_RES
<222> LOCATION: (51)..(51)
<223> OTHER INFORMATION: Gly or absent
<220> FEATURE:
<221> NAME/KEY: MOD_RES
<222> LOCATION: (52)..(52)
<223> OTHER INFORMATION: Ser or absent
<220> FEATURE:

<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Gly or absent
<220> FEATURE:
<221> NAME/KEY: MOD_RES
<222> LOCATION: (55)..(55)
<223> OTHER INFORMATION: Gly or absent
<220> FEATURE:
<221> NAME/KEY: MOD_RES
<222> LOCATION: (56)..(56)
<223> OTHER INFORMATION: Ser or absent
<220> FEATURE:
<221> NAME/KEY: MOD_RES
<222> LOCATION: (57)..(57)
<223> OTHER INFORMATION: Gly or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Gly or absent
<220> FEATURE:
<221> NAME/KEY: MOD_RES
<222> LOCATION: (60)..(60)
<223> OTHER INFORMATION: Ser or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Gly or absent
<220> FEATURE:
<221> NAME/KEY: MOD_RES
<222> LOCATION: (64)..(64)
<223> OTHER INFORMATION: Ser or absent
<220> FEATURE:
<221> NAME/KEY: MOD_RES
<222> LOCATION: (65)..(65)
<223> OTHER INFORMATION: Gly or absent
<220> FEATURE:
<221> NAME/KEY: MOD_RES
<222> LOCATION: (66)..(66)
<223> OTHER INFORMATION: Gly or absent
<220> FEATURE:
<221> NAME/KEY: MOD_RES
<222> LOCATION: (67)..(67)
<223> OTHER INFORMATION: Gly or absent
<220> FEATURE:
<221> NAME/KEY: MOD_RES
<222> LOCATION: (68)..(68)
<223> OTHER INFORMATION: Ser or absent
<220> FEATURE:
<221> NAME/KEY: MOD_RES
<222> LOCATION: (69)..(69)
<223> OTHER INFORMATION: Gly or absent
<220> FEATURE:
<221> NAME/KEY: MOD_RES
<222> LOCATION: (70)..(70)
<223> OTHER INFORMATION: Gly or absent
<220> FEATURE:
<221> NAME/KEY: MOD_RES
<222> LOCATION: (71)..(71)
<223> OTHER INFORMATION: Gly or absent
<220> FEATURE:
<221> NAME/KEY: MOD_RES
<222> LOCATION: (72)..(72)
<223> OTHER INFORMATION: Ser or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Gly or absent
<220> FEATURE:
<221> NAME/KEY: MOD_RES
<222> LOCATION: (75)..(75)
<223> OTHER INFORMATION: Gly or absent
<220> FEATURE:
<221> NAME/KEY: MOD_RES
<222> LOCATION: (76)..(76)
<223> OTHER INFORMATION: Ser or absent
<220> FEATURE:
<221> NAME/KEY: MOD_RES
<222> LOCATION: (77)..(77)
<223> OTHER INFORMATION: Gly or absent
<220> FEATURE:
<221> NAME/KEY: MOD_RES
<222> LOCATION: (78)..(78)
<223> OTHER INFORMATION: Gly or absent
<220> FEATURE:
<221> NAME/KEY: MOD_RES
<222> LOCATION: (79)..(79)
<223> OTHER INFORMATION: Gly or absent
<220> FEATURE:
<221> NAME/KEY: MOD_RES
<222> LOCATION: (80)..(80)
<223> OTHER INFORMATION: Ser or absent
<220> FEATURE:
<221> NAME/KEY: MOD_RES
<222> LOCATION: (81)..(81)
<223> OTHER INFORMATION: Gly or absent
<220> FEATURE:
<221> NAME/KEY: MOD_RES
<222> LOCATION: (82)..(82)
<223> OTHER INFORMATION: Gly or absent
<220> FEATURE:
<221> NAME/KEY: MOD_RES
<222> LOCATION: (83)..(83)
<223> OTHER INFORMATION: Gly or absent
<220> FEATURE:
<221> NAME/KEY: MOD_RES
<222> LOCATION: (84)..(84)
<223> OTHER INFORMATION: Ser or absent
<220> FEATURE:
<221> NAME/KEY: MOD_RES
<222> LOCATION: (85)..(85)
<223> OTHER INFORMATION: Gly or absent
<220> FEATURE:
<221> NAME/KEY: MOD_RES
<222> LOCATION: (86)..(86)
<223> OTHER INFORMATION: Gly or absent
<220> FEATURE:
<221> NAME/KEY: MOD_RES
<222> LOCATION: (87)..(87)
<223> OTHER INFORMATION: Gly or absent
<220> FEATURE:
<221> NAME/KEY: MOD_RES
<222> LOCATION: (88)..(88)
<223> OTHER INFORMATION: Ser or absent
<220> FEATURE:
<221> NAME/KEY: MOD_RES
<222> LOCATION: (89)..(89)
<223> OTHER INFORMATION: Gly or absent
<220> FEATURE:
<221> NAME/KEY: MOD_RES
<222> LOCATION: (90)..(90)
<223> OTHER INFORMATION: Gly or absent
<220> FEATURE:
<221> NAME/KEY: MOD_RES
<222> LOCATION: (91)..(91)
<223> OTHER INFORMATION: Gly or absent
<220> FEATURE:
<221> NAME/KEY: MOD_RES
<222> LOCATION: (92)..(92)

<223> OTHER INFORMATION: Ser or absent
<220> FEATURE:
<221> NAME/KEY: MOD_RES
<222> LOCATION: (93)..(93)
<223> OTHER INFORMATION: Gly or absent
<220> FEATURE:
<221> NAME/KEY: MOD_RES
<222> LOCATION: (94)..(94)
<223> OTHER INFORMATION: Gly or absent
<220> FEATURE:
<221> NAME/KEY: MOD_RES
<222> LOCATION: (95)..(95)
<223> OTHER INFORMATION: Gly or absent
<220> FEATURE:
<221> NAME/KEY: MOD_RES
<222> LOCATION: (96)..(96)
<223> OTHER INFORMATION: Ser or absent
<220> FEATURE:
<221> NAME/KEY: MOD_RES
<222> LOCATION: (97)..(97)
<223> OTHER INFORMATION: Gly or absent
<220> FEATURE:
<221> NAME/KEY: MOD_RES
<222> LOCATION: (98)..(98)
<223> OTHER INFORMATION: Gly or absent
<220> FEATURE:
<221> NAME/KEY: MOD_RES
<222> LOCATION: (99)..(99)
<223> OTHER INFORMATION: Gly or absent
<220> FEATURE:
<221> NAME/KEY: MOD_RES
<222> LOCATION: (100)..(100)
<223> OTHER INFORMATION: Ser or absent
<220> FEATURE:
<221> NAME/KEY: SITE
<222> LOCATION: (5)..(100)
<223> OTHER INFORMATION: This region may encompass 1-9, 14, 19 or 24
"Gly Gly Gly Ser" repeating units wherein some positions may be
absent
<220> FEATURE:
<221> NAME/KEY: MOD_RES
<222> LOCATION: (106)..(106)
<223> OTHER INFORMATION: Gly or absent
<220> FEATURE:
<221> NAME/KEY: MOD_RES
<222> LOCATION: (107)..(107)
<223> OTHER INFORMATION: Gly or absent
<220> FEATURE:
<221> NAME/KEY: MOD_RES
<222> LOCATION: (108)..(108)
<223> OTHER INFORMATION: Gly or absent
<220> FEATURE:
<221> NAME/KEY: MOD_RES
<222> LOCATION: (109)..(109)
<223> OTHER INFORMATION: Gly or absent
<220> FEATURE:
<221> NAME/KEY: MOD_RES
<222> LOCATION: (110)..(110)
<223> OTHER INFORMATION: Ser or absent
<220> FEATURE:
<221> NAME/KEY: MOD_RES
<222> LOCATION: (111)..(111)
<223> OTHER INFORMATION: Gly or absent
<220> FEATURE:
<221> NAME/KEY: MOD_RES
<222> LOCATION: (112)..(112)
<223> OTHER INFORMATION: Gly or absent
<220> FEATURE:
<221> NAME/KEY: MOD_RES
<222> LOCATION: (113)..(113)
<223> OTHER INFORMATION: Gly or absent
<220> FEATURE:
<221> NAME/KEY: MOD_RES
<222> LOCATION: (114)..(114)
<223> OTHER INFORMATION: Gly or absent
<220> FEATURE:
<221> NAME/KEY: MOD_RES
<222> LOCATION: (115)..(115)
<223> OTHER INFORMATION: Ser or absent

```
<220> FEATURE:
<221> NAME/KEY: MOD_RES
<222> LOCATION: (116)..(116)
<223> OTHER INFORMATION: Gly or absent
<220> FEATURE:
<221> NAME/KEY: MOD_RES
<222> LOCATION: (117)..(117)
<223> OTHER INFORMATION: Gly or absent
<220> FEATURE:
<221> NAME/KEY: MOD_RES
<222> LOCATION: (118)..(118)
<223> OTHER INFORMATION: Gly or absent
<220> FEATURE:
<221> NAME/KEY: MOD_RES
<222> LOCATION: (119)..(119)
<223> OTHER INFORMATION: Gly or absent
<220> FEATURE:
<221> NAME/KEY: MOD_RES
<222> LOCATION: (120)..(120)
<223> OTHER INFORMATION: Ser or absent
<220> FEATURE:
<221> NAME/KEY: MOD_RES
<222> LOCATION: (121)..(121)
<223> OTHER INFORMATION: Gly or absent
<220> FEATURE:
<221> NAME/KEY: MOD_RES
<222> LOCATION: (122)..(122)
<223> OTHER INFORMATION: Gly or absent
<220> FEATURE:
<221> NAME/KEY: MOD_RES
<222> LOCATION: (123)..(123)
<223> OTHER INFORMATION: Gly or absent
<220> FEATURE:
<221> NAME/KEY: MOD_RES
<222> LOCATION: (124)..(124)
<223> OTHER INFORMATION: Gly or absent
<220> FEATURE:
<221> NAME/KEY: MOD_RES
<222> LOCATION: (125)..(125)
<223> OTHER INFORMATION: Ser or absent
<220> FEATURE:
<221> NAME/KEY: MOD_RES
<222> LOCATION: (126)..(126)
<223> OTHER INFORMATION: Gly or absent
<220> FEATURE:
<221> NAME/KEY: MOD_RES
<222> LOCATION: (127)..(127)
<223> OTHER INFORMATION: Gly or absent
<220> FEATURE:
<221> NAME/KEY: MOD_RES
<222> LOCATION: (128)..(128)
<223> OTHER INFORMATION: Gly or absent
<220> FEATURE:
<221> NAME/KEY: MOD_RES
<222> LOCATION: (129)..(129)
<223> OTHER INFORMATION: Gly or absent
<220> FEATURE:
<221> NAME/KEY: MOD_RES
<222> LOCATION: (130)..(130)
<223> OTHER INFORMATION: Ser or absent
<220> FEATURE:
<221> NAME/KEY: MOD_RES
<222> LOCATION: (131)..(131)
<223> OTHER INFORMATION: Gly or absent
<220> FEATURE:
<221> NAME/KEY: MOD_RES
<222> LOCATION: (132)..(132)
<223> OTHER INFORMATION: Gly or absent
<220> FEATURE:
<221> NAME/KEY: MOD_RES
<222> LOCATION: (133)..(133)
<223> OTHER INFORMATION: Gly or absent
<220> FEATURE:
<221> NAME/KEY: MOD_RES
<222> LOCATION: (134)..(134)
<223> OTHER INFORMATION: Gly or absent
<220> FEATURE:
<221> NAME/KEY: MOD_RES
<222> LOCATION: (135)..(135)
```

```
<223> OTHER INFORMATION: Ser or absent
<220> FEATURE:
<221> NAME/KEY: MOD_RES
<222> LOCATION: (136)..(136)
<223> OTHER INFORMATION: Gly or absent
<220> FEATURE:
<221> NAME/KEY: MOD_RES
<222> LOCATION: (137)..(137)
<223> OTHER INFORMATION: Gly or absent
<220> FEATURE:
<221> NAME/KEY: MOD_RES
<222> LOCATION: (138)..(138)
<223> OTHER INFORMATION: Gly or absent
<220> FEATURE:
<221> NAME/KEY: MOD_RES
<222> LOCATION: (139)..(139)
<223> OTHER INFORMATION: Gly or absent
<220> FEATURE:
<221> NAME/KEY: MOD_RES
<222> LOCATION: (140)..(140)
<223> OTHER INFORMATION: Ser or absent
<220> FEATURE:
<221> NAME/KEY: MOD_RES
<222> LOCATION: (141)..(141)
<223> OTHER INFORMATION: Gly or absent
<220> FEATURE:
<221> NAME/KEY: MOD_RES
<222> LOCATION: (142)..(142)
<223> OTHER INFORMATION: Gly or absent
<220> FEATURE:
<221> NAME/KEY: MOD_RES
<222> LOCATION: (143)..(143)
<223> OTHER INFORMATION: Gly or absent
<220> FEATURE:
<221> NAME/KEY: MOD_RES
<222> LOCATION: (144)..(144)
<223> OTHER INFORMATION: Gly or absent
<220> FEATURE:
<221> NAME/KEY: MOD_RES
<222> LOCATION: (145)..(145)
<223> OTHER INFORMATION: Ser or absent
<220> FEATURE:
<221> NAME/KEY: MOD_RES
<222> LOCATION: (146)..(146)
<223> OTHER INFORMATION: Gly or absent
<220> FEATURE:
<221> NAME/KEY: MOD_RES
<222> LOCATION: (147)..(147)
<223> OTHER INFORMATION: Gly or absent
<220> FEATURE:
<221> NAME/KEY: MOD_RES
<222> LOCATION: (148)..(148)
<223> OTHER INFORMATION: Gly or absent
<220> FEATURE:
<221> NAME/KEY: MOD_RES
<222> LOCATION: (149)..(149)
<223> OTHER INFORMATION: Gly or absent
<220> FEATURE:
<221> NAME/KEY: MOD_RES
<222> LOCATION: (150)..(150)
<223> OTHER INFORMATION: Ser or absent
<220> FEATURE:
<221> NAME/KEY: MOD_RES
<222> LOCATION: (151)..(151)
<223> OTHER INFORMATION: Gly or absent
<220> FEATURE:
<221> NAME/KEY: MOD_RES
<222> LOCATION: (152)..(152)
<223> OTHER INFORMATION: Gly or absent
<220> FEATURE:
<221> NAME/KEY: MOD_RES
<222> LOCATION: (153)..(153)
<223> OTHER INFORMATION: Gly or absent
<220> FEATURE:
<221> NAME/KEY: MOD_RES
<222> LOCATION: (154)..(154)
<223> OTHER INFORMATION: Gly or absent
<220> FEATURE:
<221> NAME/KEY: MOD_RES
```

<222> LOCATION: (155)..(155)
<223> OTHER INFORMATION: Ser or absent
<220> FEATURE:
<221> NAME/KEY: MOD_RES
<222> LOCATION: (156)..(156)
<223> OTHER INFORMATION: Gly or absent
<220> FEATURE:
<221> NAME/KEY: MOD_RES
<222> LOCATION: (157)..(157)
<223> OTHER INFORMATION: Gly or absent
<220> FEATURE:
<221> NAME/KEY: MOD_RES
<222> LOCATION: (158)..(158)
<223> OTHER INFORMATION: Gly or absent
<220> FEATURE:
<221> NAME/KEY: MOD_RES
<222> LOCATION: (159)..(159)
<223> OTHER INFORMATION: Gly or absent
<220> FEATURE:
<221> NAME/KEY: MOD_RES
<222> LOCATION: (160)..(160)
<223> OTHER INFORMATION: Ser or absent
<220> FEATURE:
<221> NAME/KEY: MOD_RES
<222> LOCATION: (161)..(161)
<223> OTHER INFORMATION: Gly or absent
<220> FEATURE:
<221> NAME/KEY: MOD_RES
<222> LOCATION: (162)..(162)
<223> OTHER INFORMATION: Gly or absent
<220> FEATURE:
<221> NAME/KEY: MOD_RES
<222> LOCATION: (163)..(163)
<223> OTHER INFORMATION: Gly or absent
<220> FEATURE:
<221> NAME/KEY: MOD_RES
<222> LOCATION: (164)..(164)
<223> OTHER INFORMATION: Gly or absent
<220> FEATURE:
<221> NAME/KEY: MOD_RES
<222> LOCATION: (165)..(165)
<223> OTHER INFORMATION: Ser or absent
<220> FEATURE:
<221> NAME/KEY: MOD_RES
<222> LOCATION: (166)..(166)
<223> OTHER INFORMATION: Gly or absent
<220> FEATURE:
<221> NAME/KEY: MOD_RES
<222> LOCATION: (167)..(167)
<223> OTHER INFORMATION: Gly or absent
<220> FEATURE:
<221> NAME/KEY: MOD_RES
<222> LOCATION: (168)..(168)
<223> OTHER INFORMATION: Gly or absent
<220> FEATURE:
<221> NAME/KEY: MOD_RES
<222> LOCATION: (169)..(169)
<223> OTHER INFORMATION: Gly or absent
<220> FEATURE:
<221> NAME/KEY: MOD_RES
<222> LOCATION: (170)..(170)
<223> OTHER INFORMATION: Ser or absent
<220> FEATURE:
<221> NAME/KEY: MOD_RES
<222> LOCATION: (171)..(171)
<223> OTHER INFORMATION: Gly or absent
<220> FEATURE:
<221> NAME/KEY: MOD_RES
<222> LOCATION: (172)..(172)
<223> OTHER INFORMATION: Gly or absent
<220> FEATURE:
<221> NAME/KEY: MOD_RES
<222> LOCATION: (173)..(173)
<223> OTHER INFORMATION: Gly or absent
<220> FEATURE:
<221> NAME/KEY: MOD_RES
<222> LOCATION: (174)..(174)
<223> OTHER INFORMATION: Gly or absent
<220> FEATURE:

<221> NAME/KEY: MOD_RES
<222> LOCATION: (175)..(175)
<223> OTHER INFORMATION: Ser or absent
<220> FEATURE:
<221> NAME/KEY: MOD_RES
<222> LOCATION: (176)..(176)
<223> OTHER INFORMATION: Gly or absent
<220> FEATURE:
<221> NAME/KEY: MOD_RES
<222> LOCATION: (177)..(177)
<223> OTHER INFORMATION: Gly or absent
<220> FEATURE:
<221> NAME/KEY: MOD_RES
<222> LOCATION: (178)..(178)
<223> OTHER INFORMATION: Gly or absent
<220> FEATURE:
<221> NAME/KEY: MOD_RES
<222> LOCATION: (179)..(179)
<223> OTHER INFORMATION: Gly or absent
<220> FEATURE:
<221> NAME/KEY: MOD_RES
<222> LOCATION: (180)..(180)
<223> OTHER INFORMATION: Ser or absent
<220> FEATURE:
<221> NAME/KEY: MOD_RES
<222> LOCATION: (181)..(181)
<223> OTHER INFORMATION: Gly or absent
<220> FEATURE:
<221> NAME/KEY: MOD_RES
<222> LOCATION: (182)..(182)
<223> OTHER INFORMATION: Gly or absent
<220> FEATURE:
<221> NAME/KEY: MOD_RES
<222> LOCATION: (183)..(183)
<223> OTHER INFORMATION: Gly or absent
<220> FEATURE:
<221> NAME/KEY: MOD_RES
<222> LOCATION: (184)..(184)
<223> OTHER INFORMATION: Gly or absent
<220> FEATURE:
<221> NAME/KEY: MOD_RES
<222> LOCATION: (185)..(185)
<223> OTHER INFORMATION: Ser or absent
<220> FEATURE:
<221> NAME/KEY: MOD_RES
<222> LOCATION: (186)..(186)
<223> OTHER INFORMATION: Gly or absent
<220> FEATURE:
<221> NAME/KEY: MOD_RES
<222> LOCATION: (187)..(187)
<223> OTHER INFORMATION: Gly or absent
<220> FEATURE:
<221> NAME/KEY: MOD_RES
<222> LOCATION: (188)..(188)
<223> OTHER INFORMATION: Gly or absent
<220> FEATURE:
<221> NAME/KEY: MOD_RES
<222> LOCATION: (189)..(189)
<223> OTHER INFORMATION: Gly or absent
<220> FEATURE:
<221> NAME/KEY: MOD_RES
<222> LOCATION: (190)..(190)
<223> OTHER INFORMATION: Ser or absent
<220> FEATURE:
<221> NAME/KEY: MOD_RES
<222> LOCATION: (191)..(191)
<223> OTHER INFORMATION: Gly or absent
<220> FEATURE:
<221> NAME/KEY: MOD_RES
<222> LOCATION: (192)..(192)
<223> OTHER INFORMATION: Gly or absent
<220> FEATURE:
<221> NAME/KEY: MOD_RES
<222> LOCATION: (193)..(193)
<223> OTHER INFORMATION: Gly or absent
<220> FEATURE:
<221> NAME/KEY: MOD_RES
<222> LOCATION: (194)..(194)
<223> OTHER INFORMATION: Gly or absent
<220> FEATURE:
<221> NAME/KEY: MOD_RES
<222> LOCATION: (195)..(195)
<223> OTHER INFORMATION: Ser or absent
<220> FEATURE:
<221> NAME/KEY: MOD_RES
<222> LOCATION: (196)..(196)
<223> OTHER INFORMATION: Gly or absent
<220> FEATURE:
<221> NAME/KEY: MOD_RES
<222> LOCATION: (197)..(197)
<223> OTHER INFORMATION: Gly or absent
<220> FEATURE:
<221> NAME/KEY: MOD_RES
<222> LOCATION: (198)..(198)
<223> OTHER INFORMATION: Gly or absent
<220> FEATURE:
<221> NAME/KEY: MOD_RES
<222> LOCATION: (199)..(199)
<223> OTHER INFORMATION: Gly or absent
<220> FEATURE:
<221> NAME/KEY: MOD_RES
<222> LOCATION: (200)..(200)
<223> OTHER INFORMATION: Ser or absent
<220> FEATURE:
<221> NAME/KEY: MOD_RES
<222> LOCATION: (201)..(201)
<223> OTHER INFORMATION: Gly or absent
<220> FEATURE:
<221> NAME/KEY: MOD_RES
<222> LOCATION: (202)..(202)
<223> OTHER INFORMATION: Gly or absent
<220> FEATURE:
<221> NAME/KEY: MOD_RES
<222> LOCATION: (203)..(203)
<223> OTHER INFORMATION: Gly or absent
<220> FEATURE:
<221> NAME/KEY: MOD_RES
<222> LOCATION: (204)..(204)
<223> OTHER INFORMATION: Gly or absent
<220> FEATURE:
<221> NAME/KEY: MOD_RES
<222> LOCATION: (205)..(205)
<223> OTHER INFORMATION: Ser or absent
<220> FEATURE:
<221> NAME/KEY: MOD_RES
<222> LOCATION: (206)..(206)
<223> OTHER INFORMATION: Gly or absent
<220> FEATURE:
<221> NAME/KEY: MOD_RES
<222> LOCATION: (207)..(207)
<223> OTHER INFORMATION: Gly or absent
<220> FEATURE:
<221> NAME/KEY: MOD_RES
<222> LOCATION: (208)..(208)
<223> OTHER INFORMATION: Gly or absent
<220> FEATURE:
<221> NAME/KEY: MOD_RES
<222> LOCATION: (209)..(209)
<223> OTHER INFORMATION: Gly or absent
<220> FEATURE:
<221> NAME/KEY: MOD_RES
<222> LOCATION: (210)..(210)
<223> OTHER INFORMATION: Ser or absent
<220> FEATURE:
<221> NAME/KEY: MOD_RES
<222> LOCATION: (211)..(211)
<223> OTHER INFORMATION: Gly or absent
<220> FEATURE:
<221> NAME/KEY: MOD_RES
<222> LOCATION: (212)..(212)
<223> OTHER INFORMATION: Gly or absent
<220> FEATURE:
<221> NAME/KEY: MOD_RES
<222> LOCATION: (213)..(213)
<223> OTHER INFORMATION: Gly or absent
<220> FEATURE:
<221> NAME/KEY: MOD_RES
<222> LOCATION: (214)..(214)

```
<223> OTHER INFORMATION: Gly or absent
<220> FEATURE:
<221> NAME/KEY: MOD_RES
<222> LOCATION: (215)..(215)
<223> OTHER INFORMATION: Ser or absent
<220> FEATURE:
<221> NAME/KEY: MOD_RES
<222> LOCATION: (216)..(216)
<223> OTHER INFORMATION: Gly or absent
<220> FEATURE:
<221> NAME/KEY: MOD_RES
<222> LOCATION: (217)..(217)
<223> OTHER INFORMATION: Gly or absent
<220> FEATURE:
<221> NAME/KEY: MOD_RES
<222> LOCATION: (218)..(218)
<223> OTHER INFORMATION: Gly or absent
<220> FEATURE:
<221> NAME/KEY: MOD_RES
<222> LOCATION: (219)..(219)
<223> OTHER INFORMATION: Gly or absent
<220> FEATURE:
<221> NAME/KEY: MOD_RES
<222> LOCATION: (220)..(220)
<223> OTHER INFORMATION: Ser or absent
<220> FEATURE:
<221> NAME/KEY: MOD_RES
<222> LOCATION: (221)..(221)
<223> OTHER INFORMATION: Gly or absent
<220> FEATURE:
<221> NAME/KEY: MOD_RES
<222> LOCATION: (222)..(222)
<223> OTHER INFORMATION: Gly or absent
<220> FEATURE:
<221> NAME/KEY: MOD_RES
<222> LOCATION: (223)..(223)
<223> OTHER INFORMATION: Gly or absent
<220> FEATURE:
<221> NAME/KEY: MOD_RES
<222> LOCATION: (224)..(224)
<223> OTHER INFORMATION: Gly or absent
<220> FEATURE:
<221> NAME/KEY: MOD_RES
<222> LOCATION: (225)..(225)
<223> OTHER INFORMATION: Ser or absent
<220> FEATURE:
<221> NAME/KEY: SITE
<222> LOCATION: (106)..(225)
<223> OTHER INFORMATION: This region may encompass 1-9, 14, 19 or 24
      "Gly Gly Gly Gly Ser" repeating units wherein some positions
      may be absent

<400> SEQUENCE: 143

Gly Gly Gly Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Gly Gly Gly Gly Ser Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
```

```
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa
225


<210> SEQ ID NO 144
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Gly or absent
<220> FEATURE:
<221> NAME/KEY: MOD_RES
<222> LOCATION: (4)..(4)
<223> OTHER INFORMATION: Ser or absent
<220> FEATURE:
<221> NAME/KEY: MOD_RES
<222> LOCATION: (5)..(5)
<223> OTHER INFORMATION: Gly or absent
<220> FEATURE:
<221> NAME/KEY: MOD_RES
<222> LOCATION: (6)..(6)
<223> OTHER INFORMATION: Ser or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Ser or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Ser or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Ser or absent
<220> FEATURE:
<221> NAME/KEY: MOD_RES
<222> LOCATION: (15)..(15)
```

<223> OTHER INFORMATION: Gly or absent
<220> FEATURE:
<221> NAME/KEY: MOD_RES
<222> LOCATION: (16)..(16)
<223> OTHER INFORMATION: Ser or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Ser or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Ser or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Ser or absent
<220> FEATURE:
<221> NAME/KEY: MOD_RES
<222> LOCATION: (25)..(25)
<223> OTHER INFORMATION: Gly or absent
<220> FEATURE:
<221> NAME/KEY: MOD_RES
<222> LOCATION: (26)..(26)
<223> OTHER INFORMATION: Ser or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Ser or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Ser or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Ser or absent
<220> FEATURE:
<221> NAME/KEY: MOD_RES
<222> LOCATION: (35)..(35)
<223> OTHER INFORMATION: Gly or absent
<220> FEATURE:
<221> NAME/KEY: MOD_RES
<222> LOCATION: (36)..(36)
<223> OTHER INFORMATION: Ser or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Ser or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Ser or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Ser or absent
<220> FEATURE:
<221> NAME/KEY: MOD_RES
<222> LOCATION: (45)..(45)
<223> OTHER INFORMATION: Gly or absent
<220> FEATURE:
<221> NAME/KEY: MOD_RES
<222> LOCATION: (46)..(46)
<223> OTHER INFORMATION: Ser or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Ser or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Ser or absent
<220> FEATURE:
<221> NAME/KEY: SITE
<222> LOCATION: (3)..(50)
<223> OTHER INFORMATION: This region may encompass 1-9, 14, 19 or 24
"Gly Ser" repeating units wherein some positions may be absent

<400> SEQUENCE: 144

```
Gly Ser Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45
```

Xaa Xaa
50

<210> SEQ ID NO 145
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ser or absent
<220> FEATURE:
<221> NAME/KEY: MOD_RES
<222> LOCATION: (36)..(36)
<223> OTHER INFORMATION: Gly or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)

<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Ser or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Ser or absent
<220> FEATURE:
<221> NAME/KEY: MOD_RES
<222> LOCATION: (51)..(51)
<223> OTHER INFORMATION: Gly or absent
<220> FEATURE:
<221> NAME/KEY: MOD_RES
<222> LOCATION: (52)..(52)
<223> OTHER INFORMATION: Gly or absent
<220> FEATURE:
<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Gly or absent
<220> FEATURE:
<221> NAME/KEY: MOD_RES
<222> LOCATION: (55)..(55)
<223> OTHER INFORMATION: Ser or absent
<220> FEATURE:
<221> NAME/KEY: MOD_RES
<222> LOCATION: (56)..(56)
<223> OTHER INFORMATION: Gly or absent
<220> FEATURE:
<221> NAME/KEY: MOD_RES
<222> LOCATION: (57)..(57)
<223> OTHER INFORMATION: Gly or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Gly or absent
<220> FEATURE:
<221> NAME/KEY: MOD_RES
<222> LOCATION: (60)..(60)
<223> OTHER INFORMATION: Ser or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Gly or absent
<220> FEATURE:
<221> NAME/KEY: MOD_RES
<222> LOCATION: (64)..(64)
<223> OTHER INFORMATION: Gly or absent
<220> FEATURE:
<221> NAME/KEY: MOD_RES
<222> LOCATION: (65)..(65)
<223> OTHER INFORMATION: Ser or absent
<220> FEATURE:
<221> NAME/KEY: MOD_RES
<222> LOCATION: (66)..(66)
<223> OTHER INFORMATION: Gly or absent
<220> FEATURE:
<221> NAME/KEY: MOD_RES
<222> LOCATION: (67)..(67)
<223> OTHER INFORMATION: Gly or absent
<220> FEATURE:
<221> NAME/KEY: MOD_RES
<222> LOCATION: (68)..(68)
<223> OTHER INFORMATION: Gly or absent
<220> FEATURE:
<221> NAME/KEY: MOD_RES
<222> LOCATION: (69)..(69)
<223> OTHER INFORMATION: Gly or absent
<220> FEATURE:
<221> NAME/KEY: MOD_RES
<222> LOCATION: (70)..(70)
<223> OTHER INFORMATION: Ser or absent
<220> FEATURE:
<221> NAME/KEY: MOD_RES
<222> LOCATION: (71)..(71)
<223> OTHER INFORMATION: Gly or absent
<220> FEATURE:
<221> NAME/KEY: MOD_RES
<222> LOCATION: (72)..(72)
<223> OTHER INFORMATION: Gly or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Gly or absent
<220> FEATURE:
<221> NAME/KEY: MOD_RES
<222> LOCATION: (75)..(75)
<223> OTHER INFORMATION: Ser or absent
<220> FEATURE:
<221> NAME/KEY: MOD_RES
<222> LOCATION: (76)..(76)
<223> OTHER INFORMATION: Gly or absent
<220> FEATURE:
<221> NAME/KEY: MOD_RES
<222> LOCATION: (77)..(77)
<223> OTHER INFORMATION: Gly or absent
<220> FEATURE:
<221> NAME/KEY: MOD_RES
<222> LOCATION: (78)..(78)
<223> OTHER INFORMATION: Gly or absent
<220> FEATURE:
<221> NAME/KEY: MOD_RES
<222> LOCATION: (79)..(79)
<223> OTHER INFORMATION: Gly or absent
<220> FEATURE:
<221> NAME/KEY: MOD_RES
<222> LOCATION: (80)..(80)
<223> OTHER INFORMATION: Ser or absent
<220> FEATURE:
<221> NAME/KEY: MOD_RES
<222> LOCATION: (81)..(81)
<223> OTHER INFORMATION: Gly or absent
<220> FEATURE:

<221> NAME/KEY: MOD_RES
<222> LOCATION: (82)..(82)
<223> OTHER INFORMATION: Gly or absent
<220> FEATURE:
<221> NAME/KEY: MOD_RES
<222> LOCATION: (83)..(83)
<223> OTHER INFORMATION: Gly or absent
<220> FEATURE:
<221> NAME/KEY: MOD_RES
<222> LOCATION: (84)..(84)
<223> OTHER INFORMATION: Gly or absent
<220> FEATURE:
<221> NAME/KEY: MOD_RES
<222> LOCATION: (85)..(85)
<223> OTHER INFORMATION: Ser or absent
<220> FEATURE:
<221> NAME/KEY: MOD_RES
<222> LOCATION: (86)..(86)
<223> OTHER INFORMATION: Gly or absent
<220> FEATURE:
<221> NAME/KEY: MOD_RES
<222> LOCATION: (87)..(87)
<223> OTHER INFORMATION: Gly or absent
<220> FEATURE:
<221> NAME/KEY: MOD_RES
<222> LOCATION: (88)..(88)
<223> OTHER INFORMATION: Gly or absent
<220> FEATURE:
<221> NAME/KEY: MOD_RES
<222> LOCATION: (89)..(89)
<223> OTHER INFORMATION: Gly or absent
<220> FEATURE:
<221> NAME/KEY: MOD_RES
<222> LOCATION: (90)..(90)
<223> OTHER INFORMATION: Ser or absent
<220> FEATURE:
<221> NAME/KEY: MOD_RES
<222> LOCATION: (91)..(91)
<223> OTHER INFORMATION: Gly or absent
<220> FEATURE:
<221> NAME/KEY: MOD_RES
<222> LOCATION: (92)..(92)
<223> OTHER INFORMATION: Gly or absent
<220> FEATURE:
<221> NAME/KEY: MOD_RES
<222> LOCATION: (93)..(93)
<223> OTHER INFORMATION: Gly or absent
<220> FEATURE:
<221> NAME/KEY: MOD_RES
<222> LOCATION: (94)..(94)
<223> OTHER INFORMATION: Gly or absent
<220> FEATURE:
<221> NAME/KEY: MOD_RES
<222> LOCATION: (95)..(95)
<223> OTHER INFORMATION: Ser or absent
<220> FEATURE:
<221> NAME/KEY: MOD_RES
<222> LOCATION: (96)..(96)
<223> OTHER INFORMATION: Gly or absent
<220> FEATURE:
<221> NAME/KEY: MOD_RES
<222> LOCATION: (97)..(97)
<223> OTHER INFORMATION: Gly or absent
<220> FEATURE:
<221> NAME/KEY: MOD_RES
<222> LOCATION: (98)..(98)
<223> OTHER INFORMATION: Gly or absent
<220> FEATURE:
<221> NAME/KEY: MOD_RES
<222> LOCATION: (99)..(99)
<223> OTHER INFORMATION: Gly or absent
<220> FEATURE:
<221> NAME/KEY: MOD_RES
<222> LOCATION: (100)..(100)
<223> OTHER INFORMATION: Ser or absent
<220> FEATURE:
<221> NAME/KEY: MOD_RES
<222> LOCATION: (101)..(101)
<223> OTHER INFORMATION: Gly or absent
<220> FEATURE:
<221> NAME/KEY: MOD_RES
<222> LOCATION: (102)..(102)
<223> OTHER INFORMATION: Gly or absent
<220> FEATURE:
<221> NAME/KEY: MOD_RES
<222> LOCATION: (103)..(103)
<223> OTHER INFORMATION: Gly or absent
<220> FEATURE:
<221> NAME/KEY: MOD_RES
<222> LOCATION: (104)..(104)
<223> OTHER INFORMATION: Gly or absent
<220> FEATURE:
<221> NAME/KEY: MOD_RES
<222> LOCATION: (105)..(105)
<223> OTHER INFORMATION: Ser or absent
<220> FEATURE:
<221> NAME/KEY: MOD_RES
<222> LOCATION: (106)..(106)
<223> OTHER INFORMATION: Gly or absent
<220> FEATURE:
<221> NAME/KEY: MOD_RES
<222> LOCATION: (107)..(107)
<223> OTHER INFORMATION: Gly or absent
<220> FEATURE:
<221> NAME/KEY: MOD_RES
<222> LOCATION: (108)..(108)
<223> OTHER INFORMATION: Gly or absent
<220> FEATURE:
<221> NAME/KEY: MOD_RES
<222> LOCATION: (109)..(109)
<223> OTHER INFORMATION: Gly or absent
<220> FEATURE:
<221> NAME/KEY: MOD_RES
<222> LOCATION: (110)..(110)
<223> OTHER INFORMATION: Ser or absent
<220> FEATURE:
<221> NAME/KEY: MOD_RES
<222> LOCATION: (111)..(111)
<223> OTHER INFORMATION: Gly or absent
<220> FEATURE:
<221> NAME/KEY: MOD_RES
<222> LOCATION: (112)..(112)
<223> OTHER INFORMATION: Gly or absent
<220> FEATURE:
<221> NAME/KEY: MOD_RES
<222> LOCATION: (113)..(113)
<223> OTHER INFORMATION: Gly or absent
<220> FEATURE:
<221> NAME/KEY: MOD_RES
<222> LOCATION: (114)..(114)
<223> OTHER INFORMATION: Gly or absent
<220> FEATURE:
<221> NAME/KEY: MOD_RES
<222> LOCATION: (115)..(115)
<223> OTHER INFORMATION: Ser or absent
<220> FEATURE:
<221> NAME/KEY: MOD_RES
<222> LOCATION: (116)..(116)
<223> OTHER INFORMATION: Gly or absent
<220> FEATURE:
<221> NAME/KEY: MOD_RES
<222> LOCATION: (117)..(117)
<223> OTHER INFORMATION: Gly or absent
<220> FEATURE:
<221> NAME/KEY: MOD_RES
<222> LOCATION: (118)..(118)
<223> OTHER INFORMATION: Gly or absent
<220> FEATURE:
<221> NAME/KEY: MOD_RES
<222> LOCATION: (119)..(119)
<223> OTHER INFORMATION: Gly or absent
<220> FEATURE:
<221> NAME/KEY: MOD_RES
<222> LOCATION: (120)..(120)
<223> OTHER INFORMATION: Ser or absent
<220> FEATURE:
<221> NAME/KEY: MOD_RES
<222> LOCATION: (121)..(121)

<223> OTHER INFORMATION: Gly or absent
<220> FEATURE:
<221> NAME/KEY: MOD_RES
<222> LOCATION: (122)..(122)
<223> OTHER INFORMATION: Gly or absent
<220> FEATURE:
<221> NAME/KEY: MOD_RES
<222> LOCATION: (123)..(123)
<223> OTHER INFORMATION: Gly or absent
<220> FEATURE:
<221> NAME/KEY: MOD_RES
<222> LOCATION: (124)..(124)
<223> OTHER INFORMATION: Gly or absent
<220> FEATURE:
<221> NAME/KEY: MOD_RES
<222> LOCATION: (125)..(125)
<223> OTHER INFORMATION: Ser or absent
<220> FEATURE:
<221> NAME/KEY: SITE
<222> LOCATION: (6)..(125)
<223> OTHER INFORMATION: This region may encompass 1-9, 14, 19 or 24
      "Gly Gly Gly Gly Ser" repeating units wherein some positions may
      be absent

<400> SEQUENCE: 145

```
Gly Gly Gly Gly Ser Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125
```

<210> SEQ ID NO 146
<211> LENGTH: 75
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Gly or absent
<220> FEATURE:
<221> NAME/KEY: MOD_RES
<222> LOCATION: (5)..(5)
<223> OTHER INFORMATION: Gly or absent
<220> FEATURE:
<221> NAME/KEY: MOD_RES
<222> LOCATION: (6)..(6)
<223> OTHER INFORMATION: Ser or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:

<221> NAME/KEY: MOD_RES
<222> LOCATION: (9)..(9)
<223> OTHER INFORMATION: Ser or absent
<220> FEATURE:
<221> NAME/KEY: MOD_RES
<222> LOCATION: (10)..(10)
<223> OTHER INFORMATION: Gly or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Ser or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Ser or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Gly or absent
<220> FEATURE:
<221> NAME/KEY: MOD_RES
<222> LOCATION: (21)..(21)
<223> OTHER INFORMATION: Ser or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Ser or absent
<220> FEATURE:
<221> NAME/KEY: MOD_RES
<222> LOCATION: (25)..(25)
<223> OTHER INFORMATION: Gly or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Ser or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Ser or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Gly or absent
<220> FEATURE:
<221> NAME/KEY: MOD_RES
<222> LOCATION: (36)..(36)
<223> OTHER INFORMATION: Ser or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Ser or absent
<220> FEATURE:
<221> NAME/KEY: MOD_RES
<222> LOCATION: (40)..(40)
<223> OTHER INFORMATION: Gly or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Ser or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Ser or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)

<223> OTHER INFORMATION: Ser or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Gly or absent
<220> FEATURE:
<221> NAME/KEY: MOD_RES
<222> LOCATION: (51)..(51)
<223> OTHER INFORMATION: Ser or absent
<220> FEATURE:
<221> NAME/KEY: MOD_RES
<222> LOCATION: (52)..(52)
<223> OTHER INFORMATION: Gly or absent
<220> FEATURE:
<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Ser or absent
<220> FEATURE:
<221> NAME/KEY: MOD_RES
<222> LOCATION: (55)..(55)
<223> OTHER INFORMATION: Gly or absent
<220> FEATURE:
<221> NAME/KEY: MOD_RES
<222> LOCATION: (56)..(56)
<223> OTHER INFORMATION: Gly or absent
<220> FEATURE:
<221> NAME/KEY: MOD_RES
<222> LOCATION: (57)..(57)
<223> OTHER INFORMATION: Ser or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Gly or absent
<220> FEATURE:
<221> NAME/KEY: MOD_RES
<222> LOCATION: (60)..(60)
<223> OTHER INFORMATION: Ser or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Ser or absent
<220> FEATURE:
<221> NAME/KEY: MOD_RES
<222> LOCATION: (64)..(64)
<223> OTHER INFORMATION: Gly or absent
<220> FEATURE:
<221> NAME/KEY: MOD_RES
<222> LOCATION: (65)..(65)
<223> OTHER INFORMATION: Gly or absent
<220> FEATURE:
<221> NAME/KEY: MOD_RES
<222> LOCATION: (66)..(66)
<223> OTHER INFORMATION: Ser or absent
<220> FEATURE:
<221> NAME/KEY: MOD_RES
<222> LOCATION: (67)..(67)
<223> OTHER INFORMATION: Gly or absent
<220> FEATURE:
<221> NAME/KEY: MOD_RES
<222> LOCATION: (68)..(68)
<223> OTHER INFORMATION: Gly or absent
<220> FEATURE:
<221> NAME/KEY: MOD_RES
<222> LOCATION: (69)..(69)
<223> OTHER INFORMATION: Ser or absent
<220> FEATURE:
<221> NAME/KEY: MOD_RES
<222> LOCATION: (70)..(70)
<223> OTHER INFORMATION: Gly or absent
<220> FEATURE:
<221> NAME/KEY: MOD_RES
<222> LOCATION: (71)..(71)
<223> OTHER INFORMATION: Gly or absent
<220> FEATURE:
<221> NAME/KEY: MOD_RES
<222> LOCATION: (72)..(72)
<223> OTHER INFORMATION: Ser or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Gly or absent
<220> FEATURE:
<221> NAME/KEY: MOD_RES
<222> LOCATION: (75)..(75)
<223> OTHER INFORMATION: Ser or absent
<220> FEATURE:
<221> NAME/KEY: SITE
<222> LOCATION: (4)..(75)
<223> OTHER INFORMATION: This region may encompass 1-9, 14, 19 or 24
"Gly Gly Ser" repeating units wherein some positions may be absent

<400> SEQUENCE: 146

```
Gly Gly Ser Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa
65                  70                  75
```

<210> SEQ ID NO 147
<211> LENGTH: 100
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (5)..(5)
<223> OTHER INFORMATION: Gly or absent
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Ser or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Gly or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Ser or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Gly or absent
<220> FEATURE:
<221> NAME/KEY: MOD_RES
<222> LOCATION: (16)..(16)
<223> OTHER INFORMATION: Ser or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Ser or absent
<220> FEATURE:
<221> NAME/KEY: MOD_RES
<222> LOCATION: (25)..(25)
<223> OTHER INFORMATION: Gly or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Ser or absent
<220> FEATURE:

<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Ser or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Gly or absent
<220> FEATURE:
<221> NAME/KEY: MOD_RES
<222> LOCATION: (36)..(36)
<223> OTHER INFORMATION: Ser or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Gly or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Ser or absent
<220> FEATURE:
<221> NAME/KEY: MOD_RES
<222> LOCATION: (45)..(45)
<223> OTHER INFORMATION: Gly or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Ser or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Gly or absent
<220> FEATURE:
<221> NAME/KEY: MOD_RES
<222> LOCATION: (51)..(51)
<223> OTHER INFORMATION: Gly or absent
<220> FEATURE:
<221> NAME/KEY: MOD_RES
<222> LOCATION: (52)..(52)
<223> OTHER INFORMATION: Ser or absent
<220> FEATURE:
<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Gly or absent
<220> FEATURE:
<221> NAME/KEY: MOD_RES
<222> LOCATION: (55)..(55)
<223> OTHER INFORMATION: Gly or absent
<220> FEATURE:
<221> NAME/KEY: MOD_RES
<222> LOCATION: (56)..(56)
<223> OTHER INFORMATION: Ser or absent
<220> FEATURE:
<221> NAME/KEY: MOD_RES
<222> LOCATION: (57)..(57)
<223> OTHER INFORMATION: Gly or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Gly or absent
<220> FEATURE:
<221> NAME/KEY: MOD_RES
<222> LOCATION: (60)..(60)
<223> OTHER INFORMATION: Ser or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Gly or absent
<220> FEATURE:
<221> NAME/KEY: MOD_RES
<222> LOCATION: (64)..(64)
<223> OTHER INFORMATION: Ser or absent
<220> FEATURE:
<221> NAME/KEY: MOD_RES
<222> LOCATION: (65)..(65)
<223> OTHER INFORMATION: Gly or absent
<220> FEATURE:
<221> NAME/KEY: MOD_RES
<222> LOCATION: (66)..(66)
<223> OTHER INFORMATION: Gly or absent
<220> FEATURE:
<221> NAME/KEY: MOD_RES
<222> LOCATION: (67)..(67)
<223> OTHER INFORMATION: Gly or absent
<220> FEATURE:
<221> NAME/KEY: MOD_RES
<222> LOCATION: (68)..(68)

<223> OTHER INFORMATION: Ser or absent
<220> FEATURE:
<221> NAME/KEY: MOD_RES
<222> LOCATION: (69)..(69)
<223> OTHER INFORMATION: Gly or absent
<220> FEATURE:
<221> NAME/KEY: MOD_RES
<222> LOCATION: (70)..(70)
<223> OTHER INFORMATION: Gly or absent
<220> FEATURE:
<221> NAME/KEY: MOD_RES
<222> LOCATION: (71)..(71)
<223> OTHER INFORMATION: Gly or absent
<220> FEATURE:
<221> NAME/KEY: MOD_RES
<222> LOCATION: (72)..(72)
<223> OTHER INFORMATION: Ser or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Gly or absent
<220> FEATURE:
<221> NAME/KEY: MOD_RES
<222> LOCATION: (75)..(75)
<223> OTHER INFORMATION: Gly or absent
<220> FEATURE:
<221> NAME/KEY: MOD_RES
<222> LOCATION: (76)..(76)
<223> OTHER INFORMATION: Ser or absent
<220> FEATURE:
<221> NAME/KEY: MOD_RES
<222> LOCATION: (77)..(77)
<223> OTHER INFORMATION: Gly or absent
<220> FEATURE:
<221> NAME/KEY: MOD_RES
<222> LOCATION: (78)..(78)
<223> OTHER INFORMATION: Gly or absent
<220> FEATURE:
<221> NAME/KEY: MOD_RES
<222> LOCATION: (79)..(79)
<223> OTHER INFORMATION: Gly or absent
<220> FEATURE:
<221> NAME/KEY: MOD_RES
<222> LOCATION: (80)..(80)
<223> OTHER INFORMATION: Ser or absent
<220> FEATURE:
<221> NAME/KEY: MOD_RES
<222> LOCATION: (81)..(81)
<223> OTHER INFORMATION: Gly or absent
<220> FEATURE:
<221> NAME/KEY: MOD_RES
<222> LOCATION: (82)..(82)
<223> OTHER INFORMATION: Gly or absent
<220> FEATURE:
<221> NAME/KEY: MOD_RES
<222> LOCATION: (83)..(83)
<223> OTHER INFORMATION: Gly or absent
<220> FEATURE:
<221> NAME/KEY: MOD_RES
<222> LOCATION: (84)..(84)
<223> OTHER INFORMATION: Ser or absent
<220> FEATURE:
<221> NAME/KEY: MOD_RES
<222> LOCATION: (85)..(85)
<223> OTHER INFORMATION: Gly or absent
<220> FEATURE:
<221> NAME/KEY: MOD_RES
<222> LOCATION: (86)..(86)
<223> OTHER INFORMATION: Gly or absent
<220> FEATURE:
<221> NAME/KEY: MOD_RES
<222> LOCATION: (87)..(87)
<223> OTHER INFORMATION: Gly or absent
<220> FEATURE:
<221> NAME/KEY: MOD_RES

```
<222> LOCATION: (88)..(88)
<223> OTHER INFORMATION: Ser or absent
<220> FEATURE:
<221> NAME/KEY: MOD_RES
<222> LOCATION: (89)..(89)
<223> OTHER INFORMATION: Gly or absent
<220> FEATURE:
<221> NAME/KEY: MOD_RES
<222> LOCATION: (90)..(90)
<223> OTHER INFORMATION: Gly or absent
<220> FEATURE:
<221> NAME/KEY: MOD_RES
<222> LOCATION: (91)..(91)
<223> OTHER INFORMATION: Gly or absent
<220> FEATURE:
<221> NAME/KEY: MOD_RES
<222> LOCATION: (92)..(92)
<223> OTHER INFORMATION: Ser or absent
<220> FEATURE:
<221> NAME/KEY: MOD_RES
<222> LOCATION: (93)..(93)
<223> OTHER INFORMATION: Gly or absent
<220> FEATURE:
<221> NAME/KEY: MOD_RES
<222> LOCATION: (94)..(94)
<223> OTHER INFORMATION: Gly or absent
<220> FEATURE:
<221> NAME/KEY: MOD_RES
<222> LOCATION: (95)..(95)
<223> OTHER INFORMATION: Gly or absent
<220> FEATURE:
<221> NAME/KEY: MOD_RES
<222> LOCATION: (96)..(96)
<223> OTHER INFORMATION: Ser or absent
<220> FEATURE:
<221> NAME/KEY: MOD_RES
<222> LOCATION: (97)..(97)
<223> OTHER INFORMATION: Gly or absent
<220> FEATURE:
<221> NAME/KEY: MOD_RES
<222> LOCATION: (98)..(98)
<223> OTHER INFORMATION: Gly or absent
<220> FEATURE:
<221> NAME/KEY: MOD_RES
<222> LOCATION: (99)..(99)
<223> OTHER INFORMATION: Gly or absent
<220> FEATURE:
<221> NAME/KEY: MOD_RES
<222> LOCATION: (100)..(100)
<223> OTHER INFORMATION: Ser or absent
<220> FEATURE:
<221> NAME/KEY: SITE
<222> LOCATION: (5)..(100)
<223> OTHER INFORMATION: This region may encompass 1-9, 14, 19 or 24
      "Gly Gly Gly Ser" repeating units wherein some positions may be
      absent

<400> SEQUENCE: 147

Gly Gly Gly Ser Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa
            100
```

<210> SEQ ID NO 148
<211> LENGTH: 100
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (5)..(5)
<223> OTHER INFORMATION: Gly or absent
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Ser or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Gly or absent
<220> FEATURE:
<221> NAME/KEY: MOD_RES
<222> LOCATION: (10)..(10)
<223> OTHER INFORMATION: Gly or absent
<220> FEATURE:
<221> NAME/KEY: MOD_RES
<222> LOCATION: (11)..(11)
<223> OTHER INFORMATION: Ser or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Ser or absent
<220> FEATURE:
<221> NAME/KEY: MOD_RES
<222> LOCATION: (20)..(20)
<223> OTHER INFORMATION: Gly or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Ser or absent
<220> FEATURE:
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Gly or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Ser or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Gly or absent
<220> FEATURE:
<221> NAME/KEY: MOD_RES
<222> LOCATION: (30)..(30)
<223> OTHER INFORMATION: Gly or absent
<220> FEATURE:
<221> NAME/KEY: MOD_RES
<222> LOCATION: (31)..(31)
<223> OTHER INFORMATION: Ser or absent
<220> FEATURE:
<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Gly or absent
<220> FEATURE:
<221> NAME/KEY: MOD_RES
<222> LOCATION: (35)..(35)
<223> OTHER INFORMATION: Ser or absent
<220> FEATURE:
<221> NAME/KEY: MOD_RES
<222> LOCATION: (36)..(36)
<223> OTHER INFORMATION: Gly or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Ser or absent
<220> FEATURE:
<221> NAME/KEY: MOD_RES
<222> LOCATION: (40)..(40)
<223> OTHER INFORMATION: Gly or absent
<220> FEATURE:
<221> NAME/KEY: MOD_RES
<222> LOCATION: (41)..(41)
<223> OTHER INFORMATION: Gly or absent
<220> FEATURE:

<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Ser or absent
<220> FEATURE:
<221> NAME/KEY: MOD_RES
<222> LOCATION: (44)..(44)
<223> OTHER INFORMATION: Gly or absent
<220> FEATURE:
<221> NAME/KEY: MOD_RES
<222> LOCATION: (45)..(45)
<223> OTHER INFORMATION: Gly or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Ser or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Gly or absent
<220> FEATURE:
<221> NAME/KEY: MOD_RES
<222> LOCATION: (50)..(50)
<223> OTHER INFORMATION: Gly or absent
<220> FEATURE:
<221> NAME/KEY: MOD_RES
<222> LOCATION: (51)..(51)
<223> OTHER INFORMATION: Ser or absent
<220> FEATURE:
<221> NAME/KEY: MOD_RES
<222> LOCATION: (52)..(52)
<223> OTHER INFORMATION: Gly or absent
<220> FEATURE:
<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Gly or absent
<220> FEATURE:
<221> NAME/KEY: MOD_RES
<222> LOCATION: (55)..(55)
<223> OTHER INFORMATION: Ser or absent
<220> FEATURE:
<221> NAME/KEY: MOD_RES
<222> LOCATION: (56)..(56)
<223> OTHER INFORMATION: Gly or absent
<220> FEATURE:
<221> NAME/KEY: MOD_RES
<222> LOCATION: (57)..(57)
<223> OTHER INFORMATION: Gly or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Ser or absent
<220> FEATURE:
<221> NAME/KEY: MOD_RES
<222> LOCATION: (60)..(60)
<223> OTHER INFORMATION: Gly or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Ser or absent
<220> FEATURE:
<221> NAME/KEY: MOD_RES
<222> LOCATION: (64)..(64)
<223> OTHER INFORMATION: Gly or absent
<220> FEATURE:
<221> NAME/KEY: MOD_RES
<222> LOCATION: (65)..(65)
<223> OTHER INFORMATION: Gly or absent
<220> FEATURE:
<221> NAME/KEY: MOD_RES
<222> LOCATION: (66)..(66)
<223> OTHER INFORMATION: Gly or absent
<220> FEATURE:
<221> NAME/KEY: MOD_RES
<222> LOCATION: (67)..(67)
<223> OTHER INFORMATION: Ser or absent
<220> FEATURE:
<221> NAME/KEY: MOD_RES
<222> LOCATION: (68)..(68)
<223> OTHER INFORMATION: Gly or absent
<220> FEATURE:
<221> NAME/KEY: MOD_RES
<222> LOCATION: (69)..(69)
<223> OTHER INFORMATION: Gly or absent
<220> FEATURE:
<221> NAME/KEY: MOD_RES
<222> LOCATION: (70)..(70)
<223> OTHER INFORMATION: Gly or absent
<220> FEATURE:
<221> NAME/KEY: MOD_RES
<222> LOCATION: (71)..(71)
<223> OTHER INFORMATION: Ser or absent
<220> FEATURE:
<221> NAME/KEY: MOD_RES
<222> LOCATION: (72)..(72)
<223> OTHER INFORMATION: Gly or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Gly or absent
<220> FEATURE:
<221> NAME/KEY: MOD_RES
<222> LOCATION: (75)..(75)
<223> OTHER INFORMATION: Ser or absent
<220> FEATURE:
<221> NAME/KEY: MOD_RES
<222> LOCATION: (76)..(76)
<223> OTHER INFORMATION: Gly or absent
<220> FEATURE:
<221> NAME/KEY: MOD_RES
<222> LOCATION: (77)..(77)
<223> OTHER INFORMATION: Gly or absent
<220> FEATURE:
<221> NAME/KEY: MOD_RES
<222> LOCATION: (78)..(78)
<223> OTHER INFORMATION: Gly or absent
<220> FEATURE:
<221> NAME/KEY: MOD_RES
<222> LOCATION: (79)..(79)
<223> OTHER INFORMATION: Ser or absent
<220> FEATURE:
<221> NAME/KEY: MOD_RES
<222> LOCATION: (80)..(80)
<223> OTHER INFORMATION: Gly or absent
<220> FEATURE:
<221> NAME/KEY: MOD_RES
<222> LOCATION: (81)..(81)

<223> OTHER INFORMATION: Gly or absent
<220> FEATURE:
<221> NAME/KEY: MOD_RES
<222> LOCATION: (82)..(82)
<223> OTHER INFORMATION: Gly or absent
<220> FEATURE:
<221> NAME/KEY: MOD_RES
<222> LOCATION: (83)..(83)
<223> OTHER INFORMATION: Ser or absent
<220> FEATURE:
<221> NAME/KEY: MOD_RES
<222> LOCATION: (84)..(84)
<223> OTHER INFORMATION: Gly or absent
<220> FEATURE:
<221> NAME/KEY: MOD_RES
<222> LOCATION: (85)..(85)
<223> OTHER INFORMATION: Gly or absent
<220> FEATURE:
<221> NAME/KEY: MOD_RES
<222> LOCATION: (86)..(86)
<223> OTHER INFORMATION: Gly or absent
<220> FEATURE:
<221> NAME/KEY: MOD_RES
<222> LOCATION: (87)..(87)
<223> OTHER INFORMATION: Ser or absent
<220> FEATURE:
<221> NAME/KEY: MOD_RES
<222> LOCATION: (88)..(88)
<223> OTHER INFORMATION: Gly or absent
<220> FEATURE:
<221> NAME/KEY: MOD_RES
<222> LOCATION: (89)..(89)
<223> OTHER INFORMATION: Gly or absent
<220> FEATURE:
<221> NAME/KEY: MOD_RES
<222> LOCATION: (90)..(90)
<223> OTHER INFORMATION: Gly or absent
<220> FEATURE:
<221> NAME/KEY: MOD_RES
<222> LOCATION: (91)..(91)
<223> OTHER INFORMATION: Ser or absent
<220> FEATURE:
<221> NAME/KEY: MOD_RES
<222> LOCATION: (92)..(92)
<223> OTHER INFORMATION: Gly or absent
<220> FEATURE:
<221> NAME/KEY: MOD_RES
<222> LOCATION: (93)..(93)
<223> OTHER INFORMATION: Gly or absent
<220> FEATURE:
<221> NAME/KEY: MOD_RES
<222> LOCATION: (94)..(94)
<223> OTHER INFORMATION: Gly or absent
<220> FEATURE:
<221> NAME/KEY: MOD_RES
<222> LOCATION: (95)..(95)
<223> OTHER INFORMATION: Ser or absent
<220> FEATURE:
<221> NAME/KEY: MOD_RES
<222> LOCATION: (96)..(96)
<223> OTHER INFORMATION: Gly or absent
<220> FEATURE:
<221> NAME/KEY: MOD_RES
<222> LOCATION: (97)..(97)
<223> OTHER INFORMATION: Gly or absent
<220> FEATURE:
<221> NAME/KEY: MOD_RES
<222> LOCATION: (98)..(98)
<223> OTHER INFORMATION: Gly or absent
<220> FEATURE:
<221> NAME/KEY: MOD_RES
<222> LOCATION: (99)..(99)
<223> OTHER INFORMATION: Ser or absent
<220> FEATURE:
<221> NAME/KEY: MOD_RES
<222> LOCATION: (100)..(100)
<223> OTHER INFORMATION: Gly or absent
<220> FEATURE:
<221> NAME/KEY: SITE
<222> LOCATION: (5)..(100)
<223> OTHER INFORMATION: This region may encompass 1-9, 14, 19 or 24
      "Gly Gly Ser Gly" repeating units wherein some positions may be
      absent

<400> SEQUENCE: 148

```
Gly Gly Ser Gly Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa
            100
```

<210> SEQ ID NO 149
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Gly or absent
<220> FEATURE:
<221> NAME/KEY: MOD_RES
<222> LOCATION: (7)..(7)
<223> OTHER INFORMATION: Gly or absent
<220> FEATURE:
<221> NAME/KEY: MOD_RES
<222> LOCATION: (8)..(8)
<223> OTHER INFORMATION: Gly or absent
<220> FEATURE:
<221> NAME/KEY: MOD_RES
<222> LOCATION: (9)..(9)
<223> OTHER INFORMATION: Ser or absent
<220> FEATURE:
<221> NAME/KEY: MOD_RES
<222> LOCATION: (10)..(10)
<223> OTHER INFORMATION: Ser or absent
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Ser or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)

<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Ser or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:
<221> NAME/KEY: MOD_RES
<222> LOCATION: (24)..(24)
<223> OTHER INFORMATION: Ser or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: MOD_RES
<222> LOCATION: (26)..(26)
<223> OTHER INFORMATION: Gly or absent
<220> FEATURE:
<221> NAME/KEY: MOD_RES
<222> LOCATION: (27)..(27)
<223> OTHER INFORMATION: Gly or absent
<220> FEATURE:
<221> NAME/KEY: MOD_RES
<222> LOCATION: (28)..(28)
<223> OTHER INFORMATION: Gly or absent
<220> FEATURE:
<221> NAME/KEY: MOD_RES
<222> LOCATION: (29)..(29)
<223> OTHER INFORMATION: Ser or absent
<220> FEATURE:
<221> NAME/KEY: MOD_RES
<222> LOCATION: (30)..(30)
<223> OTHER INFORMATION: Ser or absent
<220> FEATURE:
<221> NAME/KEY: MOD_RES
<222> LOCATION: (31)..(31)
<223> OTHER INFORMATION: Gly or absent
<220> FEATURE:
<221> NAME/KEY: MOD_RES
<222> LOCATION: (32)..(32)
<223> OTHER INFORMATION: Gly or absent
<220> FEATURE:
<221> NAME/KEY: MOD_RES
<222> LOCATION: (33)..(33)
<223> OTHER INFORMATION: Gly or absent
<220> FEATURE:
<221> NAME/KEY: MOD_RES
<222> LOCATION: (34)..(34)
<223> OTHER INFORMATION: Ser or absent
<220> FEATURE:
<221> NAME/KEY: MOD_RES
<222> LOCATION: (35)..(35)
<223> OTHER INFORMATION: Ser or absent
<220> FEATURE:
<221> NAME/KEY: MOD_RES
<222> LOCATION: (36)..(36)
<223> OTHER INFORMATION: Gly or absent
<220> FEATURE:
<221> NAME/KEY: MOD_RES
<222> LOCATION: (37)..(37)
<223> OTHER INFORMATION: Gly or absent
<220> FEATURE:
<221> NAME/KEY: MOD_RES
<222> LOCATION: (38)..(38)
<223> OTHER INFORMATION: Gly or absent
<220> FEATURE:
<221> NAME/KEY: MOD_RES
<222> LOCATION: (39)..(39)
<223> OTHER INFORMATION: Ser or absent
<220> FEATURE:
<221> NAME/KEY: MOD_RES
<222> LOCATION: (40)..(40)
<223> OTHER INFORMATION: Ser or absent
<220> FEATURE:
<221> NAME/KEY: MOD_RES
<222> LOCATION: (41)..(41)
<223> OTHER INFORMATION: Gly or absent
<220> FEATURE:
<221> NAME/KEY: MOD_RES
<222> LOCATION: (42)..(42)
<223> OTHER INFORMATION: Gly or absent
<220> FEATURE:
<221> NAME/KEY: MOD_RES
<222> LOCATION: (43)..(43)
<223> OTHER INFORMATION: Gly or absent
<220> FEATURE:
<221> NAME/KEY: MOD_RES
<222> LOCATION: (44)..(44)
<223> OTHER INFORMATION: Ser or absent
<220> FEATURE:
<221> NAME/KEY: MOD_RES
<222> LOCATION: (45)..(45)
<223> OTHER INFORMATION: Ser or absent
<220> FEATURE:
<221> NAME/KEY: MOD_RES
<222> LOCATION: (46)..(46)
<223> OTHER INFORMATION: Gly or absent
<220> FEATURE:
<221> NAME/KEY: MOD_RES
<222> LOCATION: (47)..(47)
<223> OTHER INFORMATION: Gly or absent
<220> FEATURE:
<221> NAME/KEY: MOD_RES
<222> LOCATION: (48)..(48)
<223> OTHER INFORMATION: Gly or absent
<220> FEATURE:
<221> NAME/KEY: MOD_RES
<222> LOCATION: (49)..(49)
<223> OTHER INFORMATION: Ser or absent
<220> FEATURE:
<221> NAME/KEY: MOD_RES
<222> LOCATION: (50)..(50)
<223> OTHER INFORMATION: Ser or absent
<220> FEATURE:
<221> NAME/KEY: MOD_RES
<222> LOCATION: (51)..(51)
<223> OTHER INFORMATION: Gly or absent
<220> FEATURE:
<221> NAME/KEY: MOD_RES
<222> LOCATION: (52)..(52)
<223> OTHER INFORMATION: Gly or absent
<220> FEATURE:
<221> NAME/KEY: MOD_RES
<222> LOCATION: (53)..(53)
<223> OTHER INFORMATION: Gly or absent
<220> FEATURE:
<221> NAME/KEY: MOD_RES
<222> LOCATION: (54)..(54)
<223> OTHER INFORMATION: Ser or absent
<220> FEATURE:
<221> NAME/KEY: MOD_RES
<222> LOCATION: (55)..(55)
<223> OTHER INFORMATION: Ser or absent
<220> FEATURE:

<221> NAME/KEY: MOD_RES
<222> LOCATION: (56)..(56)
<223> OTHER INFORMATION: Gly or absent
<220> FEATURE:
<221> NAME/KEY: MOD_RES
<222> LOCATION: (57)..(57)
<223> OTHER INFORMATION: Gly or absent
<220> FEATURE:
<221> NAME/KEY: MOD_RES
<222> LOCATION: (58)..(58)
<223> OTHER INFORMATION: Gly or absent
<220> FEATURE:
<221> NAME/KEY: MOD_RES
<222> LOCATION: (59)..(59)
<223> OTHER INFORMATION: Ser or absent
<220> FEATURE:
<221> NAME/KEY: MOD_RES
<222> LOCATION: (60)..(60)
<223> OTHER INFORMATION: Ser or absent
<220> FEATURE:
<221> NAME/KEY: MOD_RES
<222> LOCATION: (61)..(61)
<223> OTHER INFORMATION: Gly or absent
<220> FEATURE:
<221> NAME/KEY: MOD_RES
<222> LOCATION: (62)..(62)
<223> OTHER INFORMATION: Gly or absent
<220> FEATURE:
<221> NAME/KEY: MOD_RES
<222> LOCATION: (63)..(63)
<223> OTHER INFORMATION: Gly or absent
<220> FEATURE:
<221> NAME/KEY: MOD_RES
<222> LOCATION: (64)..(64)
<223> OTHER INFORMATION: Ser or absent
<220> FEATURE:
<221> NAME/KEY: MOD_RES
<222> LOCATION: (65)..(65)
<223> OTHER INFORMATION: Ser or absent
<220> FEATURE:
<221> NAME/KEY: MOD_RES
<222> LOCATION: (66)..(66)
<223> OTHER INFORMATION: Gly or absent
<220> FEATURE:
<221> NAME/KEY: MOD_RES
<222> LOCATION: (67)..(67)
<223> OTHER INFORMATION: Gly or absent
<220> FEATURE:
<221> NAME/KEY: MOD_RES
<222> LOCATION: (68)..(68)
<223> OTHER INFORMATION: Gly or absent
<220> FEATURE:
<221> NAME/KEY: MOD_RES
<222> LOCATION: (69)..(69)
<223> OTHER INFORMATION: Ser or absent
<220> FEATURE:
<221> NAME/KEY: MOD_RES
<222> LOCATION: (70)..(70)
<223> OTHER INFORMATION: Ser or absent
<220> FEATURE:
<221> NAME/KEY: MOD_RES
<222> LOCATION: (71)..(71)
<223> OTHER INFORMATION: Gly or absent
<220> FEATURE:
<221> NAME/KEY: MOD_RES
<222> LOCATION: (72)..(72)
<223> OTHER INFORMATION: Gly or absent
<220> FEATURE:
<221> NAME/KEY: MOD_RES
<222> LOCATION: (73)..(73)
<223> OTHER INFORMATION: Gly or absent
<220> FEATURE:
<221> NAME/KEY: MOD_RES
<222> LOCATION: (74)..(74)
<223> OTHER INFORMATION: Ser or absent
<220> FEATURE:
<221> NAME/KEY: MOD_RES
<222> LOCATION: (75)..(75)
<223> OTHER INFORMATION: Ser or absent
<220> FEATURE:
<221> NAME/KEY: MOD_RES
<222> LOCATION: (76)..(76)
<223> OTHER INFORMATION: Gly or absent
<220> FEATURE:
<221> NAME/KEY: MOD_RES
<222> LOCATION: (77)..(77)
<223> OTHER INFORMATION: Gly or absent
<220> FEATURE:
<221> NAME/KEY: MOD_RES
<222> LOCATION: (78)..(78)
<223> OTHER INFORMATION: Gly or absent
<220> FEATURE:
<221> NAME/KEY: MOD_RES
<222> LOCATION: (79)..(79)
<223> OTHER INFORMATION: Ser or absent
<220> FEATURE:
<221> NAME/KEY: MOD_RES
<222> LOCATION: (80)..(80)
<223> OTHER INFORMATION: Ser or absent
<220> FEATURE:
<221> NAME/KEY: MOD_RES
<222> LOCATION: (81)..(81)
<223> OTHER INFORMATION: Gly or absent
<220> FEATURE:
<221> NAME/KEY: MOD_RES
<222> LOCATION: (82)..(82)
<223> OTHER INFORMATION: Gly or absent
<220> FEATURE:
<221> NAME/KEY: MOD_RES
<222> LOCATION: (83)..(83)
<223> OTHER INFORMATION: Gly or absent
<220> FEATURE:
<221> NAME/KEY: MOD_RES
<222> LOCATION: (84)..(84)
<223> OTHER INFORMATION: Ser or absent
<220> FEATURE:
<221> NAME/KEY: MOD_RES
<222> LOCATION: (85)..(85)
<223> OTHER INFORMATION: Ser or absent
<220> FEATURE:
<221> NAME/KEY: MOD_RES
<222> LOCATION: (86)..(86)
<223> OTHER INFORMATION: Gly or absent
<220> FEATURE:
<221> NAME/KEY: MOD_RES
<222> LOCATION: (87)..(87)
<223> OTHER INFORMATION: Gly or absent
<220> FEATURE:
<221> NAME/KEY: MOD_RES
<222> LOCATION: (88)..(88)
<223> OTHER INFORMATION: Gly or absent
<220> FEATURE:
<221> NAME/KEY: MOD_RES
<222> LOCATION: (89)..(89)
<223> OTHER INFORMATION: Ser or absent
<220> FEATURE:
<221> NAME/KEY: MOD_RES
<222> LOCATION: (90)..(90)
<223> OTHER INFORMATION: Ser or absent
<220> FEATURE:
<221> NAME/KEY: MOD_RES
<222> LOCATION: (91)..(91)
<223> OTHER INFORMATION: Gly or absent
<220> FEATURE:
<221> NAME/KEY: MOD_RES
<222> LOCATION: (92)..(92)
<223> OTHER INFORMATION: Gly or absent
<220> FEATURE:
<221> NAME/KEY: MOD_RES
<222> LOCATION: (93)..(93)
<223> OTHER INFORMATION: Gly or absent
<220> FEATURE:
<221> NAME/KEY: MOD_RES
<222> LOCATION: (94)..(94)
<223> OTHER INFORMATION: Ser or absent
<220> FEATURE:
<221> NAME/KEY: MOD_RES
<222> LOCATION: (95)..(95)

<223> OTHER INFORMATION: Ser or absent
<220> FEATURE:
<221> NAME/KEY: MOD_RES
<222> LOCATION: (96)..(96)
<223> OTHER INFORMATION: Gly or absent
<220> FEATURE:
<221> NAME/KEY: MOD_RES
<222> LOCATION: (97)..(97)
<223> OTHER INFORMATION: Gly or absent
<220> FEATURE:
<221> NAME/KEY: MOD_RES
<222> LOCATION: (98)..(98)
<223> OTHER INFORMATION: Gly or absent
<220> FEATURE:
<221> NAME/KEY: MOD_RES
<222> LOCATION: (99)..(99)
<223> OTHER INFORMATION: Ser or absent
<220> FEATURE:
<221> NAME/KEY: MOD_RES
<222> LOCATION: (100)..(100)
<223> OTHER INFORMATION: Ser or absent
<220> FEATURE:
<221> NAME/KEY: MOD_RES
<222> LOCATION: (101)..(101)
<223> OTHER INFORMATION: Gly or absent
<220> FEATURE:
<221> NAME/KEY: MOD_RES
<222> LOCATION: (102)..(102)
<223> OTHER INFORMATION: Gly or absent
<220> FEATURE:
<221> NAME/KEY: MOD_RES
<222> LOCATION: (103)..(103)
<223> OTHER INFORMATION: Gly or absent
<220> FEATURE:
<221> NAME/KEY: MOD_RES
<222> LOCATION: (104)..(104)
<223> OTHER INFORMATION: Ser or absent
<220> FEATURE:
<221> NAME/KEY: MOD_RES
<222> LOCATION: (105)..(105)
<223> OTHER INFORMATION: Ser or absent
<220> FEATURE:
<221> NAME/KEY: MOD_RES
<222> LOCATION: (106)..(106)
<223> OTHER INFORMATION: Gly or absent
<220> FEATURE:
<221> NAME/KEY: MOD_RES
<222> LOCATION: (107)..(107)
<223> OTHER INFORMATION: Gly or absent
<220> FEATURE:
<221> NAME/KEY: MOD_RES
<222> LOCATION: (108)..(108)
<223> OTHER INFORMATION: Gly or absent
<220> FEATURE:
<221> NAME/KEY: MOD_RES
<222> LOCATION: (109)..(109)
<223> OTHER INFORMATION: Ser or absent
<220> FEATURE:
<221> NAME/KEY: MOD_RES
<222> LOCATION: (110)..(110)
<223> OTHER INFORMATION: Ser or absent
<220> FEATURE:
<221> NAME/KEY: MOD_RES
<222> LOCATION: (111)..(111)
<223> OTHER INFORMATION: Gly or absent
<220> FEATURE:
<221> NAME/KEY: MOD_RES
<222> LOCATION: (112)..(112)
<223> OTHER INFORMATION: Gly or absent
<220> FEATURE:
<221> NAME/KEY: MOD_RES
<222> LOCATION: (113)..(113)
<223> OTHER INFORMATION: Gly or absent
<220> FEATURE:
<221> NAME/KEY: MOD_RES
<222> LOCATION: (114)..(114)
<223> OTHER INFORMATION: Ser or absent
<220> FEATURE:
<221> NAME/KEY: MOD_RES
<222> LOCATION: (115)..(115)
<223> OTHER INFORMATION: Ser or absent
<220> FEATURE:
<221> NAME/KEY: MOD_RES
<222> LOCATION: (116)..(116)
<223> OTHER INFORMATION: Gly or absent
<220> FEATURE:
<221> NAME/KEY: MOD_RES
<222> LOCATION: (117)..(117)
<223> OTHER INFORMATION: Gly or absent
<220> FEATURE:
<221> NAME/KEY: MOD_RES
<222> LOCATION: (118)..(118)
<223> OTHER INFORMATION: Gly or absent
<220> FEATURE:
<221> NAME/KEY: MOD_RES
<222> LOCATION: (119)..(119)
<223> OTHER INFORMATION: Ser or absent
<220> FEATURE:
<221> NAME/KEY: MOD_RES
<222> LOCATION: (120)..(120)
<223> OTHER INFORMATION: Ser or absent
<220> FEATURE:
<221> NAME/KEY: MOD_RES
<222> LOCATION: (121)..(121)
<223> OTHER INFORMATION: Gly or absent
<220> FEATURE:
<221> NAME/KEY: MOD_RES
<222> LOCATION: (122)..(122)
<223> OTHER INFORMATION: Gly or absent
<220> FEATURE:
<221> NAME/KEY: MOD_RES
<222> LOCATION: (123)..(123)
<223> OTHER INFORMATION: Gly or absent
<220> FEATURE:
<221> NAME/KEY: MOD_RES
<222> LOCATION: (124)..(124)
<223> OTHER INFORMATION: Ser or absent
<220> FEATURE:
<221> NAME/KEY: MOD_RES
<222> LOCATION: (125)..(125)
<223> OTHER INFORMATION: Ser or absent
<220> FEATURE:
<221> NAME/KEY: SITE
<222> LOCATION: (6)..(125)
<223> OTHER INFORMATION: This region may encompass 1-9, 14, 19 or 24
      "Gly Gly Gly Ser Ser" repeating units wherein some positions may
      be absent

<400> SEQUENCE: 149

```
Gly Gly Gly Ser Ser Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa
        115                 120                 125
```

<210> SEQ ID NO 150
<211> LENGTH: 20
<212> TYPE: PRT

<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (3)..(3)
<223> OTHER INFORMATION: Any amino acid or absent
<220> FEATURE:
<221> NAME/KEY: MOD_RES
<222> LOCATION: (4)..(4)
<223> OTHER INFORMATION: Pro or absent
<220> FEATURE:
<221> NAME/KEY: MOD_RES
<222> LOCATION: (5)..(5)
<223> OTHER INFORMATION: Any amino acid or absent
<220> FEATURE:
<221> NAME/KEY: MOD_RES
<222> LOCATION: (6)..(6)
<223> OTHER INFORMATION: Pro or absent
<220> FEATURE:
<221> NAME/KEY: MOD_RES
<222> LOCATION: (7)..(7)
<223> OTHER INFORMATION: Any amino acid or absent
<220> FEATURE:
<221> NAME/KEY: MOD_RES
<222> LOCATION: (8)..(8)
<223> OTHER INFORMATION: Pro or absent
<220> FEATURE:
<221> NAME/KEY: MOD_RES
<222> LOCATION: (9)..(9)
<223> OTHER INFORMATION: Any amino acid or absent
<220> FEATURE:
<221> NAME/KEY: MOD_RES
<222> LOCATION: (10)..(10)
<223> OTHER INFORMATION: Pro or absent
<220> FEATURE:
<221> NAME/KEY: MOD_RES
<222> LOCATION: (11)..(11)
<223> OTHER INFORMATION: Any amino acid or absent
<220> FEATURE:
<221> NAME/KEY: MOD_RES
<222> LOCATION: (12)..(12)
<223> OTHER INFORMATION: Pro or absent
<220> FEATURE:
<221> NAME/KEY: MOD_RES
<222> LOCATION: (13)..(13)
<223> OTHER INFORMATION: Any amino acid or absent
<220> FEATURE:
<221> NAME/KEY: MOD_RES
<222> LOCATION: (14)..(14)
<223> OTHER INFORMATION: Pro or absent
<220> FEATURE:
<221> NAME/KEY: MOD_RES
<222> LOCATION: (15)..(15)
<223> OTHER INFORMATION: Any amino acid or absent
<220> FEATURE:
<221> NAME/KEY: MOD_RES
<222> LOCATION: (16)..(16)
<223> OTHER INFORMATION: Pro or absent
<220> FEATURE:
<221> NAME/KEY: MOD_RES
<222> LOCATION: (17)..(17)
<223> OTHER INFORMATION: Any amino acid or absent
<220> FEATURE:
<221> NAME/KEY: MOD_RES
<222> LOCATION: (18)..(18)
<223> OTHER INFORMATION: Pro or absent
<220> FEATURE:
<221> NAME/KEY: MOD_RES
<222> LOCATION: (19)..(19)
<223> OTHER INFORMATION: Any amino acid or absent
<220> FEATURE:
<221> NAME/KEY: MOD_RES
<222> LOCATION: (20)..(20)

<223> OTHER INFORMATION: Pro or absent
<220> FEATURE:
<221> NAME/KEY: SITE
<222> LOCATION: (3)..(20)
<223> OTHER INFORMATION: This region may encompass 1-9 “Xaa Pro” repeating units wherein some positions may be absent
<220> FEATURE:
<223> OTHER INFORMATION: See specification as filed for detailed description of substitutions and preferred embodiments

<400> SEQUENCE: 150

Xaa Pro Xaa Xaa Xaa Xaa Xaa Xaa Xaa Xaa Xaa Xaa Xaa Xaa Xaa Xaa
1 5 10 15

Xaa Xaa Xaa Xaa
20

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (11)..(11)
<223> OTHER INFORMATION: Gly or absent
<220> FEATURE:
<221> NAME/KEY: MOD_RES
<222> LOCATION: (12)..(12)
<223> OTHER INFORMATION: Gly or absent
<220> FEATURE:
<221> NAME/KEY: MOD_RES
<222> LOCATION: (13)..(13)
<223> OTHER INFORMATION: Gly or absent
<220> FEATURE:
<221> NAME/KEY: MOD_RES
<222> LOCATION: (14)..(14)
<223> OTHER INFORMATION: Gly or absent
<220> FEATURE:
<221> NAME/KEY: MOD_RES
<222> LOCATION: (15)..(15)
<223> OTHER INFORMATION: Ser or absent
<220> FEATURE:
<221> NAME/KEY: MOD_RES
<222> LOCATION: (16)..(16)
<223> OTHER INFORMATION: Gly or absent
<220> FEATURE:
<221> NAME/KEY: MOD_RES
<222> LOCATION: (17)..(17)
<223> OTHER INFORMATION: Gly or absent
<220> FEATURE:
<221> NAME/KEY: MOD_RES
<222> LOCATION: (18)..(18)
<223> OTHER INFORMATION: Gly or absent
<220> FEATURE:
<221> NAME/KEY: MOD_RES
<222> LOCATION: (19)..(19)
<223> OTHER INFORMATION: Gly or absent
<220> FEATURE:
<221> NAME/KEY: MOD_RES
<222> LOCATION: (20)..(20)
<223> OTHER INFORMATION: Ser or absent
<220> FEATURE:
<221> NAME/KEY: MOD_RES
<222> LOCATION: (21)..(21)
<223> OTHER INFORMATION: Gly or absent
<220> FEATURE:
<221> NAME/KEY: MOD_RES
<222> LOCATION: (22)..(22)
<223> OTHER INFORMATION: Gly or absent
<220> FEATURE:
<221> NAME/KEY: MOD_RES
<222> LOCATION: (23)..(23)
<223> OTHER INFORMATION: Gly or absent
<220> FEATURE:

-continued

```
<221> NAME/KEY: MOD_RES
<222> LOCATION: (24)..(24)
<223> OTHER INFORMATION: Gly or absent
<220> FEATURE:
<221> NAME/KEY: MOD_RES
<222> LOCATION: (25)..(25)
<223> OTHER INFORMATION: Ser or absent
<220> FEATURE:
<221> NAME/KEY: SITE
<222> LOCATION: (11)..(25)
<223> OTHER INFORMATION: This region may encompass 1-3 "Gly Gly Gly Gly
      Ser" repeating units wherein some positions may be absent

<400> SEQUENCE: 151

Gly Gly Gly Gly Ser Gly Gly Gly Gly Ser Xaa Xaa Xaa Xaa Xaa Xaa
1               5                   10                  15

Xaa Xaa Xaa Xaa Xaa Xaa Xaa Xaa Xaa
            20                  25
```